US011110159B2

(12) United States Patent
Demoitie et al.

(10) Patent No.: US 11,110,159 B2
(45) Date of Patent: Sep. 7, 2021

(54) METHODS FOR INDUCING AN IMMUNE RESPONSE

(71) Applicant: GLAXOSMITHKLINE BIOLOGICALS, SA, Rixensart (BE)

(72) Inventors: Marie-Ange Demoitie, Rixensart (BE); Marie-Noelle Renelle Donner, Rixensart (BE); Nadia Ouaked, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 115 days.

(21) Appl. No.: 15/747,671

(22) PCT Filed: Jul. 25, 2016

(86) PCT No.: PCT/EP2016/067622
§ 371 (c)(1),
(2) Date: Jan. 25, 2018

(87) PCT Pub. No.: WO2017/017050
PCT Pub. Date: Feb. 2, 2017

(65) Prior Publication Data

US 2018/0250375 A1 Sep. 6, 2018

(30) Foreign Application Priority Data

Jul. 27, 2015 (GB) ..................................... 1513176

(51) Int. Cl.

| | |
|---|---|
| ***A61K 39/04*** | (2006.01) |
| ***C12N 15/86*** | (2006.01) |
| ***A61K 39/12*** | (2006.01) |
| ***C12N 7/00*** | (2006.01) |
| ***A61P 31/06*** | (2006.01) |
| ***A61K 35/761*** | (2015.01) |
| ***C07K 14/005*** | (2006.01) |
| ***C07K 14/35*** | (2006.01) |
| ***A61K 9/00*** | (2006.01) |
| ***A61K 39/39*** | (2006.01) |
| ***A61K 45/00*** | (2006.01) |
| ***C12N 15/85*** | (2006.01) |
| ***A61K 39/00*** | (2006.01) |

(52) U.S. Cl.

CPC ............ *A61K 39/04* (2013.01); *A61K 9/0019* (2013.01); *A61K 35/761* (2013.01); *A61K 39/12* (2013.01); *A61K 39/39* (2013.01); *A61K 45/05* (2013.01); *A61P 31/06* (2018.01); *C07K 14/005* (2013.01); *C07K 14/35* (2013.01); *C12N 7/00* (2013.01); *C12N 15/85* (2013.01); *C12N 15/86* (2013.01); *A61K 2039/5256* (2013.01); *A61K 2039/545* (2013.01); *C12N 2710/10321* (2013.01); *C12N 2710/10341* (2013.01); *C12N 2710/10343* (2013.01); *C12N 2740/16234* (2013.01); *C12N 2760/18534* (2013.01)

(58) Field of Classification Search
None
See application file for complete search history.

(56) References Cited

U.S. PATENT DOCUMENTS

| | | | |
|---|---|---|---|
| 5,981,225 | A | 11/1999 | Kochanek et al. |
| 6,350,456 | B1 | 2/2002 | Reed et al. |
| 8,231,880 | B2 | 7/2012 | Soumitra et al. |
| 2011/0217332 | A1 | 9/2011 | Colloca et al. |
| 2012/0027788 | A1 | 2/2012 | Colloca et al. |

FOREIGN PATENT DOCUMENTS

| | | | |
|---|---|---|---|
| WO | 97/09428 | A2 | 3/1997 |
| WO | 2003/070187 | A3 | 8/2003 |
| WO | 03070187 | A2 | 8/2003 |
| WO | 2005071093 | A3 | 8/2005 |
| WO | 2006033672 | A2 | 3/2006 |
| WO | 2006117240 | A2 | 11/2006 |
| WO | 2006133911 | A2 | 12/2006 |
| WO | 2008/107370 | A1 | 9/2008 |
| WO | 2009105084 | A2 | 8/2009 |
| WO | 2010/023260 | A1 | 3/2010 |
| WO | 2010086189 | A2 | 8/2010 |
| WO | 2011045612 | A1 | 4/2011 |
| WO | 2011130627 | A2 | 10/2011 |
| WO | 2012080369 | A1 | 6/2012 |
| WO | 2012080370 | A1 | 6/2012 |
| WO | 2013123579 | A1 | 8/2013 |
| WO | 2016/198621 | A1 | 12/2016 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Cruse et al., Illustrated Dict. of Immunology, 2nd ed., CRC Press, 2003, p. 46.*
McGuinness et al. (Mol. Microbiol., 7:505-514, 1993).*
Moudallal et al. (EMBO Journal, 1:1005-1010, 1982).*
Abaza et al. (J. Prot. Chem., 11:433-444, 1992).*
Colloca Stefano et al, "Vaccine Vectors Derived from a Large Collection of Simian Adenoviruses Induce Potent Cellular Immunity Across Multiple Species", Science Translational Medicine. American Association for the Advancement of Science, Washington, DC, vol. 4, No. 115, Jan. 1, 2012.

(Continued)

*Primary Examiner* — Brian Gangle

(57) ABSTRACT

The present invention relates to methods for inducing an immune response, in particular methods for inducing an immune response against mycobacterial infections or disease comprising (i) at least one administration of a polypeptide Rv1196 related antigen and at least one administration of an adenovirus encoding a Rv1196 related antigen or (ii) at least one administration of a polypeptide Rv0125 related antigen and at least one administration of an adenovirus encoding a Rv0125 related antigen. Associated compositions, adenoviral constructs and polynucleotide sequences are also provided.

9 Claims, 23 Drawing Sheets

Specification includes a Sequence Listing.

(56) References Cited

OTHER PUBLICATIONS

Neha Dalmia et al, "Prime-boost approaches to tuberculosis vaccine development", Expert Review of Vaccines, vol. 11, No. 10, Oct. 1, 2012.
Amit Lahiri, et al., "Engagement of TLR signaling as adjuvant: Towards smarter vaccine and beyond," Vaccine 26 (2008) 6777-6783.
Ramshaw et al., Trends: Immunology Today, 21:163-165 (2000).
Dillon et al., Infection and Immunity, 67:2941-2950 (1999).
Lewinsohn et al., Am J Respir Crit Care Med, 166:843-848 (2002).
International Preliminary Report on Patentability and Written Opinion in PCT/EP2016/067622, dated Jan. 30, 2018 (7 pages).
International Preliminary Report on Patentability and Written Opinion in PCT/EP2016/067621, dated Jan. 30, 2018 (7 pages).
Letvin et al., PNAS 94: 9378-9383 (1997).
Mortier et al., BMC Immunology, 16:63 (2015).
Idoko et al., Tuberculosis, 94:564-578 (2014).
Leroux-Roels et al., Vaccine, 31:2196-2206 (2013).
Montoya et al., J Clin Immunol, 33:1360-1375 (2013).
Penn-Nicholson et al., Vaccine, 33:4025-4034 (2015).
Thacher et al., AIDS, 28:1769-1781 (2014).
Roy et al., J Gene Med, 13:17-25 (2011).
Colloca et al., "Vaccine Vectors Derived from a Large Collection of Simian Adenoviruses Induce Potent Cellular Immunity Across Multiple Species," Science Translational Medicine, vol. 4, No. 115, (Jan. 4, 2012).
Cruse et al., Illustrated Dict. of Immunology, 2nd ed., CRC Press, 2003, pp. 46, 166, 382.
Da Costa et al., International Journal of Infectious Diseases, 32: 5-12 (2015).
Derrick et al., Vaccine, 29: 2902-2909 (2011).
Forbes et al., The Journal of Immunology, 181: 4955-4964 (2008).
Mercier et al., Vaccine, 25: 8687-8701 (2007).
Conference Report, Vaccine, 33: 3038-3046 (2015).
Zhang et al., Human Vaccines & Immunotherapeutics, 11 (7): 1803-1813 (2015).

* cited by examiner

| | 14PI Group 1: M72/AS01E | 14PII Group 1: 2x M72/AS01E | 14PI Group 2: M72-ChAd3 10^8VP | 14PII Group 2: M72-ChAd3 10^8VP / M72 AS01E | 14PI Group 3: M72-ChAd63 10^8VP | 14PII Group 3: M72-ChAd63 10^8VP / M72 AS01E | 14PI Group 4: eGFP-ChAd3 10^8VP | 14PII Group 4: eGFP-ChAd3 10^8VP / M72 AS01E | 14PI Group 5: M72/AS01E | 14PII Group 5: M72/AS01E / M72-ChAd3 10^8VP | 14PI Group 6: M72/AS01E | 14PII Group 6: M72/AS01E / M72-ChAd63 10^8VP |
|---|---|---|---|---|---|---|---|---|---|---|---|---|
| △ Pool 1 | 0.080 | 0.250 | 0.516 | 1.623 | 0.065 | 0.954 | 0.000 | 0.3484 | 0.097 | 1.5569 | 0.222 | 0.4783 |
| □ Pool 2 | 0.189 | 0.486 | 0.554 | 2.111 | 0.229 | 1.146 | 0.129 | 0.349 | 0.246 | 1.131 | 0.134 | 0.496 |
| ○ Pool 3 | 0.143 | 0.624 | 0.674 | 2.833 | 0.317 | 1.175 | 0.000 | 0.276 | 0.121 | 1.637 | 0.288 | 0.279 |
| ◇ Pool 4 | 0.130 | 0.288 | 0.428 | 2.027 | 0.353 | 0.563 | 0.018 | 0.422 | 0.161 | 0.508 | 0.114 | 0.419 |
| – Median | 0.137 | 0.387 | 0.535 | 2.069 | 0.273 | 1.050 | 0.009 | 0.349 | 0.141 | 1.344 | 0.178 | 0.449 |

Timepoint

Figure 6

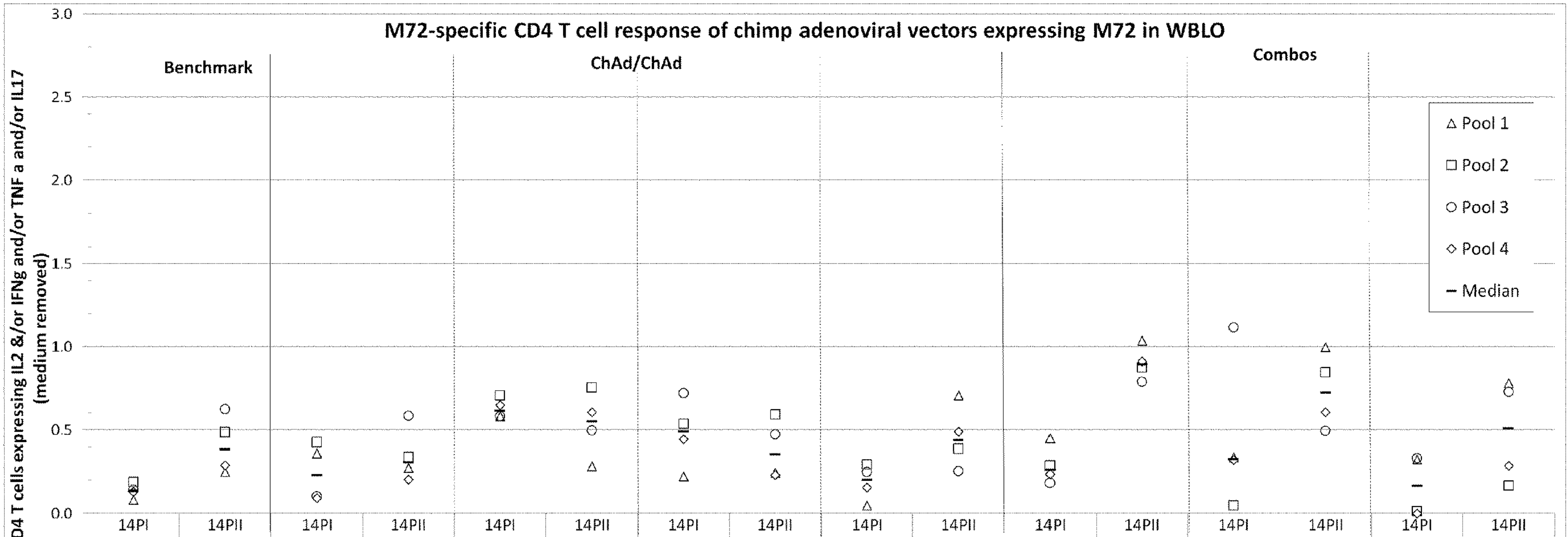

| | 14PI | 14PII | 14PI | 14PII | 14PI | 14PII | 14PI | 14PII | 14PI | 14PII | 14PI | 14PII | 14PI | 14PII | 14PI | 14PII |
|---|---|---|---|---|---|---|---|---|---|---|---|---|---|---|---|---|
| | Group 1: M72/AS01E | Group 1: 2x M72/AS01E | Group 7: M72-ChAd3 10^8VP AS01E | Group 7: 2x M72-ChAd3 10^8VP AS01E | Group 8: M72-ChAd3 10^8VP | Group 8: M72-ChAd3 10^8VP / M72-ChAd3 10^8VP | Group 9: M72-ChAd3 10^8VP | Group 9: M72-ChAd3 10^8VP / M72-ChAd63 10^8VP | Group 10: M72-ChAd63 10^8VP | Group 10: M72-ChAd63 10^8VP / M72-ChAd3 10^8VP | Group 11: M72-AS01E / M72-ChAd3 Combo | Group 11: M72-AS01E / M72-ChAd3 Combo | Group 12: M72-AS01E / M72-ChAd3 CoAd | Group 12: M72-AS01E / M72-ChAd3 CoAd | Group 13:M72-AS01E / eGFP-ChAd3 Combo | Group 13: M72-AS01E / eGFP-ChAd3 Combo |
| △ Pool 1 | 0.080 | 0.250 | 0.361 | 0.2738 | 0.581 | 0.2842 | 0.223 | 0.2433 | 0.046 | 0.707 | 0.448 | 1.0356 | 0.336 | 0.9973 | 0.322 | 0.7814 |
| □ Pool 2 | 0.189 | 0.486 | 0.426 | 0.338 | 0.707 | 0.755 | 0.535 | 0.591 | 0.293 | 0.388 | 0.288 | 0.875 | 0.047 | 0.843 | 0.013 | 0.166 |
| ○ Pool 3 | 0.143 | 0.624 | 0.103 | 0.585 | 0.582 | 0.495 | 0.720 | 0.472 | 0.249 | 0.253 | 0.183 | 0.787 | 1.116 | 0.494 | 0.330 | 0.729 |
| ◇ Pool 4 | 0.130 | 0.288 | 0.093 | 0.202 | 0.647 | 0.606 | 0.443 | 0.231 | 0.155 | 0.488 | 0.237 | 0.911 | 0.320 | 0.605 | 0.000 | 0.286 |
| − Median | 0.137 | 0.387 | 0.232 | 0.306 | 0.614 | 0.550 | 0.489 | 0.358 | 0.202 | 0.438 | 0.262 | 0.893 | 0.328 | 0.724 | 0.167 | 0.507 |

Timepoint

| | 14PI Group 1: M72/AS01E | 14PII Group 1: 2x M72/AS01E | 14PI Group 2: M72-ChAd3 10^8VP | 14PII Group 2: M72-ChAd3 10^8VP / M72 AS01E | 14PI Group 3: M72-ChAd63 10^8VP | 14PII Group 3: M72-ChAd63 10^8VP / M72 AS01E | 14PI Group 4: eGFP-ChAd3 10^8VP | 14PII Group 4: eGFP-ChAd3 10^8VP / M72 AS01E | 14PI Group 5: M72/AS01E | 14PII Group 5: M72/AS01E / M72-ChAd3 10^8VP | 14PI Group 6: M72/AS01E | 14PII Group 6: M72/AS01E / M72-ChAd63 10^8VP |
|---|---|---|---|---|---|---|---|---|---|---|---|---|
| △ Pool 1 | 0.096 | 0.000 | 10.218 | 4.412 | 7.353 | 5.001 | 0.000 | 0.0242 | 0.000 | 32.21637 | 0.041 | 7.7728 |
| □ Pool 2 | 0.065 | 0.176 | 11.755 | 8.184 | 8.480 | 6.924 | 0.000 | 0.204 | 0.093 | 41.416 | 0.049 | 17.627 |
| ○ Pool 3 | 0.016 | 0.262 | 17.252 | 10.121 | 13.022 | 7.785 | 0.000 | 0.143 | 0.024 | 27.993 | 0.153 | 17.628 |
| ◇ Pool 4 | 0.266 | 0.270 | 9.637 | 6.019 | 7.892 | 4.781 | 0.150 | 0.146 | 0.049 | 22.828 | 0.144 | 16.944 |
| − Median | 0.081 | 0.219 | 10.986 | 7.101 | 8.186 | 5.962 | 0.000 | 0.145 | 0.036 | 30.105 | 0.096 | 17.286 |

Timepoint

Figure 8

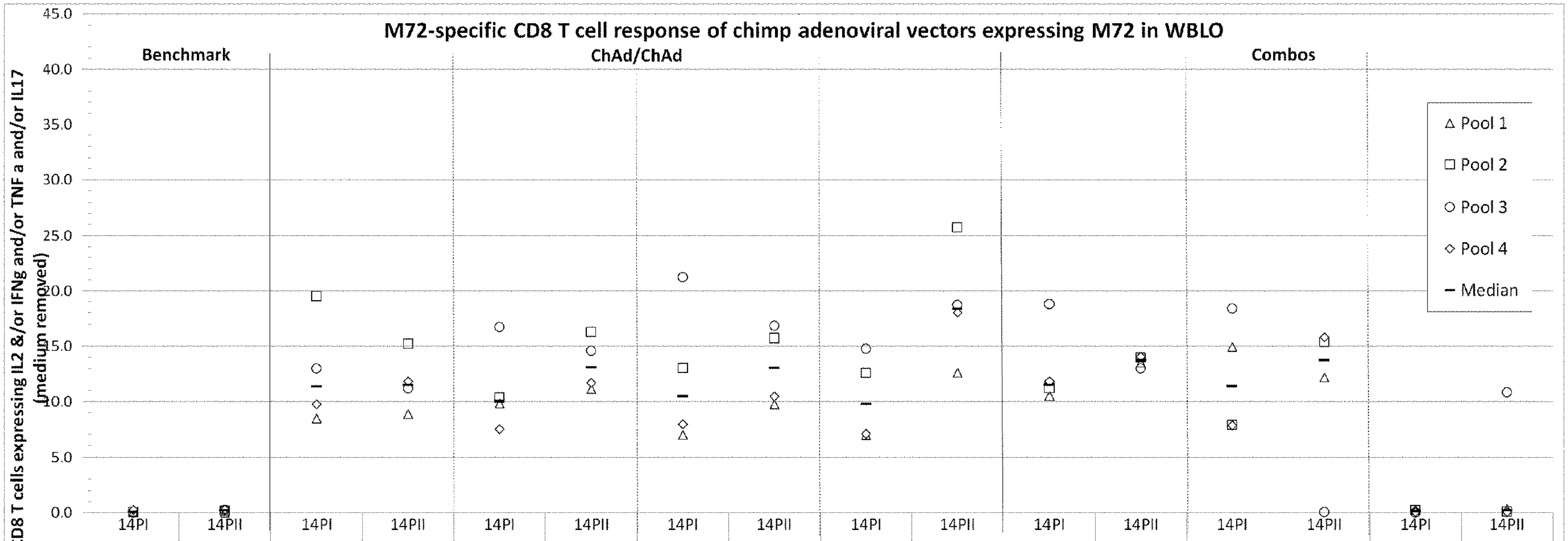

| | 14PI | 14PII | 14PI | 14PII | 14PI | 14PII | 14PI | 14PII | 14PI | 14PII | 14PI | 14PII | 14PI | 14PII | 14PI | 14PII |
|---|---|---|---|---|---|---|---|---|---|---|---|---|---|---|---|---|
| | Group 1: M72/AS01E | Group 1: 2x M72/AS01E | Group 7: M72-ChAd3 10^8VP AS01E | Group 7: 2x M72-ChAd3 10^8VP AS01E | Group 8: M72-ChAd3 10^8VP | Group 8: M72-ChAd3 10^8VP / M72-ChAd3 10^8VP | Group 9: M72-ChAd3 10^8VP | Group 9: M72-ChAd3 10^8VP / M72-ChAd63 10^8VP | Group 10: M72-ChAd63 10^8VP | Group 10: M72-ChAd63 10^8VP / M72-ChAd3 10^8VP | Group 11: M72-AS01E / M72-ChAd3 Combo | Group 11: M72-AS01E / M72-ChAd3 Combo | Group 12: M72-AS01E./ M72-ChAd3 CoAd | Group 12: M72-AS01E / M72-ChAd3 CoAd | Group 13: M72-AS01E / eGFP-ChAd3 Combo | Group 13: M72-AS01E / eGFP-ChAd3 Combo |
| △ Pool 1 | 0.096 | 0.000 | 8.451 | 8.8706 | 9.805 | 11.14912 | 6.977 | 9.7277 | 6.957 | 12.61668 | 10.495 | 13.5277 | 14.928 | 12.16355 | 0.272 | 0.35566 |
| □ Pool 2 | 0.065 | 0.176 | 19.534 | 15.193 | 10.353 | 16.281 | 13.007 | 15.717 | 12.559 | 25.729 | 11.222 | 13.957 | 7.857 | 15.350 | 0.213 | 0.104 |
| ○ Pool 3 | 0.016 | 0.262 | 12.986 | 11.182 | 16.713 | 14.583 | 21.233 | 16.846 | 14.758 | 18.736 | 18.801 | 12.970 | 18.409 | 0.032 | 0.016 | 10.815 |
| ◇ Pool 4 | 0.266 | 0.270 | 9.724 | 11.825 | 7.491 | 11.676 | 7.945 | 10.460 | 7.066 | 18.022 | 11.833 | 14.063 | 7.807 | 15.786 | 0.046 | 0.064 |
| – Median | 0.081 | 0.219 | 11.355 | 11.504 | 10.079 | 13.129 | 10.476 | 13.088 | 9.813 | 18.379 | 11.528 | 13.742 | 11.393 | 13.757 | 0.129 | 0.230 |

Timepoint

| | Group 1: 2x M72/AS01E | Group 2: M72-ChAd3 10^8VP / M72 AS01E | Group 3: M72-ChAd63 10^8VP / M72 AS01E | Group 4: eGFP-ChAd3 10^8VP / M72 AS01E | Group 5: M72/AS01E / M72-ChAd3 10^8VP | Group 6: M72/AS01E / M72-ChAd63 10^8VP | Group 7: 2x M72-ChAd3 10^8VP AS01E | Group 8: M72-ChAd3 10^8VP / M72-ChAd3 10^8VP | Group 9: M72-ChAd3 10^8VP / M72-ChAd63 10^8VP | Group 10: M72-ChAd63 10^8VP / M72-ChAd3 10^8VP | Group 11: M72-AS01E / M72-ChAd3 Combo | Group 12: M72-AS01E / M72-ChAd3 CoAd | Group 13: M72-AS01E / eGFP-ChAd3 Combo |
|---|---|---|---|---|---|---|---|---|---|---|---|---|---|
| Δ Pool 1 | 1.678 | 4.228 | 4.274 | 0.576 | 2.122 | 3.779 | 1.175 | 1.210 | 1.051 | 1.216 | 3.109 | 2.683 | 0.468 |
| □ Pool 2 | 1.668 | 3.445 | 2.875 | 0.347 | 2.620 | 0.980 | 1.357 | 1.558 | 1.059 | 0.735 | 3.629 | 2.850 | 0.770 |
| ○ Pool 3 | 0.829 | 6.163 | 3.125 | 0.476 | 3.050 | 2.064 | 1.208 | 1.573 | 1.495 | 1.277 | 3.234 | 2.172 | 0.926 |
| ◇ Pool 4 | 0.509 | 2.728 | 3.214 | 0.544 | 2.236 | 1.869 | 0.656 | 1.139 | 1.000 | 1.578 | 3.150 | 1.727 | 0.495 |
| – Median | 1.249 | 3.836 | 3.169 | 0.510 | 2.428 | 1.967 | 1.192 | 1.384 | 1.055 | 1.246 | 3.192 | 2.428 | 0.632 |

| | Group 1: 2x M72/AS01E | Group 2: M72-ChAd3 10^8VP / M72 AS01E | Group 3: M72-ChAd63 10^8VP / M72 AS01E | Group 4: eGFP-ChAd3 10^8VP / M72 AS01E | Group 5: M72/AS01E / M72-ChAd3 10^8VP | Group 6: M72/AS01E / M72-ChAd63 10^8VP | Group 7: 2x M72-ChAd3 10^8VP AS01E | Group 8: M72-ChAd3 10^8VP / M72-ChAd3 10^8VP | Group 9: M72-ChAd3 10^8VP / M72-ChAd63 10^8VP | Group 10: M72-ChAd63 10^8VP / M72-ChAd3 10^8VP | Group 11: M72-AS01E / M72-ChAd3 Combo | Group 12: M72-AS01E / M72-ChAd3 CoAd | Group 13: M72-AS01E / eGFP-ChAd3 Combo |
|---|---|---|---|---|---|---|---|---|---|---|---|---|---|
| Δ Pool 1 | 0.065 | 9.845 | 10.193 | 0.124 | 15.893 | 48.331 | 13.974 | 23.802 | 18.352 | 21.717 | 19.573 | 20.320 | 0.035 |
| □ Pool 2 | 0.049 | 12.992 | 9.297 | 0.090 | 46.950 | 27.362 | 24.104 | 27.147 | 23.664 | 24.723 | 17.891 | 25.941 | 0.285 |
| ○ Pool 3 | 0.036 | 13.618 | 9.176 | 0.084 | 35.052 | 19.992 | 19.391 | 25.577 | 22.928 | 24.699 | 18.169 | 18.020 | 0.072 |
| ◇ Pool 4 | 0.101 | 8.349 | 9.951 | 0.181 | 37.414 | 18.074 | 13.046 | 23.798 | 19.472 | 27.197 | 21.381 | 18.600 | 0.100 |
| – Median | 0.057 | 11.418 | 9.624 | 0.107 | 36.233 | 23.677 | 16.683 | 24.690 | 21.200 | 24.711 | 18.871 | 19.460 | 0.086 |

Figure 12

| | % CD4 T cells expressing cytokines (WBLO at 14PI) | | | | | | |
|---|---|---|---|---|---|---|---|
| | IL2 | IFNg | TNFa | IL2/IFNg | IL2/TNFa | IFNg/TNFa | IL2/IFNg/ TNFa |
| Group 1 | 0.000 | 0.000 | 0.018 | 0.000 | 0.072 | 0.000 | 0.029 |
| Group 2 | 0.011 | 0.071 | 0.000 | 0.032 | 0.000 | 0.166 | 0.225 |
| Group 3 | 0.000 | 0.025 | 0.017 | 0.006 | 0.006 | 0.035 | 0.064 |
| Group 4 | 0.000 | 0.000 | 0.009 | 0.000 | 0.000 | 0.000 | 0.000 |
| Group 5 | 0.016 | 0.000 | 0.048 | 0.000 | 0.056 | 0.000 | 0.000 |
| Group 6 | 0.000 | 0.000 | 0.000 | 0.013 | 0.095 | 0.000 | 0.034 |
| Group 7 | 0.000 | 0.002 | 0.079 | 0.026 | 0.000 | 0.020 | 0.041 |
| Group 8 | 0.000 | 0.137 | 0.002 | 0.000 | 0.000 | 0.148 | 0.362 |
| Group 9 | 0.000 | 0.116 | 0.000 | 0.018 | 0.000 | 0.106 | 0.190 |
| Group 10 | 0.000 | 0.027 | 0.007 | 0.023 | 0.000 | 0.018 | 0.042 |
| Group 11 | 0.000 | 0.000 | 0.043 | 0.000 | 0.008 | 0.072 | 0.091 |
| Group 12 | 0.006 | 0.032 | 0.012 | 0.000 | 0.027 | 0.060 | 0.081 |
| Group 13 | 0.000 | 0.000 | 0.030 | 0.000 | 0.059 | 0.000 | 0.000 |

Figure 14

| | % CD4 T cells expressing cytokines (WBLO at 14PI) | | | | | | | | | | | | | | |
|---|---|---|---|---|---|---|---|---|---|---|---|---|---|---|---|
| | CD4 IL2 | CD4 IFNg | CD4 TNFa | CD4 IL17 | CD4 IL2/ IFNg | CD4 IL2/ TNFa | CD4 IL2/ IL17 | CD4 IFNg/ TNFa | CD4 IFNg/ IL17 | CD4 TNFa/ IL17 | CD4 IL2/ IFNg/ TNFa | CD4 IL2/ IFNg/ IL17 | CD4 IL2/ TNFa/ IL17 | CD4 IFNg/ TNFa/ IL17 | CD4 IL2/ IFNg/ TNFa/ IL17 |
| **Group 1** | 0.000 | 0.000 | 0.000 | 0.011 | 0.009 | 0.119 | 0.000 | 0.029 | 0.000 | 0.000 | 0.112 | 0.000 | 0.000 | 0.000 | 0.000 |
| **Group 2** | 0.005 | 0.044 | 0.084 | 0.000 | 0.000 | 0.026 | 0.000 | 0.951 | 0.000 | 0.000 | 0.855 | 0.000 | 0.000 | 0.000 | 0.000 |
| **Group 3** | 0.014 | 0.009 | 0.000 | 0.016 | 0.000 | 0.009 | 0.000 | 0.370 | 0.000 | 0.000 | 0.449 | 0.000 | 0.000 | 0.000 | 0.000 |
| **Group 4** | 0.001 | 0.041 | 0.000 | 0.036 | 0.001 | 0.115 | 0.000 | 0.000 | 0.000 | 0.000 | 0.058 | 0.014 | 0.000 | 0.000 | 0.000 |
| **Group 5** | 0.000 | 0.140 | 0.090 | 0.018 | 0.011 | 0.028 | 0.000 | 0.255 | 0.000 | 0.000 | 0.649 | 0.000 | 0.000 | 0.000 | 0.000 |
| **Group 6** | 0.009 | 0.002 | 0.041 | 0.027 | 0.000 | 0.085 | 0.000 | 0.040 | 0.000 | 0.000 | 0.177 | 0.000 | 0.000 | 0.000 | 0.000 |
| **Group 7** | 0.000 | 0.051 | 0.000 | 0.000 | 0.000 | 0.000 | 0.000 | 0.068 | 0.000 | 0.000 | 0.119 | 0.000 | 0.000 | 0.000 | 0.000 |
| **Group 8** | 0.033 | 0.008 | 0.142 | 0.047 | 0.000 | 0.000 | 0.000 | 0.098 | 0.000 | 0.000 | 0.142 | 0.000 | 0.000 | 0.000 | 0.000 |
| **Group 9** | 0.000 | 0.019 | 0.007 | 0.007 | 0.008 | 0.002 | 0.000 | 0.052 | 0.000 | 0.000 | 0.157 | 0.000 | 0.000 | 0.000 | 0.000 |
| **Group 10** | 0.022 | 0.041 | 0.009 | 0.043 | 0.000 | 0.008 | 0.000 | 0.073 | 0.000 | 0.000 | 0.204 | 0.000 | 0.000 | 0.000 | 0.000 |
| **Group 11** | 0.000 | 0.063 | 0.000 | 0.019 | 0.000 | 0.016 | 0.000 | 0.365 | 0.000 | 0.000 | 0.436 | 0.000 | 0.000 | 0.000 | 0.000 |
| **Group 12** | 0.000 | 0.039 | 0.004 | 0.027 | 0.000 | 0.045 | 0.000 | 0.150 | 0.000 | 0.000 | 0.365 | 0.000 | 0.000 | 0.000 | 0.000 |
| **Group 13** | 0.028 | 0.000 | 0.013 | 0.013 | 0.000 | 0.071 | 0.000 | 0.009 | 0.000 | 0.000 | 0.059 | 0.000 | 0.000 | 0.000 | 0.000 |

Figure 16

| | % CD4 T cells expressing cytokines (lung at 14PII) | | | | | | | | | | | | | | |
|---|---|---|---|---|---|---|---|---|---|---|---|---|---|---|---|
| | CD4 IL2 | CD4 IFNg | CD4 TNFa | CD4 IL17 | CD4 IL2/ IFNg | CD4 IL2/ TNFa | CD4 IL2/ IL17 | CD4 IFNg/ TNFa | CD4 IFNg/ IL17 | CD4 TNFa/ IL17 | CD4 IL2/ IFNg/ TNFa | CD4 IL2/ IFNg/ IL17 | CD4 IL2/ TNFa/ IL17 | CD4 IFNg/ TNFa/ IL17 | CD4 IL2/ IFNg/ TNFa/ IL17 |
| **Group 1** | 0.000 | 0.000 | 0.000 | 0.011 | 0.009 | 0.119 | 0.000 | 0.029 | 0.000 | 0.000 | 0.112 | 0.000 | 0.000 | 0.000 | 0.000 |
| **Group 2** | 0.005 | 0.044 | 0.084 | 0.000 | 0.000 | 0.026 | 0.000 | 0.951 | 0.000 | 0.000 | 0.855 | 0.000 | 0.000 | 0.000 | 0.000 |
| **Group 3** | 0.014 | 0.009 | 0.000 | 0.016 | 0.000 | 0.009 | 0.000 | 0.370 | 0.000 | 0.000 | 0.449 | 0.000 | 0.000 | 0.000 | 0.000 |
| **Group 4** | 0.001 | 0.041 | 0.000 | 0.036 | 0.001 | 0.115 | 0.000 | 0.000 | 0.000 | 0.000 | 0.058 | 0.014 | 0.000 | 0.000 | 0.000 |
| **Group 5** | 0.000 | 0.140 | 0.090 | 0.018 | 0.011 | 0.028 | 0.000 | 0.255 | 0.000 | 0.000 | 0.649 | 0.000 | 0.000 | 0.000 | 0.000 |
| **Group 6** | 0.009 | 0.002 | 0.041 | 0.027 | 0.000 | 0.085 | 0.000 | 0.040 | 0.000 | 0.000 | 0.177 | 0.000 | 0.000 | 0.000 | 0.000 |
| **Group 7** | 0.000 | 0.051 | 0.000 | 0.000 | 0.000 | 0.000 | 0.000 | 0.068 | 0.000 | 0.000 | 0.119 | 0.000 | 0.000 | 0.000 | 0.000 |
| **Group 8** | 0.033 | 0.008 | 0.142 | 0.047 | 0.000 | 0.000 | 0.000 | 0.098 | 0.000 | 0.000 | 0.142 | 0.000 | 0.000 | 0.000 | 0.000 |
| **Group 9** | 0.000 | 0.019 | 0.007 | 0.007 | 0.008 | 0.002 | 0.000 | 0.052 | 0.000 | 0.000 | 0.157 | 0.000 | 0.000 | 0.000 | 0.000 |
| **Group 10** | 0.022 | 0.041 | 0.009 | 0.043 | 0.000 | 0.008 | 0.000 | 0.073 | 0.000 | 0.000 | 0.204 | 0.000 | 0.000 | 0.000 | 0.000 |
| **Group 11** | 0.000 | 0.063 | 0.000 | 0.019 | 0.000 | 0.016 | 0.000 | 0.365 | 0.000 | 0.000 | 0.436 | 0.000 | 0.000 | 0.000 | 0.000 |
| **Group 12** | 0.000 | 0.039 | 0.004 | 0.027 | 0.000 | 0.045 | 0.000 | 0.150 | 0.000 | 0.000 | 0.365 | 0.000 | 0.000 | 0.000 | 0.000 |
| **Group 13** | 0.028 | 0.000 | 0.013 | 0.013 | 0.000 | 0.071 | 0.000 | 0.009 | 0.000 | 0.000 | 0.059 | 0.000 | 0.000 | 0.000 | 0.000 |

Figure 18

| | % CD8 T cells expressing cytokines (whole blood at 14PI) | | | | | | |
|---|---|---|---|---|---|---|---|
| | **IL2** | **IFNg** | **TNFa** | **IL2/IFNg** | **IL2/TNFa** | **IFNg/TNFa** | **IL2/IFNg/ TNFa** |
| **Group 1** | 0.000 | 0.009 | 0.040 | 0.000 | 0.000 | 0.000 | 0.000 |
| **Group 2** | 0.005 | 4.528 | 0.046 | 0.047 | 0.000 | 6.451 | 0.749 |
| **Group 3** | 0.000 | 4.744 | 0.041 | 0.022 | 0.000 | 4.155 | 0.293 |
| **Group 4** | 0.000 | 0.000 | 0.000 | 0.000 | 0.000 | 0.000 | 0.000 |
| **Group 5** | 0.000 | 0.012 | 0.000 | 0.000 | 0.000 | 0.000 | 0.000 |
| **Group 6** | 0.000 | 0.021 | 0.009 | 0.000 | 0.000 | 0.019 | 0.000 |
| **Group 7** | 0.000 | 4.694 | 0.141 | 0.000 | 0.000 | 6.410 | 0.321 |
| **Group 8** | 0.000 | 4.352 | 0.000 | 0.038 | 0.000 | 5.090 | 0.410 |
| **Group 9** | 0.000 | 5.046 | 0.180 | 0.017 | 0.000 | 5.064 | 0.510 |
| **Group 10** | 0.000 | 5.515 | 0.050 | 0.009 | 0.000 | 4.455 | 0.234 |
| **Group 11** | 0.000 | 4.850 | 0.233 | 0.000 | 0.000 | 6.440 | 0.182 |
| **Group 12** | 0.000 | 4.547 | 0.118 | 0.035 | 0.000 | 6.545 | 0.385 |
| **Group 13** | 0.000 | 0.000 | 0.102 | 0.000 | 0.000 | 0.000 | 0.000 |

Figure 20

| | % CD8 T cells expressing cytokines (whole blood at 14PII) | | | | | | | | | | | | | | |
|---|---|---|---|---|---|---|---|---|---|---|---|---|---|---|---|
| | CD8 IL2 | CD8 IFNg | CD8 TNFa | CD8 IL17 | CD8 IL2/ IFNg | CD8 IL2/ TNFa | CD8 IL2/ IL17 | CD8 IFNg/ TNFa | CD8 IFNg/ IL17 | CD8 TNFa/ IL17 | CD8 IL2/ IFNg/ TNFa | CD8 IL2/ IFNg/ IL17 | CD8 IL2/ TNFa/ IL17 | CD8 IFNg/ TNFa/ IL17 | CD8 IL2/ IFNg/ TNFa/ IL17 |
| Group 1 | 0.022 | 0.000 | 0.073 | 0.000 | 0.000 | 0.013 | 0.000 | 0.000 | 0.000 | 0.000 | 0.013 | 0.000 | 0.000 | 0.000 | 0.000 |
| Group 2 | 0.000 | 1.033 | 0.358 | 0.031 | 0.011 | 0.014 | 0.000 | 5.025 | 0.000 | 0.000 | 0.611 | 0.000 | 0.000 | 0.000 | 0.000 |
| Group 3 | 0.035 | 0.939 | 0.207 | 0.027 | 0.000 | 0.000 | 0.000 | 4.370 | 0.000 | 0.000 | 0.544 | 0.000 | 0.000 | 0.000 | 0.000 |
| Group 4 | 0.009 | 0.019 | 0.010 | 0.018 | 0.000 | 0.000 | 0.000 | 0.011 | 0.003 | 0.000 | 0.014 | 0.000 | 0.000 | 0.000 | 0.000 |
| Group 5 | 0.000 | 5.514 | 0.238 | 0.000 | 0.023 | 0.000 | 0.000 | 21.497 | 0.004 | 0.000 | 1.670 | 0.000 | 0.000 | 0.011 | 0.000 |
| Group 6 | 0.009 | 3.145 | 0.208 | 0.001 | 0.000 | 0.000 | 0.000 | 11.115 | 0.009 | 0.000 | 0.837 | 0.000 | 0.000 | 0.011 | 0.000 |
| Group 7 | 0.023 | 1.196 | 0.271 | 0.030 | 0.000 | 0.000 | 0.000 | 8.742 | 0.021 | 0.000 | 0.773 | 0.000 | 0.000 | 0.000 | 0.000 |
| Group 8 | 0.019 | 2.830 | 0.401 | 0.000 | 0.017 | 0.000 | 0.000 | 8.740 | 0.002 | 0.004 | 0.584 | 0.000 | 0.000 | 0.000 | 0.000 |
| Group 9 | 0.000 | 1.771 | 0.522 | 0.000 | 0.019 | 0.000 | 0.000 | 9.275 | 0.000 | 0.000 | 1.218 | 0.000 | 0.000 | 0.000 | 0.000 |
| Group 10 | 0.014 | 3.514 | 0.346 | 0.009 | 0.039 | 0.006 | 0.000 | 12.300 | 0.008 | 0.000 | 1.220 | 0.000 | 0.000 | 0.000 | 0.000 |
| Group 11 | 0.000 | 1.141 | 0.318 | 0.010 | 0.007 | 0.007 | 0.000 | 10.800 | 0.000 | 0.000 | 1.145 | 0.000 | 0.000 | 0.000 | 0.000 |
| Group 12 | 0.000 | 1.965 | 0.204 | 0.000 | 0.024 | 0.000 | 0.000 | 8.900 | 0.000 | 0.000 | 0.910 | 0.000 | 0.000 | 0.012 | 0.000 |
| Group 13 | 0.000 | 0.019 | 0.148 | 0.018 | 0.000 | 0.006 | 0.000 | 0.011 | 0.013 | 0.000 | 0.000 | 0.000 | 0.000 | 0.000 | 0.000 |

Figure 22

| | % CD8 T cells expressing cytokines (lung at 14PII) | | | | | | | | | | | | | | |
|---|---|---|---|---|---|---|---|---|---|---|---|---|---|---|---|
| | CD8 IL2 | CD8 IFNg | CD8 TNFa | CD8 IL17 | CD8 IL2/ IFNg | CD8 IL2/ TNFa | CD8 IL2/ IL17 | CD8 IFNg/ TNFa | CD8 IFNg/ IL17 | CD8 TNFa/ IL17 | CD8 IL2/ IFNg/ TNFa | CD8 IL2/ IFNg/ IL17 | CD8 IL2/ TNFa/ IL17 | CD8 IFNg/ TNFa/ IL17 | CD8 IL2/ IFNg/ TNFa/ IL17 |
| Group 1 | 0.003 | 0.001 | 0.000 | 0.006 | 0.004 | 0.000 | 0.000 | 0.007 | 0.000 | 0.000 | 0.014 | 0.000 | 0.000 | 0.000 | 0.000 |
| Group 2 | 0.000 | 5.514 | 0.043 | 0.000 | 0.140 | 0.004 | 0.000 | 5.038 | 0.000 | 0.000 | 1.190 | 0.000 | 0.000 | 0.000 | 0.000 |
| Group 3 | 0.005 | 4.198 | 0.015 | 0.012 | 0.077 | 0.000 | 0.000 | 4.324 | 0.004 | 0.000 | 0.728 | 0.000 | 0.000 | 0.000 | 0.000 |
| Group 4 | 0.000 | 0.015 | 0.001 | 0.013 | 0.013 | 0.000 | 0.000 | 0.009 | 0.006 | 0.000 | 0.042 | 0.000 | 0.000 | 0.000 | 0.000 |
| Group 5 | 0.000 | 19.541 | 0.012 | 0.000 | 0.351 | 0.000 | 0.000 | 13.197 | 0.003 | 0.000 | 2.192 | 0.000 | 0.000 | 0.003 | 0.000 |
| Group 6 | 0.004 | 13.756 | 0.078 | 0.000 | 0.233 | 0.000 | 0.000 | 8.007 | 0.000 | 0.000 | 1.550 | 0.000 | 0.000 | 0.000 | 0.000 |
| Group 7 | 0.003 | 7.149 | 0.077 | 0.008 | 0.125 | 0.000 | 0.000 | 9.360 | 0.003 | 0.000 | 1.253 | 0.000 | 0.000 | 0.003 | 0.000 |
| Group 8 | 0.000 | 11.930 | 0.074 | 0.000 | 0.186 | 0.000 | 0.000 | 11.598 | 0.000 | 0.000 | 1.605 | 0.000 | 0.000 | 0.000 | 0.000 |
| Group 9 | 0.000 | 10.236 | 0.070 | 0.000 | 0.229 | 0.000 | 0.000 | 9.624 | 0.000 | 0.000 | 1.860 | 0.000 | 0.000 | 0.002 | 0.000 |
| Group 10 | 0.007 | 14.468 | 0.033 | 0.000 | 0.209 | 0.000 | 0.000 | 8.383 | 0.006 | 0.000 | 1.357 | 0.000 | 0.000 | 0.006 | 0.000 |
| Group 11 | 0.000 | 7.477 | 0.015 | 0.001 | 0.108 | 0.003 | 0.000 | 9.159 | 0.001 | 0.000 | 1.245 | 0.000 | 0.000 | 0.000 | 0.000 |
| Group 12 | 0.008 | 10.488 | 0.095 | 0.000 | 0.248 | 0.002 | 0.000 | 8.624 | 0.012 | 0.000 | 1.595 | 0.000 | 0.000 | 0.002 | 0.000 |
| Group 13 | 0.000 | 0.010 | 0.030 | 0.015 | 0.000 | 0.000 | 0.000 | 0.018 | 0.000 | 0.000 | 0.006 | 0.000 | 0.000 | 0.000 | 0.000 |

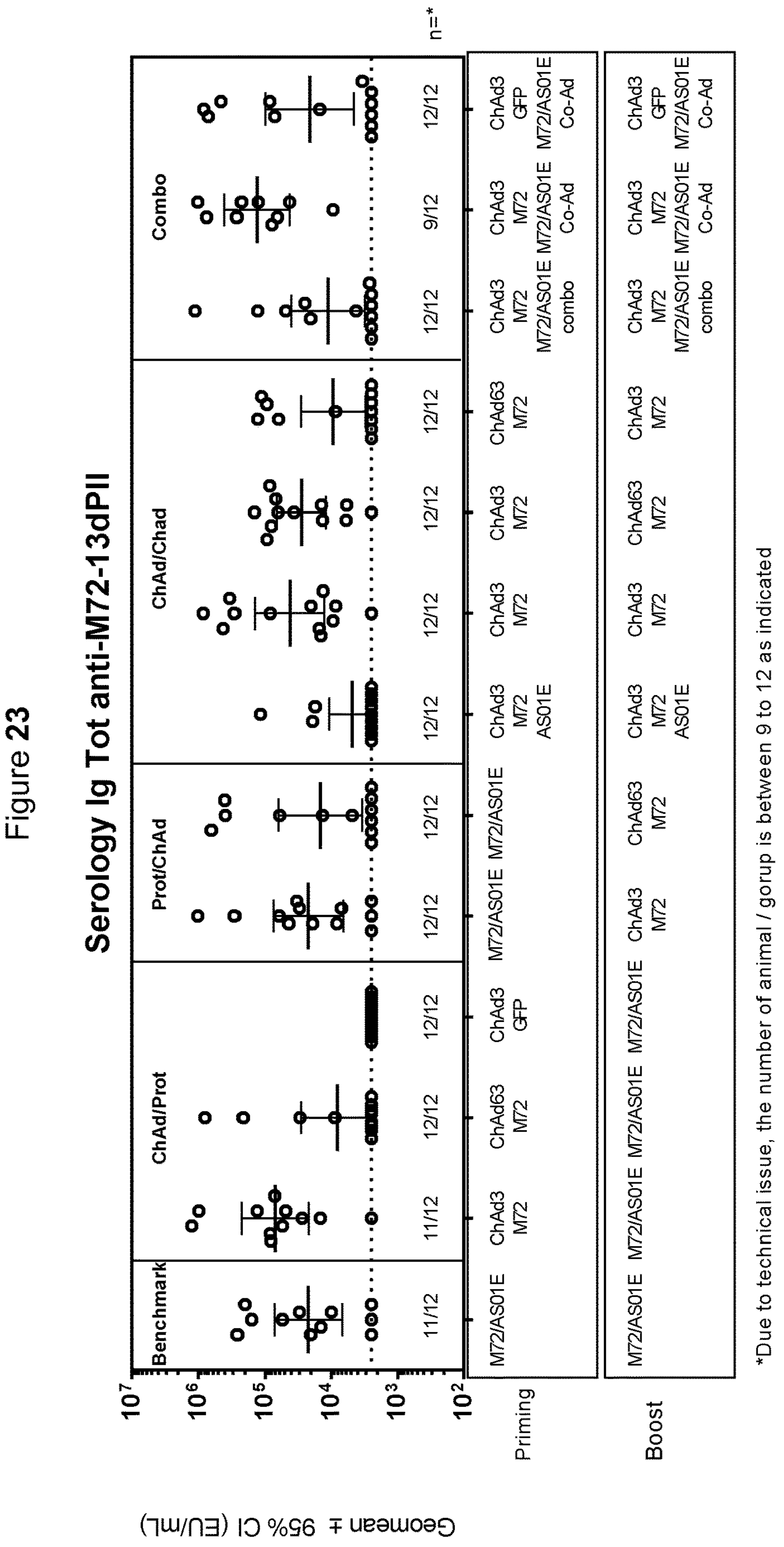
Figure 23
Serology Ig Tot anti-M72-13dPII
Geomean ± 95% CI (EU/mL)
$10^7$
$10^6$
$10^5$
$10^4$
$10^3$
$10^2$
Benchmark
ChAd/Prot
Prot/ChAd
ChAd/Chad
Combo
n=*
11/12
11/12
12/12
12/12
12/12
12/12
12/12
12/12
12/12
12/12
12/12
9/12
12/12
Priming
M72/AS01E
ChAd3 M72
ChAd63 M72
ChAd3 GFP
M72/AS01E
M72/AS01E
ChAd3 M72 AS01E
ChAd3 M72
ChAd3 M72
ChAd63 M72
ChAd3 M72 M72/AS01E combo
ChAd3 M72 M72/AS01E Co-Ad
ChAd3 GFP M72/AS01E Co-Ad
Boost
M72/AS01E
M72/AS01E
M72/AS01E
M72/AS01E
ChAd3 M72
ChAd63 M72
ChAd3 M72 AS01E
ChAd3 M72
ChAd63 M72
ChAd3 M72
ChAd3 M72 M72/AS01E combo
ChAd3 M72 M72/AS01E Co-Ad
ChAd3 GFP M72/AS01E Co-Ad
*Due to technical issue, the number of animal / gorup is between 9 to 12 as indicated

METHODS FOR INDUCING AN IMMUNE RESPONSE

CROSS-REFERENCE TO RELATED APPLICATIONS

This is the U.S. National Stage application submitted under 35 U.S.C. § 371 for International Application No. PCT/EP2016/067622, filed Jul. 25, 2016, which claims priority to Application No. GB 1513176.6, filed Jul. 27, 2015 all of which are incorporated herein by reference in their entireties.

TECHNICAL FIELD

The present invention relates to methods for inducing an immune response, in particular methods for inducing an immune response against mycobacterial infections or disease comprising (i) at least one administration of a polypeptide Rv1196 related antigen and at least one administration of an adenovirus encoding a Rv1196 related antigen or (ii) at least one administration of a polypeptide Rv0125 related antigen and at least one administration of an adenovirus encoding a Rv0125 related antigen. Associated compositions, adenoviral constructs and polynucleotide sequences are also provided.

BACKGROUND OF THE INVENTION

Vaccination is one of the most effective methods for preventing infectious diseases. However, a single administration of an antigen is often not sufficient to confer optimal immunity and/or a long-lasting response. Approaches for establishing strong and lasting immunity to specific pathogens include addition of adjuvants to vaccines and/or repeated vaccination, i.e. boosting an immune response by administration of one or more further doses of antigen. Such further administrations may be performed with the same vaccine (homologous boosting) or with a different vaccine (heterologous boosting).

Tuberculosis (TB) is a chronic infectious disease caused by infection with *Mycobacterium tuberculosis* and other *Mycobacterium* species. It is a major disease in developing countries, as well as an increasing problem in developed areas of the world.

Mtb72f and M72 are fusion protein antigens derived from the *Mycobacterium tuberculosis* proteins Rv1196 and Rv0125. Mtb72f and M72 (described, for example, in international patent applications WO2006/117240, WO2012/080369 and WO2012/080370 which are incorporated herein by reference) or fragments or derivatives thereof are protein antigens of potential benefit for the treatment or prevention of tuberculosis.

Preclinical and clinical investigations have led to M72 being administered in humans in conjunction with the immunostimulants 3-O-deacylated monophosphoryl lipid A (3D-MPL) and QS21 in a liposomal formulation and in a 0.1 month schedule using 10 ug M72 polypeptide, 25 ug 3D-MPL and 25 ug QS21 (Leroux-Roels et al *Vaccine* 2013 31 2196-2206, Montoya et al *J. Clin. Immunol.* 2013 33(8): 1360-1375; Thacher E G et al *AIDS* 2014 28(12):1769-1781; Idoko O T et al *Tuberculosis* (*Edinb*) 2014 94(6):564-578; Penn-Nicholson A, et al *Vaccine* 2015 33(32):4025-4034 doi:10.1016/j.vaccine.2015.05.088). A candidate vaccine utilising the M72 antigen is currently in a Phase IIB trial (ClinicalTrials.gov Identifier: NCT01755598) to evaluate the protective efficacy of two doses of adjuvanted protein against pulmonary TB, as compared to placebo, in adults aged 18-50 living in TB endemic countries.

WO2008107370A1 (incorporated herein by reference) describes the concomitant administration of a polypeptide antigen and an adenovirus encoding a polypeptide antigen.

WO2010023260 (incorporated herein by reference) describes the concomitant administration of a polypeptide antigen and viral vector encoding a polypeptide antigen.

There remains a need for novel methods of immunising against diseases, including tuberculosis, which are highly efficacious, safe, convenient, cost-effective, long-lasting and induce a broad spectrum of immune responses.

SUMMARY OF THE INVENTION

It has now surprisingly been found that, priming with a polypeptide Rv1196/Rv0125 related antigen and boosting with a non-human simian adenovirus encoding a Rv1196/Rv0125 related antigen, or priming with a non-human simian adenovirus encoding a Rv1196/Rv0125 related antigen with and boosting with a polypeptide Rv1196/Rv0125 related antigen can provide immune responses which are substantially improved relative to other potential approaches.

Accordingly, in a first aspect of the invention, there is provided a method for inducing an immune response in a subject comprising administration of a polypeptide Rv1196 related antigen to the subject, followed by administration of a non-human simian adenovirus encoding a Rv1196 related antigen.

In a second aspect of the invention, there is provided a method for inducing an immune response in a subject comprising administration of a non-human simian adenovirus encoding a Rv1196 related antigen, followed by administration of a polypeptide Rv1196 related antigen to the subject.

Suitably the polypeptide Rv1196 related antigen is provided in a composition which also comprises an adjuvant. Optionally, the adjuvant comprises a TLR agonist and/or an immunologically active saponin. The TLR agonist is suitably a TLR4 agonist.

Suitably the polypeptide Rv1196 related antigen is provided in a composition which does not comprise a non-human simian adenovirus encoding a Rv1196 related antigen.

Suitably the non-human simian adenovirus encoding a Rv1196 related antigen is provided in a composition which does not comprise a polypeptide Rv1196 related antigen.

In a third aspect of the invention, there is provided a method for inducing an immune response in a subject comprising administration of a polypeptide Rv0125 related antigen to the subject, followed by administration of a non-human simian adenovirus encoding a Rv0125 related antigen.

In a fourth aspect of the invention, there is provided a method for inducing an immune response in a subject comprising administration of a non-human simian adenovirus encoding a Rv0125 related antigen, followed by administration of a polypeptide Rv0125 related antigen to the subject.

Suitably the polypeptide Rv0125 related antigen is provided in a composition which also comprises an adjuvant. Optionally, the adjuvant comprises a TLR agonist and/or an immunologically active saponin. The TLR agonist is suitably a TLR4 agonist.

Suitably the polypeptide Rv0125 related antigen is provided in a composition which does not comprise a non-human simian adenovirus encoding a Rv0125 related antigen.

Suitably the non-human simian adenovirus encoding a Rv0125 related antigen is provided in a composition which does not comprise a polypeptide Rv0125 related antigen.

BRIEF DESCRIPTION OF THE FIGURES

FIG. 6: Percentage of M72-specific CD4 T cell response from whole blood of CB6F1 mice expressing IFN-gamma and/or IL-2 and/or TNF-alpha cytokines at 14 PI and 14PII using homologous (ChAd/ChAd) and in combination with M72/AS01E (admixture or co-administration) prime-boost vaccination strategies.

FIG. 8: Percentage of M72-specific CD8 T cell response from whole blood of CB6F1 mice expressing IFN-gamma and/or IL-2 and/or TNF-alpha cytokines at 14 PI and 14PII using homologous (ChAd/ChAd) and in combination with M72/AS01E (admixture or co-administration) prime-boost vaccination strategies.

FIG. 12: Table showing the data values of the cytokine profile of the M72-specific CD4 T cells response in WBLO at 14P1 in immunised CB6F1 mice.

FIG. 14: Table showing the data values of the cytokine profile of the M72-specific CD4 T cells response in WBLO at 14PII in immunised CB6F1 mice.

FIG. 16: Table showing the data values of the cytokine profile of the M72-specific CD4 T cells response in lung at 14PII in immunised CB6F1 mice.

FIG. 18: Table showing the data values of the cytokine profile of the M72-specific CD8 T cells response in WBLO at 14P1 in immunised CB6F1 mice.

FIG. 20: Table showing the data values of the cytokine profile of the M72-specific CD8 T cells response in WBLO at 14PII in immunised CB6F1 mice.

FIG. 22: Table showing the data values of the cytokine profile of the M72-specific CD8 T cells response in lung at 14PII in immunised CB6F1 mice.

FIG. 23: Anti-M72 Ig tot serology at 13dPII.

BRIEF DESCRIPTION OF THE SEQUENCE IDENTIFIERS

Figure 1:
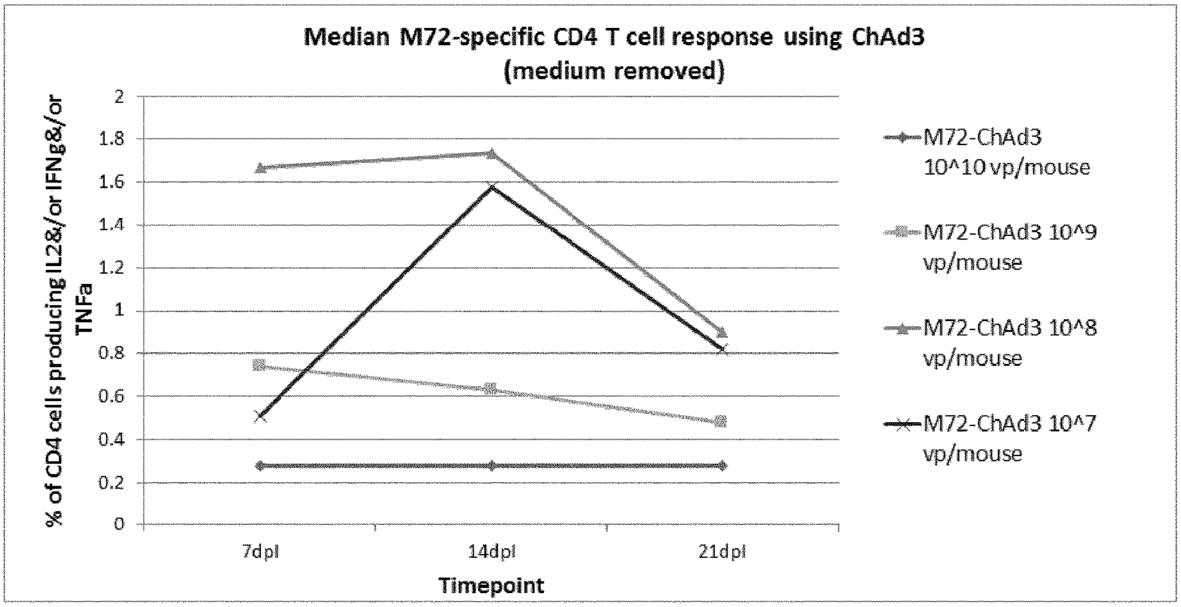
FIG. 1: Median percentage of M72-specific CD4 T cell response from CB6F1 mice expressing IFN-gamma and/or IL-2 and/or TNF-alpha cytokines at 7, 14 and 21 days post immunisation using ChAd3 in a range of doses.

SEQ ID No: 1 *Mycobacterium tuberculosis* H37Rv Rv1196 polypeptide sequence
SEQ ID No: 2 *Mycobacterium tuberculosis* F11 Rv1196 polypeptide sequence
SEQ ID No: 3 *Mycobacterium tuberculosis* H37Rv Rv0125 polypeptide sequence (mature sequence)
SEQ ID No: 4 M72 2-his polypeptide sequence
SEQ ID No: 5 M72 2-his polynucleotide
SEQ ID No: 6 M72 No his polypeptide sequence
SEQ ID No: 7 M72 No his polynucleotide
SEQ ID No: 8 M72 No his human optimised polynucleotide
SEQ ID No: 9 ChAd3 polynucleotide
SEQ ID No: 10 ChAd3 penton polypeptide sequence
SEQ ID No: 11 ChAd3 hexon polypeptide sequence
SEQ ID No: 12 ChAd3 fibre polypeptide sequence
SEQ ID No: 13 M72-ChAd3 construct DNA
SEQ ID No: 14 ChAd63 polynucleotide
SEQ ID No: 15 ChAd63 penton polypeptide sequence
SEQ ID No: 16 ChAd63 hexon polypeptide sequence
SEQ ID No: 17 ChAd63 fibre polypeptide sequence
SEQ ID No: 18 M72-ChAd63 construct DNA
SEQ ID No: 19 ChAd155 polynucleotide
SEQ ID No: 20 ChAd155 penton polypeptide sequence
SEQ ID No: 21 ChAd155 hexon polypeptide sequence
SEQ ID No: 22 ChAd155 fibre polypeptide sequence

DETAILED DESCRIPTION

Tuberculosis (TB) is a chronic infectious disease caused by infection with *Mycobacterium tuberculosis* and other *Mycobacterium* species. It is a major disease in developing countries, as well as an increasing problem in developed areas of the world. About one third of the world's population are believed to be latently infected with TB bacilli, with about 9 million new cases of active TB and 1.5 million deaths each year. Around 10% of those infected with TB bacilli will develop active TB, each person with active TB infecting an average of 10 to 15 others per year. (World Health Organisation Tuberculosis Facts 2014) *Mycobacterium tuberculosis* infects individuals through the respiratory route. Alveolar macrophages engulf the bacterium, but it is able to survive and proliferate by inhibiting phagosome fusion with acidic lysosomes. A complex immune response involving CD4+ and CD8+ T cells ensues, ultimately resulting in the formation of a granuloma. Central to the success of *Mycobacterium tuberculosis* as a pathogen is the fact that the isolated, but not eradicated, bacterium may persist for long periods, leaving an individual vulnerable to the later development of active TB.

Fewer than 5% of infected individuals develop active TB in the first years after infection. The granuloma can persist for decades and is believed to contain live *Mycobacterium tuberculosis* in a state of dormancy, deprived of oxygen and nutrients. However, it has been suggested that the majority of the bacteria in the dormancy state are located in non-macrophage cell types spread throughout the body (Locht et al, *Expert Opin. Biol. Ther.* 2007 7(11):1665-1677). The development of active TB occurs when the balance between the host's natural immunity and the pathogen changes, for example as a result of an immunosuppressive event (Anderson P *Trends in Microbiology* 2007 15(1):7-13; Ehlers S *Infection* 2009 37(2):87-95).

A dynamic hypothesis describing the balance between latent TB and active TB has also been proposed (Cardona P-J *Inflammation & Allergy—Drug Targets* 2006 6:27-39; Cardona P-J *Infection* 2009 37(2):80-86).

Although an infection may be asymptomatic for a considerable period of time, the active disease is most commonly manifested as an acute inflammation of the lungs, resulting in tiredness, weight loss, fever and a persistent cough. If untreated, serious complications and death typically result.

Tuberculosis can generally be controlled using extended antibiotic therapy, although such treatment is not sufficient to prevent the spread of the disease. Actively infected individuals may be largely asymptomatic, but contagious, for some time. In addition, although compliance with the treatment regimen (which typically lasts 6 months or more) is critical, patient behaviour is difficult to monitor. Some patients do not complete the course of treatment, which can lead to ineffective treatment and the development of drug resistance.

Multidrug-resistant TB (MDR-TB) is a form which fails to respond to first line medications. An estimated 480,000 people developed MDR-TB in 2013. MDR-TB is treatable by using second-line drugs. However, second-line treatment options are limited and recommended medicines are not always available. The extensive chemotherapy required (up to two years of treatment) is costly and can produce severe adverse drug reactions in patients.

Extensively drug-resistant TB (XDR-TB) occurs when resistance to second line medications develops on top of resistance to first line medications. It is estimated that about 9.0% of MDR-TB cases had XDR-TB (World Health Organisation Tuberculosis Facts 2014).

Even if a full course of antibiotic treatment is completed, infection with *M. tuberculosis* may not be eradicated from the infected individual and may remain as a latent infection that can be reactivated. Consequently, accurate and early diagnosis of the disease are of utmost importance.

Currently, vaccination with attenuated live bacteria is the most widely used method for inducing protective immunity. The most common *Mycobacterium* employed for this purpose is *Bacillus* Calmette-Guerin (BCG), an avirulent strain of *M. bovis* which was first developed over 60 years ago. It is administrated at birth in TB endemic regions. However, the safety and efficacy of BCG is a source of controversy—while protecting against severe disease manifestation in children, the efficacy of BCG against disease in adults is variable. Additionally, some countries, such as the United States, do not vaccinate the general public with this agent.

Several of the proteins which are strongly expressed during the early stages of *Mycobacterium* infection have been shown to provide protective efficacy in animal vaccination models. However, vaccination with antigens which are highly expressed during the early stages of infection may not provide an optimal immune response for dealing with later stages of infection. Adequate control during latent infection may require T cells which are specific for the particular antigens which are expressed at that time. Post-exposure vaccines which directly target the dormant persistent bacteria may aid in protecting against TB reactivation, thereby enhancing TB control, or even enabling clearance of the infection. A vaccine targeting latent TB could therefore significantly and economically reduce global TB infection rates.

Subunit vaccines based on late stage antigens could also be utilised in combination with early stage antigens to provide a multiphase vaccine. Alternatively, early and/or late stage antigens could be used to complement and improve BCG vaccination (either by boosting the BCG response or through the development of advanced recombinant BCG strains).

Mtb72f and M72 are fusion protein antigens of potential benefit for the treatment or prevention of tuberculosis. Mtb72f and M72 are derived from the *Mycobacterium tuberculosis* proteins Rv1196 and Rv0125, both genes are present in both virulent and avirulent strains of the *Mycobacterium tuberculosis* complex, and in BCG.

Rv1196 (described, for example, by the name Mtb39a in Dillon et al *Infection and Immunity* 1999 67(6): 2941-2950) is highly conserved, with 100% sequence identity across H37Rv, C, Haarlem, CDC1551, 94-M4241A, 98-R6041NH-RIF-EM, KZN605, KZN1435, KZN4207, KZNR506 strains, the F11 strain having a single point mutation Q30K (most other clinical isolates have in excess of 90% identity to H37Rv). An adenovirus encoding an Rv1196 related antigen is described in Lewinsohn et al *Am J Respir Crit Care Med* 2002 116:843-848.

Rv0125 (described, for example, by the name Mtb32a in Skeiky et al *Infection and Immunity* 1999 67(8): 3998-4007) is also highly conserved, with 100% sequence identity across many strains. An adenovirus (human Ad5) encoding an Rv0125 related antigen is described in Zhang et al *Human Vaccines & Therapeutics* 2015 11(7):1803-1813 doi: 10.1080/21645515.2015.1042193. Full length Rv0125 includes an N-terminal signal sequence which is cleaved to provide the mature protein.

Mtb72f has been shown to provide protection in a number of animal models (see, for example: Brandt et al *Infect. Immun.* 2004 72(11):6622-6632; Skeiky et al *J. Immunol.* 2004 172:7618-7628; Tsenova et al *Infect. Immun.* 2006 74(4):2392-2401). Mtb72f has also been the subject of clinical investigations (Von Eschen et al 2009 *Human Vaccines* 5(7):475-482). M72 is an improved antigen which incorporates a single serine to alanine mutation relative to Mtb72f, resulting in improved stability characteristics. M72 related antigens have also been shown to be of value in a latent TB model (international patent application WO2006/117240, incorporated herein by reference). Previous pre-clinical and clinical investigations have led to M72 being administered in humans in conjunction with the immunostimulants 3-O-deacylated monophosphoryl lipid A (3D-MPL) and QS21 in a liposomal formulation and in a 0.1 month schedule using 10 ug M72 polypeptide, 25 ug 3D-MPL and 25 ug QS21 (see, for example, Leroux-Roels et al *Vaccine* 2013 31 2196-2206, Montoya et al *J. Clin. Immunol.* 2013 33(8): 1360-1375; Thacher E G et al *AIDS* 2014 28(12):1769-1781; Idoko O T et al *Tuberculosis* (*Edinb*) 2014 94(6):564-578; Penn-Nicholson A, et al *Vaccine* 2015 33(32):4025-4034 doi:10.1016/j.vaccine.2015.05.088).

A candidate vaccine utilising the antigen M72 is currently in a Phase IIB trial (ClinicalTrials.gov Identifier: NCT01755598) to evaluate the protective efficacy of two doses doses of adjuvanted protein against pulmonary TB, as compared to placebo, in adults aged 18-50 living in TB endemic countries. Nevertheless, a need for improved vaccination approaches remains.

In a first aspect of the invention, there is provided a method for inducing an immune response in a subject comprising administration of a polypeptide Rv1196 related antigen to the subject, followed by administration of a non-human simian adenovirus encoding a Rv1196 related antigen.

In a second aspect of the invention, there is provided a method for inducing an immune response in a subject comprising administration of a non-human simian adenovirus encoding a Rv1196 related antigen to the subject, followed by administration of a polypeptide Rv1196 related antigen.

In a third aspect of the invention, there is provided a method for inducing an immune response in a subject comprising administration of a polypeptide Rv0125 related antigen to the subject, followed by administration of an immunogenic composition comprising a non-human simian adenovirus encoding a Rv0125 related antigen.

In a fourth aspect of the invention, there is provided a method for inducing an immune response in a subject comprising administration of a non-human simian adenovirus encoding a Rv0125 related antigen, followed by administration of a polypeptide Rv0125 related antigen to the subject.

As used herein, administration of a first composition "followed by" administration of a second composition indicates that a time interval has elapsed between administration of the first composition and administration of the second composition. Suitably the time interval between administrations is one week to two years, in particular two weeks to eighteen months, typically three weeks to fifteen months, such as three weeks to six months, for example three weeks to two months, especially three weeks to six weeks such as around four weeks.

Also provided is a polypeptide Rv1196 related antigen, for use in inducing an immune response in a subject wherein the polypeptide Rv1196 related antigen is administered to the subject, followed by the administration of a non-human simian adenovirus encoding a Rv1196 related antigen.

Similarly, there is provided a non-human simian adenovirus encoding a Rv1196 related antigen, for use in inducing an immune response in a subject wherein a polypeptide Rv1196 related antigen is administered to the subject, followed by the administration of the non-human simian adenovirus encoding a Rv1196 related antigen.

Further, there is provided the use of a polypeptide Rv1196 related antigen, in the manufacture of a medicament for inducing an immune response in a subject wherein the polypeptide Rv1196 related antigen is administered to the subject, followed by the administration of a non-human simian adenovirus encoding a Rv1196 related antigen.

Additionally, there is provided the use of a non-human simian adenovirus encoding a Rv1196 related antigen, in the manufacture of a medicament for inducing an immune response in a subject wherein a polypeptide Rv1196 related antigen is administered to the subject, followed by the administration of the non-human simian adenovirus encoding a Rv1196 related antigen.

Also provided is a polypeptide Rv1196 related antigen, for use in inducing an immune response in a subject wherein a non-human simian adenovirus encoding a Rv1196 related antigen is administered to the subject, followed by the administration of the polypeptide Rv1196 related antigen.

Similarly, there is provided a non-human simian adenovirus encoding a Rv1196 related antigen, for use in inducing an immune response in a subject wherein the non-human simian adenovirus encoding a Rv1196 related antigen is administered to the subject, followed by the administration of a polypeptide Rv1196 related antigen.

Further, there is provided the use of a polypeptide Rv1196 related antigen, in the manufacture of a medicament for inducing an immune response in a subject wherein a non-human simian adenovirus encoding a Rv1196 related antigen is administered to the subject, followed by the administration of the polypeptide Rv1196 related antigen.

Also provided is the use of a non-human simian adenovirus encoding a Rv1196 related antigen, in the manufacture of a medicament for inducing an immune response in a subject wherein the non-human simian adenovirus encoding a Rv1196 related antigen is administered to the subject, followed by the administration of a polypeptide Rv1196 related antigen.

Also provided is a polypeptide Rv0125 related antigen, for use in inducing an immune response in a subject wherein the polypeptide Rv0125 related antigen is administered to the subject, followed by the administration of a non-human simian adenovirus encoding a Rv0125 related antigen.

Similarly, there is provided a non-human simian adenovirus encoding a Rv0125 related antigen, for use in inducing an immune response in a subject wherein a polypeptide Rv0125 related antigen is administered to the subject, followed by the administration of the non-human simian adenovirus encoding a Rv0125 related antigen.

Further, there is provided the use of a polypeptide Rv0125 related antigen, in the manufacture of a medicament for inducing an immune response in a subject wherein the polypeptide Rv0125 related antigen is administered to the subject, followed by the administration of a non-human simian adenovirus encoding a Rv0125 related antigen.

Additionally, there is provided the use of a non-human simian adenovirus encoding a Rv0125 related antigen, in the manufacture of a medicament for inducing an immune response in a subject wherein a polypeptide Rv0125 related antigen is administered to the subject, followed by the administration of the non-human simian adenovirus encoding a Rv0125 related antigen.

Also provided is a polypeptide Rv0125 related antigen, for use in inducing an immune response in a subject wherein a non-human simian adenovirus encoding a Rv0125 related antigen is administered to the subject, followed by the administration of the polypeptide Rv0125 related antigen.

Similarly, there is provided a non-human simian adenovirus encoding a Rv0125 related antigen, for use in inducing an immune response in a subject wherein the non-human simian adenovirus encoding a Rv0125 related antigen is administered to the subject, followed by the administration of a polypeptide Rv0125 related antigen.

Further, there is provided the use of a polypeptide Rv0125 related antigen, in the manufacture of a medicament for inducing an immune response in a subject wherein a non-human simian adenovirus encoding a Rv0125 related antigen is administered to the subject, followed by the administration of the polypeptide Rv0125 related antigen.

Also provided is the use of a non-human simian adenovirus encoding a Rv0125 related antigen, in the manufacture of a medicament for inducing an immune response in a subject wherein the non-human simian adenovirus encoding a Rv0125 related antigen is administered to the subject, followed by the administration of a polypeptide Rv0125 related antigen.

Suitably the polypeptide Rv1196 related antigen is provided in a composition which also comprises an adjuvant. Optionally, the adjuvant comprises a TLR agonist and/or an immunologically active saponin. The TLR agonist is suitably a TLR4 agonist.

Suitably the polypeptide Rv0125 related antigen is provided in a composition which also comprises an adjuvant. Optionally, the adjuvant comprises a TLR agonist and/or an immunologically active saponin. The TLR agonist is suitably a TLR4 agonist.

Suitably the polypeptide Rv1196 related antigen is provided in a composition which is substantially free of a non-human simian adenovirus encoding a Rv1196 related antigen, such as it does not comprise a non-human simian adenovirus encoding a Rv1196 related antigen. For example, it is substantially free of or does not comprise a non-human simian adenovirus encoding a mycobacterial antigen (such as it is substantially free of or does not comprise any non-human simian adenovirus) in particular it is substantially free of or does not comprise any adenovirus encoding a mycobacterial antigen (such as it is substantially free of or does not comprise any adenovirus). In some embodiments the polypeptide Rv1196 related antigen is provided in a composition which is substantially free of or does not comprise any adenovirus encoding a mycobacterial antigen.

Furthermore, the polypeptide Rv1196 related antigen is suitably not administered within a period of one day (such as two, three or six days) of a non-human simian adenovirus encoding a Rv1196 related antigen, such a non-human simian adenovirus encoding a Rv1196 related antigen. For example, a non-human simian adenovirus encoding a mycobacterial antigen (such as any non-human simian adenovirus) in particular any adenovirus encoding a mycobacterial antigen (such as any adenovirus). The polypeptide Rv1196 related antigen is suitably not administered within a period of one day (such as two, three or six days) of any adenovirus encoding a mycobacterial antigen Suitably the non-human simian adenovirus encoding a Rv1196 related antigen is provided in a composition which is substantially free of or does not comprise a polypeptide Rv1196 related antigen. For example, it is substantially free of or does not comprise a polypeptide mycobacterial antigen (such as is substantially free of or it does not comprise any other antigens). In some embodiments the non-human simian adenovirus encoding a Rv1196 related antigen is provided in a composition which is substantially free of or does not comprise a polypeptide mycobacterial antigen.

Furthermore, the non-human simian adenovirus encoding a Rv1196 related antigen is suitably not administered within a period of one day (such as two, three or six days) of a polypeptide Rv1196 related antigen. For example, a polypeptide mycobacterial antigen (such as any other antigens). The non-human simian adenovirus encoding a Rv1196 related antigen is suitably not administered within a period of one day (such as two, three or six days) of a polypeptide mycobacterial antigen.

Suitably the polypeptide Rv0125 related antigen is provided in a composition which is substantially free of a non-human simian adenovirus encoding a Rv0125 related antigen, such as it does not comprise a non-human simian adenovirus encoding a Rv0125 related antigen. For example, it is substantially free of or does not comprise a non-human simian adenovirus encoding a mycobacterial antigen (such as it is substantially free of or does not comprise any non-human simian adenovirus) in particular it is substantially free of or does not comprise any adenovirus encoding a mycobacterial antigen (such as it is substantially free of or does not comprise any adenovirus). In some embodiments the polypeptide Rv0125 related antigen is provided in a composition which is substantially free of or does not comprise any adenovirus encoding a mycobacterial antigen.

Furthermore, the polypeptide Rv1196 related antigen is suitably not administered within a period of one day (such as two, three or six days) of a non-human simian adenovirus encoding a Rv0125 related antigen, such a non-human simian adenovirus encoding a Rv1196 related antigen. For example, a non-human simian adenovirus encoding a mycobacterial antigen (such as any non-human simian adenovirus) in particular any adenovirus encoding a mycobacterial antigen (such as any adenovirus). The polypeptide Rv0125 related antigen is suitably not administered within a period of one day (such as two, three or six days) of any adenovirus encoding a mycobacterial antigen Suitably the non-human simian adenovirus encoding a Rv0125 related antigen is provided in a composition which is substantially free of or does not comprise a polypeptide Rv0125 related antigen. For example, it is substantially free of or does not comprise a polypeptide mycobacterial antigen (such as is substantially free of or it does not comprise any other antigens). In some embodiments the non-human simian adenovirus encoding a Rv0125 related antigen is provided in a composition which is substantially free of or does not comprise a polypeptide mycobacterial antigen.

Furthermore, the non-human simian adenovirus encoding a Rv0125 related antigen is suitably not administered within a period of one day (such as two, three or six days) of a polypeptide Rv1196 related antigen. For example, a polypeptide mycobacterial antigen (such as any other antigens). The non-human simian adenovirus encoding a Rv0125 related antigen is suitably not administered within a period of one day (such as two, three or six days) of a polypeptide mycobacterial antigen.

Suitably, the subject is a mammal, such as a bovine or human. In particular, the subject is a human.

By substantially free of, in the context of adenovirus, typically means comprising less than $10^4$, such as less than $10^3$, in particular less than $10^2$ or less than $10^1$ viral particles of the relevant type per dose. Suitable methods for determining the number of viral particles include Quantitative PCR Analysis, analytical HLPC or spectrophotometric methods based on $A_{260}$ nm.

By substantially free of, in the context of polypeptide antigen, typically means comprising less than 1 ug, such as less than 0.1 ug, in particular less than 0.01 ug of the relevant antigen or antigens per dose. Suitable methods for determining the amount of peptide antigen are known to the skilled person and depending on the composition, may combine purification methods to assist in facilitating an appropriate quantification method (such as analytical HLPC or spectrophotometric methods).

Typically, the aim of the method of the invention is to induce a protective immune response, i.e. immunise or vaccinate the subject against a related pathogen. The invention may therefore be applied for the prophylaxis, treatment or amelioration of infection by mycobacteria, such as infection by *Mycobacterium bovis* or *Mycobacterium tuberculosis*, in particular *Mycobacterium tuberculosis.*

The invention may be provided for the purpose of:

prophylaxis of active tuberculosis due to infection (i.e. primary tuberculosis) or reactivation (i.e. secondary tuberculosis), such as by administering to a subject who is uninfected, or alternatively a subject who has a latent infection;

prophylaxis of latent tuberculosis, such as by administering to a subject who is uninfected;

treating latent tuberculosis;

preventing or delaying reactivation of tuberculosis, especially the delay of reactivation, for example by a period of months, years or indefinitely; or treating active tuberculosis (such as to reduce the need for chemotherapeutic treatment: such as reduced term of chemotherapeutic treatment, complexity of drug regimen or dosage of chemotherapeutic treatment; alternatively, to reduce the risk of a later relapse following chemotherapeutic treatment).

The elicited immune response may be an antigen specific T cell response (which may be a systemic and/or a local response). Systemic responses may be detected, for example, from a sample of whole blood. Local responses (for example, the local response in the lung) may be detected from an appropriate sample of tissue (for example, lung tissue) or other locally focused samply method (e.g. bronchoalveolar lavage). The antigen specific T cell response may comprise a CD4+ T cell response, such as a response involving CD4+ T cells expressing a plurality of cytokines (e.g. IFNgamma, TNFalpha or IL2, especially IFNgamma, TNFalpha and IL2). Alternatively, or additionally, the antigen specific T cell response comprises a CD8+ T cell response, such as a response involving CD8+ T cells expressing a plurality of cytokines (e.g. IFNgamma, TNFalpha or IL2, especially IFNgamma, TNFalpha and IL2).

The term "active infection" refers to an infection, e.g. infection by *M. tuberculosis*, with manifested disease symptoms and/or lesions, suitably with manifested disease symptoms.

The terms "inactive infection", "dormant infection" or "latent infection" or "latent tuberculosis" refer to an infection, e.g. infection by *M. tuberculosis*, without manifested disease symptoms and/or lesions, suitably without manifested disease symptoms. A subject with latent infection will suitably be one which tests positive for infection, e.g. by Tuberculin skin test (TST) or Interferon-Gamma Release Assays (IGRAs), but which has not demonstrated the disease symptoms and/or lesions which are associated with an active infection.

The term "primary tuberculosis" refers to clinical illness, e.g., manifestation of disease symptoms, directly following infection, e.g. infection by *M. tuberculosis*. See, *Harrison's Principles of Internal Medicine*, Chapter 150, pp. 953-966 (16th ed., Braunwald, et al., eds., 2005).

The terms "secondary tuberculosis" or "postprimary tuberculosis" refer to the reactivation of a dormant, inactive or latent infection, e.g. infection by *M. tuberculosis*. See, *Harrison's Principles of Internal Medicine*, Chapter 150, pp. 953-966 (16th ed., Braunwald, et al., eds., 2005).

The term "tuberculosis reactivation" refers to the later manifestation of disease symptoms in an individual that tests positive for infection (e.g. by Tuberculin skin test (TST) or Interferon-Gamma Release Assays (IGRAs)) but does not have apparent disease symptoms. Suitably the individual will not have been re-exposed to infection. The positive diagnostic test indicates that the individual is infected, however, the individual may or may not have previously manifested active disease symptoms that had been treated sufficiently to bring the tuberculosis into an inactive or latent state.

Suitability the methods are applied to a subject who is uninfected or who has a latent infection by mycobacteria, such as infection by *Mycobacterium tuberculosis*. In one embodiment the methods are applied to a subject who does not have an infection by *Mycobacterium tuberculosis* (in the context of human subjects) or *Mycobacterium bovis* (in the context of bovine subjects). In another embodiment the methods are applied to a subject who has a latent infection by mycobacteria, such as *Mycobacterium tuberculosis* (in the context of human subjects) or *Mycobacterium bovis* (in the context of bovine subjects).

In some embodiments, the subject has previously been vaccinated with BCG. The approaches of the present invention may, for example, be utilised for a subject at least one year after BCG vaccination, for example at least two years after BCG vaccination such as at least at least five years after BCG vaccination.

In some embodiments, the subject has previously been infected with *M. tuberculosis.*

Antigens of Use in the Invention.

T cell epitopes are short contiguous stretches of amino acids which are recognised by T cells (e.g. CD4+ or CD8+ T cells). Identification of T cell epitopes may be achieved through epitope mapping experiments which are known to the person skilled in the art (see, for example, Paul, *Fundamental Immunology,* 3rd ed., 243-247 (1993); Beiβbarth et al *Bioinformatics* 2005 21(Suppl. 1):i29-i37). In a diverse out-bred population, such as humans, different HLA types mean that particular epitopes may not be recognised by all members of the population. As a result of the crucial involvement of the T cell response in tuberculosis, to maximise the level of recognition and scale of immune response, an immunogenic derivative of a reference sequence is desirably one which contains the majority (or suitably all) T cell epitopes intact. Mortier et al *BMC Immunology* 2015 16:63 undertake sequence conservation analysis and in silico human leukocyte antigen-peptide binding predictions for Mtb72f and M72 tuberculosis candidate vaccine antigens.

The skilled person will recognise that individual substitutions, deletions or additions to a protein which alters, adds or deletes a single amino acid or a small percentage of amino acids is an "immunogenic derivative" where the alteration(s) results in the substitution of an amino acid with a functionally similar amino acid or the substitution/deletion/addition of residues which do not substantially impact the immunogenic function.

Conservative substitution tables providing functionally similar amino acids are well known in the art. In general, such conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:

1) Alanine (A), Glycine (G);
2) Aspartic acid (D), Glutamic acid (E);
3) Asparagine (N), Glutamine (Q);

4) Arginine (R), Lysine (K);

5) Isoleucine (I), Leucine (L), Methionine (M), Valine (V);

6) Phenylalanine (F), Tyrosine (Y), Tryptophan (W);

7) Serine (S), Threonine (T); and

8) Cysteine (C), Methionine (M)

(see, e.g., Creighton, Proteins 1984).

Suitably such substitutions do not occur in the region of an epitope, and do not therefore have a significant impact on the immunogenic properties of the antigen.

Immunogenic derivatives may also include those wherein additional amino acids are inserted compared to the reference sequence. Suitably such insertions do not occur in the region of an epitope, and do not therefore have a significant impact on the immunogenic properties of the antigen. One example of insertions includes a short stretch of histidine residues (e.g. 2-6 residues) to aid expression and/or purification of the antigen in question.

Immunogenic derivatives include those wherein amino acids have been deleted compared to the reference sequence. Suitably such deletions do not occur in the region of an epitope, and do not therefore have a significant impact on the immunogenic properties of the antigen.

The skilled person will recognise that a particular immunogenic derivative may comprise substitutions, deletions and additions (or any combination thereof).

The terms "identical" or percentage "identity," in the context of two or more polypeptide sequences, refer to two or more sequences or sub-sequences that are the same or have a specified percentage of amino acid residues that are the same (i.e., 70% identity, optionally 75%, 80%, 85%, 90%, 95%, 98% or 99% identity over a specified region), when compared and aligned for maximum correspondence over a comparison window, or designated region as measured using one of the following sequence comparison algorithms or by manual alignment and visual inspection. This definition also refers to the compliment of a test sequence. Optionally, the identity exists over a region that is at least 200 amino acids in length, such as at least 300 amino acids or at least 400 amino acids. Suitably, the comparison is performed over a window corresponding to the entire length of the reference sequence (as opposed to the derivative sequence).

For sequence comparison, one sequence acts as the reference sequence, to which the test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percentage sequence identities for the test sequences relative to the reference sequence, based on the program parameters.

A "comparison window", as used herein, refers to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerised implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments.

The program is run by designating specific sequences and their amino acid coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984)).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=–4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

In any event, immunogenic derivatives of a polypeptide sequence will usually have essentially the same activity as the reference sequence. By essentially the same activity is meant at least 50%, suitably at least 75% and especially at least 90% activity of the reference sequence in an in vitro restimulation assay of PBMC, whole blood, lung tissue or bronchoalveolar lavage with specific antigens (e.g. restimulation for a period of between several hours to up to two weeks, such as up to one day, 1 day to 1 week or 1 to 2 weeks) that measures the activation of the cells via lymphoproliferation, production of cytokines in the supernatant of culture (measured by ELISA, CBA etc) or characterisation of T and B cell responses by intra and extracellular staining (e.g. using antibodies specific to immune markers, such as CD3, CD4, CD8, IL2, TNF-alpha, IFN-gamma, IL-17, CD40L, CD69 etc) followed by analysis with a flow cytometer. Suitably, by essentially the same activity is meant at least 50%, suitably at least 75% and especially at least 90% activity of the reference sequence in a T cell proliferation and/or IFN-gamma production assay.

In one embodiment the polypeptide antigen and the encoded antigen are Rv1196 related antigens. The term 'Rv1196 related antigen' refers to the Rv1196 protein provided in SEQ ID No: 1 or an immunogenic derivative thereof. As used herein the term "derivative" refers to an antigen that is modified relative to the reference sequence. Immunogenic derivatives are sufficiently similar to the reference sequence to substantially retain the immunogenic properties of the reference sequence and remain capable of allowing an immune response to be raised against the reference sequence. An immunogenic derivative may, for example, comprise a modified version of the reference sequence or alternatively may consist of a modified version of the reference sequence.

The Rv1196 related antigen may for example contain 2500 amino acid residues or fewer, such 1500 amino acid residues or fewer, in particular 1200 amino acid residues or fewer, especially 1000 amino acid residues or fewer, typically 800 amino acid residues or fewer.

Suitably the Rv1196 related antigen will comprise, such as consist of, a sequence having at least 70% identity to SEQ ID No: 1, such as at least 80%, in particular at least 90%, especially at least 95%, for example at least 98%, such as at least 99%.

A specific example of an Rv1196 related antigen is Rv1196 from *Mycobacterium tuberculosis* strain H37Rv, as provided in SEQ ID No: 1. Consequently, in one embodiment of the invention the Rv1196 related antigen is a protein comprising SEQ ID No: 1. In a second embodiment of the invention the Rv1196 related antigen is a protein consisting of SEQ ID No: 1.

A further example of an Rv1196 related antigen is Rv1196 from *Mycobacterium tuberculosis* strain F11. In one embodiment of the invention the Rv1196 related antigen is a protein comprising SEQ ID No: 2. In a second embodiment of the invention the Rv1196 related antigen is a protein consisting of SEQ ID No: 2.

Typical Rv1196 related antigens will comprise (such as consist of) an immunogenic derivative of SEQ ID No: 1 having a small number of deletions, insertions and/or substitutions. Examples are those having deletions of up to 5 residues at 0-5 locations, insertions of up to 5 residues at 0-5 five locations and substitution of up to 20 residues.

Other immunogenic derivatives of Rv1196 are those comprising (such as consisting of) a fragment of SEQ ID No: 1 which is at least 200 amino acids in length, such as at least 250 amino acids in length, in particular at least 300 amino acids in length, especially at least 350 amino acids in length.

Additional immunogenic derivatives of Rv1196 are those comprising, such as consisting of, a fragment of SEQ ID No: 2 which is at least 200 amino acids in length, such as at least 250 amino acids in length, in particular at least 300 amino acids in length, especially at least 350 amino acids in length.

Rv1196 related antigens may be prepared by methods previously described (e.g. Dillon et al *Infection and Immunity* 1999 67(6): 2941-2950; WO2006/117240), those provided in the Examples, or methods analogous thereto.

In one embodiment the polypeptide antigen and the encoded antigen are Rv0125 related antigens. The term 'Rv0125 related antigen' refers to the Rv0125 protein provided in SEQ ID No: 3 or an immunogenic derivative thereof. As used herein the term "derivative" refers to an antigen that is modified relative to the reference sequence. Immunogenic derivatives are sufficiently similar to the reference sequence to substantially retain the immunogenic properties of the reference sequence and remain capable of allowing an immune response to be raised against the reference sequence. An immunogenic derivative may, for example, comprise a modified version of the reference sequence or alternatively may consist of a modified version of the reference sequence.

The Rv0125 related antigen may for example contain 2500 amino acid residues or fewer, such 1500 amino acid residues or fewer, in particular 1200 amino acid residues or fewer, especially 1000 amino acid residues or fewer, typically 800 amino acid residues or fewer.

Suitably the Rv0125 related antigen will comprise, such as consist of, a sequence having at least 70% identity to SEQ ID No: 3, such as at least 80%, in particular at least 90%, especially at least 95%, for example at least 98%, such as at least 99%.

A specific example of an Rv0125 related antigen is Rv0125 from *Mycobacterium tuberculosis* strain H37Rv, as provided in SEQ ID No: 3. Consequently, in one embodiment of the invention the Rv0125 related antigen is a protein comprising SEQ ID No: 3. In a second embodiment of the invention the Rv0125 related antigen is a protein consisting of SEQ ID No: 3.

Typical Rv0125 related antigens will comprise (such as consist of) an immunogenic derivative of SEQ ID No: 3 having a small number of deletions, insertions and/or substitutions. Examples are those having deletions of up to 5 residues at 0-5 locations, insertions of up to 5 residues at 0-5 five locations and substitution of up to 20 residues.

Other immunogenic derivatives of Rv0125 are those comprising (such as consisting of) a fragment of SEQ ID No: 3 which is at least 150 amino acids in length, such as at least 200 amino acids in length, in particular at least 250 amino acids in length, especially at least 300 amino acids in length. Particular immunogenic derivatives of Rv0125 are those comprising (such as consisting of) the fragment of SEQ ID No: 3 corresponding to residues 1-195 of SEQ ID No: 3. Further immunogenic derivatives of Rv0125 are those comprising (such as consisting of) the fragment of SEQ ID No: 3 corresponding to residues 192-323 of SEQ ID No: 3.

Particularly preferred Rv0125 related antigens are derivatives of SEQ ID No: 3 wherein at least one (for example one, two or even all three) of the catalytic triad have been substituted or deleted, such that the protease activity has been reduced and the protein more easily produced—the catalytic serine residue may be deleted or substituted (e.g. substituted with alanine) and/or the catalytic histidine residue may be deleted or substituted and/or substituted the catalytic aspartic acid residue may be deleted or substituted. Especially of interest are derivatives of SEQ ID No: 3 wherein the catalytic serine residue has been substituted (e.g. substituted with alanine). Also of interest are Rv0125 related antigens which comprise, such as consist of, a sequence having at least 70% identity to SEQ ID No: 3, such as at least 80%, in particular at least 90%, especially at least 95%, for example at least 98%, such as at least 99% and wherein at least one of the catalytic triad have been substituted or deleted or those comprising, such as consisting of, a fragment of SEQ ID No: 3 which is at least 150 amino acids in length, such as at least 200 amino acids in length, in particular at least 250 amino acids in length, especially at least 300 amino acids in length and wherein at least one of the catalytic triad have been substituted or deleted. Further immunogenic derivatives of Rv0125 are those comprising (such as consisting of) the fragment of SEQ ID No: 3 corresponding to residues 192-323 of SEQ ID No: 3 wherein at least one (for example one, two or even all three) of the catalytic triad have been substituted or deleted. Particular immunogenic derivatives of Rv0125 are those comprising (such as consisting of) the fragment of SEQ ID No: 3 corresponding to residues 1-195 of SEQ ID No: 3 wherein the catalytic serine residue (position 176 of SEQ ID No: 3) has been substituted (e.g. substituted with alanine).

In certain embodiments the polypeptide antigen and the encoded antigen are Rv1196 and Rv0125 related antigens, such as M72 related antigens. Particular derivatives of the M72 protein include those with additional His residues at the N-terminus (e.g. two His residues, as provided in SEQ ID No: 4; or a polyhistidine tag of five or particularly six His residues, which may be used for nickel affinity purification). Mtb72f which contains the original serine residue that has been mutated in M72, is a further derivative of M72, as are Mtb72f proteins with additional His residues at the N-terminus (e.g. two His residues; or a polyhistidine tag of five or particularly six His residues, which may be used for nickel affinity purification).

Nevertheless, the skilled person recognises that in some embodiments two distinct polypeptides, one being a Rv1196 related antigens and one being a Rv0125 related antigen may be provided within a composition. In such cases it will be recognised that the previously stated exclusions in respect of adenoviruses encoding a Rv1196 related antigen and adenoviruses encoding a Rv0125 related antigen may both be applied to the composition mutatis mutandis. Equally, the previously stated exclusions in respect of contemporaneous administration of adenoviruses encoding a Rv1196 related antigen and adenoviruses encoding a Rv0125 related antigen may both be applied mutatis mutandis.

Also in some embodiments a single adenovirus may encode two distinct polypeptides, one being a Rv1196 related antigen and one being a Rv0125 related antigen. In such cases it will be recognised that the previously stated exclusions in respect of a polypeptide Rv1196 related antigen and a polypeptide Rv0125 related antigen may both be applied to the composition mutatis mutandis. Equally, the previously stated exclusions in respect of contemporaneous administration of a polypeptide Rv1196 related antigen and a polypeptide Rv0125 related antigen may both be applied mutatis mutandis.

Alternatively, two distinct adenovirus constructs may be provided, one encoding an Rv1196 related antigen and one encoding an Rv0125 related antigen. In such cases it will be recognised that the previously stated exclusions in respect of a polypeptide Rv1196 related antigen and a polypeptide Rv0125 related antigen may both be applied to the composition mutatis mutandis. Equally, the previously stated exclusions in respect of contemporaneous administration of a polypeptide Rv1196 related antigen and a polypeptide Rv0125 related antigen may both be applied mutatis mutandis.

Suitably an M72 related antigen will comprise, such as consist of, a sequence having at least 70% identity to SEQ ID No. 6, such as at least 80%, in particular at least 90%, especially at least 95%, such as at least 98%, for example at least 99%.

Typical M72 related antigens will comprise, such as consist of, a derivative of SEQ ID No: 6 having a small number of deletions, insertions and/or substitutions. Examples are those having deletions of up to 5 residues at 0-5 locations, insertions of up to 5 residues at 0-5 five locations and substitution of up to 20 residues.

Other derivatives of M72 are those comprising, such as consisting of, a fragment of SEQ ID No: 6 which is at least 450 amino acids in length, such as at least 500 amino acids in length, such as at least 550 amino acids in length, such as at least 600 amino acids in length, such as at least 650 amino acids in length or at least 700 amino acids in length. As M72 is a fusion protein derived from two individual antigens, any fragment of at least 450 residues will comprise a plurality of epitopes from the full length sequence (Skeiky et al *J. Immunol.* 2004 172:7618-7628; Skeiky *Infect. Immun.* 1999 67(8):3998-4007; Dillon *Infect. Immun.* 1999 67(6):2941-2950;).

In particular embodiments the M72 related antigen will comprise residues 2-723 of SEQ ID No. 6, for example comprise (or consist of) SEQ ID No. 6.

In one embodiment, the polypeptide antigen corresponds to SEQ ID No. 4 and the encoded antigen to SEQ ID No. 6.

M72 related antigens may be prepared by methods previously described (WO2006/117240) or methods analogous thereto.

The polypeptide antigen may be the same as or may be similar to the encoded antigen. In one embodiment the polypeptide antigen is the same as the encoded antigen.

Suitably the polypeptide antigen is similar to the encoded antigen. For example, the encoded antigen may have 70% identity, such as at least 80% identity, suitably at least 90% identity, in particular at least 95% identity to the polypeptide antigen. Alternatively, the encoded antigen may comprise a fragment of at least 100 amino acid residues, such as at least 200 amino acids residues, suitably at least 300 amino acid residues of the polypeptide antigen. In some cases, the encoded antigen comprises a fragment of at least 400 amino acid residues, in particular 500 amino acid residues, such as at least 600 and suitably at least 700 residues of the polypeptide mycobacterial antigen.

The polypeptide antigen and the adenovirus may be provided in the form of immunogenic compositions which comprise one or more further antigenic components.

Additional antigenic components may be intended to strengthen or complement the immune responses solicited in the field of tuberculosis prevention and therapy or additional antigens could be associated with other pathogens and are intended for co-administration for reasons of convenience. Where a number of antigenic components are present within a composition, these may be provided in the form of individual polypeptides or fusion proteins. In some circumstances additional antigenic components may be provided as a polynucleotide (or polynucleotides) encoding one or more polypeptides.

Typically for administration to humans compositions containing a polypeptide Rv1196 related antigen will comprise between 1 ug and 100 ug of Rv1196 related antigen, such as between 1 ug and 50 ug per dose. Suitably between 1 ug and 50 ug of Rv1196 related antigen (such as between 5 ug and 50 ug), especially between 1 ug and 20 ug (such as between 5 ug and 20 ug) and in particular around or exactly 10 ug is provided.

Typically for administration to humans compositions containing a polypeptide Rv0125 related antigen will comprise between 1 ug and 100 ug of Rv0125 related antigen, such as between 1 ug and 50 ug per dose. Suitably between 1 ug and 50 ug of Rv0125 related antigen (such as between 5 ug and 50 ug), especially between 1 ug and 20 ug (such as between 5 ug and 20 ug) and in particular around or exactly 10 ug is provided.

Typically for administration to humans compositions containing a polypeptide M72 related antigen will comprise between 1 ug and 100 ug of M72 related antigen, such as between 1 ug and 50 ug per dose. Suitably between 1 ug and 50 ug of M72 related antigen (such as between 5 ug and 50 ug), especially between 1 ug and 20 ug (such as between 5 ug and 20 ug) and in particular around or exactly 10 ug is provided.

Generally, a polypeptide of use in the invention (if found in nature) will be an isolated polypeptide (i.e. separated from those components with which it may usually be found). For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Adjuvants of Use in the Invention

As described above, in one aspect of the invention, polypeptide antigen is provided in an immunogenic composition which comprises an adjuvant. Suitably the adjuvant comprises a TLR agonist and/or an immunologically active saponin.

In some embodiments the adjuvant may comprise aluminium hydroxide or aluminium phosphate.

Thus, in one embodiment, the adjuvant comprises a TLR agonist. In another embodiment, the adjuvant comprises an immunologically active saponin. In yet another embodiment, the adjuvant comprises a TLR agonist and an immunologically active saponin.

The adjuvant may comprise a TLR agonist and a saponin in a liposomal formulation. The ratio of TLR agonist to saponin may be between 5:1 and 1:5 (w/w), suitably between 2:1 and 1:2, typically around 1:1.

The use of TLR agonists in adjuvants is well-known in the art and has been reviewed e.g. by Lahiri et al. (2008) Vaccine 26:6777. TLRs that can be stimulated to achieve an adjuvant effect include TLR2, TLR4, TLR5, TLR7, TLR8 and TLR9. TLR2, TLR4, TLR7 and TLR8 agonists, particularly TLR4 agonists are preferred.

Suitable TLR4 agonists include lipopolysaccharides, such as monophosphoryl lipid A (MPL) and 3-O-deacylated monophosphoryl lipid A (3D-MPL). U.S. Pat. No. 4,436,727 discloses MPL and its manufacture. U.S. Pat. No. 4,912,094 and reexamination certificate U.S. Pat. No. 4,912,094 discloses 3D-MPL and a method for its manufacture. Another TLR4 agonist is glucopyranosyl lipid adjuvant (GLA), a synthetic lipid A-like molecule (see, e.g. Fox et al. (2012) Clin. Vaccine Immunol 19:1633). In a further embodiment, the TLR4 agonist may be a synthetic TLR4 agonist such as a synthetic disaccharide molecule, similar in structure to MPL and 3D-MPL or may be synthetic monosaccharide molecules, such as the aminoalkyl glucosaminide phosphate (AGP) compounds disclosed in, for example, WO9850399, WO0134617, WO0212258, WO3065806, WO04062599, WO06016997, WO0612425, WO03066065, and WO0190129. Such molecules have also been described in the scientific and patent literature as lipid A mimetics. Lipid A mimetics suitably share some functional and/or structural activity with lipid A, and in one aspect are recognised by TLR4 receptors. AGPs as described herein are sometimes referred to as lipid A mimetics in the art. In a preferred embodiment, the TLR4 agonist is 3D-MPL. TLR4 agonists, such as 3-O-deacylated monophosphoryl lipid A (3D-MPL), and their use as adjuvants in vaccines has e.g. been described in WO 96/33739 and WO2007/068907 and reviewed in Alving et al. (2012) *Curr Opin Immunol* 24:310.

The adjuvant may comprise an immunologically active saponin, such as an immunologically active saponin fraction, such as QS21.

Adjuvants comprising saponins have been described in the art. Saponins are described in: Lacaille-Dubois and Wagner (1996) A review of the biological and pharmacological activities of saponins. Phytomedicine vol 2:363. Saponins are known as adjuvants in vaccines. For example, Quil A (derived from the bark of the South American tree *Quillaja Saponaria* Molina), was described by Dalsgaard et al. in 1974 ("Saponin adjuvants", Archiv. fur die gesamte Virusforschung, Vol. 44, Springer Verlag, Berlin, 243) to have adjuvant activity. Purified fractions of Quil A have been isolated by HPLC which retain adjuvant activity without the toxicity associated with Quil A (Kensil et al. (1991) J. Immunol. 146: 431. Quil A fractions are also described in U.S. Pat. No. 5,057,540 and "Saponins as vaccine adjuvants", Kensil, C. R., Crit Rev Ther Drug Carrier Syst, 1996, 12 (1-2):1-55.

Two such fractions, suitable for use in the present invention, are QS7 and QS21 (also known as QA-7 and QA-21). QS21 is a preferred immunologically active saponin fraction for use in the present invention. QS21 has been reviewed in Kensil (2000) In O'Hagan: Vaccine Adjuvants: preparation methods and research protocols. Homana Press, Totowa, N.J., Chapter 15. Particulate adjuvant systems comprising fractions of Quil A, such as QS21 and QS7, are e.g. described in WO 96/33739, WO 96/11711 and WO2007/068907.

In addition to the other components, the adjuvant preferably comprises a sterol. The presence of a sterol may further reduce reactogenicity of compositions comprising saponins, see e.g. EP0822831. Suitable sterols include beta-sitosterol, stigmasterol, ergosterol, ergocalciferol and cholesterol. Cholesterol is particularly suitable. Suitably, the immunologically active saponin fraction is QS21 and the ratio of QS21:sterol is from 1:100 to 1:1 w/w, such as from 1:10 to 1:1 w/w, e.g. from 1:5 to 1:1 w/w.

In a preferred embodiment of the methods of the invention, the TLR4 agonist is 3D-MPL and the immunologically active saponin is QS21.

In some embodiments, the adjuvant is presented in the form of an oil-in-water emulsion, e.g. comprising squalene, alpha-tocopherol and a surfactant (see e.g. WO95/17210) or in the form of a liposome. A liposomal presentation is preferred.

The term "liposome" when used herein refers to uni- or multilamellar (particularly 2, 3, 4, 5, 6, 7, 8, 9, or 10 lamellar depending on the number of lipid membranes formed) lipid structures enclosing an aqueous interior. Liposomes and liposome formulations are well known in the art. Liposomal presentations are e.g. described in WO96/33739 and WO2007/068907. Lipids which are capable of forming liposomes include all substances having fatty or fat-like properties. Lipids which can make up the lipids in the liposomes may be selected from the group comprising glycerides, glycerophospholipides, glycerophosphinolipids, glycerophosphonolipids, sulfolipids, sphingolipids, phospholipids, isoprenolides, steroids, stearines, sterols, archeolipids, synthetic cationic lipids and carbohydrate containing lipids. In a particular embodiment of the invention the liposomes comprise a phospholipid. Suitable phospholipids include (but are not limited to): phosphocholine (PC) which is an intermediate in the synthesis of phosphatidylcholine; natural phospholipid derivates: egg phosphocholine, egg phosphocholine, soy phosphocholine, hydrogenated soy phosphocholine, sphingomyelin as natural phospholipids; and synthetic phospholipid derivates: phosphocholine (didecanoyl-L-a-phosphatidylcholine [DDPC], dilauroylphosphatidylcholine [DLPC], dimyristoylphosphatidylcholine [DMPC], dipalmitoyl phosphatidylcholine [DPPC], Distearoyl phosphatidylcholine [DSPC], Dioleoyl phosphatidylcholine, [DOPC], 1-palmitoyl, 2-oleoylphosphatidylcholine [POPC], Dielaidoyl phosphatidylcholine [DEPC]), phosphoglycerol (1,2-Dimyristoyl-sn-glycero-3-phosphoglycerol [DMPG], 1,2-dipalmitoyl-sn-glycero-3-phosphoglycerol [DPPG], 1,2-distearoyl-sn-glycero-3-phosphoglycerol [DSPG], 1-palmitoyl-2-oleoyl-sn-glycero-3-phosphoglycerol [POPG]), phosphatidic acid (1,2-dimyristoyl-sn-glycero-3-phosphatidic acid [DMPA], dipalmitoyl phosphatidic acid [DPPA], distearoyl-phosphatidic acid [DSPA]), phosphoethanolamine (1,2-dimyristoyl-sn-glycero-3-phosphoethanolamine [DMPE], 1,2-Dipalmitoyl-sn-glycero-3-phosphoethanolamine [DPPE], 1,2-distearoyl-sn-glycero-3-phosphoethanolamine [DSPE], 1,2-Dioleoyl-sn-Glycero-3-Phosphoethanolamine [DOPE]), phoshoserine, polyethylene glycol [PEG] phospholipid.

Liposome size may vary from 30 nm to several um depending on the phospholipid composition and the method used for their preparation. In particular embodiments of the invention, the liposome size will be in the range of 50 nm to 500 nm and in further embodiments 50 nm to 200 nm. Dynamic laser light scattering is a method used to measure the size of liposomes well known to those skilled in the art.

In a particularly suitable embodiment, liposomes used in the invention comprise DOPC and a sterol, in particular cholesterol. Thus, in a particular embodiment, compositions of the invention comprise QS21 in any amount described herein in the form of a liposome, wherein said liposome comprises DOPC and a sterol, in particular cholesterol.

Preferably, the adjuvant comprises 3D-MPL and QS21 in a liposomal formulation.

The adjuvant may comprise 1 to 100 micrograms of TLR4 agonist per dose.

The adjuvant may comprise 1 to 100 micrograms of immunologically active saponin per dose.

In one embodiment for human use, the adjuvant comprises between 12.5 and 75 micrograms of 3D-MPL and between 12.5 and 75 micrograms of QS21 per dose in a liposomal formulation.

In another embodiment, the adjuvant comprises between 12.5 and 37.5, such as between 20 and 30 micrograms (for example about or exactly 25 micrograms), of 3D-MPL and between 12.5 and 37.5, such as between 20 and 30 micrograms (for example about or exactly 25 micrograms) of QS21 in a liposomal formulation per dose. Suitably the amount of 3D-MPL is the same as the amount of QS21.

The polypeptide or adenovirus should be presented in a pharmaceutically acceptable form, appropriate to the intended delivery route. Solutions should have a pharmaceutically acceptable osmolality to avoid cell distortion or lysis. A pharmaceutically acceptable osmolality will generally mean that solutions will have an osmolality which is approximately isotonic or mildly hypertonic. Suitably the immunogenic compositions of the present invention will have an osmolality in the range of 250 to 750 mOsm/kg, for example, the osmolality may be in the range of 250 to 550 mOsm/kg, such as in the range of 280 to 500 mOsm/kg. Osmolality may be measured according to techniques known in the art, such as by the use of a commercially available osmometer, for example the Advanced® Model 2020 available from Advanced Instruments Inc. (USA). An "isotonicity agent" is a compound that is physiologically tolerated and imparts a suitable tonicity to a formulation (e.g. immunogenic compositions of the invention) to prevent the net flow of water across cell membranes that are in contact with the formulation. Aqueous adjuvant compositions are known which contain 100 mM sodium chloride or more, for example adjuvant system A (ASA) in WO 2005/112991 and WO2008/142133 or the liposomal adjuvants disclosed in WO2007/068907.

In some embodiments, the isotonicity agent used for the composition is a salt. In other embodiments, however, the composition comprises a non-ionic isotonicity agent and the concentration of sodium chloride or the ionic strength in the composition is less than 100 mM, such as less than 80 mM, e.g. less than 30 mM, such as less 10 mM or less than 5 mM. The composition may comprise a non-ionic isotonicity agent and conductivity of the composition is less than 5 mS/cm, such as less than 4 mS/cm. In a preferred embodiment, the non-ionic isotonicity agent is a polyol, such as sorbitol. The concentration of sorbitol may e.g. between about 3% and about 15% (w/v), such as between about 4% and about 10% (w/v). Adjuvants comprising an immunologically active saponin fraction and a TLR4 agonist wherein the isotonicity agent is salt or a polyol have been described in WO2012/080369 and WO2012/080370 which are incorporated herein by reference.

The pH of the immunogenic compositions should be suitable for administration. Typically the pH will be in the range 6.0 to 9.0, such as 7.0 to 9.0, especially 7.25 to 8.75, such as 7.5 to 8.5, in particular pH 7.75 to 8.25. A pH of about 8.0 is of particular interest.

For liquid compositions administered parenterally, the volume of the composition will typically be in the region of 50 ul to 2 ml (depending on the specific route). A volume of 400-600 ul, such as around 500 ul is typically used, in particular for administration by the intramuscular route.

The compositions will generally be sterile.

Adenoviral Vectors

Adenovirus has been widely used for gene transfer applications due to its ability to achieve highly efficient gene transfer in a variety of target tissues and large transgene capacity. Adenoviral vectors of use in the present invention may be derived from a range of mammalian hosts. Over 100 distinct serotypes of adenovirus have been isolated which infect various mammalian species. These adenoviral serotypes have been categorised into six subgenera (A-F; B is subdivided into B1 and B2) according to sequence homology and on their ability to agglutinate red blood cells (Tatsis and Ertl *Molecular Therapy* (2004) 10:616-629).

Examples of human-derived adenoviruses are Ad1, Ad2, Ad4, Ad5, Ad6, Ad11, Ad 24, Ad34 and Ad35. Although Ad5-based vectors have been used extensively in a number of gene therapy trials, there may be limitations on the use of Ad5 and other human group C adenoviral vectors due to preexisting immunity in the general population due to natural infection. Ad5 and other human group C members tend to be among the most seroprevalent serotypes. Additionally, immunity to existing vectors may develop as a result of exposure to the vector during treatment. These types of preexisting or developed immunity to seroprevalent vectors may limit the effectiveness of gene therapy or vaccination efforts. Alternative adenovirus serotypes, thus constitute very important targets in the pursuit of gene delivery systems capable of evading the host immune response.

The adenoviral vector of use in the present invention is derived from a non-human simian adenovirus. Numerous adenoviruses have been isolated from non-human simians such as chimpanzees, bonobos, rhesus macaques and gorillas, and vectors derived from these adenoviruses induce strong immune responses to transgenes encoded by these vectors (Colloca et al. (2012) Sci. Transl. Med. 4:1-9; Roy et al. (2004) Virol. 324: 361-372; Roy et al. (2010) J. of Gene Med. 13:17-25). Certain advantages of vectors based on non-human simian adenoviruses include the relative lack of cross-neutralising antibodies to these adenoviruses in the target population. For example, cross-reaction of certain chimpanzee adenoviruses with pre-existing neutralizing antibody responses is only present in 2% of the target population compared with 35% in the case of certain candidate human adenovirus vectors.

Specifically, the adenoviral vector is derived from a non-human simian adenovirus, in particular a chimpanzee adenovirus such as ChAd3, ChAd63, ChAd83, ChAd155, Pan 5, Pan 6, Pan 7 (also referred to as C7) or Pan 9. Examples of such strains are described in WO03/000283, WO2005/071093, WO2010/086189 and GB1510357.5 and are also available from the American Type Culture Collection, 10801 University Boulevard, Manassas, Va. 20110-2209, and other sources. Alternatively, adenoviral vectors may be derived from non-human simian adenoviruses isolated from bonobos, such as PanAd1, PanAd2 or PanAd3. Examples of such vectors described herein can be found for example in WO2005/071093 and WO2010/086189. Adenoviral vectors may also be derived from adenoviruses isolated from gorillas as described in WO2013/52799, WO2013/52811 and WO2013/52832.

Certain adenoviral vectors may demonstrate one or more following improved characteristics over other vectors: higher productivity, improved immunogenicity and increased transgene expression.

In one embodiment the adenoviral vector is a non-human simian adenovirus containing at least a penton selected from SEQ ID No: 10 or SEQ ID No: 20, a hexon selected from SEQ ID No: 11 or SEQ ID No: 21 or a fibre selected from SEQ ID No: 12 or SEQ ID No: 22, in particular a penton and hexon, penton and fibre, or hexon and fibre, such as a penton, hexon and fibre. In certain examples the adenoviral vector is a non-human simian adenovirus containing at least the penton of SEQ ID No: 10, the hexon of SEQ ID No: 11 or the fibre of SEQ ID No: 12, in particular a penton and hexon, penton and fibre, or hexon and fibre. In other examples the adenoviral vector is a non-human simian adenovirus containing at least the penton of SEQ ID No: 20, the hexon of SEQ ID No: 21 or the fibre of SEQ ID No: 22, in particular a penton and hexon, penton and fibre, or hexon and fibre.

In an embodiment the adenoviral vector is derived from as ChAd3 and contains at least a penton (SEQ ID No: 10), hexon (SEQ ID No: 11) and fibre (SEQ ID No: 12) therefrom.

In one embodiment the adenoviral vector is derived from as ChAd155 and contains a penton (SEQ ID No: 20), hexon (SEQ ID No: 21) and fibre (SEQ ID No: 22) therefrom.

In one embodiment the adenoviral vector is a non-human simian adenovirus containing at least the penton of SEQ ID No: 15, the hexon of SEQ ID No: 16 or the fibre of SEQ ID No: 17, in particular a penton and hexon, penton and fibre, or hexon and fibre. In some examples the adenoviral vector is derived from as ChAd63 containing at least the penton of SEQ ID No: 15, the hexon of SEQ ID No: 16 and the fibre of SEQ ID No: 17.

Adenoviral Vector Structure

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The hexon accounts for the majority of the structural components of the capsid, which consists of 240 trimeric hexon capsomeres and 12 penton bases. The hexon has three conserved double barrels, while the top has three towers, each tower containing a loop from each subunit that forms most of the capsid. The base of hexon is highly conserved between adenoviral serotypes, while the surface loops are variable (Tatsis and Ertl *Molecular Therapy* (2004) 10:616-629). Penton is another adenoviral capsid protein that forms a pentameric base to which fiber attaches. The trimeric fiber protein protrudes from the penton base at each of the 12 vertices of the capsid and is a knobbed rod-like structure. The primary role of the fibre protein is the tethering of the viral capsid to the cell surface via the interaction of the knob region with a cellular receptor, and variations in the flexible shaft as well as knob regions of fiber are characteristic of the different serotypes (Nicklin et al *Molecular Therapy* 2005 12:384-393).

The adenoviral genome is well characterised. The linear, double-stranded DNA is associated with the highly basic protein VII and a small peptide pX (also termed mu). Another protein, V, is packaged with this DNA-protein complex and provides a structural link to the capsid via protein VI. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITR), which is necessary for viral replication. The 5' end of the adenoviral genome contains the 5' cis-elements necessary for packaging and replication; i.e., the 5' ITR sequences (which function as origins of replication) and the native 5' packaging enhancer domains (that contain sequences necessary for packaging linear Ad genomes and enhancer elements for the E1 promoter). The 3' end of the adenoviral genome includes the 3' cis-elements (including the ITRs) necessary for packaging and encapsidation. The virus also comprises a virus-encoded protease, which is necessary for processing some of the structural proteins required to produce infectious virions. The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. During the late phase of infection, expression of the late genes L1-L5, which encode the structural components of the virus particles, is activated.

Annotation of the ChAd3 wild type sequence (SEQ ID NO: 9) sequence is provided below.

CDS (38 total)
- E1A 30.8K
  - Start: 589 End: 1544
  - Original Location Description:
    - join(589 . . . 1129, 1243 . . . 1544)
- E1A 25.5K
  - Start: 589 End: 1544
  - Original Location Description:
    - join(589 . . . 991, 1243 . . . 1544)
- E1B 22K
  - Start: 1716 End: 2279
  - Original Location Description:
    - 1716 . . . 2279
- E1B 57K
  - Start: 2021 End: 3544
  - Original Location Description:
    - 2021 . . . 3544
- IX
  - Start: 3640 End: 4104
  - Original Location Description:
    - 3640 . . . 4104
- IVa2
  - Start: 4163 End: 5790 (Complementary)
  - Original Location Description:
    - complement(4163 . . . 5499, 5778 . . . 5790)
- pol
  - Start: 5269 End: 14236 (Complementary)
  - Original Location Description:
    - complement(5269 . . . 8865, 14228 . . . 14236)
- pTP
  - Start: 8664 End: 14236 (Complementary)
  - Original Location Description:
    - complement(8664 . . . 10667, 14228 . . . 14236)
- 48K
  - Start: 11120 End: 12379
  - Original Location Description:
    - 11120 . . . 12379
- pIIIa
  - Start: 12403 End: 14181
  - Original Location Description:
    - 12403 . . . 14181
- III
  - Start: 14273 End: 16054
  - Penton
  - Original Location Description:
    - 14273 . . . 16054
- pVII
  - Start: 16069 End: 16665
  - Original Location Description:
    - 16069 . . . 16665
- V
  - Start: 16738 End: 17853
  - Original Location Description:
    - 16738 . . . 17853
- pX
  - Start: 17878 End: 18123
  - Original Location Description:
    - 17878 . . . 18123
- pVI
  - Start: 18219 End: 18974
  - Original Location Description:
    - 18219 . . . 18974
- hexon
  - Start: 19086 End: 21968
  - Original Location Description:
    - 19086 . . . 21968
- protease
  - Start: 21998 End: 22627
  - Original Location Description:
    - 21998 . . . 22627
- DBP
  - Start: 22743 End: 24395 (Complementary)
  - Original Location Description:
    - complement(22743 . . . 24395)
- 92K
  - Start: 24445 End: 26940
  - Original Location Description:
    - 24445 . . . 26940
- 22K
  - Start: 26630 End: 27229
  - Original Location Description:
    - 26630 . . . 27229
- 33K
  - Start: 26630 End: 27551
  - Original Location Description:
    - join(26630 . . . 26966, 27169 . . . 27551)
- pVIII
  - Start: 27626 End: 28309
  - Original Location Description:
    - 27626 . . . 28309
- E3 12K
  - Start: 28310 End: 28627
  - Original Location Description:
    - 28310 . . . 28627
- E3 CR1-alphap0
  - Start: 29125 End: 29325
  - Original Location Description:
    - 29125 . . . 29325
- E3 gp18K
  - Start: 29328 End: 29819
  - Original Location Description:
    - 29328 . . . 29819
- E3 33K
  - Start: 29848 End: 30738
  - Original Location Description:
    - 29848 . . . 30738

E3A 11 K
Start: 31293 End: 31589
Original Location Description:
31293 . . . 31589
E3 RID alpha
Start: 31601 End: 31873
Original Location Description:
31601 . . . 31873
E3 RID beta
Start: 31876 End: 32274
Original Location Description:
31876 . . . 32274
E3 15K
Start: 32267 End: 32653
Original Location Description:
32267 . . . 32653
U exon
Start: 32684 End: 32848 (Complementary)
Original Location Description:
complement(32684 . . . 32848)
fiber
Start: 32859 End: 34490
Original Location Description:
32859 . . . 34490
E40RF6/7
Start: 34698 End: 35858 (Complementary)
Original Location Description:
complement(34698 . . . 34973, 35685 . . . 35858)
E4 ORF6
Start: 34974 End: 35858 (Complementary)
Original Location Description:
complement(34974 . . . 35858)
E4 ORF4
Start: 35758 End: 36123 (Complementary)
Original Location Description:
complement(35758 . . . 36123)
E4 ORF3
Start: 36139 End: 36486 (Complementary)
Original Location Description:
complement(36139 . . . 36486)
E4 ORF2
Start: 36483 End: 36875 (Complementary)
Original Location Description:
complement(36483 . . . 36875)
E4 ORF1
Start: 36928 End: 37314 (Complementary)
Original Location Description:
complement(36928 . . . 37314)
Misc. Feature (3 total)
VA RNA I
Start: 10693 End: 10860
Original Location Description:
10693 . . . 10860
VA II
Start: 10927 End: 11102
Original Location Description:
10927 . . . 11102
E3 deletion—5'
Start: 28642 End: 28647
Original Location Description:
28642 . . . 28647

Annotation of the ChAd63 Wild Type Sequence (SEQ ID NO: 14) Sequence is Provided Below.

```
LOCUS          ChAd63 35994 bp DNA linear 27-JUL-2015

DEFINITION     Chimp adenovirus 163, complete genome.

COMMENT        Annotation according to alignment of ChAd63 against the human
               Adenovirus 4 reference strain NC_003266

FEATURES       Location/Qualifiers

source         1 . . . 35994
               /organism = "Chimpanzee adenovirus 63"

               /mol_type = "genomic DNA"

               /acronym = "ChAd63"

repeat_region  1 . . . 129
               /standard_name = "ITR"

               /rpt_type = inverted

gene           479 . . . 1501
               /gene = "E1A"

regulatory     479 . . . 484
               /regulatory_class = "TATA_box"

               /gene = "E1A"

CDS            join(576 . . . 1143, 1229 . . . 1437)
               /gene = "E1A"

               /product = "control protein E1A"

               /translation = "MRHLRDLPGNVFLATGNEILELVVDAMMGDDPPEPPTPFEAPSL

               YDLYDLEVDVPENDPNEEAVNDLFSDAALLAAEQANTDSGSDSDSSLHTPRPGRGEKK

               IPELKGEELDLRCYEECLPPSDDEEDEEAIRAAASEGVKVAGESFSLDCPTLPGHGCK
```

-continued

SCEFHRMNTGDKNVMCALCYMRAYNHCVYSPVSDVDETPTSECISSPPEIGEEPPEDI

IHRPVAVRVTGRRAAVESLDDLLQGGDEPLDLCTRKRPRH"

intron 1144 . . . 1228
/gene = "E1A"

regulatory 1495 . . . 1501
/regulatory_class = "polyA_signal_sequence"

/gene = "E1A"

gene 1555 . . . 3953
/gene = "E1B"

regulatory 1555 . . . 1664
/regulatory_class = "TATA_box"

/gene = "E1B"

CDS 1601 . . . 2179
/gene = "E1B"

/codon_start = 1

/product = "control protein E1B 19K"

/translation = "MEIWTVLEDFHQTRQLLENSSAEVSYLWRFCFGGPLAKLVYRAK

QDYKDQFEDILRECPGIFDSLNLGHQSHFNQSILRALDFSTPGRTTAAVAFFAFILDK

WSQETHFSRDYRLDCLAVALWRTWRCQRLNAISGYLPVQPVDTLRILSLQSPQEHQRR

QQPQQEQQQEEEEDREENLRAGLDPPVAEEEE"

CDS 1906 . . . 3420
/gene = "E1B"

/codon_start = 1

/product = "control protein E1B 55K"

/translation = "MESRNPFQQGLPSGLLSSSFVENMEVPAPECNLRLLASTAGRHA

EDPESPVTPGTPTPPAAAAGAAARGGGGPRREPESRSGPSGGGGGGVADLFPELRRVL

TRSSSGRERGIKRERHEETSHRTELTVSLMSRRRPESVWWHEVQSQGIDEVSVMHEKY

SLEQVKTCWLEPEDDWEVAIRNYAKLALKPDKKYKITKLINIRNSCYISGNGAEVEIS

TQERAAFRCCMMNMYPGVVGMEGVTFMNTRFRGDGYNGVVFMANTKLTVHGCSFFGFN

NMCIEAWGSVSVRGCSFSANWMGVVGRTKSVVSVKKCLFERCHLGVMSEGEAKVKHCA

STETGCFVLIKGNAKVKHNMICGASDERGYQMLTCAGGNSHMLATVHVASHPRKTWPE

FEHNVMTRCNVHLGSRRGMFMPYQCNMQFVKVLLEPDAMSRVSLTGVFDMNVELWKIL

RYDESKTRCRACECGGKHARLQPVCVEVTEDLRPDHLVLSCNGTEFGSSGEESD"

gene 3454 . . . 3953
/gene = "IX"

regulatory 3454 . . . 3459
/regulatory_class = "TATA_box"

/gene = "IX"

CDS 3505 . . . 3933
/gene = "IX"

/product = "capsid protein IX"

/translation = "MSGSASFEGGVFSPYLTGRLPSWAGVRQNVMGSTVDGRPVQPAN

SSTLTYATLSSSSVDAAAAAAAASAASAVRGMALGAGYYSSLVANSSSTNNPASLNEE

KLLLLMAQLEALTQRLGELTQQVAQLQAETRAAVATVKTK"

-continued

```
regulatory    3929 . . . 3934
              /regulatory_class = "polyA_signal_sequence"

              /note = "E1B, IX"

regulatory    3944 . . . 3949
              /regulatory_class = "polyA_signal_sequence"

              /note = "E1B, IX"

regulatory    3948 . . . 3953
              /regulatory_class = "polyA_signal_sequence"

              /note = "E1B, IX"

gene          complement(3992 . . . 26364)
              /gene = "E2B"

gene          complement(3992 . . . 5735)
              /gene = "IVa2"

regulatory    complement(3992 . . . 3997)
              /regulatory_class = "polyA_signal_sequence"

              /note = "IVa2, E2B"

CDS           complement(join(3993 . . . 5326, 5605 . . . 5617))
              /gene = "IVa2"

              /product = "encapsidation protein IVa2"

              /translation = "METRGRRPGAVLDQPDEPEAHPRKRPARRAPLHRDGDHADADPA

              TLEGPDPGLAGRPSPGALLPQSPQPAKRGGLLDRDALEHITELWDRLELLQQTLSKMP

              MADGLKPLKNFASLQELLSLGGERLLAELVRENMHVREMMNEVAPLLREDGSCLSLNY

              HLQPVIGVIYGPTGCGKSQLLRNLLSAQLISPAPETVFFIAPQVDMIPPSELKAWEMQ

              ICEGNYAPGIEGTFVPQSGTLRPKFIKMAYDELTQDHNYDVSDPRNVFAQAAAHGPIA

              IIMDECMENLGGHKGVSKFFHAFPSKLHDKFPKCTGYTVLVVLHNMNPRRDLGGNIAN

              LKIQAKMHLISPRMHPSQLNRFVNTYTKGLPVAISLLLKDIVQHHALRPCYDWVIYNT

              TPEHEALQWSYLHPRDGLMPMYLNIQAHLYRVLEKIHRVLNDRDRWSRAYRARKIK"

CDS           complement(join(5096 . . . 8659, 13841 . . . 13849))
              /gene = "E2B"

              /EC_number = "2.7.7.7"

              /product = "DNA polymerase"

              /translation = "MALVQTHGSRGLHPEASDPGRQPSRRRSRQSSPGAVPEPARARR

              RRAPAAPASGPRAAPAARRASSPPLLSMEPPPPKKKRGTVVAPQGHGTLQAVDVATNG

              AVEIKYHLDLPRALEKLLQVNRAPPLPTDLTPQRLRTLDSSGLRALVLALRPVRAEVW

              TCLPRGLVSMTTIEADDGHADGQDVVQHQMQPPALHCPLKFLVKGTQVQLVQHVHPVQ

              RCEHCGRLYKHKHECSARRRHFYFHHINSHSSNWWQEIQFFPIGSHPRTERLFLTYDV

              ETYTWMGSFGKQLVPFMLVMKLSGDPPLVELAHDLALQLKWDRWHGDPRTFYCVTPEK

              MAVGQQFRQYRDRLQTALAVDLWTSFLSANPHVADWALEQHGLSDPAELTYDELKKLP

              HVKGRPRFVELYIVGHNINGFDEIVLAAQVINNRAEVPQPFRITRNFMPRAGKILFND

              VTFALPNPAYKKRTDFQLWEQGGCDDLDFKHQFLKVMVRDTFALTHTSLRKAAQAYAL

              PVEKGCCAYKAVNQFYMVGSYRADQDGFPLEEYWKDREEFLLNRELWKQKGQLKYDII

              QETLDYCALDVLVTAELVAKLQDSYAHFIRDSVGLPHAHFNIFQRPTISSNSHAIFRQ

              IVYRAEKPQRSNLGTGLLAPSHELYDYVRASIRGGRCYPTYIGVLQEPLYVYDICGMY

              ASALTHPMPWGTPLSPYERALAVRDWQASLDDLGTCISYFDPELLPGIFTVDADPPDE
```

-continued

LMLDPLPPFCSRKGGRLCWTNEPLRGEVATSVDLITLHNRGWRVRIVPDELTTVFPEW

KCVAREYVQLNIAAKERADKEKNQTMRSIAKLLSNALYGSFATKLDNKKIVFSDQMDE

GLMKGVSNGTVNIKSSSFLETDNLSAEVMPAFEREYLPQQLALLDSDPEDSEDEQGPA

PFYTPPAGTPGHVAYTYKPITFLDVDEGDMCLHTLEKVDPLVDNDRYPSHVASFVLAW

TRAFVSEWAGFLYDEDRGTPLEDRPIKSVYGDTDSLFVTQRGHELMETRGKKRIKKHG

GNLVFDPDRPDLTWLVECETVCASCGADAYAPESVFLAPKLYALKSLLCPVCGHTSKG

KLRAKGHAAEALNYELMLNCYLADAQGADRERFSTSRMSLKRTLASAQPGAHPFTVTE

TTLTRTLRPWKDRTLASLDAHRLVPYSRSRPNPRNEEVCWIEMP"

intron complement(5327 . . . 5604)
/gene = "IVa2"

gene 5917 . . . 33604
/gene = "L5"

gene 5917 . . . 27469
/gene = "L4"

gene 5917 . . . 21839
/gene = "L3"

gene 5917 . . . 17466
/gene = "L2"

gene 5917 . . . 13827
/gene = "L1"

regulatory 5917 . . . 5922
/regulatory_class = "TATA_box"

/note = "L"

intron 5989 . . . 7009
/note = "between L1 and L2 leaders"

intron 7082 . . . 9518
/note = "between L2 and L3 leaders"

intron 7082 . . . 7850
/note = "between L2 and i leaders; precedes protein 13.6K CDS"

CDS join(7877 . . . 8275, 9519 . . . 9539)
/gene = "L1"

/codon_start = 1

/product = "protein 13.6K"

/translation = "MRADGEELDLLPPVGGMAVDVMEVEMPTARRALVLVFIQASAVL

ATLHGMHVLHELYLGSFDEEFQWAVERWRLHLVLYYVLAIGVAIVCLDGGHADEPARE

AGPDLGSDGSESEDEGAQAGAVQGPETLRSQGLRART"

CDS complement(join(8458 . . . 10392, 13841 . . . 13849))
/gene = "E2B"

/product = "terminal protein precursor pTP"

/translation = "MALSIHDCARLTGQTAATMNYFLPLRNIWNRVREFPRASTTAAG

ITWMSRYIYGYHRLMLEDLAPGAPATERWPLYRQPPPHFLVGYQYLVRTCNDYIFDTR

AYSRLKYHELVRPGHQTVNWSVMANCSYTINTGAYHRFVDFDDFQTTLTQIQQAILAE

RVVADLALVQPQRGFGLTRMHGRAGEEEVPVERLMQDYYKDLARCQDHAWGMADRLRI

QQAGPKDLVLLATIRRLRTAYFNFITSSIARPPPDQIPEEQETGLSLPCDCDWLEAFV

QRFSDPVDLETLRSLRGVPTGQLIRCIVSALSLPNGDPPGGHLEMRGGVFTLRPREDG

RAVTETMRRRRGETIERFIDRLPVRRRRRRAPPPPPPPEEEVEEMLVEEEEEEMEEEP

-continued

PGAFEREVRATIAELIRLLEEELTVSARNSQFFNFAVDFYEAMERLEALGDVSEMPLR

RWIMYFFVTEHIATTLNYLYQRLCNYAVFTRHVELNLAQVVMRARDPDGAVVYSRVWN

EAGMNAFSQLMGRISNDLAATVERAGRGDLQEEEIEQFMTEIAYQDNSGDVQEILRQA

AVNDTEIDSVELSFRFKLTGPVAFTQRRQIQDVNRRVVAHASLLRAQYQNLPARGADV

PLPPLPPGPEPPLPPGARPRRRF"

intron complement(8660 . . . 26296)
/gene = "E2B"

intron 9606 . . . 32253
/gene = "L5"

/note = "precedes fiber CDS"

intron 9606 . . . 26463
/gene = "L4"

/note = "precedes capsid protein precursor pVIII CDS"

intron 9606 . . . 25554
/gene = "L4"

/note = "precedes protein 33K and encapsidation protein 22K CDSs"

intron 9606 . . . 23430
/gene = "L4"

/note = "precedes hexon assembly protein 100K CDS"

intron 9606 . . . 21177
/gene = "L3"

/note = "precedes protease CDS"

intron 9606 . . . 18296
/gene = "L3"

/note = "precedes hexon CDS"

intron 9606 . . . 17508
/gene = "L3"

/note = "precedes capsid protein precursor pVI CDS"

intron 9606 . . . 17201
/gene = "L2"

/note = "precedes core protein precursor pX CDS"

intron 9606 . . . 16132
/gene = "L2"

/note = "precedes core protein V CDS"

intron 9606 . . . 15498
/gene = "L2"

/note = "precedes core protein precursor pVII CDS"

intron 9606 . . . 13887
/gene = "L2"

/note = "precedes penton base CDS"

intron 9606 . . . 12043
/gene = "L1"

/note = "precedes capsid protein precursor pIIIa CDS"

intron 9606 . . . 10844
/gene = "L1"

/note = "precedes encapsidation protein 52K CDS"

intron complement(10393 . . . 26296)
/gene = "E2B"

-continued

```
gene            10426 . . . 10585
                /gene = "VAI"

misc_RNA        10426 . . . 10585
                /gene = "VAI"

                /product = "virus-associated RNA I"

gene            10648 . . . 10818
                /gene = "VAII"

misc_RNA        10648 . . . 10818
                /gene = "VAII"

                /product = "virus-associated RNA II"

CDS             10845 . . . 12020
                /gene = "L1"

                /product = "encapsidation protein 52K"

                /translation = "MHPVLRQMRPHPPPQPPLPQQQQQPALLPPPQQQQPATTAAAAV

                SGAGVQYDLALEEGEGLARLGASSPERHPRVQMKRDAREAYVPKQNLERDRSGEEPEE

                MRASRFHAGRELRRGLDRKRVLRDEDFEADELTGISPARAHVAAANLVTAYEQTVKEE

                SNFQKSENNHVRTLIAREEVTLGLMHLWDLLEAIVQNPTSKPLTAQLFLVVQHSRDNE

                TFREALLNITEPEGRWLLDLVNILQSIVVQERGLPLSEKLAAINFSVLSLGKYYARKI

                YKTPYVPIDKEVKIDGFYMRMTLKVLTLSDDLGVYRNDRMHRAVSASRRRELSDQELM

                HSLQRALTGAGTEGESYFDMGADLRWQPSRRALEAAGGVPYVEEVDDEEEEGEYLED"

CDS             12044 . . . 13810
                /gene = "L1"

                /product = "capsid protein precursor pIIIa"

                /translation = "MQQQPPPPPPDPAMRAALQSQPSGINSSDDWTQAMQRIMALTTR

                NPEAFRQQPQANRLSAILEAVVPSRSNPTHEKVLAIVNALVENKAIRGDEAGLVYNAL

                LERVARYNSTNVQTNLDRMVTDVREAVSQREREHRESNLGSMVALNAFLSTQPANVPR

                GQEDYTNFISALRLMVAEVPQSEVYQSGPDYFFQTSRQGLQTVNLSQAFKNLQGLWGV

                QAPVGDRATVSSLLTPNSRLLLLLVAPFTDSGSVSRDSYLGYLLNLYREAIGQAHVDE

                QTYQEITHVSRALGQEDPGNLEATLNFLLTNRSQKIPPQYALSTEEERILRYVQQSVG

                LFLMQEGATPSAALDMTARNMEPSMYARNRPFINKLMDYLHRAAAMNSDYFTNAILNP

                HWLPPPGFYTGEYDMPDPNDGFLWDDVDSSVFSPRPTTTTVWKKEGGDRRPSSALSGR

                AGAAAAVPEAASPFPSLPFSLNSVRSSELGRLTRPRLLGEEEYLNDSLLKPEREKNFP

                NNGIESLVDKMSRWKTYAHEHRDEPRASSAGTRRRQRHDRQRGLVWDDEDSADDSSVL

                DLGGSGGGNPFAHLRPRIGRLM"

regulatory      13822 . . . 13827
                /regulatory_class = "polyA_signal_sequence"

                /gene = "L1"

CDS             13889 . . . 15511
                /gene = "L2"

                /product = "penton base"

                /translation = "MMRRVYPEGPPPSYESVMQQAVAAAMQPPLEAPYVPPRYLAPTE

                GRNSIRYSELAPLYDTTRLYLVDNKSADIASLNYQNDHSNFLTTVVQNNDFTPTEAST

                QTINFDERSRWGGQLKTIMHTNMPNVNEFMYSNKFKARVMVSRKTPNGVTVGDDYDGS

                QDELTYEWVEFELPEGNFSVTMTIDLMNNAIIDNYLAVGRQNGVLESDIGVKFDTRNF
```

-continued

RLGWDPVTELVMPGVYTNEAFHPDIVLLPGCGVDFTESRLSNLLGIRKRQPFQEGFQI

LYEDLEGGNIPALLDVEAYEESKEKAEAEATTAVATAATVADATVTRGDTFATQAEEA

AALAATDDSESKIVIKPVEKDSKNRSYNVLPDGKNTAYRSWYLAYNYGDPEKGVRSWT

LLTTSDVTCGVEQVYWSLPDMMQDPVTFRSTRQVSNYPVVGAELLPVYSKSFFNEQAV

YSQQLRAFTSLTHVFNRFPENQILVRPPAPTITTVSENVPALTDHGTLPLRSSIRGVQ

RVTVTDARRRTCPYVYKALGVVAPRVLSSRTF"

intron complement(14013 . . . 26296)
/gene = "E2B"

/note = "precedes DNA polymerase and terminal protein precursor pTP CDSs"

CDS 15515 . . . 16099
/gene = "L2"

/product = "core protein precursor pVII"

/translation = "MSILISPSNNTGWGLRAPSKMYGGARQRSTQHPVRVRGHFRAPW

GALKGRVRSRTTVDDVIDQVVADARNYTPAAAPASTVDAVIDSVVADARRYARAKSRR

RRIARRHRSTPAMRAARALLRRARRTGRRAMLRAARRAASGSSSAGRTRRRAATAAAA

AIASMSRPRRGNVYWVRDAATGVRVPVRTRPPRT"

CDS 16144 . . . 17181
/gene = "L2"

/product = "core protein V"

/translation = "MSKRKYKEEMLQVIAPEIYGPAAAVKEERKPRKLKRVKKDKKEE

EDDGLVEFVREFAPRRRVQWRGRKVKPVLRPGTTVVFTPGERSGSASKRSYDEVYGDE

DILEQAVERLGEFAYGKRSRPAPLKEEAVSIPLDHGNPTPSLKPVTLQQVLPSAAPRR

GFKREGGEDLYPTMQLMVPKRQKLEDVLEHMKVDPEVQPEVKVRPIKQVAPGLGVQTV

DIKIPTEPMETQTEPVKPSTSTMEVQTDPWMPAASTTTTRRRRKYGAASLLMPNYALH

PSIIPTPGYRGTRFYRGYTSSRRRKTTTRRRRRSRRSSTATSALVRRVYRSGREPLTL

PRARYHPSIAI"

CDS 17204 . . . 17437
/gene = "L2"

/product = "core protein precursor pX"

/translation = "MALTCRLRVPITGYRGRKPRRRRLTGNGLRRHHHRRRRAISKRL

GGGFLPALIPIIAAAIGAIPGIASVAVQASQRH"

regulatory 17461 . . . 17466
/regulatory_class = "polyA_signal_sequence"

/gene = "L2"

CDS 17509 . . . 18237
/gene = "L3"

/product = "capsid protein precursor pVI"

/translation = "MEDINFSSLAPRHGTRPFMGTWSDIGNSQLNGGAFNWSSLWSGL

KNFGSTLKTYGNKAWNSSTGQALREKLKEQNFQQKVVDGLASGINGVVDLANQAVQKQ

INSRLDAVPPAGSVEMPQVEEELPPLDKRGDKRPRPDAEETLLTHTDEPPPYEEAVKL

GLPTTRPVAPLATGVLKPSSSSQPATLDLPPPASRPSTVAKPLPPVAVASRAPRGRPQ

ANWQSTLNSIVGLGVQSVKRRRCY"

-continued

```
CDS             18329 . . . 21154
                /gene = "L3"

                /note = "capsid protein II"

                /product = "hexon"

                /translation = "MATPSMLPQWAYMHIAGQDASEYLSPGLVQFARATDTYFSLGNK

                FRNPTVAPTHDVTTDRSQRLTLRFVPVDREDNTYSYKVRYTLAVGDNRVLDMASTYFD

                IRGVLDRGPSFKPYSGTAYNSLAPKGAPNTSQWKDSDSKMHTFGVAAMPGVVGKKIEA

                DGLPIGIDSSSGTDTIIYADKTFQPEPQVGSDSWVDTNGAEEKYGGRALKDTTNMKPC

                YGSFARPTNKEGGQANIKDSETASTTPNYDIDLAFFDSKNIAANYDPDIVMYTENVEL

                QTPDTHIVFKPGTSDESSEANLGQQAMPNRPNYIGFRDNFIGLMYYNSTGNMGVLAGQ

                ASQLNAVVDLQDRNTELSYQLLLDSLGDRTRYFSMWNQAVDSYDPDVRIIENHGVEDE

                LPNYCFPLNGVGFTDTYQGVKVKTDTAATGTNGTQWDKDDTTVSTANEIHSGNPFAME

                INIQANLWRNFLYANVALYLPDSYKYTPANITLPTNTNTYDYMNGRVVAPSLVDAYIN

                IGARWSLDPMDNVNPFNHHRNAGLRYRSMLLGNGRYVPFHIQVPQKFFAIKSLLLLPG

                SYTYEWNFRKDVNMILQSSLGNDLRTDGASIAFTSINLYATFFPMAHNTASTLEAMLR

                NDTNDQSFNDYLSAANMLYPIPANATNVPISIPSRNWAAFRGWSFTRLKTRETPSLGS

                GFDPYFVYSGSIPYLDGTFYLNHTFKKVSITFDSSVSWPGNDRLLTPNEFEIKRTVDG

                EGYNVAQCNMTKDWFLVQMLAHYNIGYQGFYVPEGYKDRMYSFFRNFQPMSRQVVDEV

                NYKDYQAVTLAYQHNNSGFVGYLAPTMRQGQPYPANYPYPLIGKSAVASVTQKKFLCD

                RVMWRIPFSSNFMSMGALTDLGQNMLYANSAHALDMNFEVDPMDESTLLYVVFEVFDV

                VRVHQPHRGVIEAVYLRTPFSAGNATT"

CDS             21182 . . . 21802
                /gene = "L3"

                /EC_number = "3.4.22.39"

                /product = "protease"

                /translation = "TACGSGEQELRAILRDLGCGPCFLGTFDKRFPGFMAPHKLACAI

                VNTAGRETGGEHWLAFAWNPRSHTCYLFDPFGFSDERLKQIYQFEYEGLLRRSALATE

                DRCITLEKSTQTVQGPRSAACGLFCCMFLHAFVHWPDRPMDKNPTMNLLTGVPNGMLQ

                SPQVEPTLRRNQEALYRFLNAHSAYFRSHRARIEKATAFDRMNQDM"

regulatory      21834 . . . 21839
                /regulatory_class = "polyA_signal_sequence"

                /gene = "L3"

gene            complement(21877 . . . 26364)
                /gene = "E2A"

gene            complement(21877 . . . 25341)
                /gene = "E2A-L"

regulatory      complement(21877 . . .)
                /regulatory_class = "polyA_signal_sequence"

                /note = "E2A, E2A-L"

CDS             complement(21882 . . . 23417)
                /gene = "E2A"

                /product = "single-stranded DNA-binding protein"

                /translation = "MAGRGGSQSEQRRQERTPERGRGSASRPPNRESPSPPPLPQKRH

                AYRRVVSDDGQEEEIVVVSENSRSPSTSPPPPLPPKKKPRKTKHVPLQDISQDSEDER
```

-continued

QAEEELAAVGFSFPPVRITEKDGKRVFETLDENDPLTSAAATKMTVKNPLSLPIVSAW

EKGMEVMTLLMERYRVESDLKSAFQLMPEQGEVYRRICHLYVNEEHRGIPLTFTSNKT

LTTMMGRFLQGFVHSHSQIAHKNWECTGCALWLHGCTEAEGKLRCLHGTVMIQKEHTI

EMDVASENGQRALKENPDRAKITQNRWGRSVVQLANNDARCCVHDAGCATNQFSSKSC

GVFFTEGGKAQQAFRQLEAFMKAMYPGMSSEQAQMMLIPLHCDCNHKPGCVPSMGRQT

CKMTPFGMANAEDLDVEGITDATVLASVKHPALMVFQCCNPVYRNSRAQNAGPNCDFK

ISAPDLLGALQLTRKLWSDSFPDLPVPKLLIPEFKWLPKYQFRNVSLPAGHAESRQNP

FDF"

intron complement(23427 . . . 24079)
/note = "E2A, E2A-L; precedes single-stranded DNA-binding protein CDS"

CDS 23443 . . . 25842
/gene = "L4"

/product = "hexon assembly protein 100K"

/translation = "METQPSSPTSPSAPAADENQQQQNESLTAPPPSPTSDAAAAPDM

QEMEESIEIDLGYVTPAEHEEELAARFSAPEENHQEQPEQEAESEQQQAGLEHGDYLS

GAEDVLIKHLARQSIIVKDALLDRAEVPLSVAELSRAYERNLFSPRVPPKRQPNGTCE

PNPRLNFYPVFAVPEALATYHLFFKNQRIPVSCRANRTRADALLNLGPGARLPDITSL

EEVPKIFEGLGSDETRAANALQGSGEEHEHHSALVELEGDNARLAVLKRTVELTHFAY

PALNLPPKVMSAVMDQVLIKRASPLSEEEMQDPESSDEGKPVVSDEQLARWLGASSTP

QSLEERRKLMMAVVLVTVELECLRRFFADAETLRKVEENLHYLFRHGFVRQACKISNV

ELTNLVSYMGILHENRLGQNVLHTTLRGEARRDYIRDCVYLYLCHTWQTGMGVWQQCL

EEQNLKELCKLLQKNLKALWTGFDERTTASDLADLIFPERLRLTLRNGLPDFMSQSML

QNFRSFILERSGILPATCSALPSDFVPLTFRECPPPLWSHCYLLRLANYLAYHSDVIE

DVSSEGLLECHCRCNLCTPHRSLACNPQLLSETQIIGTFELQGPGEGKGGLKLTPGLW

TSAYLRKFVPEDYHPFEIRFYEDQSQPPKAELSACVITQGAILAQLQAIQKSRQEFLL

KKGHGVYLDPQTGEELNPSFPQDAPRKQQEAESGAAAAAGGFGGRLGEQSGRGDGRLG

QHSGRGGQPARQSGGGRRGGGGGRGRSSRRQTVVLGGGESKQHGYHLRSGSGSRRPGP

Q"

intron complement(24157 . . . 26296)
/note = "E2A, E2B"

intron complement(24157 . . . 25253)
/gene = "E2A-L"

regulatory complement(25336 . . . 25341)
/regulatory_class = "TATA_box"

/gene = "E2A-L"

CDS join(25556 . . . 25886, 26056 . . . 26399)
/gene = "L4"

/product = "protein 33K"

/translation = "MPRGSSKKLKVELPLPPEDLEEDWESSQAEEMEDWDSTQAEEDS

LQDSLEEEDEVEEEAEEEAAAARPSSSAEEKASSTDTISAPGRGRGGRAHSRWDETGR

FPNPTTQTAPTTVSKKRQKPSSSSRKPAAAAAARKSTAAAGGLRIAANEPAQTRELRN

RIFPTLYAIFQQSRGQEQELKVKNRSLRSLTRSCLYHKSEDQLQRTLEDAEALFNKYC

ALTLKE"

-continued

```
CDS           25556 . . . 26125
              /gene = "L4"

              /product = "encapsidation protein 22K"

              /translation = "MPRGSSKKLKVELPLPPEDLEEDWESSQAEEMEDWDSTQAEEDS

              LQDSLEEEDEVEEEAEEEAAAARPSSSAEEKASSTDTISAPGRGRGGRAHSRWDETGR

              FPNPTTQTGKKERQGYKSWRGHKNAIVSCLQACGGNISFTRRYLLFHRGVNFPRNILH

              YYRHLHSPYYCFQEEAETQQQQQKTSGSS"

intron        25887 . . . 26055
              /gene = "L4"

regulatory    complement(26388 . . . 26393)
              /regulatory_class = "TATA_box"

CDS           26471 . . . 27154
              /gene = "L4"

              /product = "capsid protein precursor pVIII"

              /translation = "MSKEIPTPYMWSYQPQMGLAAGAAQDYSTRMNWLSAGPAMISRV

              NDIRAHRNQILLEQSAITATPRHHLNPRNWPAALVYQEIPQPTTVLLPRDAQAEVQLT

              NSGVQLAGGAALCRHRPAQGIKRLVIRGRGTQLNDEVVSSSLGLRPDGVFQLAGSGRS

              SFTPRQAVLTLESSSSQPRSGGIGTLQFVEEFTPSVYFNPFSGSPGHYPDEFIPNFDA

              ISESVDGYD"

gene          26836 . . . 32075
              /gene = "E3"

regulatory    26836 . . . 26842
              /regulatory_class = "TATA_box"

              /gene = "E3"

intron        26888 . . . 31546
              /gene = "E3"

              /note = "precedes control protein E3 14.7K CDS"

intron        26888 . . . 31098
              /gene = "E3"

              /note = "precedes membrane protein E3 RID-beta CDS"

intron        26888 . . . 30849
              /gene = "E3"

              /note = "precedes membrane protein E3 RID-alpha CDS"

intron        26888 . . . 29956
              /gene = "E3"

              /note = "precedes membrane glycoprotein E3 CR1-gamma CDS"

intron        26888 . . . 28596
              /gene = "E3"

              /note = "precedes membrane glycoprotein E3 CR1-beta CDS"

intron        26888 . . . 28011
              /gene = "E3"

              /note = "precedes membrane glycoprotein E3 gp19K CDS"

intron        26888 . . . 27370
              /gene = "E3"

              /note = "precedes membrane glycoprotein E3 CR1-alpha CDS"
```

-continued

```
CDS          27155 . . . 27475
             /gene = "E3"

             /product = "control protein E3 12.5K"

             /translation = "MSHGGAADLARLRHLDHCRRFRCFARDLAEFAYFELPEEHPQGP

             AHGVRIVVEGGLDSHLLRIFSQRPILVEREQGQTLLTLYCICNHPGLHESLCCLLCTE

             YNKS"

CDS          27429 . . . 28055
             /gene = "E3"

             /product = "membrane glycoprotein E3 CR1-alpha"

             /translation = "MKVFVVCCVLSIIKAEISDYSGLDCGVPAINRSLFFTGNETELQ

             LQCKPHKKYLTWLFQGSPIAVVNHCDNDGVLLSGPANLTFSTRRSKLQLFQPFLPGTY

             QCVSGPCHHTFHLIPNTTAPLPATNNQTTHQRHRRDLSESNTTTHTGGELRGRPTSGI

             YYGPWEVVGLIALGLVAGGLLALCYLYLPCCSYLVVLCCWFKKWGRSP"

regulatory   27464 . . . 27469
             /regulatory_class = "polyA_signal_sequence"

             /gene = "L4"

CDS          28037 . . . 28570
             /gene = "E3"

             /product = "membrane glycoprotein E3 gp19K"

             /translation = "MGKITLVSCGVLVAVVLSIVGLGGAAVVKEEKADPCLHFNPDKC

             QLSFQPDGNRCTVLIKCGWECENVRIEYNNKTRNNTLASVWQPGDPEWYTVSVPGADG

             SPRTVNNTFIFAHMCDTVMWMSKQYDMWPPTKENIVVFSIAYSLCTALITAIVCLSIH

             MLIAIRPRNNAEKEKQP"

CDS          28600 . . . 29305
             /gene = "E3"

             /product = "membrane glycoprotein E3 CR1-beta"

             /translation = "MASVTALTIFLGLVGTSSTFQHINKTVYAGSNSVLPGHQSHQKV

             SWYWYDKSNTPVTLCKGHQTPINRSGIFFKCNHNNITLLSITKHYSGTYYGTNFNIKQ

             DTYYSVTVLDPTTPRTTTKPTTTKRHTKPKTTKKTTVKTTTTRTTTTTEATTSTTLAA

             TTHTHTELTLQTTNDLIALLQKGDNSTTSNEEIPRSMIGIIVAVVVCMLIIALCMVYY

             AFCYRKHRLNDKLEHL"

misc_feature 29636 . . . 29946
             /note = "residual non-functional 3'-region of membrane
             glycoprotein E3 CR1-gamma CDS that is intact in other
             members of this species; lacks splice acceptor and
             5'-region"

CDS          29961 . . . 30857
             /gene = "E3"

             /product = "membrane glycoprotein E3 CR1-delta"

             /translation = "MKAVSALVFCSLIGIVFSAGFLKNLTIYEGENATLVGISGQNVS

             WLKYHLDGWKDICDWNVTVYTCNGVNLTITNATQDQNGRFKGQSFTRNNGYESHNMFI

             YDVTVIRNETATTTQMPTTHSSTTTTMQTTQTTTFYTSTQHMTTTTAAKPSSAAPQPQ

             ALALIAAQPSTTTRTNEQTTDFLSTVESHTTATSSAFSSTANLSSLSSTPISPATTTP

             SPAPLPTPLKQTEDSGMQWQITLLIVIGLVILAVLLYYIFCRRIPNAHRKPVYKPIVD

             GQPEPLQVEGGLRNLLFSFTVW"
```

-continued

```
CDS             30865 . . . 31140
                /gene = "E3"
                /product = "membrane protein E3 RID-alpha"
                /translation = "MIPRQFLITILICLLQVCATLALVANASPDCIGPFASYVLFAFV
                TCICCCSIVCLLITFFQFIDWIFVRIAYLRHHPQYRDQRVARLLRLL"
CDS             31146 . . . 31577
                /gene = "E3"
                /codon_start = 1
                /product = "membrane protein E3 RID-beta"
                /translation = "MRALLLLALLLLVLPRPVNPRSPTQSPEEVRKCKFQEPWKFLKC
                YRQKSDMHPSWIMIIGIVNILACTLISFVIYPCFDFGWNSPEALYLPPEPDTPPQQPQ
                AHALPPPQPRPQYMPILDYEAEPQRPMLPAISYFNLTGGDD"
CDS             31570 . . . 31977
                /gene = "E3"
                /note = "12.5K family"
                /product = "control protein E3 14.7K"
                /translation = "MTDPLANNNVNDLLLDMDGRASEQRLAQLRIRQQQERAVKELQD
                GIAIHQCKKGIFCLVKQAKISYEVTQTDHRLSYELLQQRQKFTCLVGVNPIVITQQSG
                DTKGCIHCSCDSPDCVHTLIKTLCGLRDLLPMN"
regulatory      32001 . . . 32006
                /regulatory_class = "polyA_signal_sequence"
                /gene = "E3"
regulatory      32070 . . . 32075
                /regulatory_class = "polyA_signal_sequence"
                /gene = "E3"
CDS             32254 . . . 33531
                /gene = "L5"
                /note = "capsid protein IV"
                /product = "fiber"
                /translation = "MSKKRVRVDDDFDPVYPYDADNAPTVPFINPPFVSSDGFQEKPL
                GVLSLRLADPVTTKNGEITLKLGEGVDLDSSGKLISNTATKAAAPLSFSNNTISLNMD
                HPFYTKDGKLSLQVSPPLNILRTSILNTLALGFGSGLGLRGSALAVQLVSPLTFDTDG
                NIKLTLDRGLHVTTGDAIESNISWAKGLKFEDGAIATNIGNGLEFGSSSTETGVDDAY
                PIQVKLGSGLSEDSTGAIMAGNKEDDKLTLWTTPDPSPNCQILAENDAKLTLCLTKCG
                SQILATVSVLVVGSGNLNPITGTVSSAQVFLRFDANGVLLTEHSTLKKYWGYRQGDSI
                DGTPYTNAVGEMPNLKAYPKSQSSTTKNNIVGQVYMNGDVSKPMLLTITLNGTDDSNS
                TYSMSFSYTWTNGSYVGATFGANSYTESYIAQE"
regulatory      33599 . . . 33604
                /regulatory_class = "polyA_signal_sequence"
                /gene = "L5"
gene            complement(33620 . . . 36319)
                /gene = "E4"
regulatory      complement(33620 . . . 33625)
                /regulatory_class = "polyA_signal_sequence"
                /gene = "E4"
```

-continued

```
CDS             complement(join(33638 . . . 33889, 34621 . . . 34791))
                /gene = "E4"
                /product = "control protein E4orf6/7"
                /translation = "MSESNCIMTRSRARSAASRHHPYRPAPLPRCEETETRASLVEDH
                PVLPDCDTLSMHNITVIPTTEDNPQLLSCEVQMRECPEGFISLTDPRLARSETVWNVE
                TKSMSITNGVQMFKAVRGERVVYSMSWEGGGKITARIL"
CDS             complement(33886 . . . 34791)
                /gene = "E4"
                /note = "E4orf6; 34K family"
                /product = "control protein E4 34K"
                /translation = "MSESNCIMTRSRARSAASRHHPYRPAPLPRCEETETRASLVEDH
                PVLPDCDTLSMHNVSSVRGLPCSAGFAVLQEFPVPWDMVLTPEELRVLKRCMSVCLCC
                ANIDLESSQMIHGYERWVLHCHCRDPGSLRCMAGGAVLALWERRIIRGCMENQRVMWY
                REVVNRHMPKEIMYMGSVFWRGRHLIYLRIWYDGHVGSILPAMSFGWSVLNYGLLNNL
                VVLCCTYCSDLSEIRMRCCARRTRRLMLRAVGIMLRESLDPDPLSSSLTERRRQRLLR
                GLMRHHRPIPFADYDSHRRSSASSR"
intron          complement(33890 . . . 34620)
                /gene = "E4"
CDS             complement(34697 . . . 35062)
                /gene = "E4"
                /product = "control protein E4orf4"
                /translation = "MVLPVLPSPAVTETQQNCIIWLGLAHSTVVDVIRAIRHDGIFIT
                PEALDLLHGLREWLEYNENTERSKRRDRRRRSVCSARTRECYSKYENVRKQLHHDTVA
                STISRVPPSPVSAGPLTTL"
intron          complement(34815 . . . 36232)
                /gene = "E4"
                /note = "precedes control protein E4 34K CDS"
CDS             complement(35072 . . . 35425)
                /gene = "E4"
                /product = "control protein E4orf3"
                /translation = "MRVCLRMPVEGALRELFIMAGLDLPQELVRIIQGWKNENYLGMV
                QECNMMIEELENPPAFAIVLFLDVRVEALLEATVEHLENRITFDLAVIFHQHSGGERC
                HLRDLHFEVLRDRLD"
intron          complement(35136 . . . 36232)
                /gene = "E4"
                /note = "precedes control protein E4orf4 CDS"
CDS             complement(35422 . . . 35811)
                /gene = "E4"
                /product = "control protein E4orf2"
                /translation = "MLERTACIYSIVVPEALNVHLEDFSFVDFLKNCLGDFLSSYLED
                ITGSSQHAYSSLAFGNAHWGGLRFICTVACPNLIPGGPMAKNFGEDMKEYLQLLLREE
                LRDRGREFDIPLVNLLQVNQEQNILEL"
intron          complement(35455 . . . 36232)
                /gene = "E4"
                /note = "precedes control protein E4orf3 CDS"
```

-continued

```
intron          complement(35827 . . . 36232)
                /gene = "E4"

                /note = "precedes control protein E4orf2 CDS"

CDS             complement(35851 . . . 36225)
                /gene = "E4"

                /note = "genus-specific; DURP family"

                /product = "control protein E4orf1"

                /translation = "MDAEALYVYLEGSGALLPVQEGSNYILYAPENFVLHPHGIALLD

                LRLSIVVPYCFLGRFFSLADANVPGVYSSCRIIHAGHRERLSVMVENHSDNEYEGRAG

                DPVACLVLERTIYPPVRQASMV"

regulatory      complement(36314 . . . 36319)
                /regulatory_class = "TATA_box"

                /gene = "E4

repeat_region36515 . . . 36643
                /standard_name = "ITR"

                /rpt_type = inverted
```

Annotation of the ChAd155 Wild Type Sequence (SEQ ID NO: 19) Sequence is Provided Below.

```
LOCUS       ChAd155      37830 bp    DNA     linear   10-JUN-2015
DEFINITION  Chimp adenovirus 155, complete genome.
COMMENT     Annotation according to alignment of ChAd155 against
            the human
            Adenovirus 2 reference strain NC__001405
            Two putative ORFs in the E3 region added manually
FEATURES             Location/Qualifiers
     source          1..37830
                     /organism="Chimpanzee adenovirus 155"
                     /mol__type="genomic DNA"
                     /acronym="ChAd155"
     repeat__region  1..101
                     /standard__name="ITR"
                     /rpt__type=inverted
     gene            466..1622
                     /gene="E1A"
     TATA__signal    466..471
                     /gene="E1A"
     prim__transcript 497..1622
                     /gene="E1A"
     CDS             join(577..1117,1231..1532)
                     /gene="E1A"
                     /product="E1A__280R"
     CDS             join(577..979,1231..1532)
                     /gene="E1A"
                     /product="E1A__243R"
     polyA__signal   1600..1605
                     /gene="E1A"
     gene            1662..4131
                     /gene="E1B"
     TATA__signal    1662..1667
                     /gene="E1B"
     prim__transcript 1692..4131
                     /gene="E1B"
     CDS             1704..2267
                     /gene="E1B"
                     /product="E1B__19K"
     CDS             2009..3532
                     /gene="E1B"
                     /product="E1B__55K"
     gene            3571..4131
                     /gene="IX"
     TATA__signal    3571..3576
                     /gene="IX"
     prim__transcript 3601..4131
                     /gene="IX"
```

-continued

```
     CDS             3628..4092
                     /gene="IX"
                     /product="IX"
     polyA__signal   4097..4102
                     /note="E1B, IX"
     gene            complement(4117..27523)
                     /gene="E2B"
     prim__transcript complement(4117..27494)
                     /gene="E2B"
     gene            complement(4117..5896)
                     /gene="IVa2"
     prim__transcript complement(4117..5896)
                     /gene="IVa2"
     CDS             complement(join(4151..5487,5766..5778))
                     /gene="IVa2"
                     /product="E2B__IVa2"
     polyA__signal   complement(4150..4155)
                     /note="IVa2, E2B"
     CDS             complement(join(5257..8838,14209..14217))
                     /gene="E2B"
                     /product="E2B__polymerase"
     gene            6078..34605
                     /gene="L5"
     gene            6078..28612
                     /gene="L4"
     gene            6078..22658
                     /gene="L3"
     gene            6078..18164
                     /gene="L2"
     gene            6078..14216
                     /gene="L1"
     TATA__signal    6078..6083
                     /note="L"
     prim__transcript 6109..34605
                     /gene="L5"
     prim__transcript 6109..28612
                     /gene="L4"
     prim__transcript 6109..22658
                     /gene="L3"
     prim__transcript 6109..18164
                     /gene="L2"
     prim__transcript 6109..14216
                     /gene="L1"
     CDS             join(8038..8457,9722..9742)
                     /gene="L1"
                     /product="L1__13.6K"
     CDS             complement(join(8637..10640,14209..14217))
                     /gene="E2B"
                     /product="E2B__pTP"
```

-continued

| | |
|---|---|
| gene | 10671..10832<br>/gene="VAI" |
| misc_RNA | 10671..10832<br>/gene="VAI"<br>/product="VAI" |
| gene | 10902..11072<br>/gene="VAII" |
| misc_RNA | 10902..11072<br>/gene="VAII"<br>/product="VAII" |
| CDS | 11093..12352<br>/gene="L1"<br>/product="L1_52K" |
| CDS | 12376..14157<br>/gene="L1"<br>/product="L1_pIIIa" |
| polyA_signal | 14197..14202<br>/gene="L1" |
| CDS | 14254..16035<br>/gene="L2"<br>/product="L2_penton" |
| CDS | 16050..16646<br>/gene="L2"<br>/product="L2_pVII" |
| CDS | 16719..17834<br>/gene="L2"<br>/product="L2_V" |
| CDS | 17859..18104<br>/gene="L2"<br>/product="L2_pX" |
| polyA_signal | 18143..18148<br>/gene="L2" |
| CDS | 18196..18951<br>/gene="L3"<br>/product="L3_pVI" |
| CDS | 19063..21945<br>/gene="L3"<br>/product="L3_hexon" |
| CDS | 21975..22604<br>/gene="L3"<br>/product="L3_protease" |
| polyA_signal | 22630..22635<br>/gene="L3" |
| gene | complement(22632..27523)<br>/gene="E2A" |
| prim_transcript | complement(22632..27494)<br>/gene="E2A" |
| gene | complement(22632..26357)<br>/gene="E2A-L" |
| prim_transcript | complement(22632..26328)<br>/gene="E2A-L" |
| polyA_signal | complement(22649..22654)<br>/note="E2A, E2A-L" |
| CDS | complement(22715..24367)<br>/gene="E2A"<br>/note="DBP; genus-common; DBP family"<br>/codon_start=1<br>/product="E2A" |
| CDS | 24405..26915<br>/gene="L4"<br>/product="L4_100k" |
| TATA_signal | complement(26352..26357)<br>/gene="E2A-L" |
| CDS | join(26602..26941,27147..27529)<br>/gene="L4"<br>/product="L4_33K" |
| CDS | 26602..27207<br>/gene="L4"<br>/product="L4_22K" |
| TATA_signal | complement(27518..27523)<br>/note="E2A, E2B; nominal" |
| CDS | 27604..28287<br>/gene="L4"<br>/product="L4_pVIII" |
| gene | 27969..32686<br>/gene="E3B" |
| gene | 27969..31611<br>/gene="E3A" |

-continued

| | |
|---|---|
| TATA_signal | 27969..27974<br>/note="E3A, E3B" |
| prim_transcript | 27998..32686<br>/gene="E3B" |
| prim_transcript | 27998..31611<br>/gene="E3A" |
| CDS | 28288..28605<br>/gene="E3A"<br>/product="E3 ORF1" |
| polyA_signal | 28594..28599<br>/gene="L4" |
| CDS | 29103..29303<br>/gene="E3A"<br>/product="E3 ORF2" |
| CDS | 29300..29797<br>/gene="E3A"<br>/product="E3 ORF3" |
| CDS | 29826..30731<br>/gene="E3A"<br>/product="E3 ORF4" |
| CDS | 30728..31579<br>/gene="E3A"<br>/product="E3 ORF5" |
| CDS | 31283..31579<br>/gene="E3A"<br>/product="E3 ORF6" |
| polyA_signal | 31578..31584<br>/gene="E3A" |
| CDS | 31591..31863<br>/gene="E3B"<br>/product="E3 ORF7" |
| CDS | 31866..32264<br>/gene="E3B"<br>/product="E3 ORF8" |
| CDS | 32257..32643<br>/gene="E3B"<br>/product="E3 ORF9" |
| polyA_signal | 32659..32664<br>/gene="E3B" |
| gene | complement(<32678..32838)<br>/gene="U" |
| CDS | complement(<32678..32838)<br>/gene="U"<br>/note="exon encoding C terminus unidentified; genus-common"<br>/product="protein U" |
| CDS | 32849..34585<br>/gene="L5"<br>/product="L5_fiber" |
| polyA_signal | 34581..34586<br>/gene="L5" |
| gene | complement(34611..37520)<br>/gene="E4" |
| prim_transcript | complement(34611..37490)<br>/gene="E4" |
| polyA_signal | complement(34625..34630)<br>/gene="E4" |
| CDS | complement(join(34794..35069,35781..35954))<br>/gene="E4"<br>/product="E4 ORF7" |
| CDS | complement(35070..35954)<br>/gene="E4"<br>/product="E4 ORF6" |
| CDS | complement(35875..36219)<br>/gene="E4"<br>/product="E4 ORF4" |
| CDS | complement(36235..36582)<br>/gene="E4"<br>/product="E4 ORF3" |
| CDS | complement(36579..36971)<br>/gene="E4"<br>/product="E4 ORF2" |
| CDS | complement(37029..37415)<br>/gene="E4"<br>/product="E4 ORF1" |

-continued

| | |
|---|---|
| TATA_signal | complement(37515..37520)<br>/gene="E4" |
| repeat_region | 37740..37830<br>/standard_name="ITR"<br>/rpt_type=inverted |

Transgenes

Adenoviral vectors may be used to deliver desired RNA or protein sequences, for example heterologous sequences, for in vivo expression. A vector may include any genetic element including naked DNA, a phage, transposon, cosmid, episome, plasmid, or a virus. By "expression cassette" (or "minigene") is meant the combination of a selected heterologous gene (transgene) and the other regulatory elements necessary to drive translation, transcription and/or expression of the gene product in a host cell.

Typically, an adenoviral vector is designed such that the expression cassette is located in a nucleic acid molecule which contains other adenoviral sequences in the region native to a selected adenoviral gene. The expression cassette may be inserted into an existing gene region to disrupt the function of that region, if desired. Alternatively, the expression cassette may be inserted into the site of a partially or fully deleted adenoviral gene. For example, the expression cassette may be located in the site of a mutation, insertion or deletion which renders non-functional at least one gene of a genomic region selected from the group consisting of E1A, E1B, E2A, E2B, E3 and E4. The term "renders non-functional" means that a sufficient amount of the gene region is removed or otherwise disrupted, so that the gene region is no longer capable of producing functional products of gene expression. If desired, the entire gene region may be removed (and suitably replaced with the expression cassette). Suitably, E1 genes of adenovirus are deleted and replaced with an expression cassette consisting of the promoter of choice, cDNA sequence of the gene of interest and a poly A signal, resulting in a replication defective recombinant virus.

A transgene sequence may also include a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

In addition to the transgene the expression cassette also includes conventional control elements which are operably linked to the transgene in a manner that permits its transcription, translation and/or expression in a cell transfected with the adenoviral vector. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

A "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, native, constitutive, inducible and/or tissue-specific, are known in the art and may be utilized.

Examples of constitutive promoters include, without limitation, the TBG promoter, the retroviral Rous sarcoma virus LTR promoter (optionally with the enhancer), the cytomegalovirus (CMV) promoter (optionally with the CMV enhancer, see, e.g., Boshart et al, Cell, 41:521-530 (1985)), the CASI promoter (WO2012/115980), the SV40 promoter, the dihydrofolate reductase promoter, the β-actin promoter, the phosphoglycerol kinase (PGK) promoter, and the EF1a promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 378:1766-1769 (1995), see also Harvey et al, Curr. Opin. Chem. Biol, 2:512-518 (1998)). Other systems include the FK506 dimer, VP16 or p65 using castradiol, diphenol murislerone, the RU486-inducible system (Wang et al, Nat. Biotech., 15:239-243 (1997) and Wang et al, Gene Ther., 4:432-441 (1997)) and the rapamycin-inducible system (Magari et al, *J. Clin. Invest.*, 100:2865-2872 (1997)). The effectiveness of some inducible promoters increases over time. In such cases one can enhance the effectiveness of such systems by inserting multiple repressors in tandem, e.g., TetR linked to a TetR by an IRES.

The transgene may be operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see Li et al, Nat. Biotech., 17:241-245 (1999)). Examples of promoters that are tissue-specific are known for liver (albumin, Miyatake et al, J. Virol, 71:5124-32 (1997); hepatitis B virus core promoter, Sandig et al, Gene Ther., 3:1002-9 (1996); alpha-fetoprotein (AFP), Arbuthnot et al., Hum. Gene Ther., 7: 1503-14 (1996)), bone osteocalcin (Stein et al, Mol. Biol. Rep., 24:185-96 (1997)); bone sialoprotein (Chen et al., J. Bone Miner. Res., 11:654-64 (1996)), lymphocytes (CD2, Hansal et al, J. Immunol, 161:1063-8 (1998); immunoglobulin heavy chain; T cell receptor chain), neuronal such as neuron-specific enolase (NSE) promoter (Andersen et al, Cell. Mol. Neurobiol, 13:503-15 (1993)), neurofilament light-chain gene (Piccioli et al, Proc. Natl. Acad. Sci. USA, 88:5611-5 (1991)), and the neuron-specific vgf gene (Piccioli et al, Neuron, 15:373-84 (1995)), among others.

In some embodiments, the Woodchuck Hepatitis Virus Posttranscriptional Regulatory Element (WPRE) (Zuffrey et al. (1999) J Virol; 73(4):2886-9) may be operably linked to the transgene.

Adenoviral Vector Construction

Adenoviral vectors are generated by the modification of the wild type adenovirus to express heterologous genes and/or delete or inactivate undesirable adenoviral sequences. Adenoviral vectors may also have altered replication competency. For example the vector may be replication defective or have limited replication such that it has a reduced ability to replicate in non-complementing cells, compared to the wild type virus. This may be brought about by mutating the virus e.g. by functionally inactivating or deleting a gene involved in replication, for example E1a, E1b, E2, E3 or E4.

The adenoviral vectors in accordance with the present invention may comprise a functionally inactivated or deleted E1. Thus the adenoviral vectors according to the invention may be replication defective due to the absence of the ability to express adenoviral E1a and/or E1b. The recombinant adenoviruses may also bear functional inactivations in other genes (see WO 03/000283) for example, deletions in E3 or E4 genes. The adenovirus delayed early gene E3 may be eliminated from the adenovirus sequence which forms part of the recombinant virus. The function of E3 is not necessary to the production of the recombinant adenovirus particle. Thus, it is unnecessary to replace the function of this gene product in order to package a recombinant adenovirus useful in the invention. In one particular embodiment the recombinant adenoviruses have functionally deleted E1 and E3 genes. The construction of such vectors is described in Roy et al., Human Gene Therapy 15:519-530, 2004.

Recombinant adenoviruses may also be constructed having a functional deletion of the E4 gene. In a particular embodiment, the recombinant adenoviruses have functionally deleted E1 and E4 genes as described in Colloca et al. (2012) Sci. Transl. Med. 4:1-9; Roy et al. (2004) Virol. 324: 361-372. In some embodiments it may be desirable to retain the E4 ORF6 function. In one embodiment, the native E4 ORF6 region may be replaced by a heterologous E4 ORF6, such as from Ad5. Thus, in one particular embodiment, the adenoviral vector may be functionally deleted in E1 and have the E4 ORF6 region from Ad5.

Adenovirus vectors according to the invention may also contain a functional deletion in the delayed early gene E2a. Deletions may also be made in any of the late genes L1 through to L5 of the adenovirus genome. Similarly deletions in the intermediate genes IX and IVa may be useful.

Other deletions may be made in the other structural or non-structural adenovirus genes. The above deletions may be used individually, e.g. an adenovirus sequence for use in the present invention may contain deletions of E1 only. Alternatively, deletions of entire genes or portions thereof effective to destroy their biological activity may be used in any combination. For example in one exemplary vector, the adenovirus sequences may have deletions of the E1 genes and the E4 gene, or of the E1, E2a and E3 genes, or of the E1 and E3 genes (such as functional deletions in E1a and E1b, and a deletion of at least part of E3), or of the E1, E2a and E4 genes, with or without deletion of E3 and so on. Such deletions may be partial or full deletions of these genes and may be used in combination with other mutations, such as temperature sensitive mutations to achieve a desired result.

These vectors are generated using techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence. Particularly suitable methods include standard homologous recombination methods such as those provided in Colloca et al. (2012) Sci. Transl. Med. 4:1-9; Roy et al. (2004) Virol. 324: 361-372; Roy et al. (2010) J. of Gene Med. 13:17-25; and WO2010/085984 or recombineering methods as described in Warming et al. Nuc. Acids Res. (2005) 33:e36.

Suitably, an adenovirus sequence for use in the present invention will contain functional inactivation (such as deletion) of at least the E1 and E4 genes, optionally with E3 functional inactivation (such as deletion), in conjunction with Ad5E4orf6 gene substitution.

In one embodiment the adenovirus comprises functional inactivation (such as deletion) of the E1 and E4 genes, with incorporation of E4orf6 from Ad5. In such embodiments adenovirus is suitably derived from ChAd155, ChAd3 or ChAd63, particularly ChAd3.

In a second embodiment the adenovirus comprises functional inactivation (such as deletion) of the E1, E3 and E4 genes, with incorporation of E4orf6 from Ad5. In such embodiments adenovirus is suitably derived from ChAd155, ChAd3 or ChAd63, particularly ChAd63.

Adenoviral Vector Production

The adenoviral vectors can be produced using any suitable cell line in which the virus is capable of replication. In particular, complementing cell lines which provide the factors missing from the viral vector that result in its impaired replication characteristics (such as E1) can be used. Without limitation, such a cell line may be HeLa (ATCC Accession No. CCL 2), A549 (ATCC Accession No. CCL 185), HEK 293, KB (CCL 17), Detroit (e.g., Detroit 510, CCL 72) and W1-38 (CCL 75) cells, among others. These cell lines are all available from the American Type Culture Collection, 10801 University Boulevard, Manassas, Va. 20110-2209. Other suitable parent cell lines may be obtained from other sources, such as PER.C6™ cells, as represented by the cells deposited under ECACC no. 96022940 at the European Collection of Animal Cell Cultures (ECACC) at the Centre for Applied Microbiology and Research (CAMR, UK) or Her 96 cells (Crucell).

A particularly suitable complementation cell line is the Procell92 cell line. The Procell92 cell line is based on HEK 293 cells which express adenoviral E1 genes, transfected with the Tet repressor under control of the human phosphoglycerate kinase-1 (PGK) promoter, and the G418-resistance gene (Vitelli et al. PLOS One (2013) 8(e55435):1-9).

Procell92.S is adapted for growth in suspension conditions and is also useful for producing adenoviral vectors expressing toxic proteins (www.okairos.com/e/inners.php?m=00084, last accessed 13 Apr. 2015).

Adenoviral Delivery Methods and Dosage

The adenoviral vectors may be as administered in immunogenic compositions. An immunogenic composition as described herein is a composition comprising one or more recombinant vectors capable of inducing an immune response, for example a humoral (e.g., antibody) and/or cell-mediated (e.g., a cytotoxic T cell) response, against the transgene product delivered by the vector following delivery to a mammal, suitably a human. A recombinant adenovirus may comprise (suitably in any of its gene deletions) a gene encoding the desired immunogen and may therefore be used in a vaccine.

Such vaccine or other immunogenic compositions may be formulated in a suitable delivery vehicle. Generally, doses for the immunogenic compositions are in the range defined below under 'Delivery Methods and Dosage'.

Optionally, a vaccine or immunogenic composition of the invention may be formulated to contain other components, including, e.g., adjuvants, stabilizers, pH adjusters, preservatives and the like. An adjuvant can be administered with a priming DNA vaccine encoding an antigen to enhance the antigen-specific immune response compared with the immune response generated upon priming with a DNA vaccine encoding the antigen only.

The adenoviral vector may be prepared for administration by being suspended or dissolved in a pharmaceutically or physiologically acceptable carrier such as isotonic saline; isotonic salts solution or other formulations that will be apparent to those skilled in the art. The appropriate carrier will be evident to those skilled in the art and will depend in large part upon the route of administration. The compositions described herein may be administered to a mammal in a sustained release formulation using a biodegradable biocompatible polymer, or by on-site delivery using micelles, gels and liposomes.

In some embodiments, the recombinant adenovirus of the invention is administered to a subject by intramuscular injection, intravaginal injection, intravenous injection, intraperitoneal injection, subcutaneous injection, epicutaneous administration, intradermal administration, nasal administration or oral administration. Delivery to the lung may also be desirable. Intramuscular delivery may be a typical route, for reasons of simplicity and convenience.

If the therapeutic regimen involves co-administration of one or more adenoviral vectors and a further component, each formulated in different compositions, they are favourably administered co-locationally at or near the same site. For example, the components can be administered (e.g. via an administration route selected from intramuscular, transdermal, intradermal, sub-cutaneous) to the same side or extremity ("co-lateral" administration) or to opposite sides or extremities ("contra-lateral" administration).

Dosages of the viral vector will depend primarily on factors such as the condition being treated, the age, weight and health of the patient, and may thus vary among patients. For example, a therapeutically effective adult human or veterinary dosage of the viral vector generally contains $1\times10^5$ to $1\times10^{15}$ viral particles, such as from $1\times10^8$ to $1\times10^{12}$ (e.g., $1\times10^8$, $5\times10^8$, $1\times10^9$, $5\times10^9$, $1\times10^{10}$, $2.5\times10^{10}$, $5\times10^{10}$, $1\times10^{11}$ $5\times10^{11}$, $1\times10^{12}$ particles). Alternatively, a viral vector can be administered at a dose that is typically from $1\times10^5$ to $1\times10^{10}$ plaque forming units (PFU), such as $1\times10^5$ PFU, $5\times10^5$ PFU, $1\times10^6$ PFU, $5\times10^6$ PFU, $1\times10^7$ PFU, $5\times10^7$ PFU, $1\times10^8$ PFU, $5\times10^8$ PFU, $1\times10^9$ PFU, $5\times10^9$ PFU, or $1\times10^{10}$ PFU. Dosages will vary depending upon the size of the animal and the route of administration. For example, a suitable human or veterinary dosage (for about an 80 kg animal) for intramuscular injection is in the range of about $1\times10^9$ to about $5\times10^{12}$ particles per mL, for a single site. Optionally, multiple sites of administration may be used. In another example, a suitable human or veterinary dosage may be in the range of about $1\times10^{11}$ to about $1\times10^{15}$ particles for an oral formulation. The adenoviral vector can be quantified by Quantitative PCR Analysis (Q-PCR), for example with primers and probe designed on CMV promoter region using as standard curve serial dilution of plasmid DNA containing the vector genome with expression cassette including HCMV promoter. The copy number in the test sample is determined by the parallel line analysis method. Alternative methods for vector particle quantification can be analytical HPLC or spectrophotometric method based on $A_{260}$ nm.

Generally a human dose will be in a volume of between 0.5 ml and 2 ml. Thus the composition described herein can be formulated in a volume of, for example 0.5, 1.0, 1.5 or 2.0 ml human dose per individual or combined immunogenic components. A volume of 400-600 ul, such as around 500 ul is typically used, in particular for administration by the intramuscular route.

One of skill in the art may adjust these doses, depending on the route of administration and the therapeutic or vaccine application for which the recombinant vector is employed. The levels of expression of the transgene, or for an adjuvant, the level of circulating antibody, can be monitored to determine the frequency of dosage administration.

The therapeutic levels of, or level of immune response against, the protein encoded by the selected transgene can be monitored to determine the need, if any, for boosters. Following an assessment of CD8+ T cell response, or optionally, antibody titers, in the serum, optional booster immunizations may be desired. Optionally, the adenoviral vector may be delivered in a single administration or in various combination regimens, e.g., in combination with a regimen or course of treatment involving other active ingredients or in a prime-boost regimen.

M72 Transgene

A further aspect of the present invention relates to a novel polynucleotide encoding an M72 antigen which has been optimised for use in the present invention but will also have utility in other contexts. Consequently, the invention also provides a polynucleotide comprising SEQ ID No: 8 or a degenerate variant thereof having at least 95% identity to SEQ ID No: 8 (such as at least 98% identity, suitably at least 99% identity, in particular at least 99.5% identity and especially 100% identity). Also provided is a polynucleotide consisting of SEQ ID No: 8 or a degenerate variant thereof having at least 95% identity to SEQ ID No: 8 (such as at least 98% identity, in suitably at least 99% identity, particular at least 99.5% identity and especially 100% identity). By the term degenerate variant is meant a variant of the polynucleotide which encodes the same polypeptide.

The optimised polynucleotide helps ensure the benefits of the present invention are fully achieved through efficient transgene expression in human cells.

Adenoviral Constructs

A further aspect of the present invention relates to novel adenoviral constructs of use in the present invention but also having utility in other contexts. Consequently, the invention also provides a non-human simian adenovirus comprising a transgene encoding a Rv1196 or Rv0125 related antigen.

Suitably the non-human simian adenovirus comprises a penton of SEQ ID No: 10, a hexon of SEQ ID No: 11 or a fibre of SEQ ID No: 12, in particular a penton of SEQ ID No: 10, a hexon of SEQ ID No: 11 and a fibre of SEQ ID No: 12. Alternatively, the non-human simian adenovirus comprises a penton of SEQ ID No: 15, a hexon of SEQ ID No: 16 or a fibre of SEQ ID No: 17, in particular a penton of SEQ ID No: 15, a hexon of SEQ ID No: 16 and a fibre of SEQ ID No: 17. Also, the non-human simian adenovirus may comprise a penton of SEQ ID No: 20, a hexon of SEQ ID No: 21 or a fibre of SEQ ID No: 22, in particular a penton of SEQ ID No: 21, a hexon of SEQ ID No: 22 and a fibre of SEQ ID No: 23.

The transgene encoding a Rv1196 related antigen may be a sequence encoding a polypeptide comprising, such as consisting of, a sequence having at least 90% identity to SEQ ID No: 1, especially at least 95%, for example at least 98%, such as at least 99% to SEQ ID No: 1, such as SEQ ID No: 1.

The transgene encoding a Rv0125 related antigen may be a sequence encoding a polypeptide comprising, such as consisting of, a sequence having at least 90% identity to SEQ ID No: 3, especially at least 95%, for example at least 98%, such as at least 99% to SEQ ID No: 3, such as SEQ ID No: 3.

Suitably the transgene will encode an antigen comprising (such as consisting of) a sequence having at least 90% identity to SEQ ID No. 6. Alternatively, the transgene will encode an antigen comprising (such as consisting of) a fragment of SEQ ID No: 6 which is at least 450 amino acids in length. In some embodiments the transgene will encode an antigen comprising (such as consisting of) amino acids 2-723 of SEQ ID No. 6. Suitably the transgene comprises SEQ ID No: 8 or a degenerate variant thereof having at least 95% identity to SEQ ID No: 8. In some embodiments the transgene comprises SEQ ID No: 8.

Suitably the adenovirus is replication deficient. For example, the adenovirus comprises functional inactivation (such as deletion) of the E1 gene. The adenovirus may comprise functional inactivation (such as deletion) of the E4 gene. The adenovirus may also comprise functional inactivation (such as deletion) of the E3 gene. The adenovirus may also comprise an Ad5E4orf6 gene substitution.

Exemplary adenovirus constructs according to the invention are those having the polynucleotide sequence of SEQ ID No: 13 or 18.

An additional aspect of the invention is a polynucleotide sequence comprising SEQ ID No: 13 or 18, such as a polynucleotide sequence consisting of SEQ ID No: 13 or 18.

Immunisation Regimes, Target Populations and Modes of Administration

In one embodiment the subject receives a single dose of the polypeptide antigen and a single dose of the associated adenovirus. In other embodiments the subject receives two doses of the polypeptide antigen and a single dose of the associated adenovirus (the additional dose of polypeptide antigen may be given prior to initiation of the standard protein/adeno or adeno/protein methods or following completion of the standard methods). In other embodiments the subject receives one dose of the polypeptide antigen and two doses of associated adenovirus (the additional dose of the associated adenovirus may be given prior to initiation of the standard protein/adeno or adeno/protein methods or following completion of the standard methods). When two doses of adenovirus encoding antigen are provided, they may or may not make use of the same adenovirus strain and insert.

When the subject receives two doses of polypeptide antigen, suitably the additional dose is one week to three months, in particular two weeks to two months, typically three weeks to six weeks, such as three weeks to five weeks, for example around four weeks prior to initiation or following completion of the standard method.

When the subject receives two doses of associated adenovirus, suitably the additional dose is one week to three months, in particular two weeks to two months, typically three weeks to six weeks, such as three weeks to five weeks, for example around four weeks prior to initiation or following completion of the standard method.

The subject to be treated using the method of the invention may be of any age. In one aspect of the invention, the subject is human.

In one embodiment the subject is an adult human (typically aged 18-60).

The polypeptide and adenovirus compositions may be administered via various suitable routes, including parenteral, such as intramuscular or subcutaneous administration.

In one particular embodiment, the one or more of the compositions is administered intradermally. The term intradermally as used herein is intended to refer to the application of antigens into the dermis and/or epidermis of human skin. Intradermal application of an immunogenic composition may be performed by using any cutaneous method known to the skilled person including, but not limited to, delivery using a short needle device (a device comprising a microneedle that is between about 0.2 and about 0.6 mm in length) or delivery using a skin patch. Suitable devices for use with the cutaneous vaccines described herein include short needle devices such as those described in U.S. Pat. Nos. 4,886,499, 5,190,521, 5,328,483, 5,527,288, 4,270,537, 5,015,235, 5,141,496, 5,417,662 and EP1092444. Cutaneous vaccines may also be administered by devices which limit the effective penetration length of a needle into the skin, such as those described in WO99/34850. Also suitable are jet injection devices which deliver liquid vaccines to the dermis via a liquid jet injector or via a needle. Also suitable are ballistic powder/particle delivery devices which use compressed gas to accelerate vaccine in powder form through the outer layers of the skin to the dermis. Skin patches will generally comprise a backing plate which includes a solid substrate. Patches deliver the antigen and adjuvant used in the invention to the dermis or epidermis. In particular embodiment, the patches useful in the present invention comprise a plurality of microprojections. The microprojections may be of any shape suitable for piercing the stratum corneum, epidermis and/or dermis and delivery and antigen and adjuvant to the epidermis or dermis. In a particular embodiment, microprojections are biodegradable and comprise a biodegradable polymer.

In an alternative approach, the polypeptide may be administered intramuscularly and the adenovirus administered intranasally or via aerosol to the lungs.

Suitably, both compositions are administered intramuscularly.

Immunogenic compositions used in the invention may be made by admixing the antigen(s) and the adjuvant. The antigen(s) may be provided in a lyophilized form or in a liquid formulation. A kit may be provided comprising a first container comprising the antigen and a second container comprising the adjuvant.

Suitably, the compositions according to the present invention have a human dose volume of between 0.05 ml and 1 ml, such as between 0.1 and 0.5 ml, in particular a dose volume of about 0.5 ml, or 0.7 ml. The volume of the second immunogenic composition may be reduced, and e.g. be between 0.05 ml and 0.5 ml, such as between 0.1 and 0.2 ml. The volumes of the compositions used may depend on the delivery route with smaller doses being given by the intradermal route.

Additional embodiments of the invention include:

(a) A non-human simian adenovirus comprising a transgene encoding a Rv1196 or Rv0125 related antigen, said adenovirus having at least the penton of SEQ ID No: 20, the hexon of SEQ ID No: 21 or the fibre of SEQ ID No: 22.

(b) The non-human simian adenovirus according to (a), comprising the penton (SEQ ID No: 20), hexon (SEQ ID No: 21) and fibre (SEQ ID No: 22) protein from ChAd155.

(c) The non-human simian adenovirus according to either (a) or (b) wherein the encoded antigen comprises a sequence having at least 90% identity to SEQ ID No. 6.

(d) The non-human simian adenovirus according to any one of (a), (b) or (c) wherein the encoded antigen comprises a fragment of SEQ ID No: 6 which is at least 450 amino acids in length, such as 2-723 of SEQ ID No. 6.

(e) The non-human simian adenovirus according to any one of (a) to (d), which is a replication deficient adenovirus.

(f) The non-human simian adenovirus according to any one of (a) to (e), wherein the adenovirus comprises functional inactivation (such as deletion) of the E1 gene.

(g) The non-human simian adenovirus according to any one of (a) to (f), wherein the adenovirus comprises functional inactivation (such as deletion) of the E4 gene.

(h) The non-human simian adenovirus according to any one of (a) to (g), wherein the adenovirus comprises functional inactivation (such as deletion) of the E3 gene.

(i) The non-human simian adenovirus according to any one of (a) to (e), wherein the adenovirus comprises an Ad5E4orf6 gene substitution.

The teaching of all references in the present application, including patent applications and granted patents, are herein fully incorporated by reference. A composition or method or process defined as "comprising" certain elements is understood to encompass a composition, method or process (respectively) consisting of those elements. The invention will be further described by reference to the following, non-limiting, example:

EXAMPLES

Example 1—Generation of ChAd3 and ChAd63 Vectors Encoding M72 Protein

Making Constructs

An M72 DNA sequence was optimized by GeneArt® (Life Technologies Corporation) for human expression (SEQ ID No: 8). According to standard methods, the optimised DNA sequence was synthesized and cloned by GeneWiz® under control of HCMV promoterTetO system and BGH polyA sequences into the shuttle plasmid PVJ using the EcoRV-NotI restriction sites. This plasmid was cleaved with SpeI and SgfI restriction enzymes and recombined into either ChAd3 (with E1 and E4 deletions) or ChAd63 (with E1, E3 and E4 deletions) vectors by homologous recombination in *E. coli* BJ5183.

Briefly, the construction of ChAd3 vectors proceeded through the steps provided below.

The pChAd3 vector is derived from the wild type chimp adenovirus 3 genome. The wild type chimp adenovirus type 3 was isolated from a healthy young chimpanzee housed at the New Iberia Research Center facility (New Iberia Research Center; The University of Louisiana at Lafayette) using standard procedures. The viral genome was then cloned in a plasmid vector and subsequently modified to carry the following modifications in different regions of ChAd3 viral genome:

1) deletion of the E1 region (from bp 460 to bp 3543) of the viral genome;

2) deletion of the entire ChAd3 E4 coding region (spanning from nucleotide 34634-37349 of ChAd3 wild type sequence) and substitution with Ad5E4orf6 gene. The deleted region all of the E4 region with the exception of E4 native promoter and polyadenylation signal.

The construction of ChAd 63 vectors proceeded through the steps provided below.

The wild type chimp adenovirus type 63 was isolated from a healthy group of Chimpanzee housed by the New Iberia facility using standard procedures. The viral genome was then cloned in a plasmid vector and subsequently modified to carry the following modifications in different regions of ChAd3 viral genome:

1) deletion of the E1 region (from bp 456 to bp 3421) of the viral genome;

2) deletion of the E3 region (from 27208 bp to 31786 bp) of the viral genome;

3) deletion of the entire ChAd63 E4 coding region (spanning from nucleotide 33825 to 36216 of ChAd63 wt sequence) and substitution with Ad5E4orf6 gene. The deleted region contained all E4 region with the exception of E4 native promoter and polyadenylation signal.

Confirmatory Testing

Rescues and viruses amplification (from passage 1 to passage 4) were generated in procell-92.S cell line according to standard procedures and the genetic structure of the viral DNAs was checked at passage 3 (M72-ChAd63) or passage 4 (M72-ChAd3) by two different restriction patterns. Each recombinant virus was purified from 1 litre scale culture through a CsCl gradient method. Purified viruses were titred by quantitative PCR and the infectivity measured by a hexon immunostaining method.

Good M72 expression was confirmed by Western Blot, after HeLa cell line infection with purified viruses. Genomic stability was evaluated until passage 10 and the DNA sequence of complete expression cassette were confirmed by sequencing.

Example 2—Adenovirus Dose Investigation in Mice

Test Groups

The aim of this study was to assess and compare the immunogenicity of 2 chimpanzee adenoviruses encoding for the tuberculosis M72 antigen: M72-ChAd3 and M72-ChAd63. The adenoviruses were produced according to Example 1.

Female 6 week old CB6F1/OlaHsd mice, 12 mice per group, were injected by the intramuscular route with 50 ul at day 0 (ChAd 3 solution: pH 7.4, 10 mM TRIS, 10 mM histidine, 5% sucrose, 75 mM NaCl, 1 mM $MgCl_2$, 0.02% polysorbate 80, 0.1 mM EDTA, 0.5% (v/v) ethanol; ChAd63 solution: pH 6.6, 10 mM histidine, 7.5% sucrose, 35 mM NaCl, 1 mM $MgCl_2$, 0.1% polysorbate 80, 0.1 mM EDTA, 0.5% (v/v) ethanol):

| Group | Adenovirus | Number of Viral Particles |
|---|---|---|
| 1 | M72-ChAd3 | 10^10 |
| 2 | M72-ChAd3 | 10^9 |
| 3 | M72-ChAd3 | 10^8 |
| 4 | M72-ChAd3 | 10^7 |
| 5 | M72-ChAd63 | 10^10 |
| 6 | M72-ChAd63 | 10^9 |
| 7 | M72-ChAd63 | 10^8 |
| 8 | M72-ChAd63 | 10^7 |

In order to have sufficient volume, the whole blood of 4 pools of 3 mice for groups was collected at days 7, 14, and 21.

Measurement of Cellular Immune Response—Intracellular Cytokine Staining (ICS)

Leukocyte Isolation from Whole Blood

At each time point, blood was collected from each mouse and subsequently pooled (4 pools of 3 mice). Blood was collected in tubes containing, RPMI/additives (RPMI 1640, supplemented with glutamine, penicillin/streptomycin, sodium pyruvate, non-essential amino-acids and 2-mercaptoethanol) containing heparin 5000 unit/ml (Heparin Leo). Ten volumes of Lysing buffer were added to the whole blood and tubes were incubated at room temperature (RT) for 10 min. After centrifugation (335 g, 10 min at RT), the pellet was harvested in RPMI/additives and filtered (Cell strainer 100 um). Cells were pelleted again (335 g, 10 min at RT) and re-suspended in Complete Medium (RPMI 1640, supplemented with glutamine, penicillin/streptomycin, sodium pyruvate, non-essential amino-acids and 2-mercaptoethanol, and 5% heat inactivated fetal calf serum).

In Vitro Stimulation of Fresh Leukocytes

Leukocytes were plated in round bottom 96-well plates at approximately 1 million cells per well. Leukocytes were then stimulated for 6 hours (37° C., 5% $CO_2$) with anti-CD28 (clone 37.51) and anti-CD49d (clone 9C10) at 1 ug/ml, with or without 1 ug/ml of peptides covering the M72 sequence (mixture of 15-mer peptides overlapping by 11 amino acid residues). After a 2 hour stimulation period, BD GolgiPlug™ containing brefeldin A diluted in complete medium (final dilution 1/1000) was added for 4 additional hours. Plates were then transferred at 4° C., overnight.

ICS IFNg, IL-2, TNF-α

Cells were stained and analysed using a 5-colour ICS assay.

Cells were transferred to V-bottom 96-well plates, centrifuged at 189 g for 5 min at 4° C. after wash with 200 ul Flow Buffer (PBS 1×, 1% FCS), re-suspended the cells in 50 ul Flow Buffer containing anti-CD16/32 (clone 2.4G2) diluted 1/50, for 10 min at 4° C. Then, 50 ul Flow Buffer containing anti-CD4-V450 (clone RM4-5, diluted 1/50) and anti-CD8-PerCp-Cy5.5 (clone 53-6.7, diluted 1/50) antibodies and LIVE/DEAD® Pacific Orange (Life Technologies, diluted 1/500) was added for 30 min at 4° C. Cells were centrifuged (189 g for 5 min at 4° C.) and washed with 200 ul Flow Buffer.

Leukocytes were fixed and permeabilised by adding 200 ul of Cytofix/Cytoperm solution (Becton Dickinson commercial buffer) for 20 min at 4° C. Cells were centrifuged (189 g for 5 min at 4° C.) and washed with 200 ul Perm/Wash buffer (Becton Dickinson commercial buffer diluted 1:10 in distilled water). After an additional centrifugation step, cells were stained in 50 ul Perm/Wash buffer with anti-IL2-FITC (clone JES6-5H4, diluted 1/400), anti-IFNg-APC (clone XMG1.2, diluted 1/200) and anti-TNFa-PE (clone MP6-XT22, diluted 1/700) antibodies, for 1 hour at 4° C. Cells were washed twice with the Perm/Wash buffer re-suspended in 220 ul PBS. Stained cells were analysed by flow cytometry using a LSRII and the FlowJo software.

Results

Figure 2:
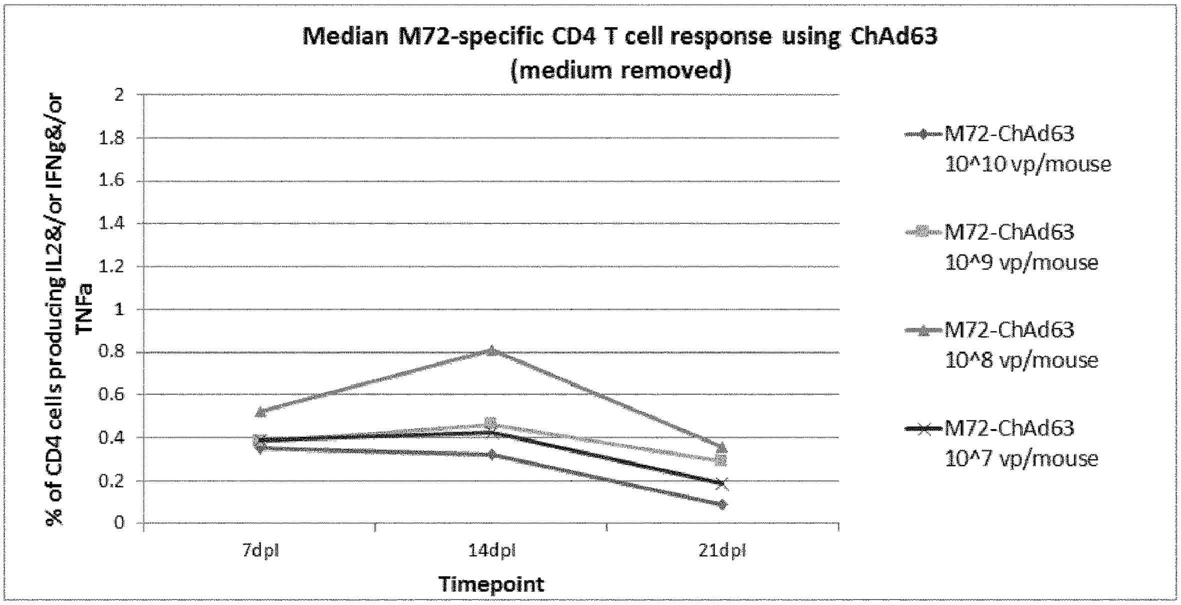
FIG. 2: Median percentage of M72-specific CD4 T cell response from CB6F1 mice expressing IFN-gamma and/or IL-2 and/or TNF-alpha cytokines at 7, 14 and 21 days post immunisation using ChAd63 in a range of doses.
Figure 3:
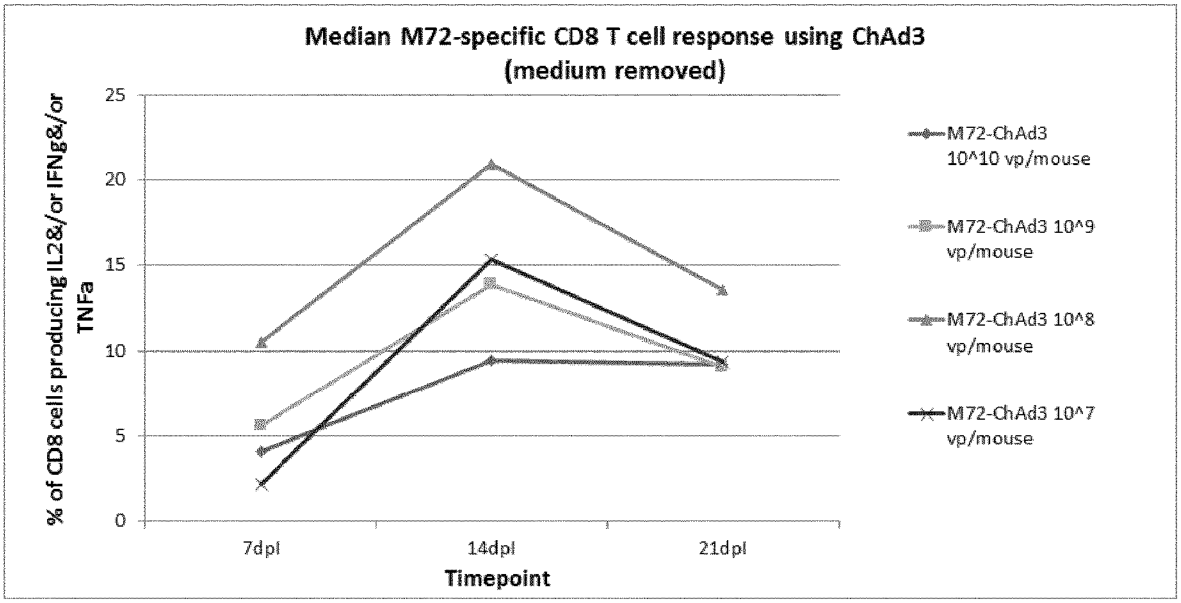
FIG. 3: Median percentage of M72-specific CD8 T cell response from CB6F1 mice expressing IFN-gamma and/or IL-2 and/or TNF-alpha cytokines at 7, 14 and 21 days post immunisation using ChAd3 in a range of doses.
Figure 4:
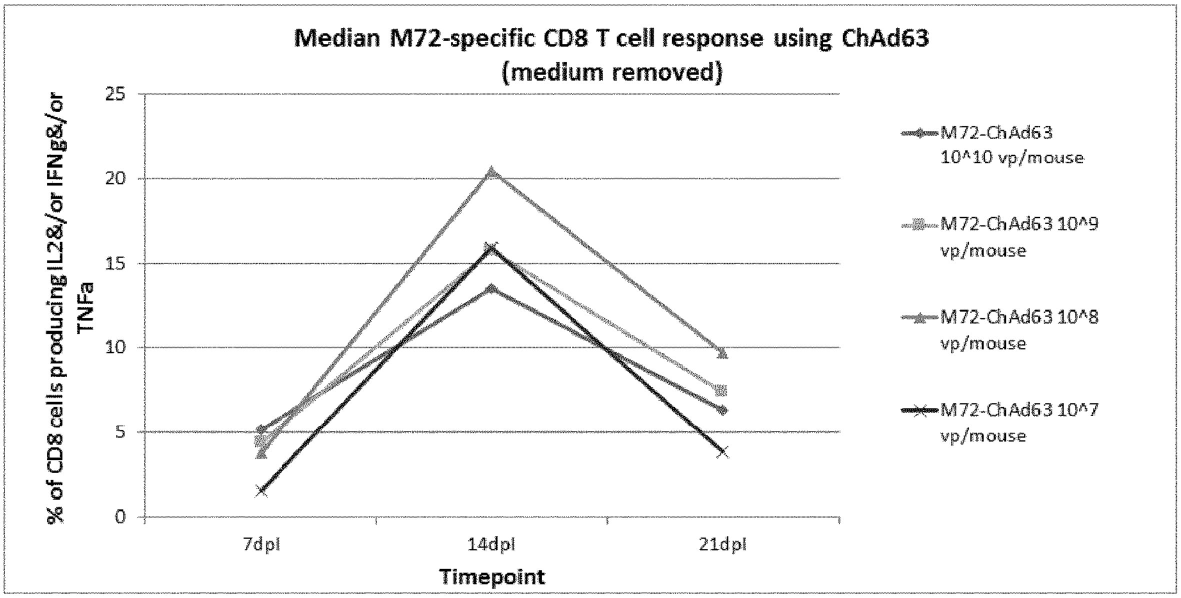
FIG. 4: Median percentage of M72-specific CD8 T cell response from CB6F1 mice expressing IFN-gamma and/or IL-2 and/or TNF-alpha cytokines at 7, 14 and 21 days post immunisation using ChAd63 in a range of doses.

As seen in FIGS. 1 and 2 (CD4 T cell response for M72-ChAd3 and M72-ChAd63 constructs respectively) and FIGS. 3 and 4 (CD8 T cell response for M72-ChAd3 and M72-ChAd63 constructs respectively) a dose of $1\times10^8$ viral particles per mouse induced the highest level M72 specific response at timepoint 14PI for both the M72-ChAd3 and M72-ChAd63 constructs.

Example 3—Investigation of the Impact of Adenovirus and Adjuvant Coformulation on Infectivity The impact of the co-formulation was evaluated with recombinant eGFP-ChAd3 or eGFP-ChAd63. These ChAd3 and ChAd 63 are controls constructed to express the green fluorescent protein instead of the M72 transgene in the respective ChAdenovirus backbones (E1-E4 deleted ChAd3 and E1-E3-E4 deleted ChAd63). Co-formulation with the AS01E (a liposomal formulation of the TLR4 agonist 3D-MPL and the saponin QS21) was evaluated via an infectivity assay based on HeLa cells.

Materials and Methods

Infectivity Test

HeLa cells were grown in an exponential growth and seeded for 24 h before infection. HeLa cells were used between passage P45 and P65 (Molbiol; GSK Rix).

DAY 0: Cell Harvest

The medium was removed from the flask and the cells rinsed carefully with DPBS to remove residual cell medium. 5 ml of Trypsin-EDTA was added onto the cells followed by observing the cells under an inverted microscope until the cell layer detached and dispersed (2 to 4 minutes). The cell suspension was gently pipetted up and down and transferred into the Falcon tube and centrifuged at 1200 rpm for 5 to 10 minutes at room temperature. The cell pellet was re-suspended in an appropriate volume and counted. The cells were seeded in a 96 well-plate at $1.5\times10^4$ cells/well (HeLa cells are expected to be at $3\times10^4$ cells/well at the day of infection DAY 1: Infection Day The HeLa cells were observed and were between 50% to 80% confluent. The entire medium was removed from the cells. The recombinant eGFP-ChAd3 and eGFP-ChAd63 stocks were diluted down to a final titre of $5\times10^7$ vp/ml in 80 ul of complete dulbecco modified eagle medium (DMEM). This volume is for 1 well. 80 ul of each sample was added in each well to infect (this is done in duplicate). A negative control of uninfected HeLa cells with a formulation with buffers alone in complete DMEM was used to measure any negative impact on the adeno-infectivity due to the adjuvant buffer. A positive infection control of HeLa cells infected with eGFP-ChAd3 (same condition of infection) was processed in identical conditions. After 3 hours at 37° C., 5% $CO_2$, 120 ul of complete DMEM was added and then cultured at 37° C., 5% $CO_2$ for approximately 24 hours.

Day 2: Harvest and FACS Read Out

The cell supernatants were harvested in a 96 well-plate. Hela cells were rinsed with 4011 of trypsin/EDTA and then incubated with an additional 4011 of the trypsin/EDTA mix. Once the cells were detaching from the plate, each well was then gently flushed to recover all the cells. The 96-well plate was then centrifuged at 1200 rpm for 10 minutes. The supernatants were discarded. The cells were suspended in 200 ul of DPBS and kept at 4° C. until FACS acquisition was done on them (LSRII Beckman Dickinson).

Results

| Test Group | Description | % GFP A | % GFP B | % GFP Average | % viability (average) |
|---|---|---|---|---|---|
| 1 | DMEM control | 0 | 0 | 0 | 89.14 |
| 2 | AS01E | 0 | 0 | 0 | 91.20 |
| 3 | AS01E + eGFP-ChAd3 | 81.9 | 84.79 | 83.35 | 89.01 |
| 4 | AS01E + eGFP-ChAd63 | 70.43 | 73.28 | 71.86 | 88.95 |
| 5 | AS buffer + eGFP-ChAd3 | 86.4 | 86.93 | 86.67 | 88.57 |
| 6 | AS buffer + eGFP-ChAd63 | 69.59 | 71.38 | 70.49 | 87.49 |
| 7 | eGFP-ChAd3 | 78.78 | 81.29 | 80.04 | 90.96 |
| 8 | eGFP-ChAd63 | 51.43 | 53.46 | 52.45 | 90.41 |

AS buffer pH 8.0, 10 mM $PO_4$, 5 mM NaCl, 4.7% sorbitol

ChAd3 buffer: pH 7.4, 10 mM TRIS, 10 mM histidine, 5% sucrose, 75 mM NaCl, 1 mM $MgCl_2$, 0.02% polysorbate 80, 0.1 mM EDTA, 0.5% (v/v) ethanol ChAd63 buffer: pH 6.6, 10 mM histidine, 7.5% sucrose, 35 mM NaCl, 1 mM $MgCl_2$, 0.1% polysorbate 80, 0.1 mM EDTA, 0.5% (v/v) ethanol The data are expressed as the percentage of cells expressing GFP correlating with the number of cells infected by the ChAd-GFP virus. For all conditions, cell viability has been recorded. This was done to assess any possible cell toxicity which could mislead the conclusion. Fortunately, this was not the case as the cell viability through all the conditions was acceptable and comparable.

According to the data, no negative impact of the AS on either ChAd3- or ChAd63-GFP is observed. The ChAd3-GFP vector co-formulated with AS01E kept its infectivity potential, which was comparable to the ChAd3-GFP alone.

Same observation was made for ChAd63-GFP. In the latter case, an increase of infectivity was even observed which may be due to the buffers used in which the adenovirus was diluted.

Example 4—Investigation of the Impact of Adenovirus and Adjuvant Coformulation on QS21 Quenching The aim of the study was to check the detoxification of QS21.

Characterisations

| Group | Description | Visual aspect | H (sticks) | Osmo (mosm/kg) |
|---|---|---|---|---|
| 1 | AS01E | Opalescent | 5.5-6 | 291 |
| 2 | eGFP-ChAd3 at $2.10 \times 10^9$ in AS01E | Slightly Opalescent | 5-5.5 | 289 |
| 3 | eGFP-ChAd63 at $2.10 \times 10^9$ in AS01E | Slightly Opalescent | 5-5.5 | 297 |
| 4 | eGFP-ChAd3 at $2.10 \times 10^9$ in AS01E buffer | Clear | 5-5.5 | 292 |
| 5 | eGFP-ChAd63 at $2.10 \times 10^9$ in AS01E buffer | Clear | 5-5.5 | 304 |
| 6 | eGFP-ChAd3 at $2.10 \times 10^9$ | Clear | 7 | 425 |
| 7 | eGFP-ChAd63 at $2.10 \times 10^9$ | Clear | 6-6.5 | 408 |

The formulated samples containing the adjuvant or the adjuvant buffer have an osmolality 285 mOsm/kg. The pH was taken on indicator stick.

Washing of Red Blood Cells

The red blood cells (10 ml) were centrifuged for 10 minutes at 1600 rpm (550 g) at 4° C. and the supernatant removed. The red blood cells were re-suspended gently with a volume of buffer DPBS equivalent to the original volume (±10 ml). The operation was repeated (min 2-3 times) until the supernatant was clear (reddish staining disappeared, but the supernatant never becomes completely translucent) and then eliminated the last supernatant after washing. The pellet was stored at 4° C. for 3 to 4 days maximum if not used directly (and washed again the day it is used) or was diluted around 10 times in buffer if used the same day.

Pre Dilutions of Red Blood Cells

Different pre dilutions of the red blood cells were performed. The pre dilution for which one a 100% of lysis is reached with an OD value (540 nm) between 1.5 and 2 was selected.

The following dilutions were prepared in haemolysis tubes:

| Dilution | Red blood cells | dPBS |
|---|---|---|
| 1/10 | 100 ul | 900 ul |
| 1/12.5 | 100 ul | 1150 ul |
| 1/15 | 100 ul | 1400 ul |

The red blood cells were centrifuged (10 ml) for 10 minutes at 1600 rpm (550 g) at 4° C. 100 ul of the predilution was removed, mixed with 900 ul of WFI and centrifuged for 5 minutes at 2000 rpm (900 g). The supernatant was transferred in a cuvette for spectroscopy and measured the OD at 540 nm. The dilution chosen gave a OD between 1.5 and 2.

QS21 Standard Curve Preparation

The standard curve of QS21 was made from a QS21 working solution (at 2 mg/ml) diluted extemporaneously to 20 ug/ml in $PO_4$/Sorbitol buffer.

Determination of lytic activity was carried out by a limit test.

1. Limit of detection (LOD) was defined as the lowest concentration of QS21 leading to an OD:

Higher than the base level (OD>0.1)

Around three times higher than OD's buffer (the "0 ug" QS21)

In the ascendant part of the curve

Determined for each test.

2. QS21 lytic activity was held to be positive in the adjuvant samples if the OD for the adjuvant sample was greater than the $OD_{LOD}$.

Example QS21 Curve

| Samples | QS21 (ug) | O.D. Sample | O.D. Buffer | Delta (O.D. sample − O.D. buffer) | *Pass/fail |
|---|---|---|---|---|---|
| AS01E | 45 | 0.151 | 0.122 | 0.029 | PASS |
| ChAd3 in AS01E | 45 | 0.148 | 0.122 | 0.026 | PASS |
| ChAd63 in AS01E | 45 | 0.143 | 0.122 | 0.021 | PASS |

*Pass: if Delta (O.D. sample − O.D buffer) < LOD (O.D.) test of the day

*Fail: if Delta (O.D. sample − O.D. buffer) > LOD (O.D.) test of the day

Conclusion

When formulating eGFP-ChAd3 and eGFP-ChAd63 separately with AS01E, the adjuvant size remains unchanged after formulation. Furthermore, there is no free QS21 after formulation, as seen by the red blood cell lysis test.

Example 5—M72 Dosage Regimes

Evaluating the application of non-replicative chimp adeno vectors expressing M72 in the context of a tuberculosis vaccine, by assessing both homologous (ChAd/ChAd) and heterologous (Prot/ChAd or ChAd/Prot) prime-boost vaccination strategies as well as in combination with M72/AS01E given as admixed or in co-administration.

Materials and Methods

Animal Model

Female mouse CB6F1/OlaHsd—6 weeks old—12 mice per group—were injected by intramuscular route with 50 ul at days 0-28 as indicated in table below.

| | Admin D0 | | | Admin D28 | | |
|---|---|---|---|---|---|---|
| Gr. | Antigen | Dose | Solution | Antigen | Dose | Solution |
| Benchmark | | | | | | |
| 1 | M72/AS01E | 1 ug | AS buffer | M72/AS01E | 1 ug | AS buffer |
| Priming: Adeno/Boost: Protein | | | | | | |
| 2 | M72-ChAd3 | 10^8 vp | ChAd3 buffer | M72/AS01E | 1 ug | AS buffer |
| 3 | M72-ChAd63 | 10^8 vp | ChAd63 buffer | | | |
| 4 | eGFP-ChAd3 | 10^8 vp | ChAd3 buffer | | | |
| Priming: Protein/Boost: Adeno | | | | | | |
| 5 | M72/AS01E | 1 ug | AS buffer | M72-ChAd3 | 10^8 vp | ChAd3 buffer |
| 6 | | 1 ug | AS buffer | M72-ChAd63 | 10^8 vp | ChAd63 buffer |
| Priming: Adeno + AS/Boost: Adeno+ AS | | | | | | |
| 7 | M72-ChAd3/ AS01E | 10^8 vp | AS buffer | M72-ChAd3/ AS01E | 10^8 vp | AS buffer |
| Priming: Adeno/Boost: Adeno | | | | | | |
| 8 | M72-ChAd3 | 10^8 vp | ChAd3 buffer | M72-ChAd3 | 10^8 vp | ChAd3 buffer |
| 9 | M72-ChAd3 | 10^8 vp | ChAd3 buffer | M72-ChAd63 | 10^8 vp | ChAd63 buffer |
| 10 | M72-ChAd63 | 10^8 vp | ChAd63 buffer | M72-ChAd3 | 10^8 vp | ChAd3 buffer |
| Combo Priming and Boost; Adeno + Protein | | | | | | |
| 11 | M72/AS01E M72-ChAd3 Combo | 1 ug 10^8 vp | AS buffer | M72/AS01E M72-ChAd3 Combo | 1 ug 10^8 vp | AS buffer |
| 12 | M72/AS01E Co-Ad M72-ChAd3 | 1 ug 10^8 vp | AS buffer (adjuvanted protein) and ChAd3 buffer (adeno) | M72/AS01E Co-Ad M72-ChAd3 | 1 ug 10^8 vp | AS buffer (adjuvanted protein) and ChAd3 buffer (adeno) |
| 13 | M72/AS01E eGFPChAd3 Combo | 1 ug 10^8 vp | AS buffer | M72/AS01E eGFPChAd3 Combo | 1 ug 10^8 vp | AS buffer |

AS buffer: approx pH 8.0, 10 mM $PO_4$, 5 mM NaCl, 4.7% sorbitol

ChAd3 buffer: pH 7.4, 10 mM TRIS, 10 mM histidine, 5% sucrose, 75 mM NaCl, 1 mM $MgCl_2$, 0.02% polysorbate 80, 0.1 mM EDTA, 0.5% (v/v) ethanol ChAd63 buffer: pH 6.6, 10 mM histidine, 7.5% sucrose, 35 mM NaCl, 1 mM $MgCl_2$, 0.1% polysorbate 80, 0.1 mM EDTA, 0.5% (v/v) ethanol

| Fluid | Test | Time point of collection | Comment |
|---|---|---|---|
| Whole Blood | ICS | D14(14PI) | Evaluation of peripheral whole blood responses of TB antigen-specific CD4 and CD8 cells, as determined by the simultaneous measurement of IFNg, IL-2, TNF-a, after restimulation with overlapping 15-mer peptide pools |
| Whole Blood/ Lung | ICS | D42(14PII)* | Evaluation of peripheral whole blood and lung responses of TB antigen-specific CD4 and CD8 cells, as determined by the simultaneous measurement of IFNg, IL-2, TNF-a, IL-17 after restimulation with overlapping 15-mer peptide pools |
| Serum | Serology anti-M72 IgTot | D41(13PII)** | |

*Limitations of +/−36 lung collection per day, therefore the study was performed in several replicates

**Due to practical constraints, serum samples were taken 1 day prior to whole blood In order to have sufficient volume, the whole blood of 4 pools of 3 mice for groups was collected at days 14, and 42. At day 42, the same process was applied for lungs.

Due to limitations of collection per day, one pool of each group was treated per day-during 4 days in order to have 4 pools per groups. Individual sera were collected at day 41.

The mice were identified in order to do the link between PI and PII for the both read-outs ICS and serology.

Cellular Immune Response-Intracellular Cytokine Staining (ICS)

Leukocyte Isolation from Whole Blood

At each time point, blood was collected from each mouse and subsequently pooled (4 pools of 3 mice). Blood was collected in tubes containing, RPMI/additives (RPMI 1640, supplemented with Glutamine, Penicillin/streptomycin, Sodium Pyruvate, non-essential amino-acids and 2-mercaptoethanol) containing heparin (1/10). Ten volumes of Lysing buffer were added to the whole blood and tubes were incubated at room temperature (RT) for 10 min. After centrifugation (335 g, 10 min at RT), the pellet was harvested in RPMI/additives and filtered (Cell strainer 100 μm). Cells were pelleted again (335 g, 10 min at RT) and re-suspended in Complete Medium (RPMI 1640, supplemented with Glutamine, Penicillin/streptomycin, Sodium Pyruvate, non-essential amino-acids and 2-mercaptoethanol, and 5% Heat inactivated Fetal Calf Serum).

Leukocyte Isolation from Lung

Lung was collected in tubes containing, RPMI/additives (RPMI 1640, supplemented with Glutamine, Penicillin/streptomycin, Sodium Pyruvate, non-essential amino-acids and 2-mercaptoethanol). The sample was transferred in to a Petri dish and the specimen cut in to small pieces (approximately 5×5 mm). The specimens were re-suspended in a gentleMACS C tube (violet) containing 10 ml of pre-warmed complete medium containing Liberase (0.0625 UI/ml=50 ul)+DNase (25 ug=25 ul). The C tube was attached upside down into the sleeve of the gentle MACS Dissociator and the Program mouse-lung 02 (40 sec) ran. At the end of the program, the C tube was detached and the C tube incubated for 30 min at 37° C. in a shaking incubator. After the incubation the sample was transferred on to a cell strainer (100 um) placed on a 50 ml falcon tube. The cell strainer was rinsed twice with 5 ml Complete Medium (RPMI 1640, supplemented with Glutamine, Penicillin/streptomycin, Sodium Pyruvate, non-essential amino-acids and 2-mercaptoethanol, and 5% Heat inactivated Fetal Calf Serum). Complete Medium was added until 45 ml. The cells were centrifuged (400 g for 10 min-4° C.), aspirated the supernatant and then re-suspended cells in 10 ml Complete Medium. This step of washing was repeated. After the second wash, the cells were re-suspended in 3 ml Percoll P30. The Percoll P30 layer containing the cells was placed on top of the Percoll P40/P75 layers gradient. The cells were centrifuged for 20 mins 754 g at RT. The cells considered were at the interphase between P40 and P75 at the end of centrifugation (lower interphase). The P30 layer was aspirated and cells collected at interphase P40-P75. The cells were collected in 15 ml tube and Complete Medium added to a final volume of 15 ml. The cells were centrifuged (900 g for 10 min-4° C.). The supernatant was aspirated and the cells washed with 15 ml Complete Medium twice. The pellet was re-suspended with Complete Medium to a volume final of 250 ul. The cells were counted with Macsquant method including viability with P1.

In Vitro Stimulation of Fresh Leukocytes

Leukocytes were plated in round bottom 96-well plates at approximately 1 million cells per well. Leukocytes were then stimulated for 6 hours (37° C., 5% $CO_2$) with anti-CD28 (clone 37.51) and anti-CD49d (clone 9C10) at 1 ug/ml, with or without 1 ug/ml of peptides covering the M72 sequence. After a 2 hour-stimulation, BD GolgiPlug™ containing brefeldin A diluted in complete medium (final dilution 1/1000) was added for 4 additional hours. Plates were then transferred at 4° C., overnight.

ICS IFNg, IL-2, TNF-α—at 14PI—WBLO

Cells were stained and analyzed using a 5-colour ICS assay.

Cells were transferred to V-bottom 96-well plates, centrifuged at 189 g for 5 min at 4° C. after wash with 200 ul Flow Buffer (PBS 1×, 1% FCS), re-suspended the cells in 50 ul Flow Buffer containing anti-CD16/32 (clone 2.4G2) diluted 1/50, for 10 min at 4° C. Then, 50 ul Flow Buffer containing anti-CD4-V450 (clone RM4-5, diluted 1/50) and anti-CD8-PerCp-Cy5.5 (clone 53-6.7, diluted 1/50) antibodies and Live & Dead PO (diluted 1/500) was added for 30 min at 4° C. Cells were centrifuged (189 g for 5 min at 4° C.) and washed with 200 ul Flow Buffer.

Leukocytes were fixed and permeabilized by adding 200 ul of Cytofix/Cytoperm solution (Becton Dickinson commercial buffer) for 20 min at 4° C. Cells were centrifuged (189 g for 5 min at 4° C.) and washed with 200 ul Perm/Wash buffer (Becton Dickinson commercial buffer diluted 1:10 in distilled water). After an additional centrifugation step, cells were stained in 50 ul Perm/Wash buffer with anti-IL2-FITC (clone JES6-5H4, diluted 1/400), anti-IFNg-APC (clone XMG1.2, diluted 1/200) and anti-TNFa-PE (clone MP6-XT22, diluted 1/700) antibodies, for 1 hour at 4° C. Cells were washed twice with the Perm/Wash buffer re-suspended in 220 ul PBS. Stained cells were analyzed by flow cytometry using a LSRII and the FlowJo software.

ICS IFNg, IL-2, TNF-α and IL-17 at 14PII—WBLO & Lung

The same protocol was used except for the step cytokine; Cells were stained in 50 ul Perm/Wash buffer with anti-IL2-FITC (clone JES6-5H4, diluted 1/400), anti-IFNg-APC (clone XMG1.2, diluted 1/200) and anti-TNFa-PE (clone MP6-XT22, diluted 1/700), anti-IL17 BV786 (clone TC11-18H10, diluted 1/50) antibodies, for 1 hour at 4° C.

Humoral Response-Anti-M72 Ig Tot Serology by ELISA 96-well Elisa plates were coated with the recombinant antigen M72 at 0.25 ug/ml in PBS and incubated overnight at 4° C. Sera from vaccinated mice at Post II were diluted at 1/5000 or 1/40000 for repeat, in PBS (0.2%)-BSA and then a 2 fold serial dilution is performed from well 1 to 12 and incubated. Serial dilutions of the standard and control material were used to calculate the anti-M72 antibody standard titres of tested sera and to ensure validity of the test. Plates were washed with PBS 0.1% tween20 buffer after each incubation step. A biotinylated goat antibody specific for mice Ig is then added and the antigen-antibody complex is revealed by incubation with a streptavidin-peroxidase complex and a peroxidase substrate ortho-phenylenediamine dihydrochlorid/$H_2O_2$. The Optical densities (O.D.) were recorded at 490-620 nm. The anti-M72 antibody titre of each individual mouse serum is determined from the standard curve of the ELISA using a regression model and expressed in ELISA unit (EU)/ml. Geometric Mean Titres (GMT) are then calculated for each group of mice.

Results

T Cell Responses

A. M72-Specific CD4 T & CD8 T Cells Responses

To evaluate the application of non-replicative chimp adeno vectors expressing M72 in the context of a tuberculosis vaccine, both homologous (ChAd/ChAd) and heterologous (Prot/ChAd or ChAd/Prot) prime-boost vaccination strategies were assessed as well as in combination with M72/AS01E4 given as admixed or in co-administration. The prime/boost and combo strategies were evaluated in a DO-D28 schedule. Whole blood was collected at 14P1 and 14PII to assess the systemic induction of M72 specific CD4 and CD8 T cells.

Figure 5:
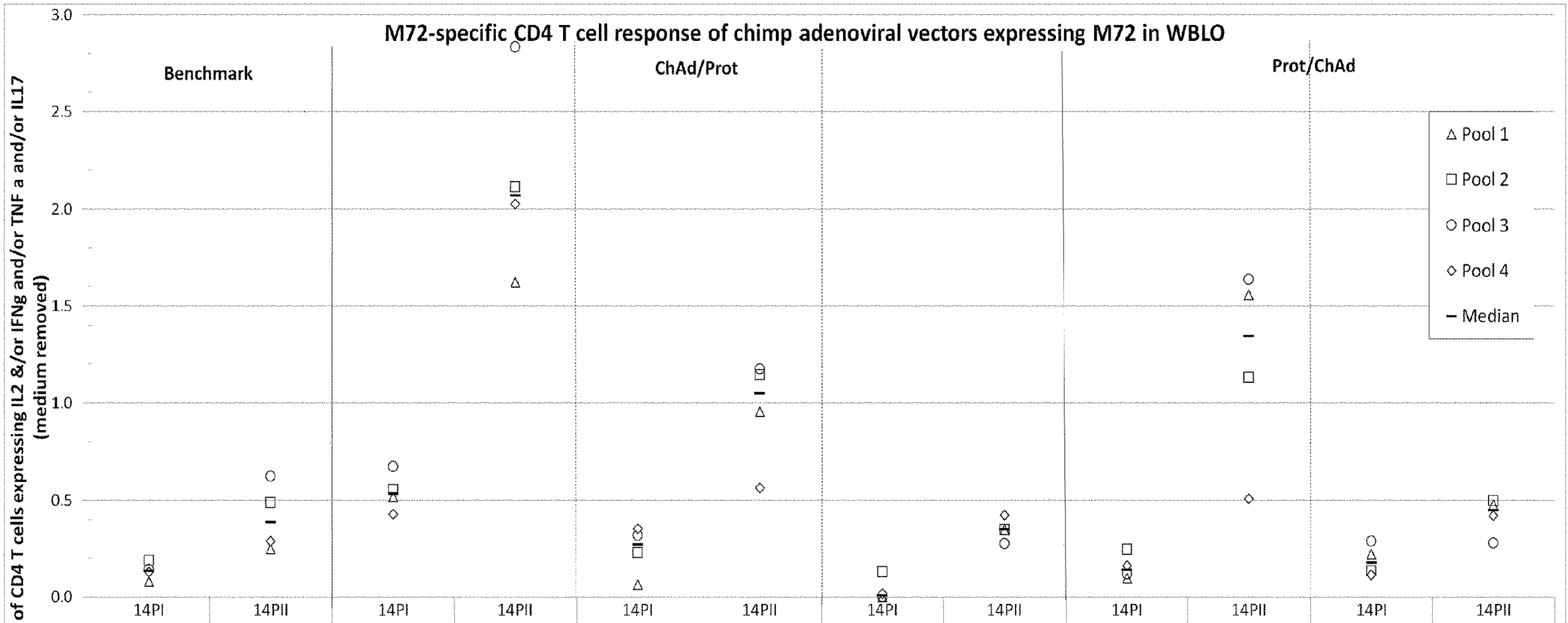
FIG. 5: Percentage of M72-specific CD4 T cell response from whole blood of CB6F1 mice expressing IFN-gamma and/or IL-2 and/or TNF-alpha cytokines at 14 PI and 14PII using heterologous (ChAd/Prot and Prot/ChAd) prime-boost vaccination strategies.

Across all groups, a specific CD4 T cell response was observed in whole blood with the peak response being below 3% (FIGS. 5 and 6). The highest levels of M72 specific CD4 T cells in whole blood were seen with the heterologous (Prot/ChAd or ChAd/Prot) vaccine strategies (FIG. 5). Priming the mice with M72-ChAd vectors and boosting with M72/AS01E induced higher level of M72 specific CD4 T cells than the opposite and in both cases the M72-ChAd3 was more potent than the M72-ChAd63 (FIG. 5). Prime-boost vaccination with M72-ChAd vectors, either homologous (M72-ChAd3/M72-ChAd3)+/−AS01E, or heterologous (M72-ChAd3/M72-ChAd63 or M72-ChAd63/M72-ChAd3), did not provide an added value in terms of the magnitude of the CD4 T cell response as compared to the M72/AS01E benchmark (FIG. 6). Combining both M72-ChAd3 and M72/AS01E slightly induced higher level of M72 specific CD4 T cells as compared to the M72/AS01E benchmark, but lower than heterologous (Prot/ChAd or ChAd/Prot) prime-boost vaccination. Co-administration induced similar M72 specific CD4 T cells levels than the combinations suggesting that physical proximity is not required (FIG. 6).

Figure 7:
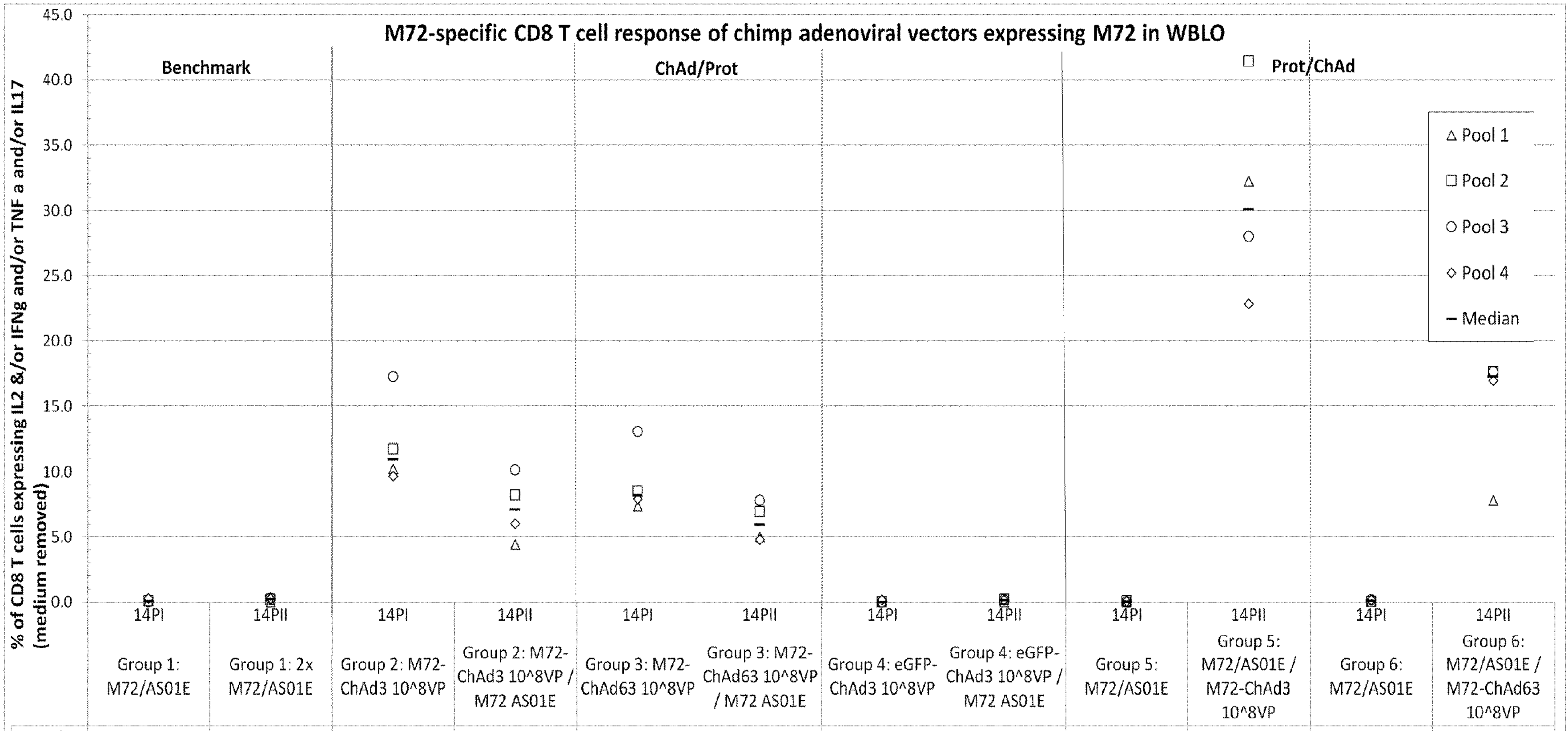
FIG. 7: Percentage of M72-specific CD8 T cell response from whole blood of CB6F1 mice expressing IFN-gamma and/or IL-2 and/or TNF-alpha cytokines at 14 PI and 14PII using heterologous (ChAd/Prot and Prot/ChAd) prime-boost vaccination strategies.

The level of M72 specific CD8 T cell was found to be highly increased in mice receiving a M72-ChAd vector either as a prime, boost or both. When the M72-ChAd vector was included during the priming, the level of M72 specific CD8 T cell did not further increase after boosting except when mice where primed with M72-ChAd63 and boosted with M72-ChAd3 (FIGS. 7 and 8). This also suggests that the M72-ChAd3 is more potent than M72-ChAd63. Boosting the M72/AS01E priming with M72-ChAd3 induced higher levels of CD8 T cells (Median=30%) than with M72-ChAd63 (Median=17%). The addition of M72-ChAd3 to the adjuvanted M72 protein in a combo also highly increased the level of M72 specific CD8 T cells (Median=13%) as compared to the current benchmark (Median=0.2%).

Figure 9:
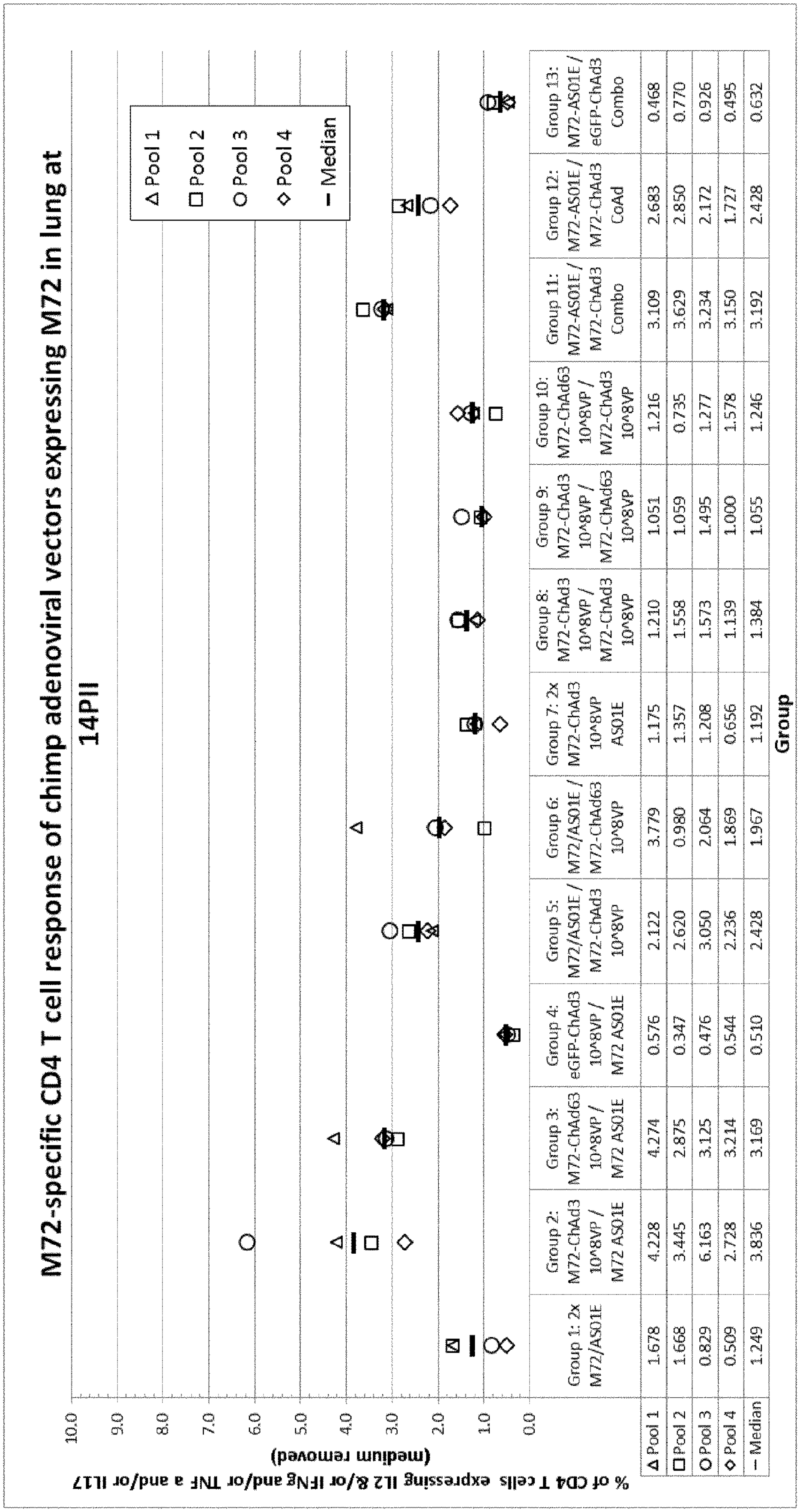
FIG. 9: Percentage of M72-specific CD4 T cell response from lung tissue of CB6F1 mice expressing IFN-gamma and/or IL-2 and/or TNF-alpha cytokines at 14PII.

The same general pattern of response was observed in the lung (FIG. 9) as compared to the whole blood (FIGS. 5 and 6) except for the admixed combination vaccine strategy. In the lungs, combination strategy induced a lower level of response than whole blood, whereby a comparable level of M72 specific CD4 T cells could be observed with the combination vaccine and with heterologous (Prot/ChAd or ChAd/Prot) prime-boost vaccination, all of which showed an increased CD4 T cell level as compared to the current benchmark.

Figure 10:
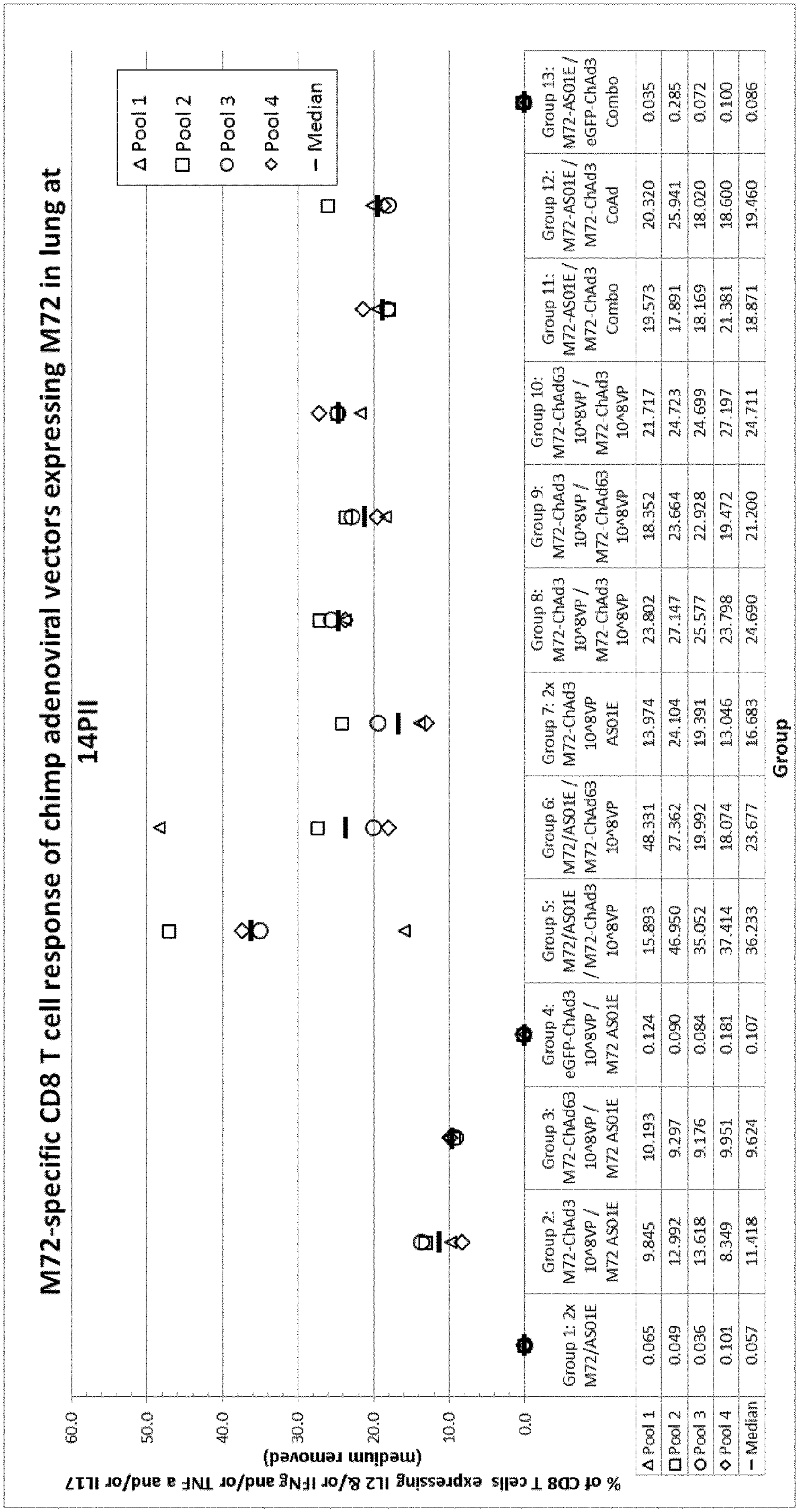
FIG. 10: Percentage of M72-specific CD8 T cell response from lung tissue of CB6F1 mice expressing IFN-gamma and/or IL-2 and/or TNF-alpha cytokines at 14PII.

The general pattern of the M72 specific CD8 T cell response in the lungs (FIG. 10) also reflected what was observed in the whole blood (FIGS. 7 and 8). Very low levels of specific CD8 T cell response was observed when mice received the benchmark M72/AS01E (FIG. 10) and addition of M72-ChAd vector highly improved the level of CD8 T cells. The highest level of M72 specific CD8 T cell was seen when mice where primed with M72/AS01E and boosted with M72-ChAd3 (Median=36%-FIG. 10).

B. Cytokine Profile of the M72-Specific CD4 & CD8 T Cells Responses

Figure 11:
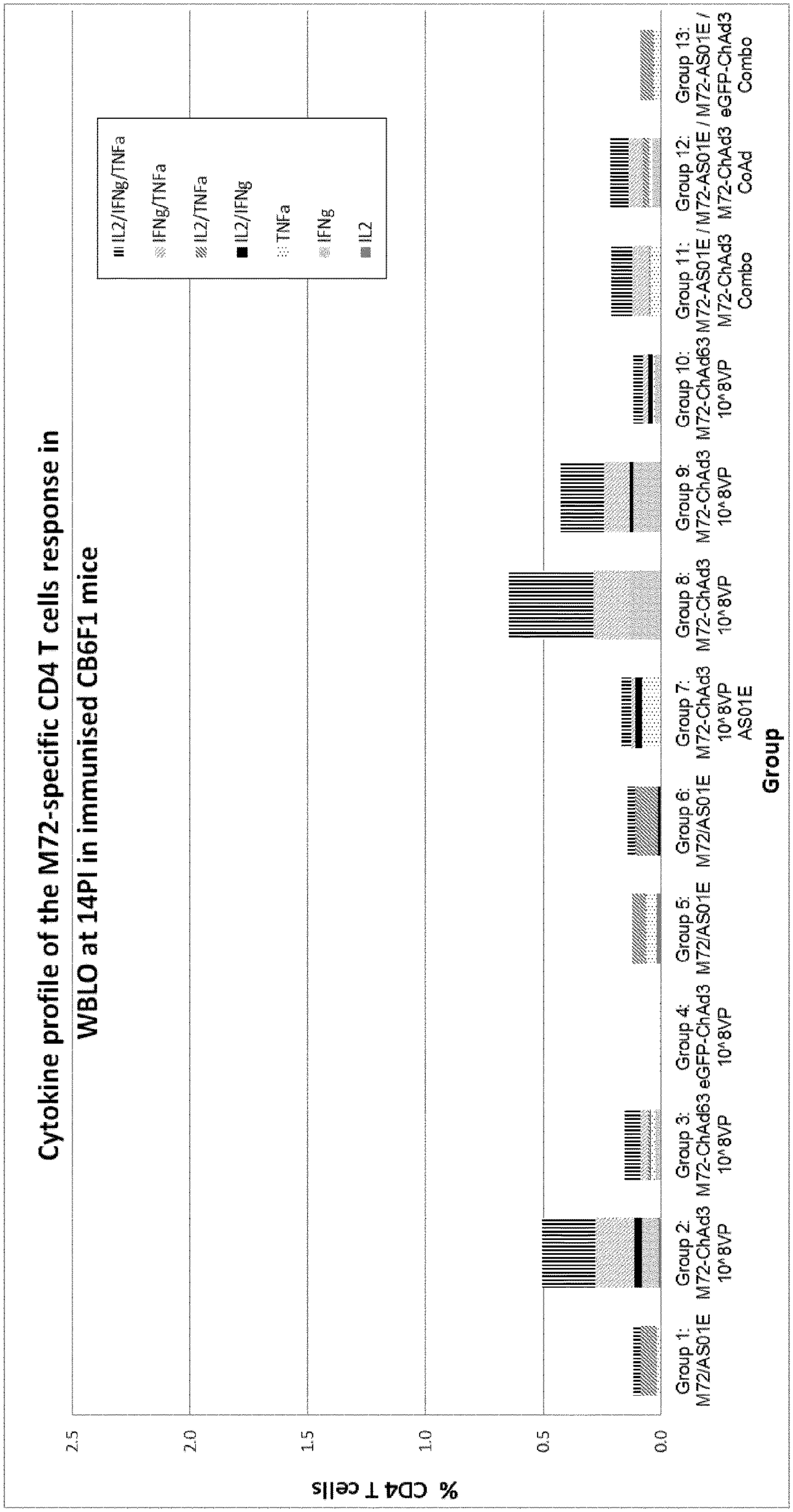
FIG. 11: Cytokine profile of the M72-specific CD4 T cells response in WBLO at 14P1 in immunised CB6F1 mice.

In groups that were primed with M72/AS01E, the M72-specific CD4+ T cell response mostly included double (IL-2/TNFa) secreting cells in the whole blood at 14P1 (FIGS. 11 and 12). In contrast, priming with a M72-ChAd vector induced a polyfunctional M72 specific CD4 T cell response with a majority of triple positive (IL2/IFNg/TNFa), and to a lower extend, double (IFNg/TNFa) and single (IFNg only) producing CD4 T cells (FIGS. 11 and 12). Combining both the protein and the ChAd vector induced low levels of triple (IL2/IFNg/TNFa), and double (IFNg/TNFa) producing CD4 T cells (FIGS. 11 and 12).

Figure 13:
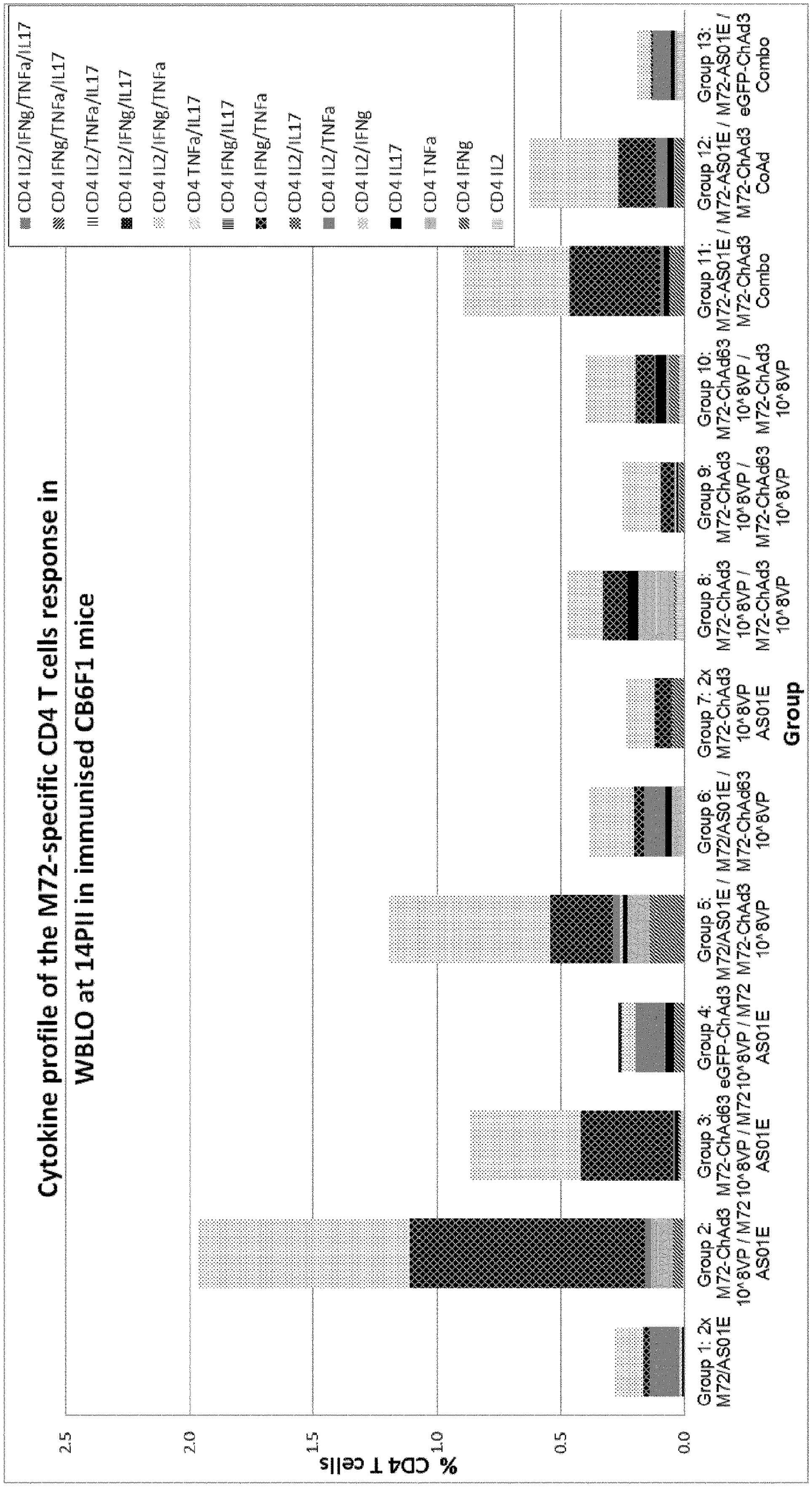
FIG. 13: Cytokine profile of the M72-specific CD4 T cells response in WBLO at 14PII in immunised CB6F1 mice.
Figure 15:
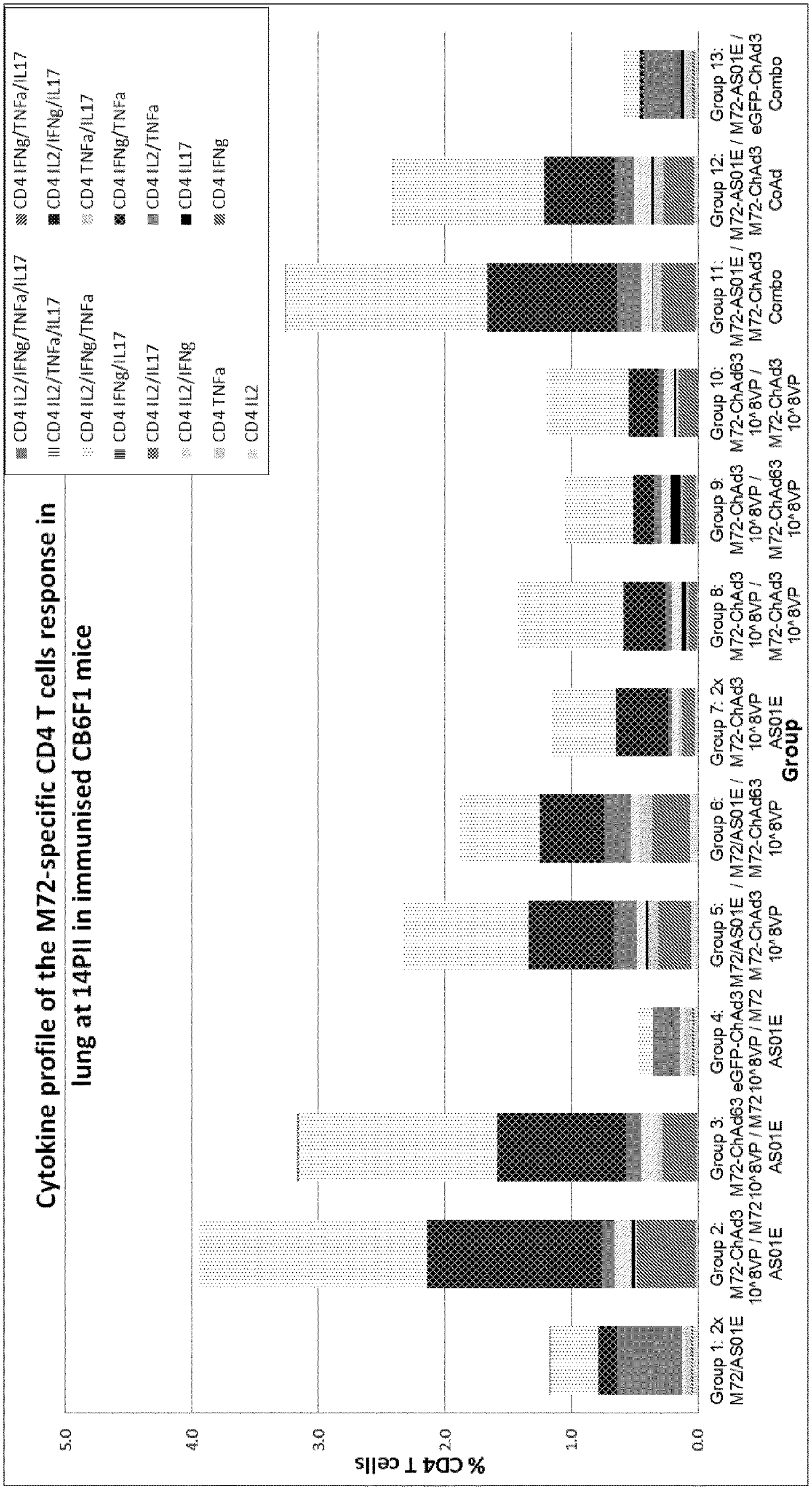
FIG. 15: Cytokine profile of the M72-specific CD4 T cells response in lung at 14PII in immunised CB6F1 mice.

A similar CD4+ T cell cytokine expression profiles was observed at 14PII in whole blood (FIGS. 13 and 14) and in the lungs (FIGS. 15 and 16) across all groups where vaccination strategy included a M72-ChAd vector. The M72-specific CD4+ T cell response included predominantly triple (IL2/IFNg/TNFa) and double (IFNg/TNFa) positive cells. In comparison to the benchmark, a reduced level of IL2/TNFa and increased level of IFNg/TNFa secreting cells were observed in the presence of a M72-ChAd vector. The IL-17 secretion was also assessed at 14dPII both in whole blood and in the lungs. However, the detected levels were extremely low across all conditions.

Figure 17:
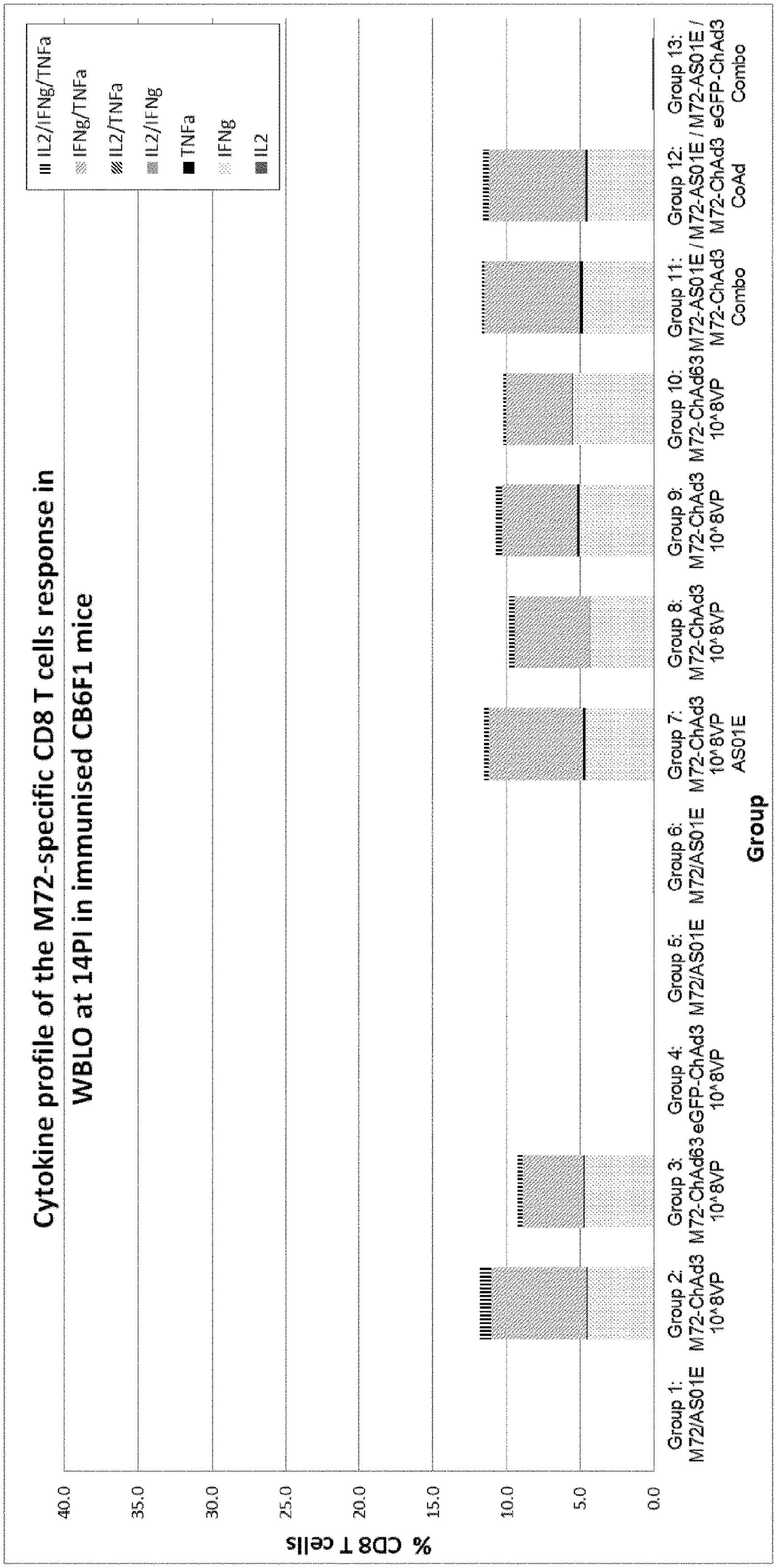
FIG. 17: Cytokine profile of the M72-specific CD8 T cells response in WBLO at 14P1 in immunised CB6F1 mice.
Figure 19:
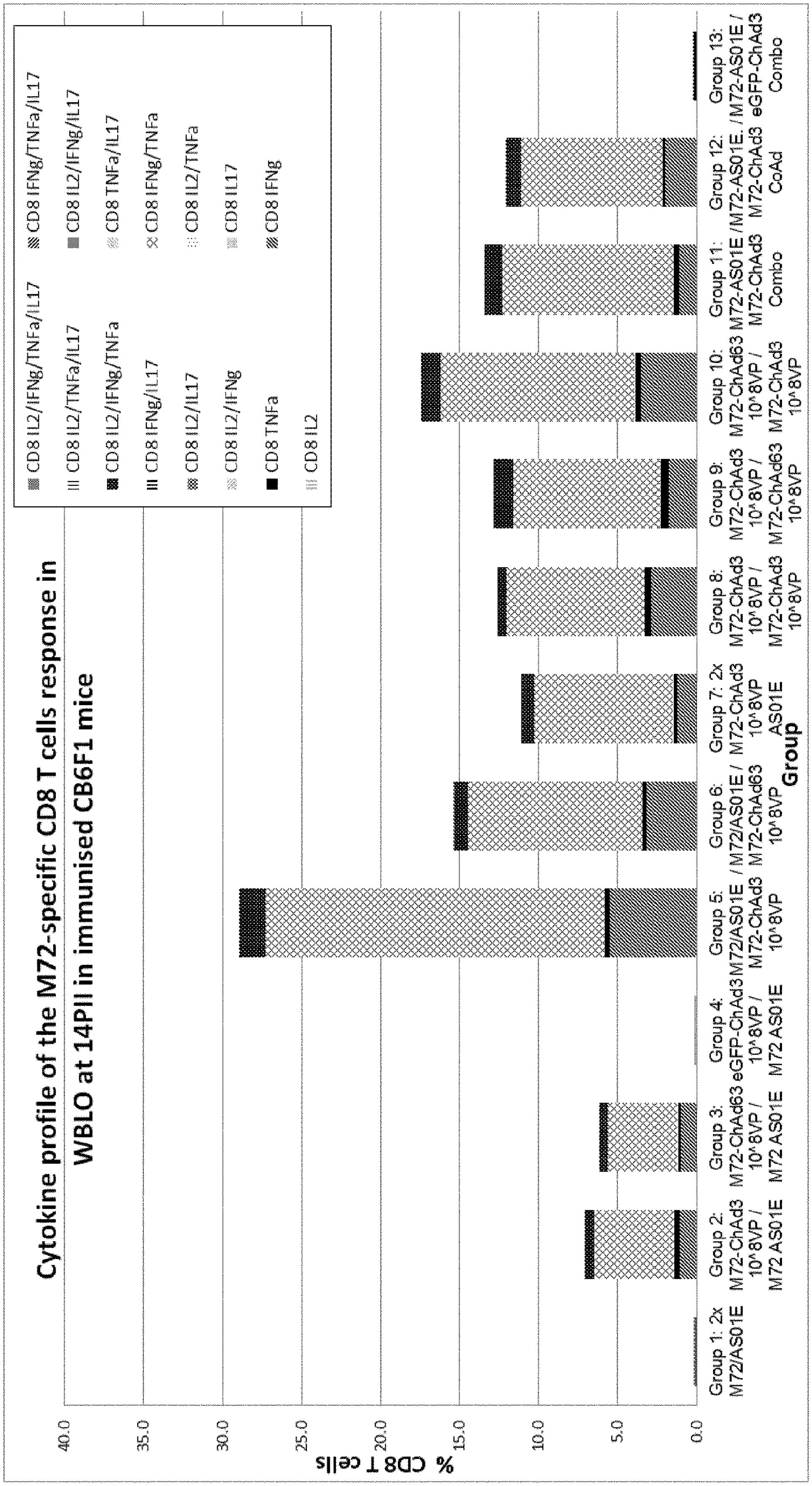
FIG. 19: Cytokine profile of the M72-specific CD8 T cells response in WBLO at 14PII in immunised CB6F1 mice.
Figure 21:
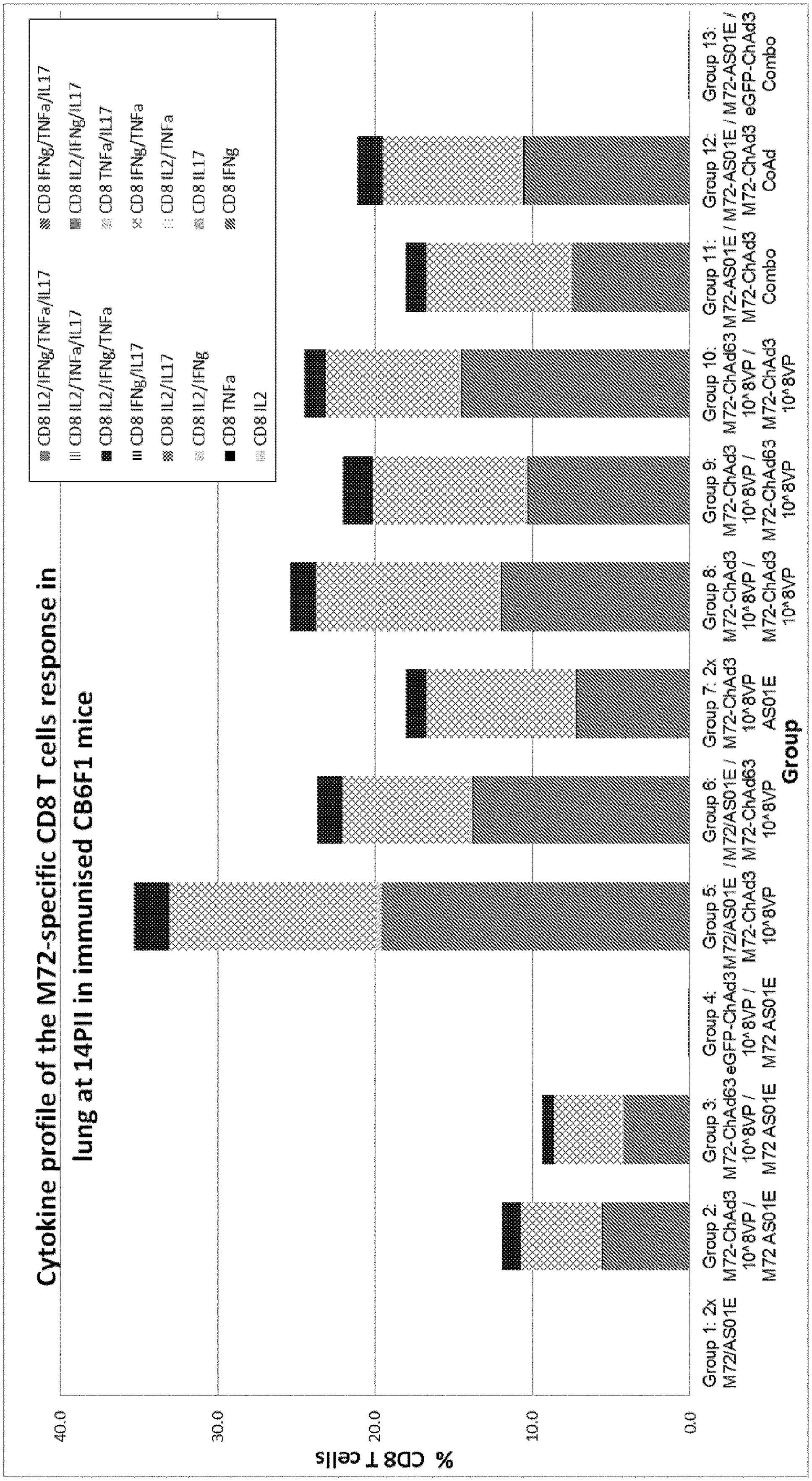
FIG. 21: Cytokine profile of the M72-specific CD8 T cells response in lung at 14PII in immunised CB6F1 mice.
Figure 24:
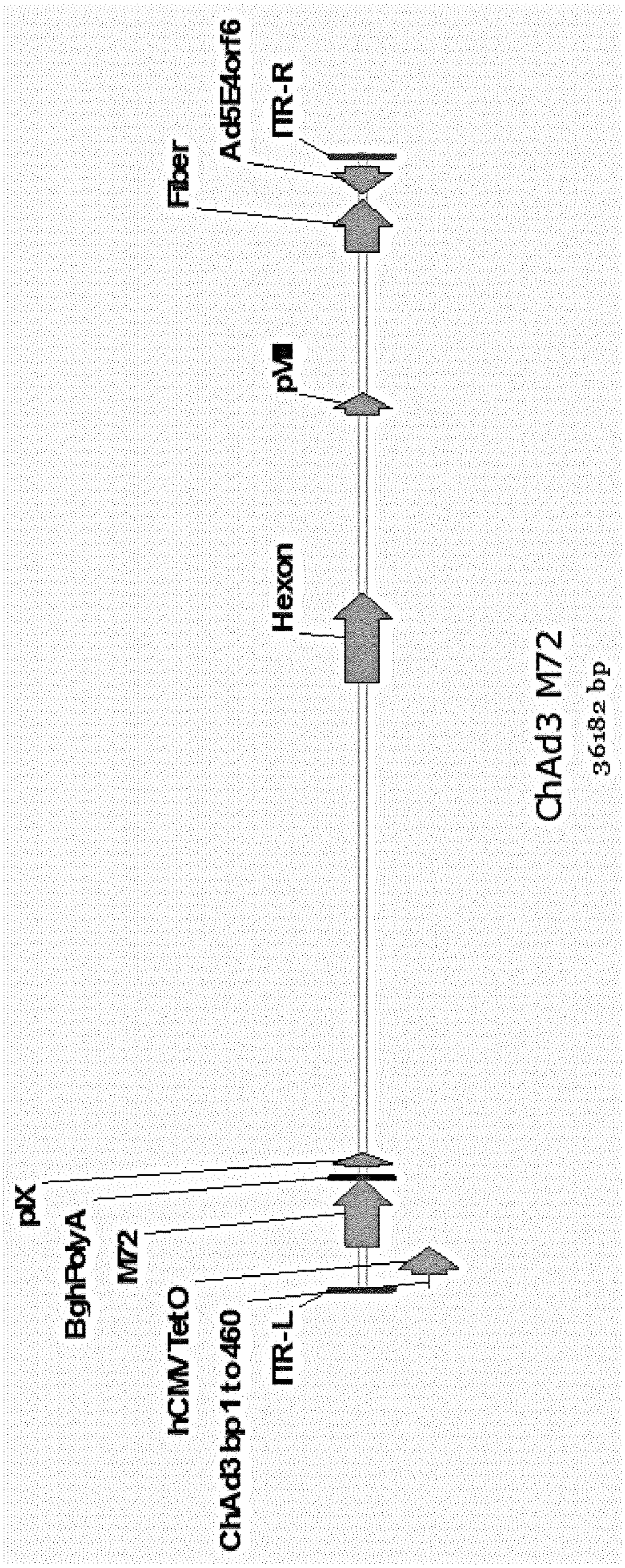
FIG. 24: Diagrammatic representation of M72-ChAd3 construct arrangement
Figure 25:
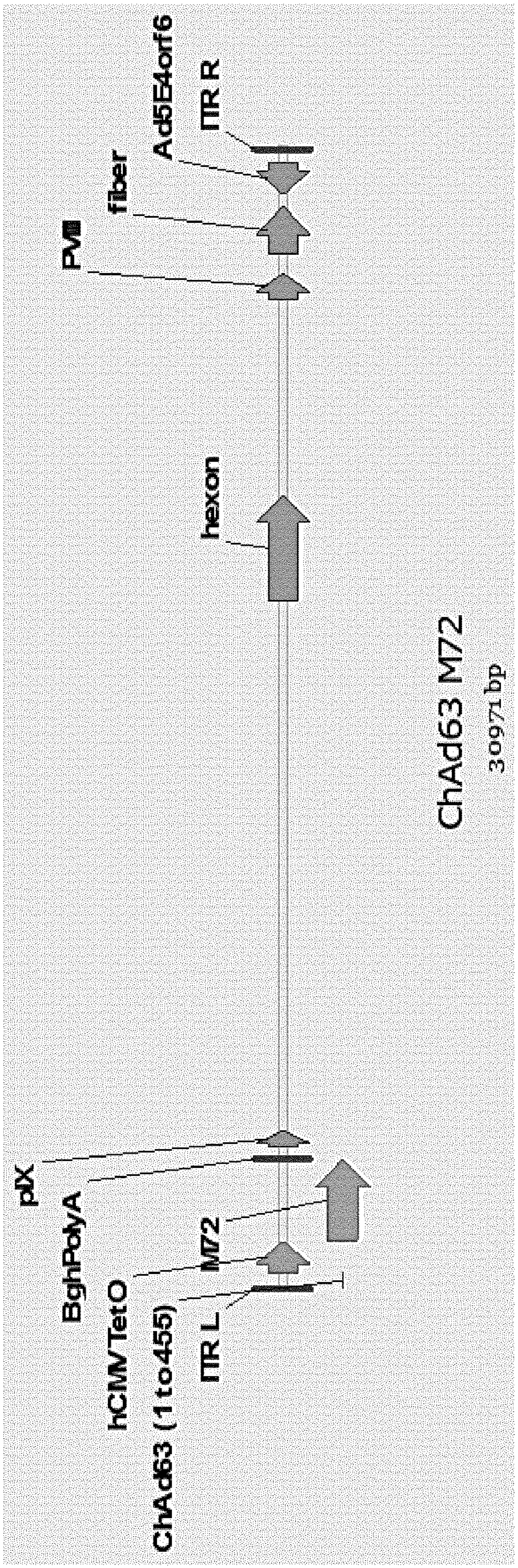
FIG. 25: Diagrammatic representation of M72-ChAd63 construct arrangement

Similar M72-specific CD8 T cell cytokine profiles were observed across all positive groups in whole blood at 14P1 (FIGS. 17 and 18), at 14PII (FIGS. 19 and 20) as well as in the lungs at 14PII (FIGS. 21 and 22). The M72-specific CD8 T cell responses were mostly composed of double (IFNg/TNFa) and single (IFNg only) producing CD8 T cells. Low levels of IL2/INFg/TNFa and very low levels of TNFa producing CD8+ T cell were also detected.

Taken together, the vaccination strategy did not notably impact the cytokine profile of M72 specific CD8 T cell.

Antibody Responses

A. Anti-M72 Ig Tot Serology

As shown in FIG. 23, the anti-M72 Ig Tot serology was highly variable across all groups and non-responders were observed with all vaccination strategies except in the combined approach given in co-administration. As for the T cell response, the M72-ChAd3 seems more potent than the M72-ChAd63 at inducing an immune response as the number of non-responding animals is increased when M72-ChAd63 is used.

Throughout the specification and the claims which follow, unless the context requires otherwise, the word ‘comprise’, and variations such as ‘comprises’ and ‘comprising’, will be understood to imply the inclusion of a stated integer, step, group of integers or group of steps but not to the exclusion of any other integer, step, group of integers or group of steps.

All documents referred to herein, including patents and patent applications, are incorporated by reference in their entirety.

The invention claimed is:

1. A method for inducing an immune response comprising a T cell response in a subject comprising:

administration of a chimpanzee adenovirus encoding a Rv1196 related antigen comprising SEQ ID NO: 1, followed by administration of a polypeptide Rv1196 related antigen to the subject, wherein the polypeptide Rv1196 related antigen is provided in a composition which also comprises an adjuvant.

2. The method of claim 1 wherein the adjuvant comprises a Toll Like Receptor (TLR) agonist and/or an immunologically active saponin.

3. The method of claim 1 wherein the adjuvant comprises 3-O-deacylated monophosphoryl lipid A (3D-MPL).

4. The method of claim 1 wherein the adjuvant comprises QS21.

5. The method of claim 1 wherein the chimpanzee adenovirus is a ChAd3.

6. The method of claim 1 wherein the chimpanzee adenovirus is a ChAd63.

7. The method of claim 1, wherein the Rv1196 related antigen comprises SEQ ID NO: 6.

8. The method of claim 1, wherein the composition in which the polypeptide Rv1196 related antigen provided is substantially free of a non-human simian adenovirus encoding the Rv1196 related antigen.

9. The method of claim 1, wherein the composition in which the polypeptide Rv1196 related antigen provided does not comprise a non-human simian adenovirus encoding the Rv1196 related antigen.

* * * * *

SEQUENCE LISTING

```
<160> NUMBER OF SEQ ID NOS: 22

<210> SEQ ID NO 1
<211> LENGTH: 391
```

<212> TYPE: PRT
<213> ORGANISM: Mycobacterium tuberculosis

<400> SEQUENCE: 1

```
Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Ala Gln Met Trp
            20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Val Ala Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Pro Val Ile Ala
            100                 105                 110

Glu Asn Arg Ala Glu Leu Met Ile Leu Ile Ala Thr Asn Leu Leu Gly
        115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Ala Val Glu Glu Ala Ser
            180                 185                 190

Asp Thr Ala Ala Ala Asn Gln Leu Met Asn Asn Val Pro Gln Ala Leu
        195                 200                 205

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
        275                 280                 285

Met Ser Ser Leu Gly Ser Ser Leu Gly Ser Ser Gly Leu Gly Gly Gly
    290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
            340                 345                 350

Gln Met Leu Gly Gly Leu Pro Val Gly Gln Met Gly Ala Arg Ala Gly
        355                 360                 365

Gly Gly Leu Ser Gly Val Leu Arg Val Pro Pro Arg Pro Tyr Val Met
    370                 375                 380

Pro His Ser Pro Ala Ala Gly
385                 390
```

<210> SEQ ID NO 2
<211> LENGTH: 391
<212> TYPE: PRT
<213> ORGANISM: Mycobacterium tuberculosis

<400> SEQUENCE: 2

```
Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Ala Lys Met Trp
            20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Val Ala Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Pro Val Ile Ala
            100                 105                 110

Glu Asn Arg Ala Glu Leu Met Ile Leu Ile Ala Thr Asn Leu Leu Gly
        115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Ala Val Glu Glu Ala Ser
            180                 185                 190

Asp Thr Ala Ala Ala Asn Gln Leu Met Asn Asn Val Pro Gln Ala Leu
        195                 200                 205

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
        275                 280                 285

Met Ser Ser Leu Gly Ser Ser Leu Gly Ser Ser Gly Leu Gly Gly Gly
    290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
            340                 345                 350

Gln Met Leu Gly Gly Leu Pro Val Gly Gln Met Gly Ala Arg Ala Gly
        355                 360                 365

Gly Gly Leu Ser Gly Val Leu Arg Val Pro Pro Arg Pro Tyr Val Met
```

```
    370                 375                 380

Pro His Ser Pro Ala Ala Gly
385                 390


<210> SEQ ID NO 3
<211> LENGTH: 323
<212> TYPE: PRT
<213> ORGANISM: Mycobacterium tuberculosis

<400> SEQUENCE: 3

Ala Pro Pro Ala Leu Ser Gln Asp Arg Phe Ala Asp Phe Pro Ala Leu
1               5                   10                  15

Pro Leu Asp Pro Ser Ala Met Val Ala Gln Val Gly Pro Gln Val Val
            20                  25                  30

Asn Ile Asn Thr Lys Leu Gly Tyr Asn Asn Ala Val Gly Ala Gly Thr
        35                  40                  45

Gly Ile Val Ile Asp Pro Asn Gly Val Val Leu Thr Asn Asn His Val
    50                  55                  60

Ile Ala Gly Ala Thr Asp Ile Asn Ala Phe Ser Val Gly Ser Gly Gln
65                  70                  75                  80

Thr Tyr Gly Val Asp Val Val Gly Tyr Asp Arg Thr Gln Asp Val Ala
                85                  90                  95

Val Leu Gln Leu Arg Gly Ala Gly Gly Leu Pro Ser Ala Ala Ile Gly
            100                 105                 110

Gly Gly Val Ala Val Gly Glu Pro Val Val Ala Met Gly Asn Ser Gly
        115                 120                 125

Gly Gln Gly Gly Thr Pro Arg Ala Val Pro Gly Arg Val Val Ala Leu
    130                 135                 140

Gly Gln Thr Val Gln Ala Ser Asp Ser Leu Thr Gly Ala Glu Glu Thr
145                 150                 155                 160

Leu Asn Gly Leu Ile Gln Phe Asp Ala Ala Ile Gln Pro Gly Asp Ser
                165                 170                 175

Gly Gly Pro Val Val Asn Gly Leu Gly Gln Val Val Gly Met Asn Thr
            180                 185                 190

Ala Ala Ser Asp Asn Phe Gln Leu Ser Gln Gly Gly Gln Gly Phe Ala
        195                 200                 205

Ile Pro Ile Gly Gln Ala Met Ala Ile Ala Gly Gln Ile Arg Ser Gly
    210                 215                 220

Gly Gly Ser Pro Thr Val His Ile Gly Pro Thr Ala Phe Leu Gly Leu
225                 230                 235                 240

Gly Val Val Asp Asn Asn Gly Asn Gly Ala Arg Val Gln Arg Val Val
                245                 250                 255

Gly Ser Ala Pro Ala Ala Ser Leu Gly Ile Ser Thr Gly Asp Val Ile
            260                 265                 270

Thr Ala Val Asp Gly Ala Pro Ile Asn Ser Ala Thr Ala Met Ala Asp
        275                 280                 285

Ala Leu Asn Gly His His Pro Gly Asp Val Ile Ser Val Thr Trp Gln
    290                 295                 300

Thr Lys Ser Gly Gly Thr Arg Thr Gly Asn Val Thr Leu Ala Glu Gly
305                 310                 315                 320

Pro Pro Ala


<210> SEQ ID NO 4
<211> LENGTH: 725
<212> TYPE: PRT
```

<213> ORGANISM: Artificial Sequence
<220> FEATURE:
<223> OTHER INFORMATION: M72 2-his
<220> FEATURE:
<221> NAME/KEY: MISC_FEATURE
<222> LOCATION: (1)..(1)
<223> OTHER INFORMATION: Start codon
<220> FEATURE:
<221> NAME/KEY: MISC_FEATURE
<222> LOCATION: (2)..(3)
<223> OTHER INFORMATION: His residues (improved expression in E. coli)
<220> FEATURE:
<221> NAME/KEY: MISC_FEATURE
<222> LOCATION: (4)..(135)
<223> OTHER INFORMATION: Rv0125 derived
<220> FEATURE:
<221> NAME/KEY: MISC_FEATURE
<222> LOCATION: (136)..(137)
<223> OTHER INFORMATION: Linkers
<220> FEATURE:
<221> NAME/KEY: MISC_FEATURE
<222> LOCATION: (138)..(528)
<223> OTHER INFORMATION: Rv1196 derived
<220> FEATURE:
<221> NAME/KEY: MISC_FEATURE
<222> LOCATION: (529)..(530)
<223> OTHER INFORMATION: Linkers
<220> FEATURE:
<221> NAME/KEY: MISC_FEATURE
<222> LOCATION: (529)..(530)
<223> OTHER INFORMATION: Linker
<220> FEATURE:
<221> NAME/KEY: MISC_FEATURE
<222> LOCATION: (531)..(725)
<223> OTHER INFORMATION: Rv0125 derived

<400> SEQUENCE: 4

```
Met His His Thr Ala Ala Ser Asp Asn Phe Gln Leu Ser Gln Gly Gly
1               5                   10                  15

Gln Gly Phe Ala Ile Pro Ile Gly Gln Ala Met Ala Ile Ala Gly Gln
            20                  25                  30

Ile Arg Ser Gly Gly Gly Ser Pro Thr Val His Ile Gly Pro Thr Ala
        35                  40                  45

Phe Leu Gly Leu Gly Val Val Asp Asn Asn Gly Asn Gly Ala Arg Val
    50                  55                  60

Gln Arg Val Val Gly Ser Ala Pro Ala Ala Ser Leu Gly Ile Ser Thr
65                  70                  75                  80

Gly Asp Val Ile Thr Ala Val Asp Gly Ala Pro Ile Asn Ser Ala Thr
                85                  90                  95

Ala Met Ala Asp Ala Leu Asn Gly His His Pro Gly Asp Val Ile Ser
            100                 105                 110

Val Thr Trp Gln Thr Lys Ser Gly Gly Thr Arg Thr Gly Asn Val Thr
        115                 120                 125

Leu Ala Glu Gly Pro Pro Ala Glu Phe Met Val Asp Phe Gly Ala Leu
    130                 135                 140

Pro Pro Glu Ile Asn Ser Ala Arg Met Tyr Ala Gly Pro Gly Ser Ala
145                 150                 155                 160

Ser Leu Val Ala Ala Ala Gln Met Trp Asp Ser Val Ala Ser Asp Leu
                165                 170                 175

Phe Ser Ala Ala Ser Ala Phe Gln Ser Val Val Trp Gly Leu Thr Val
            180                 185                 190

Gly Ser Trp Ile Gly Ser Ser Ala Gly Leu Met Val Ala Ala Ala Ser
        195                 200                 205

Pro Tyr Val Ala Trp Met Ser Val Thr Ala Gly Gln Ala Glu Leu Thr
    210                 215                 220
```

```
Ala Ala Gln Val Arg Val Ala Ala Ala Ala Tyr Glu Thr Ala Tyr Gly
225                 230                 235                 240

Leu Thr Val Pro Pro Pro Val Ile Ala Glu Asn Arg Ala Glu Leu Met
                245                 250                 255

Ile Leu Ile Ala Thr Asn Leu Leu Gly Gln Asn Thr Pro Ala Ile Ala
            260                 265                 270

Val Asn Glu Ala Glu Tyr Gly Glu Met Trp Ala Gln Asp Ala Ala Ala
        275                 280                 285

Met Phe Gly Tyr Ala Ala Ala Thr Ala Thr Ala Thr Ala Thr Leu Leu
    290                 295                 300

Pro Phe Glu Glu Ala Pro Glu Met Thr Ser Ala Gly Gly Leu Leu Glu
305                 310                 315                 320

Gln Ala Ala Ala Val Glu Glu Ala Ser Asp Thr Ala Ala Ala Asn Gln
                325                 330                 335

Leu Met Asn Asn Val Pro Gln Ala Leu Gln Gln Leu Ala Gln Pro Thr
            340                 345                 350

Gln Gly Thr Thr Pro Ser Ser Lys Leu Gly Gly Leu Trp Lys Thr Val
        355                 360                 365

Ser Pro His Arg Ser Pro Ile Ser Asn Met Val Ser Met Ala Asn Asn
    370                 375                 380

His Met Ser Met Thr Asn Ser Gly Val Ser Met Thr Asn Thr Leu Ser
385                 390                 395                 400

Ser Met Leu Lys Gly Phe Ala Pro Ala Ala Ala Ala Gln Ala Val Gln
                405                 410                 415

Thr Ala Ala Gln Asn Gly Val Arg Ala Met Ser Ser Leu Gly Ser Ser
            420                 425                 430

Leu Gly Ser Ser Gly Leu Gly Gly Gly Val Ala Ala Asn Leu Gly Arg
        435                 440                 445

Ala Ala Ser Val Gly Ser Leu Ser Val Pro Gln Ala Trp Ala Ala Ala
    450                 455                 460

Asn Gln Ala Val Thr Pro Ala Ala Arg Ala Leu Pro Leu Thr Ser Leu
465                 470                 475                 480

Thr Ser Ala Ala Glu Arg Gly Pro Gly Gln Met Leu Gly Gly Leu Pro
                485                 490                 495

Val Gly Gln Met Gly Ala Arg Ala Gly Gly Gly Leu Ser Gly Val Leu
            500                 505                 510

Arg Val Pro Pro Arg Pro Tyr Val Met Pro His Ser Pro Ala Ala Gly
        515                 520                 525

Asp Ile Ala Pro Pro Ala Leu Ser Gln Asp Arg Phe Ala Asp Phe Pro
    530                 535                 540

Ala Leu Pro Leu Asp Pro Ser Ala Met Val Ala Gln Val Gly Pro Gln
545                 550                 555                 560

Val Val Asn Ile Asn Thr Lys Leu Gly Tyr Asn Asn Ala Val Gly Ala
                565                 570                 575

Gly Thr Gly Ile Val Ile Asp Pro Asn Gly Val Val Leu Thr Asn Asn
            580                 585                 590

His Val Ile Ala Gly Ala Thr Asp Ile Asn Ala Phe Ser Val Gly Ser
        595                 600                 605

Gly Gln Thr Tyr Gly Val Asp Val Val Gly Tyr Asp Arg Thr Gln Asp
    610                 615                 620

Val Ala Val Leu Gln Leu Arg Gly Ala Gly Gly Leu Pro Ser Ala Ala
625                 630                 635                 640
```

-continued

```
Ile Gly Gly Gly Val Ala Val Gly Glu Pro Val Val Ala Met Gly Asn
                645                 650                 655

Ser Gly Gly Gln Gly Gly Thr Pro Arg Ala Val Pro Gly Arg Val Val
            660                 665                 670

Ala Leu Gly Gln Thr Val Gln Ala Ser Asp Ser Leu Thr Gly Ala Glu
        675                 680                 685

Glu Thr Leu Asn Gly Leu Ile Gln Phe Asp Ala Ala Ile Gln Pro Gly
    690                 695                 700

Asp Ala Gly Gly Pro Val Val Asn Gly Leu Gly Gln Val Val Gly Met
705                 710                 715                 720

Asn Thr Ala Ala Ser
                725
```

<210> SEQ ID NO 5
<211> LENGTH: 2178
<212> TYPE: DNA
<213> ORGANISM: Artificial Sequence
<220> FEATURE:
<223> OTHER INFORMATION: M72 2-his

<400> SEQUENCE: 5

```
atgcatcaca cggccgcgtc cgataacttc cagctgtccc agggtgggca gggattcgcc     60

attccgatcg ggcaggcgat ggcgatcgcg ggccagatcc gatcgggtgg ggggtcaccc    120

accgttcata tcgggcctac cgccttcctc ggcttgggtg ttgtcgacaa caacggcaac    180

ggcgcacgag tccaacgcgt ggtcgggagc gctccggcgg caagtctcgg catctccacc    240

ggcgacgtga tcaccgcggt cgacggcgct ccgatcaact cggccaccgc gatggcggac    300

gcgcttaacg ggcatcatcc cggtgacgtc atctcggtga cctggcaaac caagtcgggc    360

ggcacgcgta cagggaacgt gacattggcc gagggacccc cggccgaatt catggtggat    420

ttcggggcgt taccaccgga gatcaactcc gcgaggatgt acgccggccc gggttcggcc    480

tcgctggtgg ccgcggctca gatgtgggac agcgtggcga gtgacctgtt ttcggccgcg    540

tcggcgtttc agtcggtggt ctggggtctg acggtggggt cgtggatagg ttcgtcggcg    600

ggtctgatgg tggcggcggc ctcgccgtat gtggcgtgga tgagcgtcac cgcggggcag    660

gccgagctga ccgccgccca ggtccgggtt gctgcggcgg cctacgagac ggcgtatggg    720

ctgacggtgc ccccgccggt gatcgccgag aaccgtgctg aactgatgat tctgatagcg    780

accaacctct tggggcaaaa caccccggcg atcgcggtca acgaggccga atacggcgag    840

atgtgggccc aagacgccgc cgcgatgttt ggctacgccg cggcgacggc gacggcgacg    900

gcgacgttgc tgccgttcga ggaggcgccg gagatgacca gcgcgggtgg gctcctcgag    960

caggccgccg cggtcgagga ggcctccgac accgccgcgg cgaaccagtt gatgaacaat   1020

gtgccccagg cgctgcaaca gctggcccag cccacgcagg gcaccacgcc ttcttccaag   1080

ctgggtggcc tgtggaagac ggtctcgccg catcggtcgc cgatcagcaa catggtgtcg   1140

atggccaaca accacatgtc gatgaccaac tcgggtgtgt cgatgaccaa caccttgagc   1200

tcgatgttga agggctttgc tccggcggcg gccgcccagg ccgtgcaaac cgcggcgcaa   1260

aacggggtcc gggcgatgag ctcgctgggc agctcgctgg gttcttcggg tctgggcggt   1320

ggggtggccg ccaacttggg tcgggcggcc tcggtcggtt cgttgtcggt gccgcaggcc   1380

tgggccgcgg ccaaccaggc agtcaccccg gcggcgcggg cgctgccgct gaccagcctg   1440

accagcgccg cggaaagagg gcccgggcag atgctgggcg ggctgccggt ggggcagatg   1500

ggcgccaggg ccggtggtgg gctcagtggt gtgctgcgtg ttccgccgcg accctatgtg   1560
```

```
atgccgcatt ctccggcagc cggcgatatc gccccgccgg ccttgtcgca ggaccggttc   1620

gccgacttcc ccgcgctgcc cctcgacccg tccgcgatgg tcgcccaagt ggggccacag   1680

gtggtcaaca tcaacaccaa actgggctac aacaacgccg tgggcgccgg gaccggcatc   1740

gtcatcgatc ccaacggtgt cgtgctgacc aacaaccacg tgatcgcggg cgccaccgac   1800

atcaatgcgt tcagcgtcgg ctccggccaa acctacggcg tcgatgtggt cgggtatgac   1860

cgcacccagg atgtcgcggt gctgcagctg cgcggtgccg gtggcctgcc gtcggcggcg   1920

atcggtggcg gcgtcgcggt tggtgagccc gtcgtcgcga tgggcaacag cggtgggcag   1980

ggcggaacgc cccgtgcggt gcctggcagg gtggtcgcgc tcggccaaac cgtgcaggcg   2040

tcggattcgc tgaccggtgc cgaagagaca ttgaacgggt tgatccagtt cgatgccgcg   2100

atccagcccg gtgatgcggg cgggcccgtc gtcaacggcc taggacaggt ggtcggtatg   2160

aacacggccg cgtcctag                                                 2178
```

```
<210> SEQ ID NO 6
<211> LENGTH: 723
<212> TYPE: PRT
<213> ORGANISM: Artificial Sequence
<220> FEATURE:
<223> OTHER INFORMATION: M72 no his

<400> SEQUENCE: 6

Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
    130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ala Ser Pro Tyr
        195                 200                 205

Val Ala Trp Met Ser Val Thr Ala Gly Gln Ala Glu Leu Thr Ala Ala
    210                 215                 220

Gln Val Arg Val Ala Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
```

-continued

```
                245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
        275                 280                 285

Gly Tyr Ala Ala Ala Thr Ala Thr Ala Thr Ala Thr Leu Leu Pro Phe
    290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Ala Asn Gln Leu Met
                325                 330                 335

Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
        355                 360                 365

His Arg Ser Pro Ile Ser Asn Met Val Ser Met Ala Asn Asn His Met
    370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Ala Gln Ala Val Gln Thr Ala
                405                 410                 415

Ala Gln Asn Gly Val Arg Ala Met Ser Ser Leu Gly Ser Ser Leu Gly
            420                 425                 430

Ser Ser Gly Leu Gly Gly Gly Val Ala Ala Asn Leu Gly Arg Ala Ala
        435                 440                 445

Ser Val Gly Ser Leu Ser Val Pro Gln Ala Trp Ala Ala Ala Asn Gln
    450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
                485                 490                 495

Gln Met Gly Ala Arg Ala Gly Gly Gly Leu Ser Gly Val Leu Arg Val
            500                 505                 510

Pro Pro Arg Pro Tyr Val Met Pro His Ser Pro Ala Ala Gly Asp Ile
        515                 520                 525

Ala Pro Pro Ala Leu Ser Gln Asp Arg Phe Ala Asp Phe Pro Ala Leu
    530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
        595                 600                 605

Thr Tyr Gly Val Asp Val Val Gly Tyr Asp Arg Thr Gln Asp Val Ala
    610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
            660                 665                 670
```

Gly Gln Thr Val Gln Ala Ser Asp Ser Leu Thr Gly Ala Glu Glu Thr
675 680 685

Leu Asn Gly Leu Ile Gln Phe Asp Ala Ala Ile Gln Pro Gly Asp Ala
690 695 700

Gly Gly Pro Val Val Asn Gly Leu Gly Gln Val Val Gly Met Asn Thr
705 710 715 720

Ala Ala Ser

<210> SEQ ID NO 7
<211> LENGTH: 2172
<212> TYPE: DNA
<213> ORGANISM: Artificial Sequence
<220> FEATURE:
<223> OTHER INFORMATION: M72 no his

<400> SEQUENCE: 7
atgacggccg cgtccgataa cttccagctg tcccagggtg ggcagggatt cgccattccg 60
atcgggcagg cgatggcgat cgcgggccag atccgatcgg gtggggggtc acccaccgtt 120
catatcgggc ctaccgcctt cctcggcttg ggtgttgtcg acaacaacgg caacggcgca 180
cgagtccaac gcgtggtcgg gagcgctccg gcggcaagtc tcggcatctc caccggcgac 240
gtgatcaccg cggtcgacgg cgctccgatc aactcggcca ccgcgatggc ggacgcgctt 300
aacgggcatc atcccggtga cgtcatctcg gtgacctggc aaaccaagtc gggcggcacg 360
cgtacaggga acgtgacatt ggccgaggga cccccggccg aattcatggt ggatttcggg 420
gcgttaccac cggagatcaa ctccgcgagg atgtacgccg gcccgggttc ggcctcgctg 480
gtggccgcgg ctcagatgtg ggacagcgtg gcgagtgacc tgttttcggc cgcgtcggcg 540
tttcagtcgg tggtctgggg tctgacggtg gggtcgtgga taggttcgtc ggcgggtctg 600
atggtggcgg cggcctcgcc gtatgtggcg tggatgagcg tcaccgcggg gcaggccgag 660
ctgaccgccg cccaggtccg ggttgctgcg gcggcctacg agacggcgta tgggctgacg 720
gtgcccccgc cggtgatcgc cgagaaccgt gctgaactga tgattctgat agcgaccaac 780
ctcttggggc aaaacacccc ggcgatcgcg gtcaacgagg ccgaatacgg cgagatgtgg 840
gcccaagacg ccgccgcgat gtttggctac gccgcggcga cggcgacggc gacggcgacg 900
ttgctgccgt tcgaggaggc gccggagatg accagcgcgg gtgggctcct cgagcaggcc 960
gccgcggtcg aggaggcctc cgacaccgcc gcggcgaacc agttgatgaa caatgtgccc 1020
caggcgctgc aacagctggc ccagcccacg cagggcacca cgccttcttc caagctgggt 1080
ggcctgtgga agacggtctc gccgcatcgg tcgccgatca gcaacatggt gtcgatggcc 1140
aacaaccaca tgtcgatgac caactcgggt gtgtcgatga ccaacacctt gagctcgatg 1200
ttgaagggct ttgctccggc ggcggccgcc caggccgtgc aaaccgcggc gcaaaacggg 1260
gtccgggcga tgagctcgct gggcagctcg ctgggttctt cgggtctggg cggtggggtg 1320
gccgccaact tgggtcgggc ggcctcggtc ggttcgttgt cggtgccgca ggcctgggcc 1380
gcggccaacc aggcagtcac cccggcggcg cgggcgctgc cgctgaccag cctgaccagc 1440
gccgcggaaa gagggcccgg gcagatgctg ggcgggctgc cggtggggca gatgggcgcc 1500
agggccggtg gtgggctcag tggtgtgctg cgtgttccgc cgcgaccct a tgtgatgccg 1560 cattctccgg cagccggcga tatcgccccg ccggccttgt cgcaggaccg gttcgccgac 1620
ttccccgcgc tgcccctcga cccgtccgcg atggtcgccc aagtggggcc acaggtggtc 1680
aacatcaaca ccaaactggg ctacaacaac gccgtgggcg ccgggaccgg catcgtcatc 1740

-continued gatcccaacg gtgtcgtgct gaccaacaac cacgtgatcg cgggcgccac cgacatcaat 1800
gcgttcagcg tcggctccgg ccaaacctac ggcgtcgatg tggtcgggta tgaccgcacc 1860
caggatgtcg cggtgctgca gctgcgcggt gccggtggcc tgccgtcggc ggcgatcggt 1920
ggcggcgtcg cggttggtga gcccgtcgtc gcgatgggca acagcggtgg gcagggcgga 1980
acgccccgtg cggtgcctgg cagggtggtc gcgctcggcc aaaccgtgca ggcgtcggat 2040
tcgctgaccg gtgccgaaga gacattgaac gggttgatcc agttcgatgc cgcgatccag 2100
cccggtgatg cgggcgggcc cgtcgtcaac ggcctaggac aggtggtcgg tatgaacacg 2160
gccgcgtcct ag 2172

<210> SEQ ID NO 8
<211> LENGTH: 2172
<212> TYPE: DNA
<213> ORGANISM: Artificial Sequence
<220> FEATURE:
<223> OTHER INFORMATION: M72 no his human optimised

<400> SEQUENCE: 8
atgaccgccg ccagcgacaa cttccagctg tctcagggcg gccagggctt cgccatccct 60
atcggccaag ctatggccat tgctggacag atcagaagcg gcggaggcag ccctaccgtg 120
catatcggcc ctaccgcctt cctgggcctg ggcgtggtgg acaacaacgg caacggcgcc 180
agagtgcagc gggtggtcgg atctgcccct gccgcaagcc tgggcatcag caccggggat 240
gtgatcaccg ccgtggatgg cgcccctatc aacagcgcca cagccatggc cgacgccctg 300
aatggacacc accccggcga cgtgatcagc gtgacctggc agaccaagag cggaggcacc 360
agaaccggca acgtgacact ggccgaggga cctcccgccg agttcatggt ggatttcggc 420
gccctgcccc ccgagatcaa ctccgccagg atgtatgccg gccctggcag cgcctctctg 480
gtggccgctg ctcagatgtg ggacagcgtg gccagcgatc tgttcagcgc cgcctccgcc 540
ttccagtccg tggtctgggg cctgaccgtg ggcagctgga tcggaagcag tgccggcctg 600
atggtggctg ccgcctctcc ctacgtggcc tggatgtcag tcacagccgg ccaggccgaa 660
ctgactgccg ctcaagtgcg agtggctgct gctgcctatg agacagccta cggcctgaca 720
gtgcccccac ccgtgatcgc cgagaaccgg gccgagctga tgatcctgat cgccaccaac 780
ctgctgggcc agaacacccc cgccattgcc gtgaacgagg ccgagtacgg cgagatgtgg 840
gcccaggacg ccgctgccat gtttggctat gccgctgcta cagccaccgc cactgccacc 900
ctgctgccct tcgaagaggc ccccgagatg acctctgccg gcggactgct ggaacaggcc 960
gctgccgtgg aagaggccag cgacacagcc gccgctaacc agctgatgaa caacgtgccc 1020
caggccctgc agcagctggc acagcctaca cagggcacca ccccttctag caagctcggc 1080
ggcctgtgga aaaccgtgtc cccccaccgg tcccccatca gcaacatggt gtccatggcc 1140
aacaaccaca tgagcatgac caacagcggc gtgtccatga ccaataccct gagcagcatg 1200
ctgaagggct ttgccccagc cgctgccgct caggctgtgc agacagctgc tcagaatggc 1260
gtgcgggcca tgagcagcct gggcagttcc ctgggcagct ctggactggg agggggcgtg 1320
gccgccaatc tgggcagagc cgctagcgtg ggcagcctgt ctgtgcctca agcctgggct 1380
gctgccaatc aggccgtgac accagccgct agagccctgc ctctgaccag cctgacctct 1440
gctgccgaga ggggccctgg ccagatgctg ggaggactgc ctgtgggcca gatgggagcc 1500
agagccggcg gaggactgag cggcgtgctg agagtgcccc ccagacccta cgtgatgccc 1560

```
cactctcccg ccgctggcga tattgcccct cccgccctga gccaggacag attcgccgac   1620

ttccctgccc tgcccctgga tccttctgcc atggtggctc aagtgggacc ccaggtggtg   1680

aacatcaaca ccaagctggg ctacaacaac gccgtgggag ccggcaccgg catcgtgatc   1740

gaccccaatg gcgtggtgct gaccaacaat cacgtgatcg ctggcgccac cgacatcaac   1800

gccttcagcg tgggctccgg ccagacctac ggcgtggacg tggtcggata cgaccggacc   1860

caggatgtgg ccgtgctgca gctgagaggc gctggcggac tgccttctgc cgccattgga   1920

ggcggagtgg ccgtgggaga acctgtggtg gccatgggca atagcggcgg acagggcggc   1980

acacctagag ctgtgcctgg aagagtggtg gccctgggac agaccgtgca ggccagcgat   2040

agcctgacag gcgccgagga aaccctgaac ggcctgatcc agttcgacgc cgccatccag   2100

cctggggatg ctggcggacc tgtggtgaac ggactgggcc aggtggtcgg aatgaatacc   2160

gccgcctcct ga                                                       2172
```

<210> SEQ ID NO 9
<211> LENGTH: 37741
<212> TYPE: DNA
<213> ORGANISM: Pan troglodytes

<400> SEQUENCE: 9

```
catcatcaat aatatacctt attttggatt gaagccaata tgataatgag atgggcggcg     60

cgaggcgggg cgcggggcgg gaggcgggtt tgggggcggg ccggcgggcg gggcggtgtg    120

gcggaagtgg actttgtaag tgtggcggat gtgacttgct agtgccgggc gcggtaaaag    180

tgacgttttc cgtgcgcgac aacgcccccg ggaagtgaca tttttcccgc ggtttttacc    240

ggatgttgta gtgaatttgg gcgtaaccaa gtaagatttg gccattttcg cgggaaaact    300

gaaacgggga agtgaaatct gattaatttt gcgttagtca taccgcgtaa tatttgtcta    360

gggccgaggg actttggccg attacgtgga ggactcgccc aggtgttttt tgaggtgaat    420

ttccgcgttc cgggtcaaag tctccgtttt attattatag tcagctgacg cggagtgtat    480

ttataccctc tgatctcgtc aagaggccac tcttgagtgc cagcgagtag agttttctcc    540

tctgccgctc tccgctccgc tccgctcggc tctgacaccg gggaaaaaat gagacatttc    600

acctacgatg gcggtgtgct caccggccag ctggctgctg aggtcctgga caccctgatc    660

gaggaggtat tggccgataa ttatcctccc tcgactcctt ttgagccacc tacacttcac    720

gaactatacg atctggatgt ggtggggccc agcgatccga acgagcaggc ggtttccagt    780

ttttttccag agtccatgtt gttggccagc caggaggggg tcgaacttga gacccctcct    840

ccgatcgtgg attcccccga tccgccgcag ctgactaggc agcccgagcg ctgtgcggga    900

cctgagacta tgccccagct gctacctgag gtgatcgatc tcacctgtaa tgagtctggt    960

tttccaccca gcgaggatga ggacgaagag ggtgagcagt ttgtgttaga ttctgtggaa   1020

caacccgggc gaggatgcag gtcttgtcaa tatcaccgga aaaacacagg agactcccag   1080

attatgtgtt ctctgtgtta tatgaagatg acctgtatgt ttatttacag taagtttatc   1140

atcggtgggc aggtgggcta tagtgtgggt ggtggtcttt ggggggtttt ttaatatatg   1200

tcaggggtta tgctgaagac ttttttattg tgatttttaa aggtccagtg tctgagcccg   1260

agcaagaacc tgaaccggag cctgagcctt ctcgccccag gagaaagcct gtaatcttaa   1320

ctagacccag cgcaccggta gcgagaggcc tcagcagcgc ggagaccacc gactccggtg   1380

cttcctcatc acccccggag attcaccccc tggtgcccct atgtcccgtt aagcccgttg   1440

ccgtgagagt cagtgggcgg cggtctgctg tggagtgcat tgaggacttg ctttttgatt   1500
```

```
cacaggaacc tttggacttg agcttgaaac gccccaggca ttaaacctgg tcacctggac   1560
tgaatgagtt gacgcctatg tttgcttttg aatgacttaa tgtgtataga taataaagag   1620
tgagataatg ttttaattgc atggtgtgtt taacttgggc ggagtctgct gggtatataa   1680
gcttccctgg gctaaacttg gttacacttg acctcatgga ggcctgggag tgtttggaga   1740
actttgccgg agttcgtgcc ttgctggacg agagctctaa caatacctct tggtggtgga   1800
ggtatttgtg ggctctccc cagggcaagt tagtttgtag aatcaaggag gattacaagt    1860
gggaatttga agagcttttg aaatcctgtg gtgagctatt ggattctttg aatctaggcc   1920
accaggctct cttccaggag aaggtcatca ggactttgga tttttccaca ccggggcgca   1980
ttgcagccgc ggttgctttt ctagcttttt tgaaggatag atggagcgaa gagacccact   2040
tgagttcggg ctacgtcctg gattttctgg ccatgcaact gtggagagca tggatcagac   2100
acaagaacag gctgcaactg ttgtcttccg tccgcccgtt gctgattccg gcggaggagc   2160
aacaggccgg gtcagaggac cggcccgtc gggatccgga ggagagggca ccgaggccgg    2220
gcgagaggag cgcgctgaac ctgggaaccg ggctgagcgg ccatccacat cgggagtgaa   2280
tgtcgggcag gtggtggatc tttttccaga actgcggcgg attttgacta ttagggagga   2340
tgggcaattt gttaagggtc ttaagaggga gagggggct tctgagcata acgaggaggc    2400
cagtaattta gcttttagct tgatgaccag acaccgtcca gagtgcatca cttttcagca   2460
gattaaggac aattgtgcca atgagttgga tctgttgggt cagaagtata gcatagagca   2520
gctgaccact tactggctgc agccgggtga tgatctggag gaagctatta gggtgtatgc   2580
taaggtggcc ctgcggcccg attgcaagta caagctcaag ggctggtga atatcaggaa    2640
ttgttgctac atttctggca acggggcgga ggtggagata gagaccgaag acagggtggc   2700
tttcagatgc agcatgatga atatgtggcc gggggtgctg ggcatggacg gggtggtgat   2760
tatgaatgtg aggttcacgg ggcccaactt taacggcacg gtgtttttgg ggaacaccaa   2820
cctggtcctg cacggggtga gcttctatgg gtttaacaac acctgtgtgg aggcctggac   2880
cgatgtgaag gtccgcggtt gcgcctttta tggatgttgg aaggccatag tgagccgccc   2940
taagagcagg agttccatta agaaatgctt gtttgagagg tgcaccttgg ggatcctggc   3000
cgagggcaac tgcagggtgc gccacaatgt ggcctccgag tgcggttgct tcatgctagt   3060
caagagcgtg gcggtaatca agcataatat ggtgtgcggc aacagcgagg acaaggcctc   3120
acagatgctg acctgcacgg atggcaactg ccacttgctg aagaccatcc atgtaaccag   3180
ccacagccgg aaggcctggc ccgtgttcga gcacaacttg ctgacccgct gctccttgca   3240
tctgggcaac aggcgggggg tgttcctgcc ctatcaatgc aactttagtc acaccaagat   3300
cttgctagag cccgagagca tgtccaaggt gaacttgaac ggggtgtttg acatgaccat   3360
gaagatctgg aaggtgctga ggtacgacga gaccaggtcc cggtgcagac cctgcgagtg   3420
cgggggcaag catatgagga accagcccgt gatgctggat gtgaccgagg agctgaggac   3480
agaccacttg gttctggcct gcaccagggc cgagtttggt tctagcgatg aagacacaga   3540
ttgaggtggg tgagtgggcg tggcctgggg tggtcatgaa aatatataag ttgggggtct   3600
tagggtctct ttatttgtgt tgcagagacc gccggagcca tgagcgggag cagcagcagc   3660
agcagtagca gcagcgcctt ggatggcagc atcgtgagcc cttatttgac gacgcggatg   3720
ccccactggg ccggggtgcg tcagaatgtg atgggctcca gcatcgacgg ccgacccgtc   3780
ctgcccgcaa attccgccac gctgacctat gcgaccgtcg cggggacgcc gttggacgcc   3840
```

-continued

```
accgccgccg ccgccgccac cgcagccgcc tcggccgtgc gcagcctggc cacggacttt   3900
gcattcctgg gaccactggc gacaggggct acttctcggg ccgctgctgc cgccgttcgc   3960
gatgacaagc tgaccgccct gctggcgcag ttggatgcgc ttactcggga actgggtgac   4020
ctttctcagc aggtcatggc cctgcgccag caggtctcct ccctgcaagc tggcgggaat   4080
gcttctccca caaatgccgt ttaagataaa taaaaccaga ctctgtttgg attaaagaaa   4140
agtagcaagt gcattgctct ctttatttca taattttccg cgcgcgatag gccctagacc   4200
agcgttctcg gtcgttgagg gtgcggtgta tcttctccag gacgtggtag aggtggctct   4260
ggacgttgag atacatgggc atgagcccgt cccgggggtg gaggtagcac cactgcagag   4320
cttcatgctc cggggtggtg ttgtagatga tccagtcgta gcaggagcgc tgggcatggt   4380
gcctaaaaat gtccttcagc agcaggccga tggccagggg gaggcccttg gtgtaagtgt   4440
ttacaaaacg gttaagttgg gaagggtgca ttcggggaga gatgatgtgc atcttggact   4500
gtatttttag attggcgatg tttccgccca gatcccttct gggattcatg ttgtgcagga   4560
ccaccagtac agtgtatccg gtgcacttgg ggaatttgtc atgcagctta gagggaaaag   4620
cgtggaagaa cttggagacg cccttgtggc ctcccagatt ttccatgcat tcgtccatga   4680
tgatggcaat gggcccgcgg gaggcagctt gggcaaagat atttctgggg tcgctgacgt   4740
cgtagttgtg ttccagggtg aggtcgtcat aggccatttt tacaaagcgc gggcggaggg   4800
tgcccgactg gggggatgatg gtcccctctg gccctggggc gtagttgccc tcgcagatct   4860
gcatttccca ggccttaatc tcggaggggg gaatcatatc cacctgcggg gcgatgaaga   4920
aaacggtttc cggagccggg gagattaact gggatgagag caggtttcta agcagctgtg   4980
attttccaca accggtgggc ccataaataa cacctataac cggttgcagc tggtagttta   5040
gagagctgca gctgccgtcg tcccggagga ggggggccac ctcgttgagc atgtccctga   5100
cgcgcatgtt ctccccgacc agatccgcca gaaggcgctc gccgcccagg gacagcagct   5160
cttgcaagga agcaaagttt ttcagcggct tgaggccgtc cgccgtgggc atgtttttca   5220
gggtctggct cagcagctcc aggcggtccc agagctcggt gacgtgctct acggcatctc   5280
tatccagcat atctcctcgt ttcgcgggtt ggggcgactt tcgctgtagg gcaccaagcg   5340
gtggtcgtcc agcggggcca aagtcatgtc cttccatggg cgcagggtcc tcgtcagggt   5400
ggtctgggtc acggtgaagg ggtgcgctcc gggctgagcg cttgccaagg tgcgcttgag   5460
gctggttctg ctggtgctga agcgctgccg gtcttcgccc tgcgcgtcgg ccaggtagca   5520
tttgaccatg gtgtcatagt ccagcccctc cgcggcgtgt cccttggcgc gcagcttgcc   5580
cttggaggtg gcgccgcacg aggggcagag caggctcttg agcgcgtaga gcttgggggc   5640
gaggaagacc gattcggggg agtaggcgtc cgcgccgcag accccgcaca cggtctcgca   5700
ctccaccagc caggtgagct cggggcgcgc cgggtcaaaa accaggtttc ccccatgctt   5760
tttgatgcgt ttcttacctc gggtctccat gaggtggtgt ccccgctcgg tgacgaagag   5820
gctgtccgtg tctccgtaga ccgacttgag ggtcttttc tccagggggg tccctcggtc   5880
ttcctcgtag aggaactcgg accactctga gacgaaggcc cgcgtccagg ccaggacgaa   5940
ggaggctatg tgggaggggt agcggtcgtt gtccactagg gggtccacct tctccaaggt   6000
gtgaagacac atgtcgcctt cctcggcgtc caggaaggtg attggcttgt aggtgtaggc   6060
cacgtgaccg gggggttcctg acgggggggt ataaaagggg gtgggggcgc gctcgtcgtc   6120
actctcttcc gcatcgctgt ctgcgagggc cagctgctgg ggtgagtatt ccctctcgaa   6180
ggcgggcatg acctccgcgc tgaggttgtc agtttccaaa aacgaggagg atttgatgtt   6240
```

cacctgtccc gaggtgatac ctttgagggt acccgcgtcc atctggtcag aaaacacgat 6300
ctttttattg tccagcttgg tggcgaacga cccgtagagg gcgttggaga gcagcttggc 6360
gatggagcgc agggtctggt tcttgtccct gtcggcgcgc tccttggccg cgatgttgag 6420
ctgcacgtac tcgcgcgcga cgcagcgcca ctcggggaag acggtggtgc gctcgtcggg 6480
caccaggcgc acgcgccagc cgcggttgtg cagggtgacc aggtccacgc tggtggcgac 6540
ctcgccgcgc aggcgctcgt tggtccagca gagacggccg cccttgcgcg agcagaaggg 6600
gggcaggggg tcgagctggg tctcgtccgg ggggtccgcg tccacggtga aaaccccggg 6660
gcgcaggcgc gcgtcgaagt agtctatctt gcaaccttgc atgtccagcg cctgctgcca 6720
gtcgcgggcg gcgagcgcgc gctcgtaggg gttgagcggc gggccccagg gcatggggtg 6780
ggtgagtgcg gaggcgtaca tgccgcagat gtcatagacg tagaggggct cccgcaggac 6840
cccgatgtag gtggggtagc agcggccgcc gcggatgctg gcgcgcacgt agtcatacag 6900
ctcgtgcgag ggggcgagga ggtcggggcc caggttggtg cgggcggggc gctccgcgcg 6960
gaagacgatc tgcctgaaga tggcatgcga gttggaagag atggtggggc gctggaagac 7020
gttgaagctg gcgtcctgca ggccgacggc gtcgcgcacg aaggaggcgt aggagtcgcg 7080
cagcttgtgt accagctcgg cggtgacctg cacgtcgagc gcgcagtagt cgagggtctc 7140
gcggatgatg tcatatttag cctgcccctt ctttttccac agctcgcggt tgaggacaaa 7200
ctcttcgcgg tctttccagt actcttggat cgggaaaccg tccggttccg aacggtaaga 7260
gcctagcatg tagaactggt tgacggcctg gtaggcgcag cagcccttct ccacggggag 7320
ggcgtaggcc tgcgcggcct tgcggagcga ggtgtgggtc agggcgaagg tgtccctgac 7380
catgactttg aggtactggt gcttgaagtc ggagtcgtcg cagccgcccc gctcccagag 7440
cgagaagtcg gtgcgcttct tggagcgggg gttgggcaga gcgaaggtga catcgttgaa 7500
gaggattttg cccgcgcggg gcatgaagtt gcgggtgatg cggaagggcc ccggcacttc 7560
agagcggttg ttgatgacct gggcggcgag cacgatctcg tcgaagccgt tgatgttgtg 7620
gcccacgatg tagagttcca ggaagcgggg ccggcccttt acggtgggca gcttctttag 7680
ctcttcgtag gtgagctcct cgggcgaggc gaggccgtgc tcggccaggg cccagtccgc 7740
gaggtgcggg ttgtctctga ggaaggactc ccagaggtcg cgggccagga gggtctgcag 7800
gcggtccctg aaggtcctga actggcggcc cacggccatt ttttcggggg tgatgcagta 7860
gaaggtgagg gggtcttgct gccagcggtc ccagtcgagc tgcagggcga ggtcgcgcgc 7920
ggcggtgacc aggcgctcgt cgcccccgaa tttcatgacc agcatgaagg gcacgagctg 7980
ctttccgaag gcccccatcc aagtgtaggt ctctacatcg taggtgacaa agaggcgctc 8040
cgtgcgagga tgcgagccga tcgggaagaa ctggatctcc cgccaccagt tggaggagtg 8100
gctgttgatg tggtggaagt agaagtcccg tcgccgggcc gaacactcgt gctggctttt 8160
gtaaaagcga gcgcagtact ggcagcgctg cacgggctgt acctcctgca cgagatgcac 8220
ctttcgcccg cgcacgagga agccgagggg aaatctgagc cccccgcctg gctcgcggca 8280
tggctggtgc tcttctactt tggatgcgtg tccgtctccg tctggctcct cgaggggtgt 8340
tacggtggag cggaccacca cgccgcgcga gccgcaggtc cagatatcgg cgcgcggcgg 8400
tcggagtttg atgacgacat cgcgcagctg ggagctgtcc atggtctgga gctcccgcgg 8460
cggcggcagg tcagccggga gttcttgcag gttcacctcg cagagtcggg ccagggcgcg 8520
gggcaggtct aggtggtacc tgatctctag gggcgtgttg gtggcggcgt cgatggcttg 8580

```
caggagcccg catccccggg gggcgacgac ggtgccccgc ggggtggtgg tggtggtggt   8640
ggtggtggtg gtggcggtgc agctcagaag cggtgccgcg ggcgggcccc cggaggtagg   8700
gggggctccg gtcccgccgg caggggcggc agcggcacgt cggcgtggag cgcgggcagg   8760
agttggtgct gtgcccggag gttgctggcg aaggcgacga cgcggcggtt gatctcctgg   8820
atctggcgcc tctgcgtgaa gacgacgggc ccggtgagct tgaacctgaa agagagttcg   8880
acagaatcaa tctcggtgtc attgaccgcg gcctggcgca ggatctcctg cacgtctccc   8940
gagttgtctt ggtaggcgat ctcggccatg aactgctcga tctcttcctc ctggaggtct   9000
ccgcgtccgg cgcgttccac ggtggccgcc aggtcgttgg agatgcgccc catgagctgc   9060
gagaaggcgt tgagtccgcc ctcgttccag actcggctgt agaccacgcc cccctggtca   9120
tcgcgggcgc gcatgaccac ctgcgcgagg ttgagctcca cgtgccgcgc gaagacggcg   9180
tagttgcgca gacgctggaa gaggtagttg agggtggtgg cggtgtgctc ggccacgaag   9240
aagttcatga cccagcggcg caacgtggat tcgttgatgt cccccaaggc ctccagccgt   9300
tccatggcct cgtagaagtc cacggcgaag ttgaaaaact gggagttgcg cgccgacacg   9360
gtcaactcct cctccagaag acggatgagc tcggcgacgg tgtcgcgcac ctcgcgctcg   9420
aaggctatgg ggatctcttc ctccgctagc atcaccacct cctcctcttc ctcctcttct   9480
ggcacttcca tgatggcttc ctcctcttcg gggggcggcg gcggcggcgg tgggggaggg   9540
ggcgctctgc gccggcggcg gcgcaccggg aggcggtcca cgaagcgcgc gatcatctcc   9600
ccgcggcggc ggcgcatggt ctcggtgacg gcgcggccgt tctcccgggg gcgcagttgg   9660
aagacgccgc cggacatctg gtgctggggc gggtggccgt gaggcagcga aacggcgctg   9720
acgatgcatc tcaacaattg ctgcgtaggt acgccgccga gggacctgag ggagtccata   9780
tccaccggat ccgaaaacct ttcgaggaag gcgtctaacc agtcgcagtc gcaaggtagg   9840
ctgagcaccg tggcgggcgg cggggggtgg ggggagtgtc tggcggaggt gctgctgatg   9900
atgtaattga agtaggcgga cttgacacgg cggatggtcg acaggagcac catgtccttg   9960
ggtccggcct gctggatgcg gaggcggtcg gctatgcccc aggcttcgtt ctggcatcgg  10020
cgcaggtcct tgtagtagtc ttgcatgagc ctttccaccg gcacctcttc tccttcctct  10080
tctgcttctt ccatgtctgc ttcggccctg gggcggcgcc gcgccccct gccccccatg  10140
cgcgtgaccc cgaacccccct gagcggttgg agcagggcca ggtcggcgac gacgcgctcg  10200
gccaggatgg cctgctgcac ctgcgtgagg gtggtttgga agtcatccaa gtccacgaag  10260
cggtggtagg cgcccgtgtt gatggtgtag gtgcagttgg ccatgacgga ccagttgacg  10320
gtctggtggc ccggttgcga catctcggtg tacctgagtc gcgagtaggc gcgggagtcg  10380
aagacgtagt cgttgcaagt ccgcaccagg tactggtagc ccaccaggaa gtgcggcggc  10440
ggctggcggt agaggggcca gcgcagggtg gcgggggctc cgggggccag gtcttccagc  10500
atgaggcggt ggtaggcgta gatgtacctg gacatccagg tgatacccgc ggcggtggtg  10560
gaggcgcgcg ggaagtcgcg cacccggttc cagatgttgc gcaggggcag aaagtgctcc  10620
atggtaggcg tgctctgtcc agtcagacgc gcgcagtcgt tgatactcta gaccagggaa  10680
aacgaaagcc ggtcagcggg cactcttccg tggtctggtg aatagatcgc aagggtatca  10740
tggcggaggg cctcggttcg agccccgggt ccgggccgga cggtccgcca tgatccacgc  10800
ggttaccgcc cgcgtgtcga acccaggtgt gcgacgtcag acaacggtgg agtgttcctt  10860
ttggcgtttt tctggccggg cgccggcgtc gcgtaagaga ctaagccgcg aaagcgaaag  10920
cagtaagtgg ctcgctcccc gtagccggag ggatccttgc taagggttgc gttgcggcga  10980
```

accccggttc gaatcccgta ctcgggccgg ccggacccgc ggctaaggtg ttggattggc 11040
ctccccctcg tataaagacc ccgcttgcgg attgactccg gacacgggga cgagcccctt 11100
ttatttttgc tttccccaga tgcatccggt gctgcggcag atgcgccccc cgccccagca 11160
gcagcaacaa caccagcaag agcggcagca acagcagcgg gagtcatgca gggccccctc 11220
acccaccctc ggcgggccgg ccacctcggc gtccgcggcc gtgtctggcg cctgcggcgg 11280
cggcgggggg ccggctgacg accccgagga gcccccgcgg cgcagggcca gacactacct 11340
ggacctggag gagggcgagg gcctggcgcg gctgggggcg ccgtctcccg agcgccaccc 11400
gcgggtgcag ctgaagcgcg actcgcgcga ggcgtacgtg cctcggcaga acctgttcag 11460
ggaccgcgcg ggcgaggagc ccgaggagat gcgggacagg aggttcagcg cagggcggga 11520
gctgcggcag gggctgaacc gcgagcggct gctgcgcgag gaggactttg agcccgacgc 11580
gcggacgggg atcagccccg cgcgcgcgca cgtggcggcc gccgacctgg tgacggcgta 11640
cgagcagacg gtgaaccagg agatcaactt ccaaaagagt ttcaacaacc acgtgcgcac 11700
gctggtggcg cgcgaggagg tgaccatcgg gctgatgcac ctgtgggact ttgtaagcgc 11760
gctggtgcag aaccccaaca gcaagcctct gacggcgcag ctgttcctga tagtgcagca 11820
cagcagggac aacgaggcgt ttagggacgc gctgctgaac atcaccgagc ccgagggtcg 11880
gtggctgctg gacctgatta acatcctgca gagcatagtg gtgcaggagc gcagcctgag 11940
cctggccgac aaggtggcgg ccatcaacta ctcgatgctg agcctgggca agttttacgc 12000
gcgcaagatc taccagacgc cgtacgtgcc catagacaag gaggtgaaga tcgacggttt 12060
ttacatgcgc atggcgctga aggtgctcac cctgagcgac gacctgggcg tgtaccgcaa 12120
cgagcgcatc cacaaggccg tgagcgtgag ccggcggcgc gagctgagcg accgcgagct 12180
gatgcacagc ctgcagcggg cgctggcggg cgccggcagc ggcgacaggg aggcggagtc 12240
ctacttcgat gcgggggcgg acctgcgctg ggcgcccagc cggcgggccc tggaggccgc 12300
gggggtccgc gaggactatg acgaggacgg cgaggaggat gaggagtacg agctagagga 12360
gggcgagtac ctggactaaa ccgcgggtgg tgtttccggt agatgcaaga cccgaacgtg 12420
gtggacccgg cgctgcgggc ggctctgcag agccagccgt ccggccttaa ctcctcagac 12480
gactggcgac aggtcatgga ccgcatcatg tcgctgacgg cgcgtaaccc ggacgcgttc 12540
cggcagcagc cgcaggccaa caggctctcc gccatcctgg aggcggtggt gcctgcgcgc 12600
tcgaacccca cgcacgagaa ggtgctggcc atagtgaacg cgctggccga gaacagggcc 12660
atccgcccgg acgaggccgg gctggtgtac gacgcgctgc tgcagcgcgt ggcccgctac 12720
aacagcggca acgtgcagac caacctggac cggctggtgg gggacgtgcg cgaggcggtg 12780
gcgcagcgcg agcgcgcgga tcggcagggc aacctgggct ccatggtggc gctgaatgcc 12840
ttcctgagca cgcagccggc caacgtgccg cgggggcagg aagactacac caactttgtg 12900
agcgcgctgc ggctgatggt gaccgagacc ccccagagcg aggtgtacca gtcgggcccg 12960
gactacttct tccagaccag cagacagggc ctgcagacgg tgaacctgag ccaggctttc 13020
aagaacctgc gggggctgtg gggcgtgaag gcgcccaccg gcgaccgggc gacggtgtcc 13080
agcctgctga cgcccaactc gcgcctgctg ctgctgctga tcgcgccgtt cacggacagc 13140
ggcagcgtgt cccgggacac ctacctgggg cacctgctga ccctgtaccg cgaggccatc 13200
gggcaggcgc aggtggacga gcacaccttc caggagatca ccagcgtgag ccgcgcgctg 13260
gggcaggagg acacgagcag cctggaggcg actctgaact acctgctgac caaccggcgg 13320

-continued

```
cagaagattc cctcgctgca cagcctgacc tccgaggagg agcgcatctt gcgctacgtg  13380
cagcagagcg tgagcctgaa cctgatgcgc gacggggtga cgcccagcgt ggcgctggac  13440
atgaccgcgc gcaacatgga accgggcatg tacgccgcgc accggcctta catcaaccgc  13500
ctgatggact acctgcatcg cgcggcggcc gtgaaccccg agtactttac caacgccatc  13560
ctgaacccgc actggctccc gccgcccggg ttctacagcg ggggcttcga ggtcccggag  13620
gccaacgatg gcttcctgtg ggacgacatg gacgacagcg tgttctcccc gcggccgcag  13680
gcgctggcgg aagcgtccct gctgcgtccc aagaaggagg aggaggaggc gagtcgccgc  13740
cgcggcagca gcggcgtggc ttctctgtcc gagctggggg cggcagccgc cgcgcgcccc  13800
gggtccctgg gcggcagccc ctttccgagc ctggtggggt ctctgcacag cgagcgcacc  13860
acccgccctc ggctgctggg cgaggacgag tacctgaata actccctgct gcagccggtg  13920
cgggagaaaa acctgccccc cgccttcccc aacaacggga tagagagcct ggtggacaag  13980
atgagcagat ggaagaccta tgcgcaggag cacagggacg cgcccgcgct ccggccgccc  14040
acgcggcgcc agcgccacga ccggcagcgg gggctggtgt gggatgacga ggactccgcg  14100
gacgatagca gcgtgctgga cctgggaggg agcggcaacc cgttcgcgca cctgcgcccc  14160
cgcctgggga ggatgtttta aaaaaaaaaa aagcaagaag catgatgcaa aattaaataa  14220
aactcaccaa ggccatggcg accgagcgtt ggtttcttgt gttcccttca gtatgcggcg  14280
cgcggcgatg taccaggagg gacctcctcc ctcttacgag agcgtggtgg gcgcggcggc  14340
ggcggcgccc tcttctccct ttgcgtcgca gctgctggag ccgccgtacg tgcctccgcg  14400
ctacctgcgg cctacggggg ggagaaacag catccgttac tcggagctgg cgcccctgtt  14460
cgacaccacc cgggtgtacc tggtggacaa caagtcggcg gacgtggcct ccctgaacta  14520
ccagaacgac cacagcaatt ttttgaccac ggtcatccag aacaatgact acagcccgag  14580
cgaggccagc acccagacca tcaatctgga tgaccggtcg cactggggcg gcgacctgaa  14640
aaccatcctg cacaccaaca tgcccaacgt gaacgagttc atgttcacca ataagttcaa  14700
ggcgcgggtg atggtgtcgc gctcgcacac caaggaagac cgggtggagc tgaagtacga  14760
gtgggtggag ttcgagctgc cagagggcaa ctactccgag accatgacca ttgacctgat  14820
gaacaacgcg atcgtggagc actatctgaa agtgggcagg caaaacgggg tcctggagag  14880
cgacatcggg gtcaagttcg acaccaggaa cttccgcctg ggctggaccc ccgtgaccgg  14940
gctggttatg cccggggtgt acaccaacga ggccttccat cccgacatca tcctgctgcc  15000
cggctgcggg gtggacttca cttacagccg cctgagcaac ctcctgggca tccgcaagcg  15060
gcagcccttc caggagggct tcaggatcac ctacgaggac ctggaggggg gcaacatccc  15120
cgcgctcctc gatgtggagg cctaccagga tagcttgaag gaaaatgagg cgggacagga  15180
ggataccacc cccgccgcct ccgccgccgc cgagcagggc gaggatgctg ctgacaccgc  15240
ggccgcggac ggggcagagg ccgaccccgc tatggtggtg gaggctcccg agcaggagga  15300
ggatatgaat gacagtgcgg tgcgcggaga caccttcgtc acccgggggg aggaaaagca  15360
agcggaggcc gaggccgcgg ccgaggaaaa gcaactggcg gcagcagcgg cggcggcggc  15420
gttggccgcg gcggaggctg agtctgaggg gaccaagccc gccaaggagc ccgtgattaa  15480
gcccctgacc gaagatagca agaagcgcag ttacaacctg ctcaaggaca gcaccaacac  15540
cgcgtaccgc agctggtacc tggcctacaa ctacggcgac ccgtcgacgg gggtgcgctc  15600
ctggaccctg ctgtgcacgc cggacgtgac ctgcggctcg gagcaggtgt actggtcgct  15660
gcccgacatg atgcaagacc ccgtgacctt ccgctccacg cggcaggtca gcaacttccc  15720
```

ggtggtgggc gccgagctgc tgcccgtgca ctccaagagc ttctacaacg accaggccgt 15780
ctactcccag ctcatccgcc agttcacctc tctgacccac gtgttcaatc gctttcctga 15840
gaaccagatt ctggcgcgcc cgcccgcccc caccatcacc accgtcagtg aaaacgttcc 15900
tgctctcaca gatcacggga cgctaccgct gcgcaacagc atcggaggag tccagcgagt 15960
gaccgttact gacgccagac gccgcacctg cccctacgtt tacaaggcct tgggcatagt 16020
ctcgccgcgc gtcctttcca gccgcacttt ttgagcaaca ccaccatcat gtccatcctg 16080
atctcaccca gcaataactc cggctgggga ctgctgcgcg cgcccagcaa gatgttcgga 16140
ggggcgagga agcgttccga gcagcacccc gtgcgcgtgc gcgggcactt ccgcgccccc 16200
tggggagcgc acaaacgcgg ccgcgcgggg cgcaccaccg tggacgacgc catcgactcg 16260
gtggtggagc aggcgcgcaa ctacaggccc gcggtctcta ccgtggacgc ggccatccag 16320
accgtggtgc ggggcgcgcg gcggtacgcc aagctgaaga gccgccggaa gcgcgtggcc 16380
cgccgccacc gccgccgacc cggggccgcc gccaaacgcg ccgccgcggc cctgcttcgc 16440
cgggccaagc gcacgggccg ccgcgccgcc atgagggccg cgcgccgctt ggccgccggc 16500
atcaccgccg ccaccatggc cccccgtacc cgaagacgcg cggccgccgc cgccgccgcc 16560
gccatcagtg acatggccag caggcgccgg ggcaacgtgt actgggtgcg cgactcggtg 16620
accggcacgc gcgtgcccgt gcgcttccgc cccccgcgga cttgagatga tgtgaaaaaa 16680
caacactgag tctcctgctg ttgtgtgtat cccagcggcg gcggcgcgcg cagcgtcatg 16740
tccaagcgca aaatcaaaga agagatgctc caggtcgtcg cgccggagat ctatgggccc 16800
ccgaagaagg aagagcagga ttcgaagccc cgcaagataa agcgggtcaa aaagaaaaag 16860
aaagatgatg acgatgccga tggggaggtg gagttcctgc gcgccacggc gcccaggcgc 16920
ccggtgcagt ggaagggccg gcgcgtaaag cgcgtcctgc gccccggcac cgcggtggtc 16980
ttcacgcccg gcgagcgctc cacccggact ttcaagcgcg tctatgacga ggtgtacggc 17040
gacgaagacc tgctggagca ggccaacgag cgcttcggag agtttgctta cgggaagcgt 17100
cagcgggcgc tggggaagga ggacctgctg gcgctgccgc tggaccaggg caaccccacc 17160
cccagtctga agcccgtgac cctgcagcag gtgctgccga gcagcgcacc ctccgaggcg 17220
aagcggggtc tgaagcgcga gggcggcgac ctggcgccca ccgtgcagct catggtgccc 17280
aagcggcaga ggctggagga tgtgctggag aaaatgaaag tagaccccgg tctgcagccg 17340
gacatcaggg tccgtcccat caagcaggtg gcgccgggcc tcggcgtgca gaccgtggac 17400
gtggtcatcc ccaccggcaa ctcccccgcc gccaccacca ctaccgctgc ctccacggac 17460
atggagacac agaccgatcc cgccgcagcc gcagccgccg ccgcagccgc gacctcctcg 17520
gcggaggtgc agacggaccc ctggctgccg ccggcgatgt cagctccccg cgcgcgccgc 17580
ggacgcagaa agtacggcgc cgccaacgcg ctcctgcccg agtacgcctt gcatccttcc 17640
atcgcgccca cccccggcta ccgaggctat acctaccgcc cgcgaagagc caagggttcc 17700
acccgccgtc cccgccgacg cgccgccgcc accacccgcc gccgccgccg cagacgccag 17760
cccgcactgg ctccagtctc cgtgaggaga gtggcgcgcg acggacacac cctggtgctg 17820
cccagggcgc gctaccaccc cagcatcgtt taaaagcctg ttgtggttct tgcagatatg 17880
gccctcactt gccgcctccg tttcccggtg ccgggatacc gaggaggaag atcgcgccgc 17940
aggaggggtc tggccggccg cggcctgagc ggaggcagcc gccgcgcgca ccggcggcga 18000
cgcgccacca gccgacgcat gcgcggcggg gtgctgcccc tgttaatccc cctgatcgcc 18060

-continued

```
gcggcgatcg gcgccgtgcc cgggatcgcc tccgtggcct tgcaagcgtc ccagaggcat  18120
tgacagactt gcaaacttgc aaatatggaa aaaaaaaaaa aaccccaata aaaagtctag  18180
actctcacgc tcgcttggtc ctgtgactat tttgtagaat ggaagacatc aactttgcgt  18240
cgctggcccc gcgtcacggc tcgcgcccgt tcctgggaca ctggaacgat atcggcacca  18300
gcaacatgag cggtggcgcc ttcagttggg gctctctgtg gagcggcatt aaaagtatcg  18360
ggtctgccgt taaaaattac ggctcccggg cctggaacag cagcacgggc cagatgttga  18420
gagacaagtt gaaagagcag aacttccagc agaaggtggt ggagggcctg gcctccggca  18480
tcaacggggt ggtggacctg gccaaccagg ccgtgcagaa taaaatcaac agcagactgg  18540
acccccggcc gccggtggag gaggtgccgc cggcgctgga gacggtgtcc cccgatgggc  18600
gtggcgagaa gcgcccgcgg cccgataggg aagagaccac tctggtcacg cagaccgatg  18660
agccgccccc gtatgaggag gccctaaagc aaggtctgcc caccacgcgg cccatcgcgc  18720
ccatggccac cggggtggtg ggccgccaca cccccgccac gctggacttg cctccgcccg  18780
ccgatgtgcc gcagcagcag aaggcggcac agccgggccc gcccgcgacc gcctcccgtt  18840
cctccgccgg tcctctgcgc cgcgcggcca gcggcccccg cggggggggtc gcgaggcacg  18900
gcaactggca gagcacgctg aacagcatcg tgggtctggg ggtgcggtcc gtgaagcgcc  18960
gccgatgcta ctgaatagct tagctaacgt gttgtatgtg tgtatgcgcc ctatgtcgcc  19020
gccagaggag ctgctgagtc gccgccgttc gcgcgcccac caccaccgcc actccgcccc  19080
tcaagatggc gaccccatcg atgatgccgc agtggtcgta catgcacatc tcgggccagg  19140
acgcctcgga gtacctgagc cccgggctgg tgcagttcgc ccgcgccacc gagagctact  19200
tcagcctgag taacaagttt aggaacccca cggtggcgcc cacgcacgat gtgaccaccg  19260
accggtctca gcgcctgacg ctgcggttca ttcccgtgga ccgcgaggac accgcgtact  19320
cgtacaaggc gcggttcacc ctggccgtgg gcgacaaccg cgtgctggac atggcctcca  19380
cctactttga catccgcggg gtgctggacc ggggtcccac tttcaagccc tactctggca  19440
ccgcctacaa ctccctggcc cccaagggcg ctcccaactc ctgcgagtgg gagcaagagg  19500
aaactcaggc agttgaagaa gcagcagaag aggaagaaga agatgctgac ggtcaagctg  19560
aggaagagca agcagctacc aaaaagactc atgtatatgc tcaggctccc ctttctggcg  19620
aaaaaattag taaagatggt ctgcaaatag gaacggacgc tacagctaca gaacaaaaac  19680
ctatttatgc agaccctaca ttccagcccg aaccccaaat cggggagtcc cagtggaatg  19740
aggcagatgc tacagtcgcc ggcggtagag tgctaaagaa atctactccc atgaaaccat  19800
gctatggttc ctatgcaaga cccacaaatg ctaatggagg tcagggtgta ctaacggcaa  19860
atgcccaggg acagctagaa tctcaggttg aaatgcaatt cttttcaact tctgaaaacg  19920
cccgtaacga ggctaacaac attcagccca aattggtgct gtatagtgag gatgtgcaca  19980
tggagacccc ggatacgcac ctttcttaca agcccgcaaa aagcgatgac aattcaaaaa  20040
tcatgctggg tcagcagtcc atgcccaaca gacctaatta catcggcttc agagacaact  20100
ttatcggcct catgtattac aatagcactg gcaacatggg agtgcttgca ggtcaggcct  20160
ctcagttgaa tgcagtggtg gacttgcaag acagaaacac agaactgtcc taccagctct  20220
tgcttgattc catgggtgac agaaccagat acttttccat gtggaatcag gcagtggaca  20280
gttatgaccc agatgttaga attattgaaa atcatggaac tgaagacgag ctccccaact  20340
attgtttccc tctgggtggc ataggggtaa ctgacactta ccaggctgtt aaaaccaaca  20400
atggcaataa cgggggccag gtgacttgga caaaagatga aacttttgca gatcgcaatg  20460
```

```
aaataggggt gggaaacaat ttcgctatgg agatcaacct cagtgccaac ctgtggagaa  20520
acttcctgta ctccaacgtg gcgctgtacc taccagacaa gcttaagtac aacccctcca  20580
atgtggacat ctctgacaac cccaacacct acgattacat gaacaagcga gtggtggccc  20640
cggggctggt ggactgctac atcaacctgg gcgcgcgctg gtcgctggac tacatggaca  20700
acgtcaaccc cttcaaccac caccgcaatg cgggcctgcg ctaccgctcc atgctcctgg  20760
gcaacgggcg ctacgtgccc ttccacatcc aggtgcccca gaagttcttt gccatcaaga  20820
acctcctcct cctgccgggc tcctacacct acgagtggaa cttcaggaag gatgtcaaca  20880
tggtcctcca gagctctctg ggtaacgatc tcagggtgga cggggccagc atcaagttcg  20940
agagcatctg cctctacgcc accttcttcc ccatggccca caacacggcc tccacgctcg  21000
aggccatgct caggaacgac accaacgacc agtccttcaa tgactacctt tccgccgcca  21060
acatgctcta ccccataccc gccaacgcca ccaacgtccc catctccatc cctcgcgca   21120
actgggcggc cttccgcggc tgggccttca cccgcctcaa gaccaaggag accccctccc  21180
tgggctcggg attcgacccc tactacacct actcgggctc tattccctac ctggacggca  21240
ccttctacct caaccacact ttcaagaagg tctcggtcac cttcgactcc tcggtcagct  21300
ggccgggcaa cgaccgtctg ctcacccccca acgagttcga gatcaagcgc tcggtcgacg  21360
gggaaggcta caacgtggcc cagtgcaaca tgaccaagga ctggttcctg gtccagatgc  21420
tggccaacta caacatcggc taccagggct tctacatccc agagagctac aaggacagga  21480
tgtactcctt cttcaggaac ttccagccca tgagccggca ggtggtggac cagaccaagt  21540
acaaggacta ccaggaggtg ggcatcatcc accagcacaa caactcgggc ttcgtgggct  21600
acctcgcccc caccatgcgc gagggacagg cctaccccgc caacttcccc tacccgctca  21660
taggcaagac cgcggtcgac agcatcaccc agaaaaagtt cctctgcgac cgcaccctct  21720
ggcgcatccc cttctccagc aacttcatgt ccatgggtgc gctctcggac ctgggccaga  21780
acttgctcta cgccaactcc gcccacgccc tcgacatgac cttcgaggtc gaccccatgg  21840
acgagcccac ccttctctat gttctgttcg aagtctttga cgtggtccgg gtccaccagc  21900
cgcaccgcgg cgtcatcgag accgtgtacc tgcgtacgcc cttctcggcc ggcaacgcca  21960
ccacctaaag aagcaagccg cagtcatcgc cgcctgcatg ccgtcgggtt ccaccgagca  22020
agagctcagg gccatcgtca gagacctggg atgcgggccc tatttttggg gcaccttcga  22080
caagcgcttc cctggctttg tctccccaca caagctggcc tgcgccatcg tcaacacggc  22140
cggccgcgag accgggggcg tgcactggct ggcctttgcc tggaacccgc gctccaaaac  22200
atgcttcctc tttgacccct tcggcttttc ggaccagcgg ctcaagcaaa tctacgagtt  22260
cgagtacgag ggcttgctgc gtcgcagcgc catcgcctcc tcgcccgacc gctgcgtcac  22320
cctcgaaaag tccacccaga ccgtgcaggg gcccgactcg gccgcctgcg gtctcttctg  22380
ctgcatgttt ctgcacgcct ttgtgcactg gcctcagagt cccatggacc gcaaccccac  22440
catgaacttg ctgacggggg tgcccaactc catgctccaa agcccccagg tcgagcccac  22500
cctgcgccgc aaccaggagc agctctacag cttcctggag cgccactcgc cctacttccg  22560
ccgccacagc gcacagatca ggagggccac ctccttctgc cacttgcaag agatgcaaga  22620
agggtaataa cgatgtacac actttttttct caataaatgg catttttttt ttatttatac  22680
aagctctctg ggtattcatt ttcccaccac caccacccgc cgttgtcgcc atctggctct  22740
atttagaaat cgaaagggtt ctgccgggag tcgccgtgcg ccacgggcag ggacacgttg  22800
```

-continued

```
cgatactggt agcgggtgcc ccacttgaac tcgggcacca ccaggcgagg cagctcgggg  22860
aagttttcgc tccacaggct gcgggtcagc accagcgcgt tcatcaggtc gggcgccgag  22920
atcttgaagt cgcagttggg gccgccgccc tgcgcgcgcg agttgcggta caccgggttg  22980
cagcactgga acaccaacag cgccgggtgc ttcacgctgg ccagcacgct gcggtcggag  23040
atcagctcgg cgtccaggtc ctccgcgttg ctcagcgcga acggggtcat cttgggcact  23100
tgccgcccca ggaagggcgc gtgccccggt ttcgagttgc agtcgcagcg cagcgggatc  23160
agcaggtgcc cgtgcccgga ctcggcgttg ggtacagcg cgcgcatgaa ggcctgcatc  23220
tggcggaagg ccatctgggc cttggcgccc tccgagaaga acatgccgca ggacttgccc  23280
gagaactggt ttgcggggca gctggcgtcg tgcaggcagc agcgcgcgtc ggtgttggcg  23340
atctgcacca cgttgcgccc ccaccggttc ttcacgatct tggccttgga cgattgctcc  23400
ttcagcgcgc gctgcccgtt ctcgctggtc acatccatct cgatcacatg ttccttgttc  23460
accatgctgc tgccgtgcag acacttcagc tcgccctccg tctcggtgca gcggtgctgc  23520
cacagcgcgc agcccgtggg ctcgaaagac ttgtaggtca cctccgcgaa ggactgcagg  23580
tacccctgca aaaagcggcc catcatggtc acgaaggtct tgttgctgct gaaggtcagc  23640
tgcagcccgc ggtgctcctc gttcagccag gtcttgcaca cggccgccag cgcctccacc  23700
tggtcgggca gcatcttgaa gttcaccttc agctcattct ccacgtggta cttgtccatc  23760
agcgtgcgcg ccgcctccat gcccttctcc caggccgaca ccagcggcag gctcacgggg  23820
ttcttcacca tcaccgtggc cgccgcctcc gccgcgcttt cgctttccgc cccgctgttc  23880
tcttcctctt cctcctcttc ctcgccgccg cccactcgca gcccccgcac cacggggtcg  23940
tcttcctgca ggcgctgcac cttgcgcttg ccgttgcgcc cctgcttgat gcgcacgggc  24000
gggttgctga agcccaccat caccagcgcg gcctcttctt gctcgtcctc gctgtccaga  24060
atgacctccg gggagggggg gttggtcatc ctcagtaccg aggcacgctt ctttttcttc  24120
ctgggggcgt tcgccagctc cgcggctgcg gccgctgccg aggtcgaagg ccgagggctg  24180
ggcgtgcgcg gcaccagcgc gtcttgcgag ccgtcctcgt cctcctcgga ctcgagacgg  24240
aggcgggccc gcttcttcgg gggcgcgcgg ggcggcggag gcggcggcgg cgacggagac  24300
ggggacgaga catcgtccag ggtgggtgga cggcgggccg cgccgcgtcc gcgctcgggg  24360
gtggtttcgc gctggtcctc ttcccgactg gccatctccc actgctcctt ctcctatagg  24420
cagaaagaga tcatggagtc tctcatgcga gtcgagaagg aggaggacag cctaaccgcc  24480
ccctctgagc cctccaccac cgccgccacc accgccaatg ccgccgcgga cgacgcgccc  24540
accgagacca ccgccagtac caccctcccc agcgacgcac cccgctcgga gaatgaagtg  24600
ctgatcgagc aggacccggg ttttgtgagc ggagaggagg atgaggtgga tgagaaggag  24660
aaggaggagg tcgccgcctc agtgccaaaa gaggataaaa agcaagacca ggacgacgca  24720
gataaggatg agacagcagt cgggcggggg aacggaagcc atgatgctga tgacggctac  24780
ctagacgtgg gagacgacgt gctgcttaag cacctgcacc gccagtgcgt catcgtctgc  24840
gacgcgctgc aggagcgctg cgaagtgccc ctggacgtgg cggaggtcag ccgcgcctac  24900
gagcggcacc tcttcgcgcc gcacgtgccc cccaagcgcc gggagaacgg cacctgcgag  24960
cccaacccgc gtctcaactt ctacccggtc ttcgcggtac ccgaggtgct ggccacctac  25020
cacatcttct tccaaaactg caagatcccc ctctcctgcc gcgctaaccg cacccgcgcc  25080
gacaaaaccc tgaccctgcg gcagggcgcc cacatacctg atattgcctc tctggaggaa  25140
gtgcccaaga tcttcgaggg tctcggtcgc gacgagaaac gggcggcgaa cgctctgcac  25200
```

```
ggagacagcg aaaacgagag tcactcgggg gtgctggtgg agctcgaggg cgacaacgcg  25260
cgcctggccg tactcaagcg cagcatagag gtcacccact ttgcctaccc ggcgctcaac  25320
ctgcccccca aggtcatgag tgtggtcatg ggcgagctca tcatgcgccg cgctcagccc  25380
ctggccgcgg atgcaaactt gcaagagtcc tccgaggaag gcctgcccgc ggtcagcgac  25440
gagcagctag cgcgctggct ggagacccgc gaccccgcgc agctggagga gcggcgcaag  25500
ctcatgatgg ccgcggtgct ggtcaccgtg gagctcgagt gtctgcagcg cttcttcgcg  25560
gaccccgaga tgcagcgcaa gctcgaggag accctgcact acaccttccg ccagggctac  25620
gtgcgccagg cctgcaagat ctccaacgtg gagctctgca acctggtctc ctacctgggc  25680
atcctgcacg agaaccgcct cgggcagaac gtcctgcact ccaccctcaa aggggaggcg  25740
cgccgcgact acatccgcga ctgcgcctac ctcttcctct gctacacctg gcagacggcc  25800
atgggggtct ggcagcagtg cctggaggag cgcaacctca aggagctgga aaagctactc  25860
aagcgcaccc tcagggacct ctggacgggc ttcaacgagc gctcggtggc cgccgcgctg  25920
gcggacatca tcttccccga gcgcctgctc aagaccctgc agcagggcct gcccgacttc  25980
accagccaga gcatgctgca gaactttagg actttcatcc tggagcgctc gggcatcctg  26040
cctgccactt gctgcgcgct gcccagcgac ttcgtgccca tcaagtacag ggagtgcccg  26100
ccgccgctct ggggccactg ctacctcttc cagctggcca actacctcgc ctaccactcg  26160
gacctcatgg aagacgtgag cggcgagggc ctgctcgagt gccactgccg ctgcaacctc  26220
tgcacgcccc accgctctct agtctgcaac ccgcagctgc tcagcgagag tcagattatc  26280
ggtaccttcg agctgcaggg tccctcgcct gacgagaagt ccgcggctcc ggggctgaaa  26340
ctcactccgg ggctgtggac ttccgcctac ctacgcaaat ttgtacctga ggactaccac  26400
gcccacgaga tcaggttcta cgaagaccaa tcccgcccgc ccaaggcgga gctcaccgcc  26460
tgcgtcatca cccaggggca catcctgggc caattgcaag ccatcaacaa agcccgccga  26520
gagttcttgc tgaaaaaggg tcgggggtg tacctggacc cccagtccgg cgaggagcta  26580
aacccgctac ccccgccgcc gccccagcag cgggaccttg cttcccagga tggcacccag  26640
aaagaagcag cagccgccgc cgccgcagcc atacatgctt ctggaggaag aggaggagga  26700
ctgggacagt caggcagagg aggtttcgga cgaggagcag gaggagatga tggaagactg  26760
ggaggaggac agcagcctag acgaggaagc ttcagaggcc gaagaggtgg cagacgcaac  26820
accatcaccc tcggtcgcag cccccctcgcc ggggcccctg aaatcctccg aacccagcac  26880
cagcgctata acctccgctc ctccggcgcc ggcgccaccc gcccgcagac ccaaccgtag  26940
atgggacacc acaggaaccg gggtcggtaa gtccaagtgc ccgccgccgc caccgcagca  27000
gcagcagcag cgccagggct accgctcgtg gcgcgggcac aagaacgcca tagtcgcctg  27060
cttgcaagac tgcgggggca acatctcttt cgcccggcgc ttcctgctat tccaccacgg  27120
ggtcgccttt ccccgcaatg tcctgcatta ctaccgtcat ctctacagcc cctactgcag  27180
cggcgaccca gaggcggcag cggcagccac agcggcgacc accacctagg aagatatcct  27240
ccgcgggcaa gacagcggca gcagcggcca ggagacccgc ggcagcagcg gcgggagcgg  27300
tgggcgcact gcgcctctcg cccaacgaac ccctctcgac ccgggagctc agacacagga  27360
tcttccccac tttgtatgcc atcttccaac agagcagagg ccaggagcag gagctgaaaa  27420
taaaaaacag atctctgcgc tccctcaccc gcagctgtct gtatcacaaa agcgaagatc  27480
agcttcggcg cacgctggag gacgcggagg cactcttcag caaatactgc gcgctcactc  27540
```

-continued

```
ttaaagacta gctccgcgcc cttctcgaat ttaggcggga gaaaactacg tcatcgccgg  27600
ccgccgccca gcccgcccag ccgagatgag caaagagatt cccacgccat acatgtggag  27660
ctaccagccg cagatgggac tcgcggcggg agcggcccag gactactcca cccgcatgaa  27720
ctacatgagc gcgggacccc acatgatctc acaggtcaac gggatccgcg cccagcgaaa  27780
ccaaatactg ctggaacagg cggccatcac cgccacgccc cgccataatc tcaacccccg  27840
aaattggccc gccgccctcg tgtaccagga aacccccctcc gccaccaccg tactacttcc  27900
gcgtgacgcc caggccgaag tccagatgac taactcaggg gcgcagctcg cgggcggctt  27960
tcgtcacggg gcgcggccgc tccgaccagg tataagacac ctgatgatca gaggccgagg  28020
tatccagctc aacgacgagt cggtgagctc ttcgctcggt ctccgtccgg acggaacttt  28080
ccagctcgcc ggatccggcc gctcttcgtt cacgccccgc caggcgtacc tgactctgca  28140
gacctcgtcc tcggagcccc gctccggagg catcggaacc ctccagttcg tggaggagtt  28200
cgtgccctcg gtctacttca acccccttctc gggacctccc ggacgctacc ccgaccagtt  28260
cattccgaac tttgacgcgg tgaaggactc ggcggacggc tacgactgaa tgtcaggtgc  28320
cgaggcagag cagcttcgcc tgagacacct cgagcactgc cgccgccaca agtgcttcgc  28380
ccgcggttcc ggtgagttct gctactttca gctacccgag gagcataccg aggggccggc  28440
gcacggcgtc cgcctgacca cccagggcga ggttacctgt tccctcatcc gggagttcac  28500
cctccgtccc ctgctagtgg agcgggagcg gggtccctgt gtcctaacta tcgcctgcaa  28560
ctgccctaac cctggattac atcaagatct ttgctgtcat ctctgtgctg agtttaataa  28620
acgctgagat cagaatctac tggggctcct gtcgccatcc tgtgaacgcc accgtcttca  28680
cccaccccga ccaggcccag gcgaacctca cctgcggtct gcatcggagg gccaagaagt  28740
acctcacctg gtacttcaac ggcacccccct ttgtggttta caacagcttc gacggggacg  28800
gagtctccct gaaagaccag ctctccggtc tcagctactc catccacaag aacaccaccc  28860
tccaactctt ccctccctac ctgccgggaa cctacgagtg cgtcaccggc cgctgcaccc  28920
acctcacccg cctgatcgta aaccagagct ttccgggaac agataactcc ctcttcccca  28980
gaacaggagg tgagctcagg aaactccccg gggaccaggg cggagacgta ccttcgaccc  29040
ttgtggggtt aggatttttt attaccgggt tgctggctct tttaatcaaa gcttccttga  29100
gatttgttct ttccttctac gtgtatgaac acctcagcct ccaataactc tacccttttct  29160
tcggaatcag gtgacttctc tgaaatcggg cttggtgtgc tgcttactct gttgattttt  29220
ttccttatca tactcagcct tctgtgcctc aggctcgccg cctgctgcgc acacatctat  29280
atctactgct ggttgctcaa gtgcaggggt cgccacccaa gatgaacagg tacatggtcc  29340
tatcgatcct aggcctgctg gccctggcgg cctgcagcgc cgccaaaaaa gagattacct  29400
ttgaggagcc cgcttgcaat gtaactttca agcccgaggg tgaccaatgc accaccctcg  29460
tcaaatgcgt taccaatcat gagaggctgc gcatcgacta caaaaacaaa actggccagt  29520
ttgcggtcta tagtgtgttt acgcccggag accccctctaa ctactctgtc accgtcttcc  29580
agggcggaca gtctaagata ttcaattaca ctttcccttt ttatgagtta tgcgatgcgg  29640
tcatgtacat gtcaaaacag tacaacctgt ggcctccctc tccccaggcg tgtgtggaaa  29700
atactgggtc ttactgctgt atggctttgg caatcactac gctcgctcta atctgcacgg  29760
tgctatacat aaaattcagg cagaggcgaa tctttatcga tgaaaagaaa atgccttgat  29820
cgctaacacc ggctttctat ctgcagaatg aatgcaatca cctccctact aatcaccacc  29880
accctccttg cgattgccca tgggttgaca cgaatcgaag tgccagtggg gtccaatgtc  29940
```

accatggtgg gccccgccgg caattccacc ctcatgtggg aaaaatttgt ccgcaatcaa 30000
tgggttcatt tctgctctaa ccgaatcagt atcaagccca gagccatctg cgatgggcaa 30060
aatctaactc tgatcaatgt gcaaatgatg gatgctgggt actattacgg gcagcgggga 30120
gaaatcatta attactggcg accccacaag gactacatgc tgcatgtagt cgaggcactt 30180
cccactacca cccccactac cacctctccc accaccacta ccaccactac tactactact 30240
actaccacta ccgctgcccg ccatacccgc aaaagcacca tgattagcac aaagcccccct 30300
cgtgctcact cccacgccgg cgggcccatc ggtgcgacct cagaaaccac cgagctttgc 30360
ttctgccaat gcactaacgc cagcgctcat gaactgttcg acctggagaa tgaggatgcc 30420
cagcagagct ccgcttgcct gacccaggag gctgtggagc ccgttgccct gaagcagatc 30480
ggtgattcaa taattgactc ttcttctttt gccactcccg aataccctcc cgattctact 30540
ttccacatca cgggtaccaa agaccctaac ctctctttct acctgatgct gctgctctgt 30600
atctctgtgg tctcttccgc gctgatgtta ctggggatgt tctgctgcct gatctgccgc 30660
agaaagagaa aagctcgctc tcagggccaa ccactgatgc ccttccccta ccccccggat 30720
tttgcagata acaagatatg agctcgctgc tgacactaac cgctttacta gcctgcgctc 30780
taacccttgt cgcttgcgac tcgagattcc acaatgtcac agctgtggca ggagaaaatg 30840
ttactttcaa ctccacggcc gatacccagt ggtcgtggag tggctcaggt agctacttaa 30900
ctatctgcaa tagctccact tcccccagca tatccccaac caagtaccaa tgcaatgcca 30960
gcctgttcac cctcatcaac gcttccaccc tggacaatgg actctatgta ggctatgtac 31020
cctttggtgg gcaaggaaag acccacgctt acaacctgga agttcgccag cccagaacca 31080
ctacccaagc ttctcccacc accaccacca ccaccaccac caccatcacc agcagcagca 31140
gcagccacag cagcagcagc agattattga ctttggtttt ggccagctca tctgccgcta 31200
cccaggccat ctacagctct gtgcccgaaa ccactcagat ccaccgccca gaaacgacca 31260
ccgccaccac cctacacacc tccagcgatc agatgccgac caacatcacc ccccttggctc 31320
ttcaaatggg acttacaagc ccactccaa aaccagtgga tgcggccgag gtctccgccc 31380
tcgtcaatga ctgggcgggg ctgggaatgt ggtggttcgc cataggcatg atggcgctct 31440
gcctgcttct gctctggctc atctgctgcc tccaccgcag gcgagccaga ccccccatct 31500
atagacccat cattgtcctg aaccccgata atgatgggat ccatagattg gatggcctga 31560
aaaacctact tttttctttt acagtatgat aaattgagac atgcctcgca ttttcttgta 31620
catgttcctt ctcccacctt ttctggggtg ttctacgctg gccgctgtgt ctcacctgga 31680
ggtagactgc ctctcaccct tcactgtcta cctgctttac ggattggtca ccctcactct 31740
catctgcagc ctaatcacag taatcatcgc cttcatccag tgcattgatt acatctgtgt 31800
gcgcctcgca tacttcagac accacccgca gtaccgagac aggaacattg cccaacttct 31860
aagactgctc taatcatgca taagactgtg atctgccttc tgatcctctg catcctgccc 31920
accctcacct cctgccagta caccacaaaa tctccgcgca aaagacatgc ctcctgccgc 31980
ttcacccaac tgtggaatat acccaaatgc tacaacgaaa agagcgagct ctccgaagct 32040
tggctgtatg gggtcatctg tgtcttagtt ttctgcagca ctgtctttgc cctcatgatc 32100
tacccctact ttgatttggg atggaacgcg atcgatgcca tgaattaccc cacctttccc 32160
gcacccgaga taattccact gcgacaagtt gtacccgttg tcgttaatca acgcccccca 32220
tcccctacgc ccactgaaat cagctacttt aacctaacag gcggagatga ctgacgccct 32280
agatctagaa atggacggca tcagtaccga gcagcgtctc ctagagaggc gcaggcaggc 32340
ggctgagcaa gagcgcctca atcaggagct ccgagatctc gttaacctgc accagtgcaa 32400
aagaggcatc ttttgtctgg taaagcaggc caaagtcacc tacgagaaga ccggcaacag 32460
ccaccgcctc agttacaaat tgcccaccca gcgccagaag ctggtgctca tggtgggtga 32520
gaatcccatc accgtcaccc agcactcggt agagaccgag ggtgtctgc actctccctg 32580
tcggggtcca gaagacctct gcaccctggt aaagaccctg tgcggtctca gagatttagt 32640
cccctttaac taatcaaaca ctggaatcaa taaaaagaat cacttactta aaatcagaca 32700
gcaggtctct gtccagttta ttcagcagca cctccttccc ctcctcccaa ctctggtact 32760
ccaaacgcct tctggcggca aacttcctcc acaccctgaa gggaatgtca gattcttgct 32820
cctgtccctc cgcacccact atcttcatgt tgttgcagat gaagcgcacc aaaacgtctg 32880
acgagagctt caaccccgtg tacccctatg acacggaaag cggccctccc tccgtccctt 32940
tcctcacccc tcccttcgtg tctcccgatg gattccaaga aagcccccccc ggggtcctgt 33000
ctctgaacct ggccgagccc ctggtcactt cccacggcat gctcgccctg aaaatgggaa 33060
gtggcctctc cctggacgac gctggcaacc tcacctctca agatatcacc accgctagcc 33120
ctcccctcaa aaaaaccaag accaacctca gcctagaaac ctcatccccc ctaactgtaa 33180
gcacctcagg cgccctcacc gtagcagccg ccgctcccct ggcagtggcc ggcacctccc 33240
tcaccatgca atcagaggcc cccctgacag tacaggatgc aaaactcacc ctggccacca 33300
aaggcccccct gaccgtgtct gaaggcaaac tggccttgca aacatcggcc ccgctgacgg 33360
ccgctgacag cagcaccctc accgttagcg ccacaccacc aattaatgta agcagtggaa 33420
gtttaggctt agacatggaa gaccctatgt atactcacga tggaaaactg ggaataagaa 33480
ttgggggtcc actaagagta gtagacagct tgcacacact cactgtagtt accggaaatg 33540
gactaactgt agataacaat gccctccaaa ctagagttac gggcgcccta ggttatgaca 33600
catcaggaaa tctacaattg agagctgcag gaggtatgcg aattgatgca aatggccaac 33660
ttatccttaa tgtggcatac ccatttgatg ctcagaacaa tctcagcctt agacttggtc 33720
agggacccct gtatataaac acagaccaca acctggattt gaattgcaac agaggtctaa 33780
ccacaactac caccaacaac acaaaaaaac ttgagactaa aattagctca ggcttagact 33840
atgacaccaa tggtgctgtc attattaaac ttggcactgg tctaagcttc gacaacacag 33900
gcgccctaac tgtgggaaac actggtgatg ataaactgac tctgtggacg accccagacc 33960
catctccaaa ttgcagaatt cactcagaca aagactgcaa gtttactcta gtcctaacta 34020
agtgtggaag ccaaatcctg gcctctgtcg ccgccctagc ggtatcagga aatctggctt 34080
cgataacagg caccgttgcc agcgttacca tctttctcag atttgatcag aatggagtgc 34140
ttatggaaaa ctcctcgcta gacaggcagt actggaactt cagaaatggc aactcaacta 34200
acgctgcccc ctacaccaat gcagttgggt tcatgccaaa cctcgcagca taccccaaaa 34260
cgcaaagcca gactgctaaa aacaacattg taagtcaggt ttacttgaat ggagacaaat 34320
ccaaacccat gacccttacc atcaccctca atggaactaa tgaatccagt gaaactagcc 34380
aggtgagtca ctactccatg tcatttacat gggcttggga aagtgggcaa tatgccactg 34440
aaacctttgc caccaactcc ttcacctttt cttacattgc tgaacaataa aaagcatgac 34500
actgatgttc atttctgatt cttattttat tattttcaaa cacaacaaaa tcattcaagt 34560
cattcttcca tcttagctta atagacacag tagcttaata gacccagtag tgcaaagccc 34620
cattctagct tatagatcag acagtgataa ttaaccacca ccaccaccat accttttgat 34680

```
tcaggaaatc atgatcatca caggatccta gtcttcaggc cgccccctcc ctcccaagac  34740
acagaataca cagtcctctc cccccgactg gctttaaata acaccatctg gttggtcaca  34800
gacatgttct taggggttat attccacacg gtctcctgcc gcgccaggcg ctcgtcggtg  34860
atgttgataa actctcccgg cagctcgctc aagttcacgt cgctgtccag cggctgaacc  34920
tccggctgac gcgataactg tgcgaccggc tgctggacaa acggaggccg cgcctacaag  34980
ggggtagagt cataatcctc ggtcaggata gggcggtgat gcagcagcag cgagcgaaac  35040
atctgctgcc gccgccgctc cgtccggcag gaaaacaaca agccggtggt ctcctccgcg  35100
ataatccgca ccgcccgcag catcagcttc ctcgttctcc gcgcgcagca cctcaccctg  35160
atctcgctca agtcggcgca gtaggtacag cacagcacca cgatgttatt catgatccca  35220
cagtgcaggg cgctgtatcc aaagctcatg ccgggaacca ccgcccccac gtggccatcg  35280
taccacaagc gcacgtaaat taagtgtcga cccctcatga acgtgctgga cacaaacatt  35340
acttccttgg gcatgttgta attcaccacc tcccggtacc agataaacct ctggttaaac  35400
agggcacctt ccaccaccat cctgaaccaa gaggccagaa cctgcccacc ggctatgcac  35460
tgcagggaac ccgggttgga acaatgacaa tgcagactcc aaggctcgta accgtggatc  35520
atccggctgc tgaaggcatc gatgttggca caacacagac acacgtgcat gcactttctc  35580
atgattagca gctcttccct cgtcaggatc atatcccaag gaataaccca ttcttgaatc  35640
aacgtaaaac ccacacagca gggaaggcct cgcacataac tcacgttgtg catggtcagc  35700
gtgttgcatt ctggaaacag cggatgatcc tccagtatcg aggcgcgggt ctccttctca  35760
cagggaggta aagggtccct gctgtacgga ctgcgccggg acgaccgaga tcgtgttgag  35820
cgtagtgtca tggaaaaggg aacgccggac gtggtcatac ttcttgaagc agaaccaggt  35880
tcgcgcgtgg caggcctcct tgcgtctgcg gtctcgccgt ctagctcgct ccgtgtgata  35940
gttgtagtac agccactccc gcagagcgtc gaggcgcacc ctggcttccg gatctatgta  36000
gactccgtct tgcaccgcgg ccctgataat atccaccacc gtagaataag caacacccag  36060
ccaagcaata cactcgctct gcgagcggca gacaggagga gcgggcagag atgggagaac  36120
catgataaaa aacttttttt aaagaatatt ttccaattct tcgaaagtaa gatctatcaa  36180
gtggcagcgc tcccctccac tggcgcggtc aaactctacg gccaaagcac agacaacggc  36240
atttctaaga tgttccttaa tggcgtccaa aagacacacc gctctcaagt tgcagtaaac  36300
tatgaatgaa aacccatccg gctgattttc caatatagac gcgccggcgg cgtccaccaa  36360
acccagataa ttttcttctc tccagcggtt tagaatctgt ctaagcaaat cccttatatc  36420
aagtccggcc atgccaaaaa tctgctcaag agcgccctcc accttcatga ccaagcagcg  36480
catcatgatt gcaaaaattc aggttcttca gagacctgta taagattcaa aatgggaaca  36540
ttaacaaaaa ttcctctgtc gcgcagatcc cttcgcaggg caagctgaac ataatcagac  36600
aggtctgaac ggaccagtga ggccaaatcc ccaccaggaa ccagatccag agaccctata  36660
ctgattatga cgcgcatact cggggctatg ctgaccagcg tagcgccgat gtaggcgtgc  36720
tgcatgggcg gcgagataaa atgcaaagtg ctggttaaaa aatcaggcaa agcctcgcgc  36780
aaaaaagcta acacatcata atcatgctca tgcaggtagt tgcaggtaag ctcaggaacc  36840
aaaacggaat aacacacgat ttcctctcaa aacatgactt cgcggatact gcgtaaaaca  36900
aaaattataa ataaaaaatt aattaactta aacattggaa gcctgtctca caacaggaaa  36960
aaccacttta atcaacataa gacgggccac gggcatgccg gcatagccgt aaaaaaattg  37020
```

```
gtccccgtga ttaacaagta ccacagacag ctcccggtc atgtcggggg tcatcatgtg  37080

agactctgta tacacgtctg gattgtgaac atcagacaaa caaagaaatc gagccacgta  37140

gcccggaggt ataatcaccc gcaggcggag gtacagcaaa acgaccccca taggaggaat  37200

cacaaaatta gtaggagaaa aaaatacata aacaccagaa aaaccctgtt gctgaggcaa  37260

aatagcgccc tcccgatcca aaacaacata aagcgcttcc acaggagcag ccataacaaa  37320

gacccgagtc ttaccagtaa aagaaaaaag atctctcaac gcagcaccag caccaacact  37380

tcgcagtgta aaaggccaag tgccgagaga gtatatatag gaataaaaag tgacgtaaac  37440

gggcaaagtc caaaaaacgc ccagaaaaac cgcacgcgaa cctacgcccc gaaacgaaag  37500

ccaaaaaaca ctagacactc ccttccggcg tcaacttccg ctttcccacg ctacgtcact  37560

tgccccagtc aaacaaacta catatcccga acttccaagt cgccacgccc aaaacaccgc  37620

ctacacctcc ccgcccgccg gcccgccccc aaacccgcct cccgccccgc gccccgcctc  37680

gcgccgccca tctcattatc atattggctt caatccaaaa taaggtatat tattgatgat  37740

g                                                                  37741
```

<210> SEQ ID NO 10
<211> LENGTH: 593
<212> TYPE: PRT
<213> ORGANISM: Pan troglodytes

<400> SEQUENCE: 10

```
Met Arg Arg Ala Ala Met Tyr Gln Glu Gly Pro Pro Pro Ser Tyr Glu
1               5                   10                  15

Ser Val Val Gly Ala Ala Ala Ala Ala Pro Ser Ser Pro Phe Ala Ser
            20                  25                  30

Gln Leu Leu Glu Pro Pro Tyr Val Pro Pro Arg Tyr Leu Arg Pro Thr
        35                  40                  45

Gly Gly Arg Asn Ser Ile Arg Tyr Ser Glu Leu Ala Pro Leu Phe Asp
    50                  55                  60

Thr Thr Arg Val Tyr Leu Val Asp Asn Lys Ser Ala Asp Val Ala Ser
65                  70                  75                  80

Leu Asn Tyr Gln Asn Asp His Ser Asn Phe Leu Thr Thr Val Ile Gln
                85                  90                  95

Asn Asn Asp Tyr Ser Pro Ser Glu Ala Ser Thr Gln Thr Ile Asn Leu
            100                 105                 110

Asp Asp Arg Ser His Trp Gly Gly Asp Leu Lys Thr Ile Leu His Thr
        115                 120                 125

Asn Met Pro Asn Val Asn Glu Phe Met Phe Thr Asn Lys Phe Lys Ala
    130                 135                 140

Arg Val Met Val Ser Arg Ser His Thr Lys Glu Asp Arg Val Glu Leu
145                 150                 155                 160

Lys Tyr Glu Trp Val Glu Phe Glu Leu Pro Glu Gly Asn Tyr Ser Glu
                165                 170                 175

Thr Met Thr Ile Asp Leu Met Asn Asn Ala Ile Val Glu His Tyr Leu
            180                 185                 190

Lys Val Gly Arg Gln Asn Gly Val Leu Glu Ser Asp Ile Gly Val Lys
        195                 200                 205

Phe Asp Thr Arg Asn Phe Arg Leu Gly Leu Asp Pro Val Thr Gly Leu
    210                 215                 220

Val Met Pro Gly Val Tyr Thr Asn Glu Ala Phe His Pro Asp Ile Ile
225                 230                 235                 240
```

```
Leu Leu Pro Gly Cys Gly Val Asp Phe Thr Tyr Ser Arg Leu Ser Asn
            245                 250                 255

Leu Leu Gly Ile Arg Lys Arg Gln Pro Phe Gln Glu Gly Phe Arg Ile
            260                 265                 270

Thr Tyr Glu Asp Leu Glu Gly Gly Asn Ile Pro Ala Leu Leu Asp Val
        275                 280                 285

Glu Ala Tyr Gln Asp Ser Leu Lys Glu Asn Glu Ala Gly Gln Glu Asp
    290                 295                 300

Thr Thr Pro Ala Ala Ser Ala Ala Ala Glu Gln Gly Glu Asp Ala Ala
305                 310                 315                 320

Asp Thr Ala Ala Ala Asp Gly Ala Glu Ala Asp Pro Ala Met Val Val
            325                 330                 335

Glu Ala Pro Glu Gln Glu Glu Asp Met Asn Asp Ser Ala Val Arg Gly
            340                 345                 350

Asp Thr Phe Val Thr Arg Gly Glu Glu Lys Gln Ala Glu Ala Glu Ala
        355                 360                 365

Ala Ala Glu Glu Lys Gln Leu Ala Ala Ala Ala Ala Ala Ala Ala Leu
    370                 375                 380

Ala Ala Ala Glu Ala Glu Ser Glu Gly Thr Lys Pro Ala Lys Glu Pro
385                 390                 395                 400

Val Ile Lys Pro Leu Thr Glu Asp Ser Lys Lys Arg Ser Tyr Asn Leu
            405                 410                 415

Leu Lys Asp Ser Thr Asn Thr Ala Tyr Arg Ser Trp Tyr Leu Ala Tyr
            420                 425                 430

Asn Tyr Gly Asp Pro Ser Thr Gly Val Arg Ser Trp Thr Leu Leu Cys
        435                 440                 445

Thr Pro Asp Val Thr Cys Gly Ser Glu Gln Val Tyr Trp Ser Leu Pro
    450                 455                 460

Asp Met Met Gln Asp Pro Val Thr Phe Arg Ser Thr Arg Gln Val Ser
465                 470                 475                 480

Asn Phe Pro Val Val Gly Ala Glu Leu Leu Pro Val His Ser Lys Ser
            485                 490                 495

Phe Tyr Asn Asp Gln Ala Val Tyr Ser Gln Leu Ile Arg Gln Phe Thr
            500                 505                 510

Ser Leu Thr His Val Phe Asn Arg Phe Pro Glu Asn Gln Ile Leu Ala
        515                 520                 525

Arg Pro Pro Ala Pro Thr Ile Thr Thr Val Ser Glu Asn Val Pro Ala
    530                 535                 540

Leu Thr Asp His Gly Thr Leu Pro Leu Arg Asn Ser Ile Gly Gly Val
545                 550                 555                 560

Gln Arg Val Thr Val Thr Asp Ala Arg Arg Arg Thr Cys Pro Tyr Val
            565                 570                 575

Tyr Lys Ala Leu Gly Ile Val Ser Pro Arg Val Leu Ser Ser Arg Thr
            580                 585                 590

Phe


<210> SEQ ID NO 11
<211> LENGTH: 960
<212> TYPE: PRT
<213> ORGANISM: Pan troglodytes

<400> SEQUENCE: 11

Met Ala Thr Pro Ser Met Met Pro Gln Trp Ser Tyr Met His Ile Ser
1               5                   10                  15
```

-continued

```
Gly Gln Asp Ala Ser Glu Tyr Leu Ser Pro Gly Leu Val Gln Phe Ala
            20                  25                  30

Arg Ala Thr Glu Ser Tyr Phe Ser Leu Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Glu Glu Thr Gln Ala Val Glu
    130                 135                 140

Glu Ala Ala Glu Glu Glu Glu Glu Asp Ala Asp Gly Gln Ala Glu Glu
145                 150                 155                 160

Glu Gln Ala Ala Thr Lys Lys Thr His Val Tyr Ala Gln Ala Pro Leu
                165                 170                 175

Ser Gly Glu Lys Ile Ser Lys Asp Gly Leu Gln Ile Gly Thr Asp Ala
            180                 185                 190

Thr Ala Thr Glu Gln Lys Pro Ile Tyr Ala Asp Pro Thr Phe Gln Pro
        195                 200                 205

Glu Pro Gln Ile Gly Glu Ser Gln Trp Asn Glu Ala Asp Ala Thr Val
    210                 215                 220

Ala Gly Gly Arg Val Leu Lys Lys Ser Thr Pro Met Lys Pro Cys Tyr
225                 230                 235                 240

Gly Ser Tyr Ala Arg Pro Thr Asn Ala Asn Gly Gly Gln Gly Val Leu
                245                 250                 255

Thr Ala Asn Ala Gln Gly Gln Leu Glu Ser Gln Val Glu Met Gln Phe
            260                 265                 270

Phe Ser Thr Ser Glu Asn Ala Arg Asn Glu Ala Asn Asn Ile Gln Pro
        275                 280                 285

Lys Leu Val Leu Tyr Ser Glu Asp Val His Met Glu Thr Pro Asp Thr
    290                 295                 300

His Leu Ser Tyr Lys Pro Ala Lys Ser Asp Asp Asn Ser Lys Ile Met
305                 310                 315                 320

Leu Gly Gln Gln Ser Met Pro Asn Arg Pro Asn Tyr Ile Gly Phe Arg
                325                 330                 335

Asp Asn Phe Ile Gly Leu Met Tyr Tyr Asn Ser Thr Gly Asn Met Gly
            340                 345                 350

Val Leu Ala Gly Gln Ala Ser Gln Leu Asn Ala Val Val Asp Leu Gln
        355                 360                 365

Asp Arg Asn Thr Glu Leu Ser Tyr Gln Leu Leu Leu Asp Ser Met Gly
    370                 375                 380

Asp Arg Thr Arg Tyr Phe Ser Met Trp Asn Gln Ala Val Asp Ser Tyr
385                 390                 395                 400

Asp Pro Asp Val Arg Ile Ile Glu Asn His Gly Thr Glu Asp Glu Leu
                405                 410                 415

Pro Asn Tyr Cys Phe Pro Leu Gly Gly Ile Gly Val Thr Asp Thr Tyr
            420                 425                 430

Gln Ala Val Lys Thr Asn Asn Gly Asn Asn Gly Gly Gln Val Thr Trp
```

```
        435                 440                 445

Thr Lys Asp Glu Thr Phe Ala Asp Arg Asn Glu Ile Gly Val Gly Asn
    450                 455                 460

Asn Phe Ala Met Glu Ile Asn Leu Ser Ala Asn Leu Trp Arg Asn Phe
465                 470                 475                 480

Leu Tyr Ser Asn Val Ala Leu Tyr Leu Pro Asp Lys Leu Lys Tyr Asn
                485                 490                 495

Pro Ser Asn Val Asp Ile Ser Asp Asn Pro Asn Thr Tyr Asp Tyr Met
            500                 505                 510

Asn Lys Arg Val Val Ala Pro Gly Leu Val Asp Cys Tyr Ile Asn Leu
        515                 520                 525

Gly Ala Arg Trp Ser Leu Asp Tyr Met Asp Asn Val Asn Pro Phe Asn
    530                 535                 540

His His Arg Asn Ala Gly Leu Arg Tyr Arg Ser Met Leu Leu Gly Asn
545                 550                 555                 560

Gly Arg Tyr Val Pro Phe His Ile Gln Val Pro Gln Lys Phe Phe Ala
                565                 570                 575

Ile Lys Asn Leu Leu Leu Leu Pro Gly Ser Tyr Thr Tyr Glu Trp Asn
            580                 585                 590

Phe Arg Lys Asp Val Asn Met Val Leu Gln Ser Ser Leu Gly Asn Asp
        595                 600                 605

Leu Arg Val Asp Gly Ala Ser Ile Lys Phe Glu Ser Ile Cys Leu Tyr
    610                 615                 620

Ala Thr Phe Phe Pro Met Ala His Asn Thr Ala Ser Thr Leu Glu Ala
625                 630                 635                 640

Met Leu Arg Asn Asp Thr Asn Asp Gln Ser Phe Asn Asp Tyr Leu Ser
                645                 650                 655

Ala Ala Asn Met Leu Tyr Pro Ile Pro Ala Asn Ala Thr Asn Val Pro
            660                 665                 670

Ile Ser Ile Pro Ser Arg Asn Trp Ala Ala Phe Arg Gly Trp Ala Phe
        675                 680                 685

Thr Arg Leu Lys Thr Lys Glu Thr Pro Ser Leu Gly Ser Gly Phe Asp
    690                 695                 700

Pro Tyr Tyr Thr Tyr Ser Gly Ser Ile Pro Tyr Leu Asp Gly Thr Phe
705                 710                 715                 720

Tyr Leu Asn His Thr Phe Lys Lys Val Ser Val Thr Phe Asp Ser Ser
                725                 730                 735

Val Ser Trp Pro Gly Asn Asp Arg Leu Leu Thr Pro Asn Glu Phe Glu
            740                 745                 750

Ile Lys Arg Ser Val Asp Gly Glu Gly Tyr Asn Val Ala Gln Cys Asn
        755                 760                 765

Met Thr Lys Asp Trp Phe Leu Val Gln Met Leu Ala Asn Tyr Asn Ile
    770                 775                 780

Gly Tyr Gln Gly Phe Tyr Ile Pro Glu Ser Tyr Lys Asp Arg Met Tyr
785                 790                 795                 800

Ser Phe Phe Arg Asn Phe Gln Pro Met Ser Arg Gln Val Val Asp Gln
                805                 810                 815

Thr Lys Tyr Lys Asp Tyr Gln Glu Val Gly Ile Ile His Gln His Asn
            820                 825                 830

Asn Ser Gly Phe Val Gly Tyr Leu Ala Pro Thr Met Arg Glu Gly Gln
        835                 840                 845

Ala Tyr Pro Ala Asn Phe Pro Tyr Pro Leu Ile Gly Lys Thr Ala Val
    850                 855                 860
```

Asp Ser Ile Thr Gln Lys Lys Phe Leu Cys Asp Arg Thr Leu Trp Arg
865 870 875 880

Ile Pro Phe Ser Ser Asn Phe Met Ser Met Gly Ala Leu Ser Asp Leu
885 890 895

Gly Gln Asn Leu Leu Tyr Ala Asn Ser Ala His Ala Leu Asp Met Thr
900 905 910

Phe Glu Val Asp Pro Met Asp Glu Pro Thr Leu Leu Tyr Val Leu Phe
915 920 925

Glu Val Phe Asp Val Val Arg Val His Gln Pro His Arg Gly Val Ile
930 935 940

Glu Thr Val Tyr Leu Arg Thr Pro Phe Ser Ala Gly Asn Ala Thr Thr
945 950 955 960

<210> SEQ ID NO 12
<211> LENGTH: 543
<212> TYPE: PRT
<213> ORGANISM: Pan troglodytes

<400> SEQUENCE: 12

Met Lys Arg Thr Lys Thr Ser Asp Glu Ser Phe Asn Pro Val Tyr Pro
1 5 10 15

Tyr Asp Thr Glu Ser Gly Pro Pro Ser Val Pro Phe Leu Thr Pro Pro
20 25 30

Phe Val Ser Pro Asp Gly Phe Gln Glu Ser Pro Pro Gly Val Leu Ser
35 40 45

Leu Asn Leu Ala Glu Pro Leu Val Thr Ser His Gly Met Leu Ala Leu
50 55 60

Lys Met Gly Ser Gly Leu Ser Leu Asp Asp Ala Gly Asn Leu Thr Ser
65 70 75 80

Gln Asp Ile Thr Thr Ala Ser Pro Pro Leu Lys Lys Thr Lys Thr Asn
85 90 95

Leu Ser Leu Glu Thr Ser Ser Pro Leu Thr Val Ser Thr Ser Gly Ala
100 105 110

Leu Thr Val Ala Ala Ala Ala Pro Leu Ala Val Ala Gly Thr Ser Leu
115 120 125

Thr Met Gln Ser Glu Ala Pro Leu Thr Val Gln Asp Ala Lys Leu Thr
130 135 140

Leu Ala Thr Lys Gly Pro Leu Thr Val Ser Glu Gly Lys Leu Ala Leu
145 150 155 160

Gln Thr Ser Ala Pro Leu Thr Ala Ala Asp Ser Ser Thr Leu Thr Val
165 170 175

Ser Ala Thr Pro Pro Ile Asn Val Ser Ser Gly Ser Leu Gly Leu Asp
180 185 190

Met Glu Asp Pro Met Tyr Thr His Asp Gly Lys Leu Gly Ile Arg Ile
195 200 205

Gly Gly Pro Leu Arg Val Val Asp Ser Leu His Thr Leu Thr Val Val
210 215 220

Thr Gly Asn Gly Leu Thr Val Asp Asn Asn Ala Leu Gln Thr Arg Val
225 230 235 240

Thr Gly Ala Leu Gly Tyr Asp Thr Ser Gly Asn Leu Gln Leu Arg Ala
245 250 255

Ala Gly Gly Met Arg Ile Asp Ala Asn Gly Gln Leu Ile Leu Asn Val
260 265 270

Ala Tyr Pro Phe Asp Ala Gln Asn Asn Leu Ser Leu Arg Leu Gly Gln

```
        275                 280                 285

Gly Pro Leu Tyr Ile Asn Thr Asp His Asn Leu Asp Leu Asn Cys Asn
    290                 295                 300

Arg Gly Leu Thr Thr Thr Thr Thr Asn Asn Thr Lys Lys Leu Glu Thr
305                 310                 315                 320

Lys Ile Ser Ser Gly Leu Asp Tyr Asp Thr Asn Gly Ala Val Ile Ile
                325                 330                 335

Lys Leu Gly Thr Gly Leu Ser Phe Asp Asn Thr Gly Ala Leu Thr Val
            340                 345                 350

Gly Asn Thr Gly Asp Asp Lys Leu Thr Leu Trp Thr Thr Pro Asp Pro
        355                 360                 365

Ser Pro Asn Cys Arg Ile His Ser Asp Lys Asp Cys Lys Phe Thr Leu
    370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ala Ser Val
                405                 410                 415

Thr Ile Phe Leu Arg Phe Asp Gln Asn Gly Val Leu Met Glu Asn Ser
            420                 425                 430

Ser Leu Asp Arg Gln Tyr Trp Asn Phe Arg Asn Gly Asn Ser Thr Asn
        435                 440                 445

Ala Ala Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540
```

<210> SEQ ID NO 13
<211> LENGTH: 36182
<212> TYPE: DNA
<213> ORGANISM: Artificial Sequence
<220> FEATURE:
<223> OTHER INFORMATION: M72-ChAd3 construct

<400> SEQUENCE: 13

```
catcatcaat aatatacctt attttggatt gaagccaata tgataatgag atgggcggcg     60

cgaggcgggg cgcggggcgg gaggcgggtt tgggggcggg ccggcgggcg ggcggtgtg     120

gcggaagtgg actttgtaag tgtggcggat gtgacttgct agtgccgggc gcggtaaaag    180

tgacgttttc cgtgcgcgac aacgcccccg ggaagtgaca tttttcccgc ggtttttacc    240

ggatgttgta gtgaatttgg gcgtaaccaa gtaagatttg gccattttcg cgggaaaact    300

gaaacgggga agtgaaatct gattaatttt gcgttagtca taccgcgtaa tatttgtcta    360

gggccgaggg actttggccg attacgtgga ggactcgccc aggtgttttt tgaggtgaat    420

ttccgcgttc cgggtcaaag tctccgtttt attattatag gatatcccat tgcatacgtt    480

gtatccatat cataatatgt acatttatat tggctcatgt ccaacattac cgccatgttg    540

acattgatta ttgactagtt attaatagta atcaattacg gggtcattag ttcatagccc    600
```

```
atatatggag ttccgcgtta cataacttac ggtaaatggc ccgcctggct gaccgcccaa    660
cgacccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgccccat tgacgcaaat   1080
gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg gaacggtgca ttggaacgcg gattccccgt gccaagagtg agatcttccg   1320
tttatctagg taccagatat cgccaccatg accgccgcca gcgacaactt ccagctgtct   1380
cagggcggcc agggcttcgc catccctatc ggccaagcta tggccattgc tggacagatc   1440
agaagcggcg gaggcagccc taccgtgcat atcggcccta ccgccttcct gggcctgggc   1500
gtggtggaca acaacggcaa cggcgccaga gtgcagcggg tggtcggatc tgcccctgcc   1560
gcaagcctgg gcatcagcac cggggatgtg atcaccgccg tggatggcgc ccctatcaac   1620
agcgccacag ccatggccga cgccctgaat ggacaccacc ccggcgacgt gatcagcgtg   1680
acctggcaga ccaagagcgg aggcaccaga accggcaacg tgacactggc cgagggacct   1740
cccgccgagt tcatggtgga tttcggcgcc ctgccccccg agatcaactc cgccaggatg   1800
tatgccggcc ctggcagcgc ctctctggtg gccgctgctc agatgtggga cagcgtggcc   1860
agcgatctgt tcagcgccgc ctccgccttc cagtccgtgg tctggggcct gaccgtgggc   1920
agctggatcg gaagcagtgc cggcctgatg gtggctgccg cctctcccta cgtggcctgg   1980
atgtcagtca cagccggcca ggccgaactg actgccgctc aagtgcgagt ggctgctgct   2040
gcctatgaga cagcctacgg cctgacagtg cccccacccg tgatcgccga gaaccgggcc   2100
gagctgatga tcctgatcgc caccaacctg ctgggccaga acacccccgc cattgccgtg   2160
aacgaggccg agtacggcga gatgtgggcc caggacgccg ctgccatgtt tggctatgcc   2220
gctgctacag ccaccgccac tgccaccctg ctgcccttcg aagaggcccc cgagatgacc   2280
tctgccggcg gactgctgga acaggccgct gccgtggaag aggccagcga cacagccgcc   2340
gctaaccagc tgatgaacaa cgtgccccag gccctgcagc agctggcaca gcctacacag   2400
ggcaccaccc cttctagcaa gctcggcggc ctgtggaaaa ccgtgtcccc ccaccggtcc   2460
cccatcagca acatggtgtc catggccaac aaccacatga gcatgaccaa cagcggcgtg   2520
tccatgacca ataccctgag cagcatgctg aagggctttg ccccagccgc tgccgctcag   2580
gctgtgcaga cagctgctca gaatggcgtg cgggccatga gcagcctggg cagttccctg   2640
ggcagctctg gactgggagg gggcgtggcc gccaatctgg gcagagccgc tagcgtgggc   2700
agcctgtctg tgcctcaagc ctgggctgct gccaatcagg ccgtgacacc agccgctaga   2760
gccctgcctc tgaccagcct gacctctgct gccgagaggg gccctggcca gatgctggga   2820
ggactgcctg tgggccagat gggagccaga gccggcggag gactgagcgg cgtgctgaga   2880
gtgcccccca gaccctacgt gatgccccac tctcccgccg ctggcgatat tgcccctccc   2940
```

-continued

```
gccctgagcc aggacagatt cgccgacttc cctgccctgc ccctggatcc ttctgccatg   3000
gtggctcaag tgggacccca ggtggtgaac atcaacacca agctgggcta caacaacgcc   3060
gtgggagccg gcaccggcat cgtgatcgac cccaatggcg tggtgctgac caacaatcac   3120
gtgatcgctg gcgccaccga catcaacgcc ttcagcgtgg gctccggcca gacctacggc   3180
gtggacgtgg tcggatacga ccggacccag gatgtggccg tgctgcagct gagaggcgct   3240
ggcggactgc cttctgccgc cattggaggc ggagtggccg tgggagaacc tgtggtggcc   3300
atgggcaata gcggcggaca gggcggcaca cctagagctg tgcctggaag agtggtggcc   3360
ctgggacaga ccgtgcaggc cagcgatagc ctgacaggcg ccgaggaaac cctgaacggc   3420
ctgatccagt tcgacgccgc catccagcct ggggatgctg gcggacctgt ggtgaacgga   3480
ctgggccagg tggtcggaat gaataccgcc gcctcctaat agtgagcggc cgcgatctgc   3540
tgtgccttct agttgccagc catctgttgt ttgcccctcc cccgtgcctt ccttgaccct   3600
ggaaggtgcc actcccactg tcctttccta ataaaatgag gaaattgcat cgcattgtct   3660
gagtaggtgt cattctattc tggggggtgg ggtggggcag gacagcaagg gggaggattg   3720
ggaagacaat agcaggcatg ctggggatgc ggtgggctct agatatcagc gatcgctgag   3780
gtgggtgagt gggcgtggcc tggggtggtc atgaaaatat ataagttggg ggtcttaggg   3840
tctctttatt tgtgttgcag agaccgccgg agccatgagc gggagcagca gcagcagcag   3900
tagcagcagc gccttggatg gcagcatcgt gagcccttat ttgacgacgc ggatgcccca   3960
ctgggccggg gtgcgtcaga atgtgatggg ctccagcatc gacggccgac ccgtcctgcc   4020
cgcaaattcc gccacgctga cctatgcgac cgtcgcgggg acgccgttgg acgccaccgc   4080
cgccgccgcc gccaccgcag ccgcctcggc cgtgcgcagc ctggccacgg actttgcatt   4140
cctgggacca ctggcgacag gggctacttc tcgggccgct gctgccgccg ttcgcgatga   4200
caagctgacc gccctgctgg cgcagttgga tgcgcttact cgggaactgg gtgacctttc   4260
tcagcaggtc atggccctgc gccagcaggt ctcctccctg caagctggcg ggaatgcttc   4320
tcccacaaat gccgtttaag ataaataaaa ccagactctg tttggattaa agaaaagtag   4380
caagtgcatt gctctcttta tttcataatt ttccgcgcgc gataggccct agaccagcgt   4440
tctcggtcgt tgagggtgcg gtgtatcttc tccaggacgt ggtagaggtg gctctggacg   4500
ttgagataca tgggcatgag cccgtcccgg gggtggaggt agcaccactg cagagcttca   4560
tgctccgggg tggtgttgta gatgatccag tcgtagcagg agcgctgggc atggtgccta   4620
aaaatgtcct tcagcagcag gccgatggcc agggggaggc ccttggtgta agtgtttaca   4680
aaacggttaa gttgggaagg gtgcattcgg ggagagatga tgtgcatctt ggactgtatt   4740
tttagattgg cgatgtttcc gcccagatcc cttctgggat tcatgttgtg caggaccacc   4800
agtacagtgt atccggtgca cttggggaat ttgtcatgca gcttagaggg aaaagcgtgg   4860
aagaacttgg agacgccctt gtggcctccc agattttcca tgcattcgtc catgatgatg   4920
gcaatgggcc cgcgggaggc agcttgggca aagatatttc tggggtcgct gacgtcgtag   4980
ttgtgttcca gggtgaggtc gtcataggcc atttttacaa agcgcgggcg gagggtgccc   5040
gactggggga tgatggtccc ctctggccct ggggcgtagt tgccctcgca gatctgcatt   5100
tcccaggcct taatctcgga ggggggaatc atatccacct gcggggcgat gaagaaaacg   5160
gtttccggag ccggggagat taactgggat gagagcaggt ttctaagcag ctgtgatttt   5220
ccacaaccgg tgggcccata aataacacct ataaccggtt gcagctggta gtttagagag   5280
ctgcagctgc cgtcgtcccg gaggaggggg gccacctcgt tgagcatgtc cctgacgcgc   5340
```

atgttctccc cgaccagatc cgccagaagg cgctcgccgc ccagggacag cagctcttgc 5400
aaggaagcaa agtttttcag cggcttgagg ccgtccgccg tgggcatgtt tttcagggtc 5460
tggctcagca gctccaggcg gtcccagagc tcggtgacgt gctctacggc atctctatcc 5520
agcatatctc ctcgtttcgc gggttggggc gactttcgct gtagggcacc aagcggtggt 5580
cgtccagcgg ggccaaagtc atgtccttcc atgggcgcag ggtcctcgtc agggtggtct 5640
gggtcacggt gaaggggtgc gctccgggct gagcgcttgc caaggtgcgc ttgaggctgg 5700
ttctgctggt gctgaagcgc tgccggtctt cgccctgcgc gtcggccagg tagcatttga 5760
ccatggtgtc atagtccagc ccctccgcgg cgtgtccctt ggcgcgcagc ttgcccttgg 5820
aggtggcgcc gcacgagggg cagagcaggc tcttgagcgc gtagagcttg gggcgagga 5880
agaccgattc gggggagtag gcgtccgcgc cgcagacccc gcacacggtc tcgcactcca 5940
ccagccaggt gagctcgggg cgcgccgggt caaaaaccag gtttccccca tgctttttga 6000
tgcgtttctt acctcgggtc tccatgaggt ggtgtccccg ctcggtgacg aagaggctgt 6060
ccgtgtctcc gtagaccgac ttgaggggtc ttttctccag gggggtccct cggtcttcct 6120
cgtagaggaa ctcggaccac tctgagacga aggcccgcgt ccaggccagg acgaaggagg 6180
ctatgtggga ggggtagcgg tcgttgtcca ctagggggtc caccttctcc aaggtgtgaa 6240
gacacatgtc gccttcctcg gcgtccagga aggtgattgg cttgtaggtg taggccacgt 6300
gaccgggggt tcctgacggg ggggtataaa agggggtggg ggcgcgctcg tcgtcactct 6360
cttccgcatc gctgtctgcg agggccagct gctggggtga gtattccctc tcgaaggcgg 6420
gcatgacctc cgcgctgagg ttgtcagttt ccaaaaacga ggaggatttg atgttcacct 6480
gtcccgaggt gatacctttg agggtacccg cgtccatctg gtcagaaaac acgatctttt 6540
tattgtccag cttggtggcg aacgacccgt agagggcgtt ggagagcagc ttggcgatgg 6600
agcgcagggt ctggttcttg tccctgtcgg cgcgctcctt ggccgcgatg ttgagctgca 6660
cgtactcgcg cgcgacgcag cgccactcgg ggaagacggt ggtgcgctcg tcgggcacca 6720
ggcgcacgcg ccagccgcgg ttgtgcaggg tgaccaggtc cacgctggtg gcgacctcgc 6780
cgcgcaggcg ctcgttggtc cagcagagac ggccgccctt gcgcgagcag aagggggggca 6840
gggggtcgag ctgggtctcg tccgggggggt ccgcgtccac ggtgaaaacc ccggggcgca 6900
ggcgcgcgtc gaagtagtct atcttgcaac cttgcatgtc cagcgcctgc tgccagtcgc 6960
gggcggcgag cgcgcgctcg taggggttga gcggcgggcc ccagggcatg gggtgggtga 7020
gtgcggaggc gtacatgccg cagatgtcat agacgtagag gggctcccgc aggaccccga 7080
tgtaggtggg gtagcagcgg ccgccgcgga tgctggcgcg cacgtagtca tacagctcgt 7140
gcgagggggc gaggaggtcg gggcccaggt tggtgcgggc ggggcgctcc gcgcggaaga 7200
cgatctgcct gaagatggca tgcgagttgg aagagatggt ggggcgctgg aagacgttga 7260
agctggcgtc ctgcaggccg acggcgtcgc gcacgaagga ggcgtaggag tcgcgcagct 7320
tgtgtaccag ctcggcggtg acctgcacgt cgagcgcgca gtagtcgagg gtctcgcgga 7380
tgatgtcata tttagcctgc cccttctttt tccacagctc gcggttgagg acaaactctt 7440
cgcggtcttt ccagtactct tggatcggga aaccgtccgg ttccgaacgg taagagccta 7500
gcatgtagaa ctggttgacg gcctggtagg cgcagcagcc cttctccacg gggagggcgt 7560
aggcctgcgc ggccttgcgg agcgaggtgt gggtcagggc gaaggtgtcc ctgaccatga 7620
ctttgaggta ctggtgcttg aagtcggagt cgtcgcagcc gccccgctcc cagagcgaga 7680

```
agtcggtgcg cttcttggag cgggggttgg gcagagcgaa ggtgacatcg ttgaagagga   7740
ttttgcccgc gcggggcatg aagttgcggg tgatgcggaa gggccccggc acttcagagc   7800
ggttgttgat gacctgggcg gcgagcacga tctcgtcgaa gccgttgatg ttgtggccca   7860
cgatgtagag ttccaggaag cggggccggc cctttacggt gggcagcttc tttagctctt   7920
cgtaggtgag ctcctcgggc gaggcgaggc cgtgctcggc cagggcccag tccgcgaggt   7980
gcgggttgtc tctgaggaag gactcccaga ggtcgcgggc caggagggtc tgcaggcggt   8040
ccctgaaggt cctgaactgg cggcccacgg ccatttttc ggggggtgatg cagtagaagg   8100
tgagggggtc ttgctgccag cggtcccagt cgagctgcag ggcgaggtcg cgcgcggcgg   8160
tgaccaggcg ctcgtcgccc ccgaatttca tgaccagcat gaagggcacg agctgctttc   8220
cgaaggcccc catccaagtg taggtctcta catcgtaggt gacaaagagg cgctccgtgc   8280
gaggatgcga gccgatcggg aagaactgga tctcccgcca ccagttggag gagtggctgt   8340
tgatgtggtg gaagtagaag tcccgtcgcc gggccgaaca ctcgtgctgg cttttgtaaa   8400
agcgagcgca gtactggcag cgctgcacgg gctgtacctc ctgcacgaga tgcacctttc   8460
gcccgcgcac gaggaagccg aggggaaatc tgagcccccc gcctggctcg cggcatggct   8520
ggtgctcttc tactttggat gcgtgtccgt ctccgtctgg ctcctcgagg ggtgttacgg   8580
tggagcggac caccacgccg cgcgagccgc aggtccagat atcggcgcgc ggcggtcgga   8640
gtttgatgac gacatcgcgc agctgggagc tgtccatggt ctggagctcc cgcggcggcg   8700
gcaggtcagc cgggagttct tgcaggttca cctcgcagag tcgggccagg gcgcggggca   8760
ggtctaggtg gtacctgatc tctaggggcg tgttggtggc ggcgtcgatg gcttgcagga   8820
gcccgcatcc ccgggggggcg acgacggtgc cccgcggggt ggtggtggtg gtggtggtgg   8880
tggtggtggc ggtgcagctc agaagcggtg ccgcgggcgg gcccccggag gtaggggggg   8940
ctccggtccc gccggcaggg gcggcagcgg cacgtcggcg tggagcgcgg gcaggagttg   9000
gtgctgtgcc cggaggttgc tggcgaaggc gacgacgcgg cggttgatct cctggatctg   9060
gcgcctctgc gtgaagacga cgggcccggt gagcttgaac ctgaaagaga gttcgacaga   9120
atcaatctcg gtgtcattga ccgcggcctg gcgcaggatc tcctgcacgt ctcccgagtt   9180
gtcttggtag gcgatctcgg ccatgaactg ctcgatctct tcctcctgga ggtctccgcg   9240
tccggcgcgt tccacggtgg ccgccaggtc gttggagatg cgccccatga gctgcgagaa   9300
ggcgttgagt ccgccctcgt tccagactcg gctgtagacc acgccccccct ggtcatcgcg   9360
ggcgcgcatg accacctgcg cgaggttgag ctccacgtgc cgcgcgaaga cggcgtagtt   9420
gcgcagacgc tggaagaggt agttgagggt ggtggcggtg tgctcggcca cgaagaagtt   9480
catgacccag cggcgcaacg tggattcgtt gatgtccccc aaggcctcca gccgttccat   9540
ggcctcgtag aagtccacgg cgaagttgaa aaactgggag ttgcgcgccg acacggtcaa   9600
ctcctcctcc agaagacgga tgagctcggc gacggtgtcg cgcacctcgc gctcgaaggc   9660
tatggggatc tcttcctccg ctagcatcac cacctcctcc tcttcctcct cttctggcac   9720
ttccatgatg gcttcctcct cttcgggggg cggcggcggc ggcggtgggg gaggggggcgc   9780
tctgcgccgg cggcggcgca ccgggaggcg gtccacgaag cgcgcgatca tctccccgcg   9840
gcggcggcgc atggtctcgg tgacggcgcg gccgttctcc cgggggcgca gttggaagac   9900
gccgccggac atctggtgct ggggcgggtg gccgtgaggc agcgaaacgg cgctgacgat   9960
gcatctcaac aattgctgcg taggtacgcc gccgagggac ctgagggagt ccatatccac  10020
cggatccgaa aacctttcga ggaaggcgtc taaccagtcg cagtcgcaag gtaggctgag  10080
```

caccgtggcg ggcggcgggg ggtgggggga gtgtctggcg gaggtgctgc tgatgatgta 10140
attgaagtag gcggacttga cacggcggat ggtcgacagg agcaccatgt ccttgggtcc 10200
ggcctgctgg atgcggaggc ggtcggctat gccccaggct tcgttctggc atcggcgcag 10260
gtccttgtag tagtcttgca tgagcctttc caccggcacc tcttctcctt cctcttctgc 10320
ttcttccatg tctgcttcgg ccctggggcg gcgccgcgcc cccctgcccc ccatgcgcgt 10380
gaccccgaac cccctgagcg gttggagcag ggccaggtcg gcgacgacgc gctcggccag 10440
gatggcctgc tgcacctgcg tgagggtggt ttggaagtca tccaagtcca cgaagcggtg 10500
gtaggcgccc gtgttgatgg tgtaggtgca gttggccatg acggaccagt tgacggtctg 10560
gtggcccggt tgcgacatct cggtgtacct gagtcgcgag taggcgcggg agtcgaagac 10620
gtagtcgttg caagtccgca ccaggtactg gtagcccacc aggaagtgcg gcggcggctg 10680
gcggtagagg ggccagcgca gggtggcggg ggctccgggg gccaggtctt ccagcatgag 10740
gcggtggtag gcgtagatgt acctggacat ccaggtgata cccgcggcgg tggtggaggc 10800
gcgcgggaag tcgcgcaccc ggttccagat gttgcgcagg ggcagaaagt gctccatggt 10860
aggcgtgctc tgtccagtca gacgcgcgca gtcgttgata ctctagacca gggaaaacga 10920
aagccggtca gcgggcactc ttccgtggtc tggtgaatag atcgcaaggg tatcatggcg 10980
gagggcctcg gttcgagccc cgggtccggg ccggacggtc cgccatgatc cacgcggtta 11040
ccgcccgcgt gtcgaaccca ggtgtgcgac gtcagacaac ggtggagtgt tccttttggc 11100
gtttttctgg ccgggcgccg gcgtcgcgta agagactaag ccgcgaaagc gaaagcagta 11160
agtggctcgc tccccgtagc cggagggatc cttgctaagg gttgcgttgc ggcgaacccc 11220
ggttcgaatc ccgtactcgg gccggccgga cccgcggcta aggtgttgga ttggcctccc 11280
cctcgtataa agaccccgct tgcggattga ctccggacac ggggacgagc cccttttatt 11340
tttgctttcc ccagatgcat ccggtgctgc ggcagatgcg ccccccgccc cagcagcagc 11400
aacaacacca gcaagagcgg cagcaacagc agcgggagtc atgcagggcc ccctcaccca 11460
ccctcggcgg gccggccacc tcggcgtccg cggccgtgtc tggcgcctgc ggcggcggcg 11520
gggggccggc tgacgacccc gaggagcccc cgcggcgcag ggccagacac tacctggacc 11580
tggaggaggg cgagggcctg gcgcggctgg gggcgccgtc tcccgagcgc cacccgcggg 11640
tgcagctgaa gcgcgactcg cgcgaggcgt acgtgcctcg gcagaacctg ttcagggacc 11700
gcgcgggcga ggagcccgag gagatgcggg acaggaggtt cagcgcaggg cgggagctgc 11760
ggcaggggct gaaccgcgag cggctgctgc gcgaggagga ctttgagccc gacgcgcgga 11820
cggggatcag ccccgcgcgc gcgcacgtgg cggccgccga cctggtgacg gcgtacgagc 11880
agacggtgaa ccaggagatc aacttccaaa agagtttcaa caaccacgtg cgcacgctgg 11940
tggcgcgcga ggaggtgacc atcgggctga tgcacctgtg ggactttgta agcgcgctgg 12000
tgcagaaccc caacagcaag cctctgacgg cgcagctgtt cctgatagtg cagcacagca 12060
gggacaacga ggcgtttagg gacgcgctgc tgaacatcac cgagcccgag ggtcggtggc 12120
tgctggacct gattaacatc ctgcagagca tagtggtgca ggagcgcagc ctgagcctgg 12180
ccgacaaggt ggcggccatc aactactcga tgctgagcct gggcaagttt tacgcgcgca 12240
agatctacca gacgccgtac gtgcccatag acaaggaggt gaagatcgac ggtttttaca 12300
tgcgcatggc gctgaaggtg ctcaccctga gcgacgacct gggcgtgtac cgcaacgagc 12360
gcatccacaa ggccgtgagc gtgagccggc ggcgcgagct gagcgaccgc gagctgatgc 12420
acagcctgca gcgggcgctg gcgggcgccg gcagcggcga cagggaggcg gagtcctact 12480
tcgatgcggg ggcggacctg cgctgggcgc ccagccggcg ggccctggag gccgcggggg 12540
tccgcgagga ctatgacgag gacggcgagg aggatgagga gtacgagcta gaggagggcg 12600
agtacctgga ctaaaccgcg ggtggtgttt ccggtagatg caagacccga acgtggtgga 12660
cccggcgctg cgggcggctc tgcagagcca gccgtccggc cttaactcct cagacgactg 12720
gcgacaggtc atggaccgca tcatgtcgct gacggcgcgt aacccggacg cgttccggca 12780
gcagccgcag gccaacaggc tctccgccat cctggaggcg gtggtgcctg cgcgctcgaa 12840
ccccacgcac gagaaggtgc tggccatagt gaacgcgctg gccgagaaca gggccatccg 12900
cccggacgag gccgggctgg tgtacgacgc gctgctgcag cgcgtggccc gctacaacag 12960
cggcaacgtg cagaccaacc tggaccggct ggtgggggac gtgcgcgagg cggtggcgca 13020
gcgcgagcgc gcggatcggc agggcaacct gggctccatg gtggcgctga atgccttcct 13080
gagcacgcag ccggccaacg tgccgcgggg gcaggaagac tacaccaact ttgtgagcgc 13140
gctgcggctg atggtgaccg agacccccca gagcgaggtg taccagtcgg gcccggacta 13200
cttcttccag accagcagac agggcctgca gacggtgaac ctgagccagg ctttcaagaa 13260
cctgcggggg ctgtggggcg tgaaggcgcc caccggcgac cgggcgacgg tgtccagcct 13320
gctgacgccc aactcgcgcc tgctgctgct gctgatcgcg ccgttcacgg acagcggcag 13380
cgtgtcccgg gacacctacc tggggcacct gctgaccctg taccgcgagg ccatcgggca 13440
ggcgcaggtg gacgagcaca ccttccagga gatcaccagc gtgagccgcg cgctggggca 13500
ggaggacacg agcagcctgg aggcgactct gaactacctg ctgaccaacc ggcggcagaa 13560
gattccctcg ctgcacagcc tgacctccga ggaggagcgc atcttgcgct acgtgcagca 13620
gagcgtgagc ctgaacctga tgcgcgacgg ggtgacgccc agcgtggcgc tggacatgac 13680
cgcgcgcaac atggaaccgg gcatgtacgc cgcgcaccgg ccttacatca accgcctgat 13740
ggactacctg catcgcgcgg cggccgtgaa ccccgagtac tttaccaacg ccatcctgaa 13800
cccgcactgg ctcccgccgc ccgggttcta cagcgggggc ttcgaggtcc cggaggccaa 13860
cgatggcttc ctgtgggacg acatggacga cagcgtgttc tccccgcggc cgcaggcgct 13920
ggcggaagcg tccctgctgc gtcccaagaa ggaggaggag gaggcgagtc gccgccgcgg 13980
cagcagcggc gtggcttctc tgtccgagct gggggcggca gccgccgcgc gccccgggtc 14040
cctgggcggc agcccctttc cgagcctggt ggggtctctg cacagcgagc gcaccacccg 14100
ccctcggctg ctgggcgagg acgagtacct gaataactcc ctgctgcagc cggtgcggga 14160
gaaaaacctg ccccccgcct tccccaacaa cgggatagag agcctggtgg acaagatgag 14220
cagatggaag acctatgcgc aggagcacag ggacgcgccc gcgctccggc cgcccacgcg 14280
gcgccagcgc cacgaccggc agcgggggct ggtgtgggat gacgaggact ccgcggacga 14340
tagcagcgtg ctggacctgg gagggagcgg caacccgttc gcgcacctgc gcccccgcct 14400
ggggaggatg ttttaaaaaa aaaaaaagca agaagcatga tgcaaaatta aataaaactc 14460
accaaggcca tggcgaccga gcgttggttt cttgtgttcc cttcagtatg cggcgcgcgg 14520
cgatgtacca ggagggacct cctccctctt acgagagcgt ggtgggcgcg gcggcggcgg 14580
cgccctcttc tccctttgcg tcgcagctgc tggagccgcc gtacgtgcct ccgcgctacc 14640
tgcggcctac ggggggggaga aacagcatcc gttactcgga gctggcgccc ctgttcgaca 14700
ccacccgggt gtacctggtg gacaacaagt cggcggacgt ggcctccctg aactaccaga 14760
acgaccacag caattttttg accacggtca tccagaacaa tgactacagc ccgagcgagg 14820
ccagcaccca gaccatcaat ctggatgacc ggtcgcactg gggcggcgac ctgaaaacca 14880
tcctgcacac caacatgccc aacgtgaacg agttcatgtt caccaataag ttcaaggcgc 14940
gggtgatggt gtcgcgctcg cacaccaagg aagaccgggt ggagctgaag tacgagtggg 15000
tggagttcga gctgccagag ggcaactact ccgagaccat gaccattgac ctgatgaaca 15060
acgcgatcgt ggagcactat ctgaaagtgg gcaggcaaaa cggggtcctg gagagcgaca 15120
tcggggtcaa gttcgacacc aggaacttcc gcctggggct ggaccccgtg accgggctgg 15180
ttatgcccgg ggtgtacacc aacgaggcct tccatcccga catcatcctg ctgcccggct 15240
gcggggtgga cttcacttac agccgcctga gcaacctcct gggcatccgc aagcggcagc 15300
ccttccagga gggcttcagg atcacctacg aggacctgga ggggggcaac atccccgcgc 15360
tcctcgatgt ggaggcctac caggatagct tgaaggaaaa tgaggcggga caggaggata 15420
ccacccccgc cgcctccgcc gccgccgagc agggcgagga tgctgctgac accgcggccg 15480
cggacggggc agaggccgac cccgctatgg tggtggaggc tcccgagcag gaggaggata 15540
tgaatgacag tgcggtgcgc ggagacacct tcgtcacccg gggggaggaa aagcaagcgg 15600
aggccgaggc cgcggccgag gaaaagcaac tggcggcagc agcggcggcg gcggcgttgg 15660
ccgcggcgga ggctgagtct gaggggacca agcccgccaa ggagcccgtg attaagcccc 15720
tgaccgaaga tagcaagaag cgcagttaca acctgctcaa ggacagcacc aacaccgcgt 15780
accgcagctg gtacctggcc tacaactacg gcgacccgtc gacgggggtg cgctcctgga 15840
ccctgctgtg cacgccggac gtgacctgcg gctcggagca ggtgtactgg tcgctgcccg 15900
acatgatgca agaccccgtg accttccgct ccacgcggca ggtcagcaac ttcccggtgg 15960
tgggcgccga gctgctgccc gtgcactcca agagcttcta caacgaccag gccgtctact 16020
cccagctcat ccgccagttc acctctctga cccacgtgtt caatcgcttt cctgagaacc 16080
agattctggc gcgcccgccc gcccccacca tcaccaccgt cagtgaaaac gttcctgctc 16140
tcacagatca cgggacgcta ccgctgcgca acagcatcgg aggagtccag cgagtgaccg 16200
ttactgacgc cagacgccgc acctgcccct acgtttacaa ggccttgggc atagtctcgc 16260
cgcgcgtcct ttccagccgc actttttgag caacaccacc atcatgtcca tcctgatctc 16320
acccagcaat aactccggct ggggactgct gcgcgcgccc agcaagatgt tcggaggggc 16380
gaggaagcgt tccgagcagc accccgtgcg cgtgcgcggg cacttccgcg ccccctgggg 16440
agcgcacaaa cgcggccgcg cggggcgcac caccgtggac gacgccatcg actcggtggt 16500
ggagcaggcg cgcaactaca ggcccgcggt ctctaccgtg gacgcggcca tccagaccgt 16560
ggtgcggggc gcgcggcggt acgccaagct gaagagccgc cggaagcgcg tggcccgccg 16620
ccaccgccgc cgacccgggg ccgccgccaa acgcgccgcc gcggccctgc ttcgccgggc 16680
caagcgcacg ggccgccgcg ccgccatgag ggccgcgcgc cgcttggccg ccggcatcac 16740
cgccgccacc atggcccccc gtacccgaag acgcgcggcc gccgccgccg ccgccgccat 16800
cagtgacatg gccagcaggc gccggggcaa cgtgtactgg gtgcgcgact cggtgaccgg 16860
cacgcgcgtg cccgtgcgct tccgcccccc gcggacttga gatgatgtga aaaaacaaca 16920
ctgagtctcc tgctgttgtg tgtatcccag cggcggcggc gcgcgcagcg tcatgtccaa 16980
gcgcaaaatc aaagaagaga tgctccaggt cgtcgcgccg gagatctatg ggcccccgaa 17040
gaaggaagag caggattcga agccccgcaa gataaagcgg gtcaaaaaga aaaagaaaga 17100
tgatgacgat gccgatgggg aggtggagtt cctgcgcgcc acggcgccca ggcgcccggt 17160
gcagtggaag ggccggcgcg taaagcgcgt cctgcgcccc ggcaccgcgg tggtcttcac 17220
gcccggcgag cgctccaccc ggactttcaa gcgcgtctat gacgaggtgt acggcgacga 17280
agacctgctg gagcaggcca acgagcgctt cggagagttt gcttacggga agcgtcagcg 17340
ggcgctgggg aaggaggacc tgctggcgct gccgctggac cagggcaacc ccaccccag 17400 tctgaagccc gtgaccctgc agcaggtgct gccgagcagc gcaccctccg aggcgaagcg 17460
gggtctgaag cgcgagggcg gcgacctggc gcccaccgtg cagctcatgg tgcccaagcg 17520
gcagaggctg gaggatgtgc tggagaaaat gaaagtagac cccggtctgc agccggacat 17580
cagggtccgt cccatcaagc aggtggcgcc gggcctcggc gtgcagaccg tggacgtggt 17640
catccccacc ggcaactccc ccgccgccac caccactacc gctgcctcca cggacatgga 17700
gacacagacc gatcccgccg cagccgcagc cgccgccgca gccgcgacct cctcggcgga 17760
ggtgcagacg gacccctggc tgccgccggc gatgtcagct ccccgcgcgc gccgcggacg 17820
cagaaagtac ggcgccgcca acgcgctcct gcccgagtac gccttgcatc cttccatcgc 17880
gcccaccccc ggctaccgag gctataccta ccgcccgcga agagccaagg gttccacccg 17940
ccgtccccgc cgacgcgccg ccgccaccac ccgccgccgc cgccgcagac gccagcccgc 18000
actggctcca gtctccgtga ggagagtggc gcgcgacgga cacaccctgg tgctgcccag 18060
ggcgcgctac caccccagca tcgtttaaaa gcctgttgtg gttcttgcag atatggccct 18120
cacttgccgc ctccgtttcc cggtgccggg ataccgagga ggaagatcgc gccgcaggag 18180
gggtctggcc ggccgcggcc tgagcggagg cagccgccgc gcgcaccggc ggcgacgcgc 18240
caccagccga cgcatgcgcg gcggggtgct gcccctgtta atcccccctga tcgccgcggc 18300 gatcggcgcc gtgcccggga tcgcctccgt ggccttgcaa gcgtcccaga ggcattgaca 18360
gacttgcaaa cttgcaaata tggaaaaaaa aaaaaaaccc caataaaaag tctagactct 18420
cacgctcgct tggtcctgtg actattttgt agaatggaag acatcaactt tgcgtcgctg 18480
gccccgcgtc acggctcgcg cccgttcctg ggacactgga acgatatcgg caccagcaac 18540
atgagcggtg gcgccttcag ttggggctct ctgtggagcg gcattaaaag tatcgggtct 18600
gccgttaaaa attacggctc ccgggcctgg aacagcagca cgggccagat gttgagagac 18660
aagttgaaag agcagaactt ccagcagaag gtggtggagg gcctggcctc cggcatcaac 18720
ggggtggtgg acctggccaa ccaggccgtg cagaataaaa tcaacagcag actggacccc 18780
cggccgccgg tggaggaggt gccgccggcg ctggagacgg tgtcccccga tgggcgtggc 18840
gagaagcgcc cgcggcccga tagggaagag accactctgg tcacgcagac cgatgagccg 18900
cccccgtatg aggaggccct aaagcaaggt ctgcccacca cgcggcccat cgcgcccatg 18960
gccaccgggg tggtgggccg ccacaccccc gccacgctgg acttgcctcc gcccgccgat 19020
gtgccgcagc agcagaaggc ggcacagccg ggcccgcccg cgaccgcctc ccgttcctcc 19080
gccggtcctc tgcgccgcgc ggccagcggc ccccgcgggg gggtcgcgag gcacggcaac 19140
tggcagagca cgctgaacag catcgtgggt ctgggggtgc ggtccgtgaa gcgccgccga 19200
tgctactgaa tagcttagct aacgtgttgt atgtgtgtat gcgccctatg tcgccgccag 19260
aggagctgct gagtcgccgc cgttcgcgcg cccaccacca ccgccactcc gcccctcaag 19320
atggcgaccc catcgatgat gccgcagtgg tcgtacatgc acatctcggg ccaggacgcc 19380
tcggagtacc tgagccccgg gctggtgcag ttcgcccgcg ccaccgagag ctacttcagc 19440
ctgagtaaca agtttaggaa ccccacggtg gcgcccacgc acgatgtgac caccgaccgg 19500
tctcagcgcc tgacgctgcg gttcattccc gtggaccgcg aggacaccgc gtactcgtac 19560
aaggcgcggt tcaccctggc cgtgggcgac aaccgcgtgc tggacatggc ctccacctac 19620
tttgacatcc gcggggtgct ggaccggggt cccactttca agccctactc tggcaccgcc 19680
tacaactccc tggcccccaa gggcgctccc aactcctgcg agtgggagca agaggaaact 19740
caggcagttg aagaagcagc agaagaggaa gaagaagatg ctgacggtca agctgaggaa 19800
gagcaagcag ctaccaaaaa gactcatgta tatgctcagg ctcccctttc tggcgaaaaa 19860
attagtaaag atggtctgca aataggaacg gacgctacag ctacagaaca aaaacctatt 19920
tatgcagacc ctacattcca gcccgaaccc caaatcgggg agtcccagtg gaatgaggca 19980
gatgctacag tcgccggcgg tagagtgcta aagaaatcta ctcccatgaa accatgctat 20040
ggttcctatg caagacccac aaatgctaat ggaggtcagg gtgtactaac ggcaaatgcc 20100
cagggacagc tagaatctca ggttgaaatg caattctttt caacttctga aaacgcccgt 20160
aacgaggcta acaacattca gcccaaattg gtgctgtata gtgaggatgt gcacatggag 20220
accccggata cgcacctttc ttacaagccc gcaaaaagcg atgacaattc aaaaatcatg 20280
ctgggtcagc agtccatgcc caacagacct aattacatcg gcttcagaga caactttatc 20340
ggcctcatgt attacaatag cactggcaac atgggagtgc ttgcaggtca ggcctctcag 20400
ttgaatgcag tggtggactt gcaagacaga aacacagaac tgtcctacca gctcttgctt 20460
gattccatgg gtgacagaac cagatacttt tccatgtgga atcaggcagt ggacagttat 20520
gacccagatg ttagaattat tgaaaatcat ggaactgaag acgagctccc caactattgt 20580
ttccctctgg gtggcatagg ggtaactgac acttaccagg ctgttaaaac caacaatggc 20640
aataacgggg gccaggtgac ttggacaaaa gatgaaactt ttgcagatcg caatgaaata 20700
ggggtgggaa acaatttcgc tatggagatc aacctcagtg ccaacctgtg gagaaacttc 20760
ctgtactcca acgtggcgct gtacctacca gacaagctta agtacaaccc ctccaatgtg 20820
gacatctctg acaaccccaa cacctacgat tacatgaaca agcgagtggt ggccccgggg 20880
ctggtggact gctacatcaa cctgggcgcg cgctggtcgc tggactacat ggacaacgtc 20940
aacccettca accaccaccg caatgcgggc ctgcgctacc gctccatgct cctgggcaac 21000
gggcgctacg tgcccttcca catccaggtg ccccagaagt tctttgccat caagaacctc 21060
ctcctcctgc cgggctccta cacctacgag tggaacttca ggaaggatgt caacatggtc 21120
ctccagagct ctctgggtaa cgatctcagg gtggacgggg ccagcatcaa gttcgagagc 21180
atctgcctct acgccacctt cttccccatg gcccacaaca cggcctccac gctcgaggcc 21240
atgctcagga acgacaccaa cgaccagtcc ttcaatgact acctttccgc cgccaacatg 21300
ctctacccca tacccgccaa cgccaccaac gtccccatct ccatcccctc gcgcaactgg 21360
gcggccttcc gcggctgggc cttcacccgc ctcaagacca aggagacccc ctccctgggc 21420
tcgggattcg acccctacta cacctactcg ggctctattc cctacctgga cggcaccttc 21480
tacctcaacc acactttcaa gaaggtctcg gtcaccttcg actcctcggt cagctggccg 21540
ggcaacgacc gtctgctcac ccccaacgag ttcgagatca agcgctcggt cgacggggaa 21600
ggctacaacg tggcccagtg caacatgacc aaggactggt tcctggtcca gatgctggcc 21660
aactacaaca tcggctacca gggcttctac atcccagaga gctacaagga caggatgtac 21720
tccttcttca ggaacttcca gcccatgagc cggcaggtgg tggaccagac caagtacaag 21780
gactaccagg aggtgggcat catccaccag cacaacaact cgggcttcgt gggctacctc 21840
gcccccacca tgcgcgaggg acaggcctac cccgccaact tcccctaccc gctcataggc 21900
aagaccgcgg tcgacagcat cacccagaaa aagttcctct gcgaccgcac cctctggcgc 21960
atccccttct ccagcaactt catgtccatg ggtgcgctct cggacctggg ccagaacttg 22020
ctctacgcca actccgccca cgccctcgac atgaccttcg aggtcgaccc catggacgag 22080
cccacccttc tctatgttct gttcgaagtc tttgacgtgg tccgggtcca ccagccgcac 22140
cgcggcgtca tcgagaccgt gtacctgcgt acgcccttct cggccggcaa cgccaccacc 22200
taaagaagca agccgcagtc atcgccgcct gcatgccgtc gggttccacc gagcaagagc 22260
tcagggccat cgtcagagac ctgggatgcg ggccctattt tttgggcacc ttcgacaagc 22320
gcttccctgg ctttgtctcc ccacacaagc tggcctgcgc catcgtcaac acggccggcc 22380
gcgagaccgg gggcgtgcac tggctggcct ttgcctggaa cccgcgctcc aaaacatgct 22440
tcctctttga ccccttcggc ttttcggacc agcggctcaa gcaaatctac gagttcgagt 22500
acgagggctt gctgcgtcgc agcgccatcg cctcctcgcc cgaccgctgc gtcaccctcg 22560
aaaagtccac ccagaccgtg caggggcccg actcggccgc ctgcggtctc ttctgctgca 22620
tgtttctgca cgcctttgtg cactggcctc agagtcccat ggaccgcaac cccaccatga 22680
acttgctgac gggggtgccc aactccatgc tccaaagccc ccaggtcgag cccaccctgc 22740
gccgcaacca ggagcagctc tacagcttcc tggagcgcca ctcgccctac ttccgccgcc 22800
acagcgcaca gatcaggagg gccacctcct tctgccactt gcaagagatg caagaagggt 22860
aataacgatg tacacacttt tttctcaata aatggcattt tttttttatt tatacaagct 22920
ctctggggta ttcatttccc accaccacca cccgccgttg tcgccatctg gctctattta 22980
gaaatcgaaa gggttctgcc gggagtcgcc gtgcgccacg ggcagggaca cgttgcgata 23040
ctggtagcgg gtgccccact tgaactcggg caccaccagg cgaggcagct cggggaagtt 23100
ttcgctccac aggctgcggg tcagcaccag cgcgttcatc aggtcgggcg ccgagatctt 23160
gaagtcgcag ttggggccgc cgccctgcgc gcgcgagttg cggtacaccg ggttgcagca 23220
ctggaacacc aacagcgccg ggtgcttcac gctggccagc acgctgcggt cggagatcag 23280
ctcggcgtcc aggtcctccg cgttgctcag cgcgaacggg gtcatcttgg gcacttgccg 23340
ccccaggaag ggcgcgtgcc ccggtttcga gttgcagtcg cagcgcagcg ggatcagcag 23400
gtgcccgtgc ccggactcgg cgttggggta cagcgcgcgc atgaaggcct gcatctggcg 23460
gaaggccatc tgggccttgg cgccctccga gaagaacatg ccgcaggact tgcccgagaa 23520
ctggtttgcg gggcagctgg cgtcgtgcag gcagcagcgc gcgtcggtgt tggcgatctg 23580
caccacgttg cgcccccacc ggttcttcac gatcttggcc ttggacgatt gctccttcag 23640
cgcgcgctgc ccgttctcgc tggtcacatc catctcgatc acatgttcct tgttcaccat 23700
gctgctgccg tgcagacact tcagctcgcc ctccgtctcg gtgcagcggt gctgccacag 23760
cgcgcagccc gtgggctcga aagacttgta ggtcacctcc gcgaaggact gcaggtaccc 23820
ctgcaaaaag cggcccatca tggtcacgaa ggtcttgttg ctgctgaagg tcagctgcag 23880
cccgcggtgc tcctcgttca gccaggtctt gcacacggcc gccagcgcct ccacctggtc 23940
gggcagcatc ttgaagttca ccttcagctc attctccacg tggtacttgt ccatcagcgt 24000
gcgcgccgcc tccatgccct tctcccaggc cgacaccagc ggcaggctca cggggttctt 24060
caccatcacc gtggccgccg cctccgccgc gctttcgctt tccgccccgc tgttctcttc 24120
ctcttcctcc tcttcctcgc cgccgcccac tcgcagcccc cgcaccacgg ggtcgtcttc 24180
ctgcaggcgc tgcaccttgc gcttgccgtt gcgcccctgc ttgatgcgca cgggcgggtt 24240
gctgaagccc accatcacca gcgcggcctc ttcttgctcg tcctcgctgt ccagaatgac 24300
ctccggggag ggggggttgg tcatcctcag taccgaggca cgcttctttt tcttcctggg 24360
ggcgttcgcc agctccgcgg ctgcggccgc tgccgaggtc gaaggccgag ggctgggcgt 24420
gcgcggcacc agcgcgtctt gcgagccgtc ctcgtcctcc tcggactcga gacggaggcg 24480
ggcccgcttc ttcgggggcg cgcggggcgg cggaggcggc ggcggcgacg gagacgggga 24540
cgagacatcg tccagggtgg gtggacggcg ggccgcgccg cgtccgcgct cgggggtggt 24600
ttcgcgctgg tcctcttccc gactggccat ctcccactgc tccttctcct ataggcagaa 24660
agagatcatg gagtctctca tgcgagtcga gaaggaggag gacagcctaa ccgccccctc 24720
tgagccctcc accaccgccg ccaccaccgc caatgccgcc gcggacgacg cgcccaccga 24780
gaccaccgcc agtaccaccc tccccagcga cgcacccccg ctcgagaatg aagtgctgat 24840
cgagcaggac ccgggttttg tgagcggaga ggaggatgag gtggatgaga aggagaagga 24900
ggaggtcgcc gcctcagtgc caaaagagga taaaaagcaa gaccaggacg acgcagataa 24960
ggatgagaca gcagtcgggc gggggaacgg aagccatgat gctgatgacg gctacctaga 25020
cgtgggagac gacgtgctgc ttaagcacct gcaccgccag tgcgtcatcg tctgcgacgc 25080
gctgcaggag cgctgcgaag tgcccctgga cgtggcggag gtcagccgcg cctacgagcg 25140
gcacctcttc gcgccgcacg tgccccccaa gcgccgggag aacggcacct gcgagcccaa 25200
cccgcgtctc aacttctacc cggtcttcgc ggtacccgag gtgctggcca cctaccacat 25260
cttcttccaa aactgcaaga tcccccctctc ctgccgcgct aaccgcaccc gcgccgacaa 25320
aaccctgacc ctgcggcagg gcgcccacat acctgatatt gcctctctgg aggaagtgcc 25380
caagatcttc gagggtctcg gtcgcgacga gaaacgggcg gcgaacgctc tgcacggaga 25440
cagcgaaaac gagagtcact cgggggtgct ggtggagctc gagggcgaca acgcgcgcct 25500
ggccgtactc aagcgcagca tagaggtcac ccactttgcc tacccggcgc tcaacctgcc 25560
ccccaaggtc atgagtgtgg tcatgggcga gctcatcatg cgccgcgctc agcccctggc 25620
cgcggatgca aacttgcaag agtcctccga ggaaggcctg cccgcggtca gcgacgagca 25680
gctagcgcgc tggctggaga cccgcgaccc cgcgcagctg gaggagcggc gcaagctcat 25740
gatggccgcg gtgctggtca ccgtggagct cgagtgtctg cagcgcttct tcgcggaccc 25800
cgagatgcag cgcaagctcg aggagaccct gcactacacc ttccgccagg gctacgtgcg 25860
ccaggcctgc aagatctcca acgtggagct ctgcaacctg gtctcctacc tgggcatcct 25920
gcacgagaac cgcctcgggc agaacgtcct gcactccacc ctcaaagggg aggcgcgccg 25980
cgactacatc cgcgactgcg cctacctctt cctctgctac acctggcaga cggccatggg 26040
ggtctggcag cagtgcctgg aggagcgcaa cctcaaggag ctggaaaagc tactcaagcg 26100
caccctcagg gacctctgga cgggcttcaa cgagcgctcg gtggccgccg cgctggcgga 26160
catcatcttc cccgagcgcc tgctcaagac cctgcagcag ggcctgcccg acttcaccag 26220
ccagagcatg ctgcagaact ttaggacttt catcctggag cgctcgggca tcctgcctgc 26280
cacttgctgc gcgctgccca gcgacttcgt gcccatcaag tacagggagt gcccgccgcc 26340
gctctggggc cactgctacc tcttccagct ggccaactac ctcgcctacc actcggacct 26400
catggaagac gtgagcggcg agggcctgct cgagtgccac tgccgctgca acctctgcac 26460
gccccaccgc tctctagtct gcaacccgca gctgctcagc gagagtcaga ttatcggtac 26520
cttcgagctg cagggtccct cgcctgacga gaagtccgcg gctccggggc tgaaactcac 26580
tccggggctg tggacttccg cctacctacg caaatttgta cctgaggact accacgccca 26640

```
cgagatcagg ttctacgaag accaatcccg cccgcccaag gcggagctca ccgcctgcgt  26700
catcacccag gggcacatcc tgggccaatt gcaagccatc aacaaagccc gccgagagtt  26760
cttgctgaaa aagggtcggg gggtgtacct ggaccccag tccggcgagg agctaaaccc  26820
gctacccccg ccgccgcccc agcagcggga ccttgcttcc caggatggca cccagaaaga  26880
agcagcagcc gccgccgccg cagccataca tgcttctgga ggaagaggag gaggactggg  26940
acagtcaggc agaggaggtt tcggacgagg agcaggagga gatgatggaa gactgggagg  27000
aggacagcag cctagacgag gaagcttcag aggccgaaga ggtggcagac gcaacaccat  27060
caccctcggt cgcagccccc tcgccggggc ccctgaaatc ctccgaaccc agcaccagcg  27120
ctataacctc cgctcctccg gcgccggcgc cacccgcccg cagacccaac cgtagatggg  27180
acaccacagg aaccggggtc ggtaagtcca agtgcccgcc gccgccaccg cagcagcagc  27240
agcagcgcca gggctaccgc tcgtggcgcg ggcacaagaa cgccatagtc gcctgcttgc  27300
aagactgcgg gggcaacatc tctttcgccc ggcgcttcct gctattccac cacggggtcg  27360
cctttccccg caatgtcctg cattactacc gtcatctcta cagcccctac tgcagcggcg  27420
acccagaggc ggcagcggca gccacagcgg cgaccaccac ctaggaagat atcctccgcg  27480
ggcaagacag cggcagcagc ggccaggaga cccgcggcag cagcggcggg agcggtgggc  27540
gcactgcgcc tctcgcccaa cgaacccctc tcgacccggg agctcagaca caggatcttc  27600
cccactttgt atgccatctt ccaacagagc agaggccagg agcaggagct gaaaataaaa  27660
aacagatctc tgcgctccct cacccgcagc tgtctgtatc acaaaagcga agatcagctt  27720
cggcgcacgc tggaggacgc ggaggcactc ttcagcaaat actgcgcgct cactcttaaa  27780
gactagctcc gcgcccttct cgaatttagg cgggagaaaa ctacgtcatc gccggccgcc  27840
gcccagcccg cccagccgag atgagcaaag agattcccac gccatacatg tggagctacc  27900
agccgcagat gggactcgcg gcgggagcgg cccaggacta ctccacccgc atgaactaca  27960
tgagcgcggg accccacatg atctcacagg tcaacgggat ccgcgcccag cgaaaccaaa  28020
tactgctgga acaggcggcc atcaccgcca cgccccgcca taatctcaac ccccgaaatt  28080
ggcccgccgc cctcgtgtac caggaaaccc cctccgccac caccgtacta cttccgcgtg  28140
acgcccaggc cgaagtccag atgactaact caggggcgca gctcgcgggc ggctttcgtc  28200
acggggcgcg gccgctccga ccaggtataa gacacctgat gatcagaggc cgaggtatcc  28260
agctcaacga cgagtcggtg agctcttcgc tcggtctccg tccggacgga actttccagc  28320
tcgccggatc cggccgctct tcgttcacgc cccgccaggc gtacctgact ctgcagacct  28380
cgtcctcgga gccccgctcc ggaggcatcg gaaccctcca gttcgtggag gagttcgtgc  28440
cctcggtcta cttcaacccc ttctcgggac ctcccggacg ctaccccgac cagttcattc  28500
cgaactttga cgcggtgaag gactcggcgg acggctacga ctgaatgtca ggtgccgagg  28560
cagagcagct tcgcctgaga cacctcgagc actgccgccg ccacaagtgc ttcgcccgcg  28620
gttccggtga gttctgctac tttcagctac ccgaggagca taccgagggg ccggcgcacg  28680
gcgtccgcct gaccacccag ggcgaggtta cctgttccct catccgggag ttcaccctcc  28740
gtcccctgct agtggagcgg gagcggggtc cctgtgtcct aactatcgcc tgcaactgcc  28800
ctaaccctgg attacatcaa gatctttgct gtcatctctg tgctgagttt aataaacgct  28860
gagatcagaa tctactgggg ctcctgtcgc catcctgtga acgccaccgt cttcacccac  28920
cccgaccagg cccaggcgaa cctcacctgc ggtctgcatc ggagggccaa gaagtacctc  28980
acctggtact tcaacggcac cccctttgtg gtttacaaca gcttcgacgg ggacggagtc  29040
```

tccctgaaag accagctctc cggtctcagc tactccatcc acaagaacac caccctccaa 29100
ctcttccctc cctacctgcc gggaacctac gagtgcgtca ccggccgctg cacccacctc 29160
acccgcctga tcgtaaacca gagctttccg ggaacagata actccctctt ccccagaaca 29220
ggaggtgagc tcaggaaact ccccggggac cagggcggag acgtaccttc gacccttgtg 29280
gggttaggat tttttattac cgggttgctg gctcttttaa tcaaagcttc cttgagattt 29340
gttctttcct tctacgtgta tgaacacctc agcctccaat aactctaccc tttcttcgga 29400
atcaggtgac ttctctgaaa tcgggcttgg tgtgctgctt actctgttga tttttttcct 29460
tatcatactc agccttctgt gcctcaggct cgccgcctgc tgcgcacaca tctatatcta 29520
ctgctggttg ctcaagtgca ggggtcgcca cccaagatga acaggtacat ggtcctatcg 29580
atcctaggcc tgctggccct ggcggcctgc agcgccgcca aaaaagagat tacctttgag 29640
gagcccgctt gcaatgtaac tttcaagccc gagggtgacc aatgcaccac cctcgtcaaa 29700
tgcgttacca atcatgagag gctgcgcatc gactacaaaa acaaaactgg ccagtttgcg 29760
gtctatagtg tgtttacgcc cggagacccc tctaactact ctgtcaccgt cttccagggc 29820
ggacagtcta agatattcaa ttacactttc cctttttatg agttatgcga tgcggtcatg 29880
tacatgtcaa aacagtacaa cctgtggcct ccctctcccc aggcgtgtgt ggaaaatact 29940
gggtcttact gctgtatggc tttggcaatc actacgctcg ctctaatctg cacggtgcta 30000
tacataaaat tcaggcagag gcgaatcttt atcgatgaaa agaaaatgcc ttgatcgcta 30060
acaccggctt tctatctgca gaatgaatgc aatcacctcc ctactaatca ccaccaccct 30120
ccttgcgatt gcccatgggt tgacacgaat cgaagtgcca gtggggtcca atgtcaccat 30180
ggtgggcccc gccggcaatt ccaccctcat gtgggaaaaa tttgtccgca atcaatgggt 30240
tcatttctgc tctaaccgaa tcagtatcaa gcccagagcc atctgcgatg ggcaaaatct 30300
aactctgatc aatgtgcaaa tgatggatgc tgggtactat tacgggcagc ggggagaaat 30360
cattaattac tggcgacccc acaaggacta catgctgcat gtagtcgagg cacttcccac 30420
taccaccccc actaccacct ctcccaccac cactaccacc actactacta ctactactac 30480
cactaccgct gcccgccata cccgcaaaag caccatgatt agcacaaagc cccctcgtgc 30540
tcactcccac gccggcgggc ccatcggtgc gacctcagaa accaccgagc tttgcttctg 30600
ccaatgcact aacgccagcg ctcatgaact gttcgacctg gagaatgagg atgcccagca 30660
gagctccgct tgcctgaccc aggaggctgt ggagcccgtt gccctgaagc agatcggtga 30720
ttcaataatt gactcttctt cttttgccac tcccgaatac cctcccgatt ctactttcca 30780
catcacgggt accaaagacc ctaacctctc tttctacctg atgctgctgc tctgtatctc 30840
tgtggtctct tccgcgctga tgttactggg gatgttctgc tgcctgatct gccgcagaaa 30900
gagaaaagct cgctctcagg gccaaccact gatgcccttc ccctaccccc cggattttgc 30960
agataacaag atatgagctc gctgctgaca ctaaccgctt tactagcctg cgctctaacc 31020
cttgtcgctt gcgactcgag attccacaat gtcacagctg tggcaggaga aaatgttact 31080
ttcaactcca cggccgatac ccagtggtcg tggagtggct caggtagcta cttaactatc 31140
tgcaatagct ccacttcccc cagcatatcc ccaaccaagt accaatgcaa tgccagcctg 31200
ttcaccctca tcaacgcttc caccctggac aatggactct atgtaggcta tgtacccttt 31260
ggtgggcaag gaaagaccca cgcttacaac ctggaagttc gccagcccag aaccactacc 31320
caagcttctc ccaccaccac caccaccacc accaccacca tcaccagcag cagcagcagc 31380

-continued

```
cacagcagca gcagcagatt attgactttg gttttggcca gctcatctgc cgctacccag  31440
gccatctaca gctctgtgcc cgaaaccact cagatccacc gcccagaaac gaccaccgcc  31500
accaccctac acacctccag cgatcagatg ccgaccaaca tcaccccctt ggctcttcaa  31560
atgggactta caagccccac tccaaaacca gtggatgcgg ccgaggtctc cgccctcgtc  31620
aatgactggg cggggctggg aatgtggtgg ttcgccatag gcatgatggc gctctgcctg  31680
cttctgctct ggctcatctg ctgcctccac cgcaggcgag ccagaccccc catctataga  31740
cccatcattg tcctgaaccc cgataatgat gggatccata gattggatgg cctgaaaaac  31800
ctactttttt cttttacagt atgataaatt gagacatgcc tcgcattttc ttgtacatgt  31860
tccttctccc accttttctg ggtgttctta cgctggccgc tgtgtctcac ctggaggtag  31920
actgcctctc acccttcact gtctacctgc tttacggatt ggtcacccctc actctcatct  31980
gcagcctaat cacagtaatc atcgccttca tccagtgcat tgattacatc tgtgtgcgcc  32040
tcgcatactt cagacaccac ccgcagtacc gagacaggaa cattgcccaa cttctaagac  32100
tgctctaatc atgcataaga ctgtgatctg ccttctgatc ctctgcatcc tgcccaccct  32160
cacctcctgc cagtacacca caaaatctcc gcgcaaaaga catgcctcct gccgcttcac  32220
ccaactgtgg aatataccca aatgctacaa cgaaaagagc gagctctccg aagcttggct  32280
gtatggggtc atctgtgtct tagttttctg cagcactgtc tttgccctca tgatctaccc  32340
ctactttgat ttgggatgga acgcgatcga tgccatgaat taccccacct ttcccgcacc  32400
cgagataatt ccactgcgac aagttgtacc cgttgtcgtt aatcaacgcc ccccatcccc  32460
tacgcccact gaaatcagct actttaacct aacaggcgga gatgactgac gccctagatc  32520
tagaaatgga cggcatcagt accgagcagc gtctcctaga gaggcgcagg caggcggctg  32580
agcaagagcg cctcaatcag gagctccgag atctcgttaa cctgcaccag tgcaaaagag  32640
gcatcttttg tctggtaaag caggccaaag tcacctacga gaagaccggc aacagccacc  32700
gcctcagtta caaattgccc acccagcgcc agaagctggt gctcatggtg ggtgagaatc  32760
ccatcaccgt cacccagcac tcggtagaga ccgaggggtg tctgcactct ccctgtcggg  32820
gtccagaaga cctctgcacc ctggtaaaga ccctgtgcgg tctcagagat ttagtcccct  32880
ttaactaatc aaacactgga atcaataaaa agaatcactt acttaaaatc agacagcagg  32940
tctctgtcca gtttattcag cagcacctcc ttcccctcct cccaactctg gtactccaaa  33000
cgccttctgg cggcaaactt cctccacacc ctgaagggaa tgtcagattc ttgctcctgt  33060
ccctccgcac ccactatctt catgttgttg cagatgaagc gcaccaaaac gtctgacgag  33120
agcttcaacc ccgtgtaccc ctatgacacg gaaagcggcc ctccctccgt ccctttcctc  33180
acccctccct tcgtgtctcc cgatggattc caagaaagcc cccccggggt cctgtctctg  33240
aacctggccg agcccctggt cacttcccac ggcatgctcg ccctgaaaat gggaagtggc  33300
ctctccctgg acgacgctgg caacctcacc tctcaagata tcaccaccgc tagccctccc  33360
ctcaaaaaaa ccaagaccaa cctcagccta gaaacctcat ccccccctaac tgtaagcacc  33420
tcaggcgccc tcaccgtagc agccgccgct cccctggcag tggccggcac ctccctcacc  33480
atgcaatcag aggccccccct gacagtacag gatgcaaaac tcaccctggc caccaaaggc  33540
cccctgaccg tgtctgaagg caaactggcc ttgcaaacat cggccccgct gacggccgct  33600
gacagcagca ccctcaccgt tagcgccaca ccaccaatta atgtaagcag tggaagttta  33660
ggcttagaca tggaagaccc tatgtatact cacgatggaa aactgggaat aagaattggg  33720
ggtccactaa gagtagtaga cagcttgcac acactcactg tagttaccgg aaatggacta  33780
```

actgtagata acaatgccct ccaaactaga gttacgggcg ccctaggtta tgacacatca 33840
ggaaatctac aattgagagc tgcaggaggt atgcgaattg atgcaaatgg ccaacttatc 33900
cttaatgtgg catacccatt tgatgctcag aacaatctca gccttagact tggtcaggga 33960
cccctgtata taaacacaga ccacaacctg gatttgaatt gcaacagagg tctaaccaca 34020
actaccacca acaacacaaa aaaacttgag actaaaatta gctcaggctt agactatgac 34080
accaatggtg ctgtcattat taaacttggc actggtctaa gcttcgacaa cacaggcgcc 34140
ctaactgtgg gaaacactgg tgatgataaa ctgactctgt ggacgacccc agacccatct 34200
ccaaattgca gaattcactc agacaaagac tgcaagttta ctctagtcct aactaagtgt 34260
ggaagccaaa tcctggcctc tgtcgccgcc ctagcggtat caggaaatct ggcttcgata 34320
acaggcaccg ttgccagcgt taccatcttt ctcagatttg atcagaatgg agtgcttatg 34380
gaaaactcct cgctagacag gcagtactgg aacttcagaa atggcaactc aactaacgct 34440
gcccccctaca ccaatgcagt tgggttcatg ccaaacctcg cagcataccc caaaacgcaa 34500
agccagactg ctaaaaacaa cattgtaagt caggtttact tgaatggaga caaatccaaa 34560
cccatgaccc ttaccatcac cctcaatgga actaatgaat ccagtgaaac tagccaggtg 34620
agtcactact ccatgtcatt tacatgggct tgggaaagtg ggcaatatgc cactgaaacc 34680
tttgccacca actccttcac cttttcttac attgctgaac aataaaaagc atgacactga 34740
tgttcatttc tgattcttat tttattattt tcaaacacaa caaaatcatt caagtcattc 34800
ttccatctta gcttaataga cacagtagct taatagaccc agtagtgcaa agccccattc 34860
tagcttataa ctagtggaga agtactcgcc tacatggggg tagagtcata atcgtgcatc 34920
aggatagggc ggtggtgctg cagcagcgcg cgaataaact gctgccgccg ccgctccgtc 34980
ctgcaggaat acaacatggc agtggtctcc tcagcgatga ttcgcaccgc ccgcagcata 35040
aggcgccttg tcctccgggc acagcagcgc accctgatct cacttaaatc agcacagtaa 35100
ctgcagcaca gcaccacaat attgttcaaa atcccacagt gcaaggcgct gtatccaaag 35160
ctcatggcgg ggaccacaga acccacgtgg ccatcatacc acaagcgcag gtagattaag 35220
tggcgacccc tcataaacac gctggacata aacattacct cttttggcat gttgtaattc 35280
accacctccc ggtaccatat aaacctctga ttaaacatgg cgccatccac caccatccta 35340
aaccagctgg ccaaaacctg cccgccggct atacactgca gggaaccggg actggaacaa 35400
tgacagtgga gagcccagga ctcgtaacca tggatcatca tgctcgtcat gatatcaatg 35460
ttggcacaac acaggcacac gtgcatacac ttcctcagga ttacaagctc ctcccgcgtt 35520
agaaccatat cccagggaac aacccattcc tgaatcagcg taaatcccac actgcaggga 35580
agacctcgca cgtaactcac gttgtgcatt gtcaaagtgt tacattcggg cagcagcgga 35640
tgatcctcca gtatggtagc gcgggtttct gtctcaaaag gaggtagacg atccctactg 35700
tacggagtgc gccgagacaa ccgagatcgt gttggtcgta gtgtcatgcc aaatggaacg 35760
ccggacgtag tcatatttcc tgaagtctta gatctctcaa cgcagcacca gcaccaacac 35820
ttcgcagtgt aaaaggccaa gtgccgagag agtatatata ggaataaaaa gtgacgtaaa 35880
cgggcaaagt ccaaaaaacg cccagaaaaa ccgcacgcga acctacgccc cgaaacgaaa 35940
gccaaaaaac actagacact cccttccggc gtcaacttcc gctttcccac gctacgtcac 36000
ttgccccagt caaacaaact acatatcccg aacttccaag tcgccacgcc caaaacaccg 36060
cctacacctc cccgcccgcc ggcccgcccc caaacccgcc tcccgccccg cgccccgccc 36120

-continued cgcgccgccc atctcattat catattggct tcaatccaaa ataaggtata ttattgatga 36180
tg 36182

<210> SEQ ID NO 14
<211> LENGTH: 36643
<212> TYPE: DNA
<213> ORGANISM: Pan troglodytes

<400> SEQUENCE: 14
catcatcaat aatatacctc aaacttttgg tgcgcgttaa tatgcaaatg aggtgtttga 60
atttggggat gcggggcgct gattggctga gagacgggcg accgttaggg gcggggcggg 120
tgacgttttg atgacgtggc cgtgaggcgg agccggtttg caagttctcg tgggaaaagt 180
gacgtcaaac gaggtgtggt ttgaacacgg aaatactcaa ttttcccgcg ctctctgaca 240
ggaaatgagg tgtttctggg cggatgcaag tgaaaacggg ccattttcgc gcgaaaactg 300
aatgaggaag tgaaaatctg agtaattccg cgtttatggc agggaggagt atttgccgag 360
ggccgagtag actttgaccg attacgtggg ggtttcgatt accgtatttt tcacctaaat 420
ttccgcgtac ggtgtcaaag tccggtgttt ttacgtaggc gtcagctgat cgccagggta 480
tttaaacctg cgctctctag tcaagaggcc actcttgagt gccagcgagt agagttttct 540
cctccgcgcc gcgagtcaga tctacacttt gaaagatgag gcacctgaga gacctgcccg 600
gtaatgtttt cctggctact gggaacgaga ttctggaact ggtggtggac gccatgatgg 660
gtgacgaccc tcccgagccc cctaccccat ttgaggcgcc ttcgctgtac gatttgtatg 720
atctggaggt ggatgtgccc gagaacgacc ccaacgagga ggcggtgaat gatttgttta 780
gcgatgccgc gctgctggct gccgagcagg ctaatacgga ctctggctca gacagcgatt 840
cctctcttca taccccgaga cccggcagag gtgagaaaaa gatccccgag cttaaagggg 900
aagagctcga cctgcgctgc tatgaggaat gcttgcctcc gagcgatgat gaggaggacg 960
aggaggcgat tcgagctgca gcgagcgagg gagtgaaagt tgcgggcgag agctttagcc 1020
tggactgtcc tactctgccc ggacacggct gtaagtcttg tgaatttcat cgcatgaata 1080
ctggagataa gaatgtgatg tgtgccctgt gctatatgag agcttacaac cattgtgttt 1140
acagtaagtg tgattaactt tagttgggaa ggcagagggt gactgggtgc tgactggttt 1200
atttatgtat atgttttttt atgtgtaggt cccgtctctg acgtagatga gacccccact 1260
tcagagtgca tttcatcacc cccagaaatt ggcgaggaac cgcccgaaga tattattcat 1320
agaccagttg cagtgagagt caccgggcgg agagcagctg tggagagttt ggatgacttg 1380
ctacagggtg gggatgaacc tttggacttg tgtacccgga aacgccccag gcactaagtg 1440
ccacacatgt gtgtttactt aaggtgatgt cagtatttat agggtgtgga gtgcaataaa 1500
aatatgtgtt gactttaagt gcgtggttta tgactcaggg gtggggactg tgggtatata 1560
agcaggtgca gacctgtgtg gtcagttcag agcaggactc atggagatct ggacggtctt 1620
ggaagacttt caccagacta gacagctgct agagaactca tcggcggaag tctcttacct 1680
gtggagattc tgcttcggtg ggcctctagc taagctagtc tatagggcca agcaggatta 1740
taaggatcaa tttgaggata ttttgagaga gtgtcctggt atttttgact ctctcaactt 1800
gggccatcag tctcacttta accagagtat tctgagagcc cttgactttt ccactcctgg 1860
cagaactacc gccgcggtag cctttttttgc ctttatcctt gacaaatgga gtcaagaaac 1920
ccatttcagc agggattacc gtctggactg cttagcagta gctttgtgga gaacatggag 1980
gtgccagcgc ctgaatgcaa tctccggcta cttgccagta cagccggtag acacgctgag 2040

```
gatcctgagt ctccagtcac cccaggaaca ccaacgccgc cagcagccgc agcaggagca   2100
gcagcaagag gaggaggagg accgagaaga gaacctgaga gccggtctgg accctccggt   2160
ggcggaggag gaggagtagc tgacttgttt cccgagctgc gccgggtgct gactaggtct   2220
tccagtggac gggagagggg gattaagcgg gagaggcatg aggagactag ccacagaact   2280
gaactgactg tcagtctgat gagccgcagg cgcccagaat cggtgtggtg gcatgaggtg   2340
cagtcgcagg ggatagatga ggtctcagtg atgcatgaga aatattccct agaacaagtc   2400
aagacttgtt ggttggagcc tgaggatgat tgggaggtag ccatcaggaa ttatgccaag   2460
ctggctctga agccagacaa gaagtacaag attaccaaac tgattaatat cagaaattcc   2520
tgctacattt cagggaatgg ggccgaggtg gagatcagta cccaggagag ggcggccttc   2580
agatgttgta tgatgaatat gtacccgggg gtggtgggca tggagggagt cacctttatg   2640
aacacgaggt tcaggggtga tgggtataat ggggtggtct ttatggccaa caccaagttg   2700
acagtgcacg gatgctcctt ctttggcttc aataacatgt gcatcgaggc ctggggcagt   2760
gtttcagtga ggggatgcag cttttcagcc aactggatgg gggtcgtggg cagaaccaag   2820
agcgtggttt cagtgaagaa atgcctgttt gagaggtgcc acctgggggt gatgagcgag   2880
ggcgaagcca aagtcaaaca ctgcgcctct accgagacgg gctgctttgt gctgatcaag   2940
ggcaatgcca aagtcaagca taacatgatc tgtggggcct cggatgagcg cggctaccag   3000
atgctgacct gcgccggtgg gaacagccat atgctggcca ccgtgcatgt ggcctcgcac   3060
ccccgcaaga catggcccga gttcgagcac aacgtcatga cccgctgcaa tgtgcacctg   3120
gggtcccgcc gaggcatgtt catgccctac cagtgcaaca tgcaatttgt gaaggtgctg   3180
ctggagcccg atgccatgtc cagagtgagc ctgacggggg tgtttgacat gaatgtggag   3240
ctgtggaaaa ttctgagata tgatgaatcc aagaccaggt gccgggcctg cgaatgcgga   3300
ggcaagcacg ccaggcttca gcccgtgtgt gtggaggtga cggaggacct gcgacccgat   3360
catttggtgt tgtcctgcaa cgggacggag ttcggctcca gcggggaaga atctgactag   3420
agtgagtagt gtttgggggt gggtgggagc ctgcatgatg ggcagaatga ctaaaatctg   3480
tgtttttctg tgtgttgcag cagcatgagc ggaagcgcct cctttgaggg aggggtattc   3540
agcccttatc tgacggggcg tctcccctcc tgggcgggag tgcgtcagaa tgtgatggga   3600
tccacggtgg acggccggcc cgtgcagccc gcgaactctt caaccctgac ctacgcgacc   3660
ctgagctcct cgtccgtgga cgcagctgcc gccgcagctg ctgcttccgc cgccagcgcc   3720
gtgcgcggaa tggccctggg cgccggctac tacagctctc tggtggccaa ctcgagttcc   3780
accaataatc ccgccagcct gaacgaggag aagctgttgc tgctgatggc ccagctcgag   3840
gccctgaccc agcgcctggg cgagctgacc cagcaggtgg ctcagctgca ggcggagacg   3900
cgggccgcgg ttgccacggt gaaaaccaaa taaaaaatga atcaataaat aaacggagac   3960
ggttgttgat tttaacacag agtcttgaat ctttatttga tttttcgcgc gcggtaggcc   4020
ctggaccacc ggtctcgatc attgagcacc cggtggatct tttccaggac ccggtagagg   4080
tgggcttgga tgttgaggta catgggcatg agcccgtccc gggggtggag gtagctccat   4140
tgcagggcct cgtgctcggg ggtggtgttg taaatcaccc agtcatagca ggggcgcagg   4200
gcgtggtgct gcacgatgtc tttgaggagg agactgatgg ccacgggcag ccccttggtg   4260
taggtgttga cgaacctatt gagctgggag ggatgcatgc ggggggagat gagatgcatc   4320
ttggcctgga tcttgagatt ggcgatgttc ccgcccagat cccgccgggg gttcatgttg   4380
```

-continued

```
tgcaggacca ccagcacggt gtatccggtg cacttgggga atttgtcatg caacttggaa   4440
gggaaggcgt gaaagaattt ggagacgccc ttgtgaccgc ccaggttttc catgcactca   4500
tccatgatga tggcgatggg cccgtgggcg gcggcctggg caaagacgtt tcgggggtcg   4560
gacacatcgt agttgtggtc ctgggtgagc tcgtcatagg ccattttaat gaatttgggg   4620
cggagggtac ccgactgggg gacaaaggtg ccctcgatcc cgggggcgta gttcccctcg   4680
cagatctgca tctcccaggc cttgagctcg gagggggga tcatgtccac ctgcggggcg    4740
atgaaaaaaa cggtttccgg ggcgggggag atgagctgcg ccgaaagcag gttccggagc   4800
agctgggact tgccgcagcc ggtggggccg tagatgaccc cgatgaccgg ctgcaggtgg   4860
tagttgaggg agagacagct gccgtcctcg cggaggaggg gggccacctc gttcatcatc   4920
tcgcgcacat gcatgttctc gcgcacgagt tccgccagga ggcgctcgcc ccccagcgag   4980
aggagctctt gcagcgaggc gaagtttttc agcggcttga gcccgtcggc catgggcatt   5040
ttggagaggg tctgttgcaa gagttccaga cggtcccaga gctcggtgat gtgctctagg   5100
gcatctcgat ccagcagacc tcctcgtttc gcgggttggg gcgactgcgg gagtagggca   5160
ccaggcgatg ggcgtccagc gaggccaggg tccggtcctt ccagggtcgc agggtccgcg   5220
tcagcgtggt ctccgtcacg gtgaaggggt gcgcgccggg ctgggcgctt gcgagggtgc   5280
gcttcaggct catccggctg gtcgagaacc gctcccggtc ggcgccctgc gcgtcggcca   5340
ggtagcaatt gagcatgagt tcgtagttga gcgcctcggc cgcgtggccc ttggcgcgga   5400
gcttaccttt ggaagtgtgt ccgcagacgg gacagaggag ggacttgagg gcgtagagct   5460
tgggggcgag gaagacggac tcgggggcgt aggcgtccgc gccgcagctg gcgcagacgg   5520
tctcgcactc cacgagccag gtgaggtcgg ggcggtcggg gtcaaaaacg aggtttcctc   5580
cgtgcttttt gatgcgtttc ttacctctgg tctccatgag ctcgtgtccc cgctgggtga   5640
caaagaggct gtccgtgtcc ccgtagaccg actttatggg ccggtcctcg agcggggtgc   5700
cgcggtcctc gtcgtagagg aaccccgccc actccgagac gaaggcccgg gtccaggcca   5760
gcacgaagga ggccacgtgg gaggggtagc ggtcgttgtc caccagcggg tccaccttct   5820
ccagggtatg caagcacatg tccccctcgt ccacatccag gaaggtgatt ggcttgtaag   5880
tgtaggccac gtgaccgggg gtcccggccg ggggggtata aaagggggcg ggcccctgct   5940
cgtcctcact gtcttccgga tcgctgtcca ggagcgccag ctgttggggt aggtattccc   6000
tctcgaaggc gggcatgacc tcggcactca ggttgtcagt ttctagaaac gaggaggatt   6060
tgatattgac ggtgccgttg gagacgcctt tcatgagccc ctcgtccatc tggtcagaaa   6120
agacgatctt tttgttgtcg agcttggtgg cgaaggagcc gtagagggcg ttggagagca   6180
gcttggcgat ggagcgcatg gtctggttct tttccttgtc ggcgcgctcc ttggcggcga   6240
tgttgagctg cacgtactcg cgcgccacgc acttccattc ggggaagacg gtggtgagct   6300
cgtcgggcac gattctgacc cgccagccgc ggttgtgcag ggtgatgagg tccacgctgg   6360
tggccacctc gccgcgcagg ggctcgttgg tccagcagag gcgcccgccc ttgcgcgagc   6420
agaagggggg cagcgggtcc agcatgagct cgtcgggggg gtcggcgtcc acggtgaaga   6480
tgccgggcag gagctcgggg tcgaagtagc tgatgcaggt gcccagatcg tccagacttg   6540
cttgccagtc gcgcacggcc agcgcgcgct cgtaggggct gaggggcgtg ccccagggca   6600
tggggtgcgt gagcgcggag gcgtacatgc cgcagatgtc gtagacgtag aggggctcct   6660
ggaggacgcc gatgtaggtg ggtagcagc gccccccgcg gatgctggcg cgcacgtagt    6720
cgtacagctc gtgcgagggc gcgaggagcc ccgtgccgag attggagcgc tgcggctttt   6780
```

```
cggcgcggta gacgatctgg cggaagatgg cgtgggagtt ggaggagatg gtgggcctct   6840
ggaagatgtt gaagtgggca tggggcagtc cgaccgagtc cctgatgaag tgggcgtagg   6900
agtcctgcag cttggcgacg agctcggcgg tgacgaggac gtccagggcg cagtagtcga   6960
gggtctcttg gatgatgtcg tacttgagct ggcccttctg cttccacagc tcgcggttga   7020
gaaggaactc ttcgcggtcc ttccagtact cttcgagggg gaacccgtcc tgatcggcac   7080
ggtaagagcc caccatgtag aactggttga cggccttgta ggcgcagcag cccttctcca   7140
cggggagggc gtaagcttgc gcggccttgc gcagggaggt gtgggtgagg gcgaaggtgt   7200
cgcgcaccat gactttgagg aactggtgct tgaagtcgag gtcgtcgcag ccgccctgct   7260
cccagagctg gaagtccgtg cgcttcttgt aggcggggtt gggcaaagcg aaagtaacat   7320
cgttgaagag gatcttgccc gcgcggggca tgaagttgcg agtgatgcgg aaaggctggg   7380
gcacctcggc ccggttgttg atgacctggg cggcgaggac gatctcgtcg aagccgttga   7440
tgttgtgccc gacgatgtag agttccacga atcgcgggcg gcccttgacg tggggcagct   7500
tcttgagctc gtcgtaggtg agctcggcgg ggtcgctgag cccgtgctgc tcgagggccc   7560
agtcggcgac gtgggggttg gcgctgagga aggaagtcca gagatccacg gccagggcgg   7620
tctgcaagcg gtcccggtac tgacggaact gctggcccac ggccattttt tcgggggtga   7680
cgcagtagaa ggtgcggggg tcgccgtgcc agcggtccca cttgagctgg agggcgaggt   7740
cgtgggcgag ctcgacgagc ggcgggtccc cggagagttt catgaccagc atgaagggga   7800
cgagctgctt gccgaaggac cccatccagg tgtaggtttc cacatcgtag gtgaggaaga   7860
gcctttcggt gcgaggatgc gagccgatgg ggaagaactg gatctcctgc caccagttgg   7920
aggaatggct gttgatgtga tggaagtaga aatgccgacg gcgcgccgag cactcgtgct   7980
tgtgtttata caagcgtccg cagtgctcgc aacgctgcac gggatgcacg tgctgcacga   8040
gctgtacctg ggttcctttg acgaggaatt tcagtgggca gtggagcgct ggcggctgca   8100
tctggtgctg tactacgtcc tggccatcgg cgtggccatc gtctgcctcg atggtggtca   8160
tgctgacgag cccgcgcggg aggcaggtcc agacctcggc tcggacgggt cggagagcga   8220
ggacgagggc gcgcaggccg gagctgtcca gggtcctgag acgctgcgga gtcaggtcag   8280
tgggcagcgg cggcgcgcgg ttgacttgca ggagcttttc cagggcgcgc gggaggtcca   8340
gatggtactt gatctccacg gcgccgttgg tggcgacgtc cacggcttgc agggtcccgt   8400
gcccctgggg cgccaccacc gtgccccgtt tcttcttggg cggcggcggc tccatgctta   8460
gaagcggcgg cgaggacgcg cgccgggcgg caggggcggc tcggggcccg gaggcagggg   8520
cggcaggggc acgtcggcgc cgcgcgcggg caggttctgg tactgcgccc ggagaagact   8580
ggcgtgagcg acgacgcgac ggttgacgtc ctggatctga cgcctctggg tgaaggccac   8640
gggacccgtg agtttgaacc tgaaagagag ttcgacagaa tcaatctcgg tatcgttgac   8700
ggcggcctgc cgcaggatct cttgcacgtc gcccgagttg tcctggtagg cgatctcggt   8760
catgaactgc tcgatctcct cctcctgaag gtctccgcgg ccggcgcgct cgacggtggc   8820
cgcgaggtcg ttggagatgc ggcccatgag ctgcgagaag gcgttcatgc cggcctcgtt   8880
ccagacgcgg ctgtagacca cggctccgtc ggggtcgcgc gcgcgcatga ccacctgggc   8940
gaggttgagc tcgacgtggc gcgtgaagac cgcgtagttg cagaggcgct ggtagaggta   9000
gttgagcgtg gtggcgatgt gctcggtgac gaagaagtac atgatccagc ggcggagcgg   9060
catctcgctg acgtcgccca gggcttccaa gcgctccatg gcctcgtaga agtccacggc   9120
```

-continued

```
gaagttgaaa aactgggagt tgcgcgccga gacggtcaac tcctcctcca gaagacggat   9180
gagctcggcg atggtggcgc gcacctcgcg ctcgaaggcc ccggggggct cctcttccat   9240
ttcctcctct tcctcctcca ctaacatctc ttctacttcc tcctcaggag gcggcggcgg   9300
gggaggggcc ctgcgtcgcc ggcggcgcac gggcagacgg tcgatgaagc gctcgatggt   9360
ctccccgcgc cggcgacgca tggtctcggt gacggcgcgc ccgtcctcgc ggggccgcag   9420
cgtgaagacg ccgccgcgca tctccaggtg gccgccgggg gggtctccgt tgggcaggga   9480
gagggcgctg acgatgcatc ttatcaattg acccgtaggg actccgcgca aggacctgag   9540
cgtctcgaga tccacgggat ccgaaaaccg ctgaacgaag gcttcgagcc agtcgcagtc   9600
gcaaggtagg ctgagcccgg tttcttgttc ttcgggtatt tggtcgggag gcgggcgggc   9660
gatgctgctg gtgatgaagt tgaagtaggc ggtcctgaga cggcggatgg tggcgaggag   9720
caccaggtcc ttgggcccgg cttgctggat gcgcagacgg tcggccatgc cccaggcgtg   9780
gtcctgacac ctggcgaggt ccttgtagta gtcctgcatg agccgctcca cgggcacctc   9840
ctcctcgccc gcgcggccgt gcatgcgcgt gagcccgaac ccgcgctgcg gctggacgag   9900
cgccaggtcg gcgacgacgc gctcggcgag gatggcctgc tggatctggg tgagggtggt   9960
ctggaagtcg tcgaagtcga cgaagcggtg gtaggctccg gtgttgatgg tgtaggagca  10020
gttggccatg acggaccagt tgacggtctg gtggccgggg cgcacgagct cgtggtactt  10080
gaggcgcgag taggcgcgcg tgtcgaagat gtagtcgttg caggtgcgca cgaggtactg  10140
gtatccgacg aggaagtgcg gcggcggctg gcggtagagc ggccatcgct cggtggcggg  10200
ggcgccgggc gcgaggtcct cgagcatgag gcggtggtag ccgtagatgt acctggacat  10260
ccaggtgatg ccggcggcgg tggtggaggc gcgcgggaac tcgcggacgc ggttccagat  10320
gttgcgcagc ggcaggaagt agttcatggt ggccgcggtc tggcccgtga ggcgcgcgca  10380
gtcgtggatg ctctagacat acgggcaaaa acgaaagcgg tcagcggctc gactccgtgg  10440
cctggaggct aagcgaacgg gttgggctgc gcgtgtaccc cggttcgaat ctcgaatcag  10500
gctggagccg cagctaacgt ggtactggca ctcccgtctc gacccaagcc tgctaacgaa  10560
acctccagga tacggaggcg ggtcgttttt tggccttggt cgctggtcat gaaaaactag  10620
taagcgcgga aagcggccgc ccgcgatggc tcgctgccgt agtctggaga aagaatcgcc  10680
agggttgcgt tgcggtgtgc cccggttcga gcctcagcgc tcggcgccgg ccggattccg  10740
cggctaacgt gggcgtggct gccccgtcgt ttccaagacc ccttagccag ccgacttctc  10800
cagttacgga gcgagcccct cttttttttct tgtgtttttg ccagatgcat cccgtactgc  10860
ggcagatgcg cccccaccct ccaccacaac cgcccctacc gcagcagcag caacagccgg  10920
cgcttctgcc cccgccccag cagcagcagc cagccactac cgcggcggcc gccgtgagcg  10980
gagccggcgt tcagtatgac ctggccttgg aagagggcga ggggctggcg cggctggggg  11040
cgtcgtcgcc ggagcggcac ccgcgcgtgc agatgaaaag ggacgctcgc gaggcctacg  11100
tgcccaagca gaacctgttc agagacagga gcggcgagga gcccgaggag atgcgcgcct  11160
cccgcttcca cgcggggcgg gagctgcggc gcggcctgga ccgaaagcgg gtgctgaggg  11220
acgaggattt cgaggcggac gagctgacgg ggatcagccc cgcgcgcgcg cacgtggccg  11280
cggccaacct ggtcacggcg tacgagcaga ccgtgaagga ggagagcaac ttccaaaaat  11340
ccttcaacaa ccacgtgcgc acgctgatcg cgcgcgagga ggtgaccctg ggcctgatgc  11400
acctgtggga cctgctggag gccatcgtgc agaaccccac gagcaagccg ctgacggcgc  11460
agctgtttct ggtggtgcag cacagtcggg acaacgagac gttcagggag gcgctgctga  11520
```

atatcaccga gcccgagggc cgctggctcc tggacctggt gaacattctg cagagcatcg 11580
tggtgcagga gcgcgggctg ccgctgtccg agaagctggc ggccatcaac ttctcggtgc 11640
tgagcctggg caagtactac gctaggaaga tctacaagac cccgtacgtg cccatagaca 11700
aggaggtgaa gatcgatggg ttttacatgc gcatgaccct gaaagtgctg accctgagcg 11760
acgatctggg ggtgtaccgc aacgacagga tgcaccgcgc ggtgagcgcc agccgccggc 11820
gcgagctgag cgaccaggag ctgatgcaca gcctgcagcg ggccctgacc ggggccggga 11880
ccgaggggga gagctacttt gacatgggcg cggacctgcg ctggcagccc agccgccggg 11940
ccttggaagc tgccggcggc gtgccctacg tggaggaggt ggacgatgag gaggaggagg 12000
gcgagtacct ggaagactga tggcgcgacc gtatttttgc tagatgcagc aacagccacc 12060
gccgccgcct cctgatcccg cgatgcgggc ggcgctgcag agccagccgt ccggcattaa 12120
ctcctcggac gattggaccc aggccatgca acgcatcatg gcgctgacga cccgcaatcc 12180
cgaagccttt agacagcagc ctcaggccaa ccggctctcg gccatcctgg aggccgtggt 12240
gccctcgcgc tcgaacccca cgcacgagaa ggtgctggcc atcgtgaacg cgctggtgga 12300
gaacaaggcc atccgcggcg acgaggccgg gctggtgtac aacgcgctgc tggagcgcgt 12360
ggcccgctac aacagcacca acgtgcagac gaacctggac cgcatggtga ccgacgtgcg 12420
cgaggcggtg tcgcagcgcg agcggttcca ccgcgagtcg aacctgggct ccatggtggc 12480
gctgaacgcc ttcctgagca cgcagcccgc caacgtgccc cggggccagg aggactacac 12540
caacttcatc agcgcgctgc ggctgatggt ggccgaggtg ccccagagcg aggtgtacca 12600
gtcggggccg gactacttct tccagaccag tcgccagggc ttgcagaccg tgaacctgag 12660
ccaggctttc aagaacttgc agggactgtg gggcgtgcag gccccggtcg gggaccgcgc 12720
gacggtgtcg agcctgctga cgccgaactc gcgcctgctg ctgctgctgg tggcgccctt 12780
cacggacagc ggcagcgtga gccgcgactc gtacctgggc tacctgctta acctgtaccg 12840
cgaggccatc gggcaggcgc acgtggacga gcagacctac caggagatca cccacgtgag 12900
ccgcgcgctg ggccaggagg acccgggcaa cctggaggcc accctgaact tcctgctgac 12960
caaccggtcg cagaagatcc cgccccagta cgcgctgagc accgaggagg agcgcatcct 13020
gcgctacgtg cagcagagcg tggggctgtt cttgatgcag gagggggcca cgcccagcgc 13080
cgcgctcgac atgaccgcgc gcaacatgga gcccagcatg tacgcccgca accgcccgtt 13140
catcaataag ctgatggact acttgcatcg ggcggccgcc atgaactcgg actactttac 13200
caacgccatc ttgaacccgc actggctccc gccgcccggg ttctacacgg gcgagtacga 13260
catgcccgac cccaacgacg ggttcctgtg ggacgacgtg gacagcagcg tgttctcgcc 13320
gcggcccacc accaccaccg tgtggaagaa agagggcggg gaccggcggc cgtcctcggc 13380
gctgtccggt cgcgcgggtg ctgccgcggc ggtgcccgag gctgccagcc ccttcccgag 13440
cctgcccttt tcgctgaaca gcgtgcgcag cagcgagctg ggtcggctga cgcggccgcg 13500
cctgctgggc gaggaggagt acctgaacga ctccttgttg aagcccgagc gcgagaagaa 13560
cttccccaat aacgggatag agagcctggt ggacaagatg agccgctgga agacgtacgc 13620
gcacgagcac agggacgagc cccgagctag cagcgcaggc acccgtagac gccagcggca 13680
cgacaggcag cggggactgg tgtgggacga tgaggattcc gccgacgaca gcagcgtgtt 13740
ggacttgggt gggagtggtg gtggtaaccc gttcgctcac ctgcgccccc gtatcgggcg 13800
cctgatgtaa gaatctgaaa aaataaaaga cggtactcac caaggccatg gcgaccagcg 13860

-continued

```
tgcgttcttc tctgttgttt gtagtagtat gatgaggcgc gtgtacccgg agggtcctcc  13920
tccctcgtac gagagcgtga tgcagcaggc ggtggcggcg gcgatgcagc cccgctgga   13980
ggcgccttac gtgcccccgc ggtacctggc gcctacggag gggcggaaca gcattcgtta  14040
ctcggagctg gcacccttgt acgataccac ccggttgtac ctggtggaca acaagtcggc  14100
ggacatcgcc tcgctgaact accagaacga ccacagcaac ttcctgacca ccgtggtgca  14160
gaacaacgat ttcacccccca cggaggccag cacccagacc atcaactttg acgagcgctc 14220
gcggtggggc ggccagctga aaaccatcat gcacaccaac atgcccaacg tgaacgagtt  14280
catgtacagc aacaagttca aggcgcgggt gatggtctcg cgcaagaccc ccaacggggt  14340
cacggtaggg gatgattatg atggtagtca ggacgagctg acctacgagt gggtggagtt  14400
tgagctgccc gagggcaact tctcggtgac catgaccatc gatctgatga acaacgccat  14460
catcgacaac tacttggcgg tggggcggca gaacggggtg ctggagagcg acatcggcgt  14520
gaagttcgac acgcgcaact tccggctggg ctgggacccc gtgaccgagc tggtgatgcc  14580
gggcgtgtac accaacgagg ccttccaccc cgacatcgtc ctgctgcccg gctgcggcgt  14640
ggacttcacc gagagccgcc tcagcaacct gctgggcatc cgcaagcggc agcccttcca  14700
ggagggcttc cagatcctgt acgaggacct ggaggggggc aacatccccg cgctcttgga  14760
tgtcgaagcc tatgaagaaa gtaaggaaaa agcagaggct gaggcaacta cagccgtggc  14820
taccgccgcg actgtggcag atgccactgt caccaggggc gatacattcg ccacccaggc  14880
ggaggaagca gccgccctag cggcgaccga tgatagtgaa agtaagatag tcatcaagcc  14940
ggtggagaag gacagcaaga acaggagcta caacgttcta ccggatggaa agaacaccgc  15000
ctaccgcagc tggtacctgg cctacaacta cggcgacccc gagaagggcg tgcgctcctg  15060
gacgctgctc accacctcgg acgtcacctg cggcgtggag caagtctact ggtcgctgcc  15120
cgacatgatg caagacccgg tcaccttccg ctccacgcga caagttagca actacccggt  15180
ggtgggcgcc gagctcctgc ccgtctactc caagagcttc ttcaacgagc aggccgtcta  15240
ctcgcagcag ctgcgtgcct tcacctcgct cacgcacgtc ttcaaccgct tccccgagaa  15300
ccagatcctc gtccgcccgc ccgcgcccac cattaccacc gtcagtgaaa acgttcctgc  15360
tctcacagat cacgggaccc tgccgctgcg cagcagtatc cggggagtcc agcgcgtgac  15420
cgtcactgac gccagacgcc gcacctgccc ctacgtctac aaggccctgg gcgtagtcgc  15480
gccgcgcgtc ctctcgagcc gcaccttcta aaaaatgtcc attctcatct cgcccagtaa  15540
taacaccggt tggggcctgc gcgcgcccag caagatgtac ggaggcgctc gccaacgctc  15600
cacgcaacac cccgtgcgcg tgcgcgggca cttccgcgct ccctggggcg ccctcaaggg  15660
ccgcgtgcgc tcgcgcacca ccgtcgacga cgtgatcgac caggtggtgg ccgacgcgcg  15720
caactacacg cccgccgccg cgcccgcctc caccgtggac gccgtcatcg acagcgtggt  15780
ggccgacgcg cgccggtacg cccgcgccaa gagccggcgg cggcgcatcg cccggcggca  15840
ccggagcacc cccgccatgc gcgcggcgcg agccttgctg cgcagggcca ggcgcacggg  15900
acgcagggcc atgctcaggg cggccagacg cgcggcctcc ggcagcagca gcgccggcag  15960
gacccgcaga cgcgcggcca cggcggcggc ggcggccatc gccagcatgt cccgcccgcg  16020
gcgcggcaac gtgtactggg tgcgcgacgc cgccaccggt gtgcgcgtgc ccgtgcgcac  16080
ccgccccccct cgcacttgaa gatgctgact tcgcgatgtt gatgtgtccc agcggcgagg 16140
aggatgtcca agcgcaaata caaggaagag atgctccagg tcatcgcgcc tgagatctac  16200
ggccccgcgg cggcggtgaa ggaggaaaga aagccccgca aactgaagcg ggtcaaaaag  16260
```

```
gacaaaaagg aggaggaaga tgacggactg gtggagtttg tgcgcgagtt cgccccccgg  16320
cggcgcgtgc agtggcgcgg gcggaaagtg aaaccggtgc tgcggcccgg caccacggtg  16380
gtcttcacgc ccggcgagcg ttccggctcc gcctccaagc gctcctacga cgaggtgtac  16440
ggggacgagg acatcctcga gcaggcggtc gagcgtctgg gcgagtttgc ttacggcaag  16500
cgcagccgcc ccgcgccctt gaaagaggag gcggtgtcca tcccgctgga ccacggcaac  16560
cccacgccga gcctgaagcc ggtgaccctg cagcaggtgc tgccgagcgc ggcgccgcgc  16620
cggggcttca agcgcgaggg cggcgaggat ctgtacccga ccatgcagct gatggtgccc  16680
aagcgccaga agctggagga cgtgctggag cacatgaagg tggaccccga ggtgcagccc  16740
gaggtcaagg tgcggcccat caagcaggtg gccccgggcc tgggcgtgca gaccgtggac  16800
atcaagatcc ccacggagcc catggaaacg cagaccgagc ccgtgaagcc cagcaccagc  16860
accatggagg tgcagacgga tccctggatg ccagcggctt ccaccaccac cactcgccga  16920
agacgcaagt acggcgcggc cagcctgctg atgcccaact acgcgctgca tccttccatc  16980
atccccacgc cgggctaccg cggcacgcgc ttctaccgcg gctacaccag cagccgccgc  17040
cgcaagacca ccacccgccg ccgtcgtcgc agccgccgca gcagcaccgc gacttccgcc  17100
ttggtgcgga gagtgtatcg cagcgggcgc gagcctctga ccctgccgcg cgcgcgctac  17160
cacccgagca tcgccattta actaccgcct cctacttgca gatatggccc tcacatgccg  17220
cctccgcgtc cccattacgg gctaccgagg aagaaagccg cgccgtagaa ggctgacggg  17280
gaacgggctg cgtcgccatc accaccggcg gcggcgcgcc atcagcaagc ggttgggggg  17340
aggcttcctg cccgcgctga tccccatcat cgccgcggcg atcggggcga tccccggcat  17400
agcttccgtg gcggtgcagg cctctcagcg ccactgagac acaaaaaagc atggatttgt  17460
aataaaaaaa tggactgacg ctcctggtcc tgtgatgtgt gtttttagat ggaagacatc  17520
aatttttcgt ccctggcacc gcgacacggc acgcggccgt ttatgggcac ctggagcgac  17580
atcggcaaca gccaactgaa cgggggcgcc ttcaattgga gcagtctctg gagcgggctt  17640
aagaatttcg ggtccacgct caaaacctat ggcaacaagg cgtggaacag cagcacaggg  17700
caggcgctga gggaaaagct gaaagagcag aacttccagc agaaggtggt cgatggcctg  17760
gcctcgggca tcaacggggt ggtggacctg gccaaccagg ccgtgcagaa acagatcaac  17820
agccgcctgg acgcggtccc gcccgcgggg tccgtggaga tgccccaggt ggaggaggag  17880
ctgcctcccc tggacaagcg cggcgacaag cgaccgcgtc ccgacgcgga ggagacgctg  17940
ctgacgcaca cggacgagcc gcccccgtac gaggaggcgg tgaaactggg tctgcccacc  18000
acgcggcccg tggcgcctct ggccaccggg gtgctgaaac ccagcagcag cagccagccc  18060
gcgaccctgg acttgcctcc gcctgcttcc cgcccctcca cagtggctaa gcccctgccg  18120
ccggtggccg tcgcgtcgcg cgccccccga ggccgccccc aggcgaactg gcagagcact  18180
ctgaacagca tcgtgggtct gggagtgcag agtgtgaagc gccgccgctg ctattaaaag  18240
acactgtagc gcttaacttg cttgtctgtg tgtgtatatg tatgtccgcc gaccagaagg  18300
aggaagaggc gcgtcgccga gttgcaagat ggccacccca tcgatgctgc cccagtgggc  18360
gtacatgcac atcgccggac aggacgcttc ggagtacctg agtccgggtc tggtgcagtt  18420
cgcccgcgcc acagacacct acttcagtct ggggaacaag tttaggaacc ccacggtggc  18480
gcccacgcac gatgtgacca ccgaccgcag ccagcggctg acgctgcgct tcgtgcccgt  18540
ggaccgcgag gacaacacct actcgtacaa agtgcgctac acgctggccg tgggcgacaa  18600
```

```
ccgcgtgctg gacatggcca gcacctactt tgacatccgc ggcgtgctgg atcggggccc  18660
cagcttcaaa ccctactccg gcaccgccta caacagccta gctcccaagg gagcgcccaa  18720
cacctcacag tggaaggatt ccgacagcaa aatgcatact tttggagttg ctgccatgcc  18780
cggtgttgtt ggtaaaaaaa tagaagccga tggtctgcct attggaatag attcatcctc  18840
tggaactgac accataattt atgctgataa aactttccaa ccagagccac aggttggaag  18900
tgacagttgg gtcgacacca atggtgcaga ggaaaaatat ggaggtagag ctcttaagga  18960
cactacaaac atgaagccct gctacggttc ttttgccagg cctaccaaca aagaaggtgg  19020
acaggctaac ataaaagatt ctgaaactgc cagcactact cctaactatg atatagattt  19080
ggcattcttt gacagcaaaa atattgcagc taactacgat ccagatattg taatgtacac  19140
agaaaatgtt gagttgcaaa ctccagatac tcatattgtg tttaagccag gaacttcaga  19200
tgaaagttca gaagccaatt tgggccagca ggccatgccc aacagaccca actacatcgg  19260
gttcagagac aactttatcg ggctcatgta ctacaacagc actggcaata tgggtgtact  19320
ggctggtcag gcctcccagc taaatgctgt ggtggacttg caggacagaa acaccgaact  19380
gtcctaccag ctcttgcttg actctctggg tgacagaacc aggtatttca gtatgtggaa  19440
tcaggcggtg gacagctatg accccgatgt gcgcattatt gaaaatcacg gtgtggagga  19500
tgaactcccc aattattgct tccctttgaa tggtgtaggc tttacagata cttaccaggg  19560
tgttaaagtt aagacagata cagccgctac tggtaccaat ggaacgcagt gggacaaaga  19620
tgataccaca gtcagcactg ccaatgagat ccactcaggc aatcctttcg ccatggagat  19680
caacatccag gccaacctgt ggcggaactt cctctacgcg aacgtggcgc tgtacctgcc  19740
cgactcctac aagtacacgc cggccaacat cacgctgccg accaacacca acacctacga  19800
ttacatgaac ggccgcgtgg tggcgccctc gctggtggac gcctacatca acatcggggc  19860
gcgctggtcg ctggacccca tggacaacgt caacccettc aaccaccacc gcaacgcggg  19920
cctgcgctac cgctccatgc tcctgggcaa cgggcgctac gtgcccttcc acatccaggt  19980
gccccaaaag tttttcgcca tcaagagcct cctgctcctg cccgggtcct acacctacga  20040
gtggaacttc cgcaaggacg tcaacatgat cctgcagagc tccctcggca acgacctgcg  20100
cacggacggg gcctccatcg ccttcaccag catcaacctc tacgccacct tcttccccat  20160
ggcgcacaac accgcctcca cgctcgaggc catgctgcgc aacgacacca acgaccagtc  20220
cttcaacgac tacctctcgg cggccaacat gctctacccc atcccggcca acgccaccaa  20280
cgtgcccatc tccatcccct cgcgcaactg ggccgccttc cgcggatggt ccttcacgcg  20340
cctcaagacc cgcgagacgc cctcgctcgg ctccgggttc gacccctact tcgtctactc  20400
gggctccatc ccctacctcg acggcacctt ctacctcaac cacaccttca agaaggtctc  20460
catcaccttc gactcctccg tcagctggcc cggcaacgac cgcctcctga cgcccaacga  20520
gttcgaaatc aagcgcaccg tcgacggaga gggatacaac gtggcccagt gcaacatgac  20580
caaggactgg ttcctggtcc agatgctggc ccactacaac atcggctacc agggcttcta  20640
cgtgcccgag ggctacaagg accgcatgta ctccttcttc cgcaacttcc agcccatgag  20700
ccgccaggtc gtggacgagg tcaactacaa ggactaccag gccgtcaccc tggcctacca  20760
gcacaacaac tcgggcttcg tcggctacct cgcgcccacc atgcgccagg gccagcccta  20820
ccccgccaac taccccctacc cgctcatcgg caagagcgcc gtcgccagcg tcacccagaa  20880
aaagttcctc tgcgaccggg tcatgtggcg catccccttc tccagcaact tcatgtccat  20940
gggcgcgctc accgacctcg gccagaacat gctctacgcc aactccgccc acgcgctaga  21000
```

catgaatttc gaagtcgacc ccatggatga gtccaccctt ctctatgttg tcttcgaagt 21060
cttcgacgtc gtccgagtgc accagcccca ccgcggcgtc atcgaggccg tctacctgcg 21120
cacgcccttc tcggccggca acgccaccac ctaaagcccc gctcttgctt cttgcaagat 21180
gacggcctgt ggctccggcg agcaggagct cagggccatc ctccgcgacc tgggctgcgg 21240
gccctgcttc ctgggcacct tcgacaagcg cttcccggga ttcatggccc cgcacaagct 21300
ggcctgcgcc atcgtcaaca cggccggccg cgagaccggg ggcgagcact ggctggcctt 21360
cgcctggaac ccgcgctccc acacctgcta cctcttcgac cccttcgggt tctcggacga 21420
gcgcctcaag cagatctacc agttcgagta cgagggcctg ctgcgccgca gcgccctggc 21480
caccgaggac cgctgcatca ccctggaaaa gtccacccag accgtgcagg gtccgcgctc 21540
ggccgcctgc gggctcttct gctgcatgtt cctgcacgcc ttcgtgcact ggcccgaccg 21600
ccccatggac aagaacccca ccatgaactt gctgacgggg gtgcccaacg gcatgctcca 21660
gtcgccccag gtggaaccca ccctgcgccg caaccaggag gcgctctacc gcttcctcaa 21720
cgcccactcc gcctactttc gctcccaccg cgcgcgcatc gagaaggcca ccgccttcga 21780
ccgcatgaat caagacatgt aaactgtgtg tatgtgaatg ctttattcat cataataaac 21840
agcacatgtt tatgccacct tctctgaggc tctgacttta tttagaaatc gaaggggttc 21900
tgccggctct cggcgtgccc cgcgggcagg gatacgttgc ggaactggta cttgggcagc 21960
cacttgaact cggggatcag cagcttcggc acggggaggt cggggaacga gtcgctccac 22020
agcttgcgcg tgagttgcag ggcgcccagc aggtcgggcg cggagatctt gaaatcgcag 22080
ttgggacccg cgttctgcgc gcgagagttg cggtacacgg ggttgcagca ctggaacacc 22140
atcagggccg ggtgcttcac gctcgccagc accgtcgcgt cggtgatgcc ctccacgtcc 22200
agatcctcgg cgttggccat cccgaagggg gtcatcttgc aggtctgccg ccccatgctg 22260
ggcacgcagc cgggcttgtg gttgcaatcg cagtgcaggg ggatcagcat catctgagcc 22320
tgctcggagc tcatgcccgg gtacatggcc ttcatgaaag cctccagctg gcggaaggcc 22380
tgctgcgcct tgccgccctc ggtgaagaag accccacagg acttgctaga gaactggttg 22440
gtggcgcagc ccgcgtcgtg cacgcagcag cgcgcgtcgt tgttggccag ctgcaccacg 22500
ctgcgccccc agcggttctg ggtgatcttg gcccggtcgg ggttctcctt cagcgcgcgc 22560
tgcccgttct cgctcgccac atccatctcg atcgtgtgct ccttctggat catcacggtc 22620
ccgtgcaggc accgcagctt gccctcggcc tcggtgcacc cgtgcagcca cagcgcgcag 22680
ccggtgcact cccagttctt gtgggcgatc tgggagtgcg agtgcacgaa gccctgcagg 22740
aagcggccca tcatcgtggt cagggtcttg ttgctggtga aggtcagcgg gatgccgcgg 22800
tgctcctcgt tcacatacag gtggcagatg cggcggtaca cctcgccctg ctcgggcatc 22860
agctggaagg cggacttcag gtcgctctcc acgcggtacc gctccatcag cagcgtcatc 22920
acttccatgc ccttctccca ggccgaaacg atcggcaggc tcagggggtt cttcaccgtc 22980
atcttagtcg ccgccgccga agtcaggggg tcgttctcgt ccagggtctc aaacactcgc 23040
ttgccgtcct tctcggtgat gcgcacgggg ggaaagctga agcccacggc cgccagctcc 23100
tcctcggcct gcctttcgtc ctcgctgtcc tggctgatgt cttgcaaagg cacatgcttg 23160
gtcttgcggg gtttcttttt gggcggcaga ggcggcggcg gagacgtgct gggcgagcgc 23220
gagttctcgc tcaccacgac tatttcttct tcttggccgt cgtccgagac cacgcggcgg 23280
taggcatgcc tcttctgggg cagaggcgga ggcgacgggc tctcgcggtt cggcgggcgg 23340

```
ctggcagagc cccttccgcg ttcgggggtg cgctcctggc ggcgctgctc tgactgactt  23400
cctccgcggc cggccattgt gttctcctag ggagcaacaa gcatggagac tcagccatcg  23460
tcgccaacat cgccatctgc ccccgccgcc gacgagaacc agcagcagca gaatgaaagc  23520
ttaaccgccc cgccgcccag ccccacctcc gacgccgccg cggccccaga catgcaagag  23580
atggaggaat ccatcgagat tgacctgggc tacgtgacgc ccgcggagca cgaggaggag  23640
ctggcagcgc gcttttcagc cccggaagag aaccaccaag agcagccaga gcaggaagca  23700
gagagcgagc agcagcaggc tgggctcgag catggcgact acctgagcgg ggcagaggac  23760
gtgctcatca agcatctggc ccgccaaagc atcatcgtca aggacgcgct gctcgaccgc  23820
gccgaggtgc ccctcagcgt ggcggagctc agccgcgcct acgagcgcaa cctcttctcg  23880
ccgcgcgtgc cccccaagcg ccagcccaac ggcacctgcg agcccaaccc gcgcctcaac  23940
ttctacccgg tcttcgcggt gcccgaggcc ctggccacct accacctctt tttcaagaac  24000
caaaggatcc ccgtctcctg ccgcgccaac cgcacccgcg ccgacgccct gctcaacctg  24060
ggtcccggcg cccgcctacc tgatatcacc tccttggaag aggttcccaa gatcttcgag  24120
ggtctgggca gcgacgagac tcgggccgcg aacgctctgc aaggaagcgg agaggagcat  24180
gagcaccaca gcgccctggt ggagttggaa ggcgacaacg cgcgcctggc ggtgctcaag  24240
cgcacggtcg agctgaccca cttcgcctac ccggcgctca acctgccccc caaggtcatg  24300
agcgccgtca tggaccaggt gctcatcaag cgcgcctcgc ccctctcaga ggaggagatg  24360
caggaccccg agagctcgga cgagggcaag cccgtggtca gcgacgagca gctggcgcgc  24420
tggctgggag cgagcagcac cccccagagc ctggaagagc ggcgcaagct catgatggcc  24480
gtggtcctgg tgaccgtgga gctggagtgt ctgcgccgct tcttcgccga cgcggagacc  24540
ctgcgcaagg tcgaggagaa cctgcactac ctcttcaggc acgggttcgt gcgccaggcc  24600
tgcaagatct ccaacgtgga gctgaccaac ctggtctcct acatgggcat cctgcacgag  24660
aaccgcctgg ggcagaacgt gctgcacacc accctgcgcg gggaggcccg ccgcgactac  24720
atccgcgact gcgtctacct gtacctctgc cacacctggc agacgggcat gggcgtgtgg  24780
cagcagtgcc tggaggagca gaacctgaaa gagctctgca agctcctgca gaagaacctc  24840
aaggccctgt ggaccgggtt cgacgagcgc accaccgcct cggacctggc cgacctcatc  24900
ttccccgagc gcctgcggct gacgctgcgc aacgggctgc ccgactttat gagccaaagc  24960
atgttgcaaa actttcgctc tttcatcctc gaacgctccg ggatcctgcc cgccacctgc  25020
tccgcactgc cctcggactt cgtgccgctg accttccgcg agtgcccccc gccgctctgg  25080
agccactgct acttgctgcg cctggccaac tacctggcct accactcgga cgtgatcgag  25140
gacgtcagca gcgagggtct gctcgagtgc cactgccgct gcaacctctg cacgccgcac  25200
cgctccttgg cctgcaaccc ccagctgctg agcgagaccc agatcatcgg caccttcgag  25260
ttgcaaggcc ccggcgaggg caaggggggt ctcaaactca ccccggggct gtggacctcg  25320
gcctacttgc gcaagttcgt gcccgaggac taccatccct tcgagatcag gttctacgag  25380
gaccaatccc agccgcccaa ggccgagctg tcggcctgcg tcatcaccca gggggccatc  25440
ctggcccaat tgcaagccat ccagaaatcc cgccaagaat ttctgctgaa aaagggccac  25500
ggggtctact tggaccccca gaccggagag gagctcaacc ccagcttccc ccaggatgcc  25560
ccgaggaagc agcaagaagc tgaaagtgga gctgccgctg ccgccggagg atttggagga  25620
agactgggag agcagtcagg cagaggagat ggaagactgg gacagcactc aggcagagga  25680
ggacagcctg caagacagtc tggaggagga agacgaggtg gaggaggagg cagaggaaga  25740
```

```
agcagccgcc gccagaccgt cgtcctcggc ggaggagaaa gcaagcagca cggataccat  25800
ctccgctccg ggtcggggtc gcggcggccg ggcccacagt agatgggacg agaccgggcg  25860
cttcccgaac cccaccaccc agaccggtaa gaaggagcgg cagggataca agtcctggcg  25920
ggggcacaaa aacgccatcg tctcctgctt gcaagcctgc gggggcaaca tctccttcac  25980
ccggcgctac ctgctcttcc accgcggggt gaacttcccc cgcaacatct tgcattacta  26040
ccgtcacctc cacagcccct actactgttt ccaagaagag gcagaaaccc agcagcagca  26100
gcagaaaacc agcggcagca gcagcagcta gaaaatccac agcggcggca ggtggactga  26160
ggatcgcggc gaacgagccg gcgcagaccc gggagctgag gaaccggatc tttcccaccc  26220
tctatgccat cttccagcag agtcgggggc aggagcagga actgaaagtc aagaaccgtt  26280
ctctgcgctc gctcacccgc agttgtctgt atcacaagag cgaagaccaa cttcagcgca  26340
ctctcgagga cgccgaggct ctcttcaaca agtactgcgc gctcactctt aaagagtagc  26400
ccgcgcccgc ccacacacgg aaaaaggcgg gaattacgtc accacctgcg cccttcgccc  26460
gaccatcatc atgagcaaag agattcccac gccttacatg tggagctacc agccccagat  26520
gggcctggcc gccggcgccg cccaggacta ctccacccgc atgaactggc tcagtgccgg  26580
gcccgcgatg atctcacggg tgaatgacat ccgcgcccac cgaaaccaga tactcctaga  26640
acagtcagcg atcaccgcca cgccccgcca tcaccttaat ccgcgtaatt ggcccgccgc  26700
cctggtgtac caggaaattc cccagcccac gaccgtacta cttccgcgag acgcccaggc  26760
cgaagtccag ctgactaact caggtgtcca gctggccggc ggcgccgccc tgtgtcgtca  26820
ccgccccgct cagggtataa agcggctggt gatccgaggc agaggcacac agctcaacga  26880
cgaggtggtg agctcttcgc tgggtctgcg acctgacgga gtcttccaac tcgccggatc  26940
ggggagatct tccttcacgc ctcgtcaggc cgtcctgact ttggagagtt cgtcctcgca  27000
gccccgctcg ggcggcatcg gcactctcca gttcgtggag gagttcactc cctcggtcta  27060
cttcaacccc ttctccggct cccccggcca ctacccggac gagttcatcc cgaacttcga  27120
cgccatcagc gagtcggtgg acggctacga ttgaatgtcc catggtggcg cggctgacct  27180
agctcggctt cgacacctgg accactgccg ccgcttccgc tgcttcgctc gggatctcgc  27240
cgagtttgcc tactttgagc tgcccgagga gcaccctcag ggcccggccc acggagtgcg  27300
gatcgtcgtc gaagggggcc tcgactccca cctgcttcgg attttcagcc agcgtccgat  27360
cctggtcgag cgcgagcaag gacagaccct tctgaccctg tactgcatct gcaaccaccc  27420
cggcctgcat gaaagtcttt gttgtctgct gtgtactgag tataataaaa gctgagatca  27480
gcgactactc cggactcgat tgtggtgttc ctgctatcaa ccggtccctg ttcttcaccg  27540
ggaacgagac cgagctccag ctccagtgta agccccacaa gaagtatctc acctggctgt  27600
tccagggctc tccgatcgcc gttgtcaacc actgcgacaa cgacggagtc ctgctgagcg  27660
gccctgccaa ccttactttt tccacccgca gaagcaagct ccagctcttc caacccttcc  27720
tccccgggac ctatcagtgc gtctcgggac cctgccatca caccttccac ctgatcccga  27780
ataccacagc gccgctcccc gctactaaca accaaactac ccaccaacgc caccgtcgcg  27840
acctttctga atctaatact accacccaca ccggaggtga gctccgaggt cgaccaacct  27900
ctgggattta ctacggcccc tgggaggtgg tagggttaat agcgctaggc ctagttgcgg  27960
gtgggctttt ggctctctgc tacctatacc tcccttgctg ttcgtactta gtggtgctgt  28020
gttgctggtt taagaaatgg ggaagatcac cctagtgagc tgcggtgtgc tggtggcggt  28080
```

```
ggtgctttcg attgtgggac tgggcggcgc ggctgtagtg aaggaggaga aggccgatcc  28140
ctgcttgcat ttcaatcccg acaaatgcca gctgagtttt cagcccgatg gcaatcggtg  28200
cacggtgctg atcaagtgcg gatgggaatg cgagaacgtg agaatcgagt acaataacaa  28260
gactcggaac aatactctcg cgtccgtgtg gcagcccggg gaccccgagt ggtacaccgt  28320
ctctgtcccc ggtgctgacg gctccccgcg caccgtgaac aatactttca tttttgcgca  28380
catgtgcgac acggtcatgt ggatgagcaa gcagtacgat atgtggcccc ccacgaagga  28440
gaacatcgtg gtcttctcca tcgcttacag cctgtgcacg gcgctaatca ccgctatcgt  28500
gtgcctgagc attcacatgc tcatcgctat tcgccccaga aataatgccg aaaaagagaa  28560
acagccataa cacgtttttt cacacacctt tttcagacca tggcctctgt tactgcccta  28620
actatttttt tgggccttgt gggtactagc agcacttttc agcatataaa caaaactgtt  28680
tatgctggtt ctaattctgt attacctggg catcaatcac accagaaagt ttcatggtac  28740
tggtatgata aaagtaacac gccagtcaca ctctgcaagg gtcatcaaac acccataaac  28800
cgtagtggaa tttttttaa atgtaatcat aataatatta cactactttc aattacaaag  28860
cactattctg gtacttacta tggaaccaat tttaacataa aacaggacac ttactatagt  28920
gtcacagtat tggatccaac tactcctaga acaactacaa aacccacaac tactaagagg  28980
cacactaaac ctaaaactac caagaaaacc actgtcaaaa ctacaacaac taggaccacc  29040
acaactacag aggctaccac cagcacaaca cttgctgcca ctacacacac acacactgag  29100
ctaaccttac agaccactaa tgatttgatc gccctgttgc aaaaggggga taacagcacc  29160
acttccaatg aggagatacc cagatccatg attggcatta ttgttgctgt agtggtgtgc  29220
atgttgatca tcgccttgtg catggtgtac tatgccttct gctacagaaa gcacagactg  29280
aacgacaagc tggaacactt actaagtgtt gaattttaat tttttagaac catgaagatc  29340
ctaggccttt ttagtttttc tatcattacc tctactcttt gtgaatcagt ggataaagat  29400
gttactatta ccactggttc taattataca ctgaaagggc caccctcagg tatgctttcg  29460
tggtattgct attttggaac tgacactgat caaactgaat tatgcaattt tcaaaaaggc  29520
aaaacctcaa actctaaaat ctctaattat caatgcaatg gcactgatct gatactactc  29580
aatgtcacga aagcatatgg tggcagttat tcttgccctg gacaaaacac tgaggatatg  29640
attttttaca aagtggaagt ggttgatccc actactccac cgcccaccac cacaactact  29700
cacaccacac acacagaaca aacaccagag gcagcagaag cagagttggc cttccaggtt  29760
cacggagatt cctttgctgt caataccct acacccgatc agcggtgtcc ggggctgctc  29820
gtcagcggca ttgtcggtgt gctttcggga ttagcagtca taatcatctg catgttcatt  29880
tttgcttgct gctatagaag gctttaccga caaaaatcag acccactgct gaacctctat  29940
gtttaatttt ttccagagcc atgaaggcag ttagcgctct agtttttgt tctttgattg  30000
gcattgtttt tagtgctggg tttttgaaaa atcttaccat ttatgaaggt gagaatgcca  30060
ctctagtggg catcagtggt caaaatgtca gctggctaaa ataccatcta gatgggtgga  30120
aagacatttg cgattggaat gtcactgtgt atacatgtaa tggagttaac ctcaccatta  30180
ctaatgccac ccaagatcag aatggtaggt ttaagggcca gagtttcact agaaataatg  30240
ggtatgaatc ccataacatg tttatctatg acgtcactgt catcagaaat gagactgcca  30300
ccaccacaca gatgcccact acacacagtt ctaccactac taccatgcaa accacacaga  30360
caaccacttt ttatacatca actcagcata tgaccaccac tacagcagca aagccaagta  30420
gtgcagcgcc tcagccccag gctttggctt tgatagctgc acaacctagt acaactacta  30480
```

ggaccaatga gcagactact gatttttttgt ccactgtcga gagccacacc acagctacct 30540
ccagtgcctt ctctagcacc gccaatctct cctcgctttc ctctacacca atcagtcccg 30600
ctactactac tcctagcccc gctcctcttc ccactcccct gaagcaaact gaggacagcg 30660
gcatgcaatg gcagatcacc ctgctcattg tgatcgggtt ggtcattctg gccgtgttgc 30720
tctactacat cttctgccgc cgcattccca acgcgcaccg caagccggtc tacaagccca 30780
tcgttgacgg gcaaccggag ccgcttcagg tggaaggggg tctaaggaat cttctcttct 30840
cttttacagt atggtgattg aactatgatt cctagacaat tcttgatcac tattcttatc 30900
tgcctcctcc aagtctgtgc caccctcgct ctggtggcca acgccagtcc agactgtatt 30960
gggcccttcg cctcctacgt gctctttgcc ttcgtcacct gcatctgctg ctgtagcata 31020
gtctgcctgc ttatcacctt cttccagttc attgactgga tctttgtgcg catcgcctac 31080
ctgcgccacc acccccagta ccgcgaccag cgagtggcgc ggctgctcag gctcctctga 31140
taagcatgcg ggctctgcta cttctcgcgc ttctgctgtt agtgctcccc cgtcccgtca 31200
acccccggtc ccccactcag tcccccgagg aggtccgcaa atgcaaattc caagaaccct 31260
ggaaattcct caaatgctac cgccaaaaat cagacatgca tcccagctgg atcatgatca 31320
ttgggatcgt gaacattctg gcctgcaccc tcatctcctt tgtgatttac ccctgctttg 31380
actttggttg gaactcgcca gaggcgctct atctcccgcc tgaacctgac acaccaccac 31440
agcaacctca ggcacacgca ctaccaccac cacagcctag gccacaatac atgcccatat 31500
tagactatga ggccgagcca cagcgaccca tgctccccgc tattagttac ttcaatctaa 31560
ccggcggaga tgactgaccc actggccaac aacaacgtca acgaccttct cctggacatg 31620
gacggccgcg cctcggagca gcgactcgcc caacttcgca ttcgccagca gcaggagaga 31680
gccgtcaagg agctgcagga cggcatagcc atccaccagt gcaagaaagg catcttctgc 31740
ctggtgaaac aggccaagat ctcctacgag gtcacccaga ccgaccatcg cctctcctac 31800
gagctcctgc agcagcgcca gaagttcacc tgcctggtcg gagtcaaccc catcgtcatc 31860
acccagcagt cgggcgatac caaggggtgc atccactgct cctgcgactc ccccgactgc 31920
gtccacactc tgatcaagac cctctgcggc ctccgcgacc tcctccccat gaactaatca 31980
ccccccttatc cagtgaaata aagatcatat tgatgatgat tttacagaaa taaagataca 32040
atcatattga tgatttgagt ttaataaaaa ataaagaatc acttacttga aatctgatac 32100
caggtctctg tccatgtttt ctgccaacac cacttcactc ccctcttccc agctctggta 32160
ctgcaggccc cggcgggctg caaacttcct ccacacgctg aaggggatgt caaattcctc 32220
ctgtccctca atcttcattt tatcttctat cagatgtcca aaaagcgcgt ccgggtggat 32280
gatgacttcg accccgtcta cccctacgat gcagacaacg caccgaccgt gcccttcatc 32340
aacccccccct tcgtctcttc agatggattc caagagaagc ccctgggggt gctgtccctg 32400
cgactggccg accccgtcac caccaagaac ggggaaatca ccctcaagct gggagagggg 32460
gtggacctcg actcctcggg aaaactcatc tccaacacgg ccaccaaggc cgccgcccct 32520
ctcagttttt ccaacaacac catttccctt aacatggatc accccttttta cactaaagat 32580
ggaaaattat ccttacaagt ttctccacca ttaaatatac tgagaacaag cattctaaac 32640
acactagctt taggttttgg atcaggttta ggactccgtg gctctgcctt ggcagtacag 32700
ttagtctctc cacttacatt tgatactgat ggaaacataa agcttacctt agacagaggt 32760
ttgcatgtta caacaggaga tgcaattgaa agcaacataa gctgggctaa aggtttaaaa 32820

```
tttgaagatg gagccatagc aaccaacatt ggaaatgggt tagagtttgg aagcagtagt  32880
acagaaacag gtgttgatga tgcttaccca atccaagtta aacttggatc tggccttagc  32940
tttgacagta caggagccat aatggctggt aacaaagaag acgataaact cactttgtgg  33000
acaacacctg atccatcgcc aaactgtcaa atactcgcag aaaatgatgc aaaactaaca  33060
ctttgcttga ctaaatgtgg tagtcaaata ctggccactg tgtcagtctt agttgtagga  33120
agtggaaacc taaaccccat tactggcacc gtaagcagtg ctcaggtgtt tctacgtttt  33180
gatgcaaacg gtgttctttt aacagaacat tctacactaa aaaaatactg gggtataggg  33240
cagggagata gcatagatgg cactccatat accaatgctg taggattcat gcccaattta  33300
aaagcttatc caaagtcaca aagttctact actaaaaata atatagtagg gcaagtatac  33360
atgaatggag atgtttcaaa acctatgctt ctcactataa ccctcaatgg tactgatgac  33420
agcaacagta catattcaat gtcattttca tacacctgga ctaatggaag ctatgttgga  33480
gcaacatttg gggctaactc ttataccttc tcatacatcg cccaagaatg aacactgtat  33540
cccaccctgc atgccaaccc ttcccacccc actctgtgga aaaaactctg aaacacaaaa  33600
taaaataaag ttcaagtgtt ttattgattc aacagtttta caggattcga gcagttattt  33660
ttcctccacc ctcccaggac atggaataca ccaccctctc cccccgcaca gccttgaaca  33720
tctgaacgcc attggtgatg gacatgcttt tggtctccac gttccacaca gtttcagagc  33780
gagccagtct cgggtcggtc agggagatga aaccctccgg gcactcccgc atctgcacct  33840
cacagctcaa cagctgagga ttgtcctcgg tggtcgggat cacggttatc tggaagaagc  33900
agaagagcgg cggtgggaat catagtccgc gaacgggatc ggccggtggt gtcgcatcag  33960
gccccgcagc agtcgctgtc gccgccgctc cgtcaagctg ctgctcaggg ggtccgggtc  34020
cagggactcc ctcagcatga tgcccacggc cctcagcatc agtcgtctgg tgcggcgggc  34080
gcagcagcgc atgcggatct cgctcaggtc gctgcagtac gtgcaacaca ggaccaccag  34140
gttgttcaac agtccatagt tcaacacgct ccagccgaaa ctcatcgcgg gaaggatgct  34200
acccacgtgg ccgtcgtacc agatcctcag gtaaatcaag tggcgccccc tccagaacac  34260
gctgcccatg tacatgatct ccttgggcat gtggcggttc accacctccc ggtaccacat  34320
caccctctgg ttgaacatgc agccccggat gatcctgcgg aaccacaggg ccagcaccgc  34380
cccgcccgcc atgcagcgaa gagaccccgg gtcccggcaa tggcaatgga ggacccaccg  34440
ctcgtacccg tggatcatct gggagctgaa caagtctatg ttggcacagc acaggcacac  34500
gctcatgcat ctcttcagca ctctcagctc ctcgggggtc aaaaccatat cccagggcac  34560
ggggaactct tgcaggacag cgaaccccgc agaacagggc aatcctcgca cagaacttac  34620
attgtgcatg gacagggtat cgcaatcagg cagcaccggg tgatcctcca ccagggaagc  34680
gcgggtctcg gtctcctcac agcgtggtaa gggggccggc cgatacgggt gatggcggga  34740
cgcggctgat cgtgctcgcg accgtgtcat gatgcagttg ctttcggaca ttttcgtact  34800
tgctgtagca gaacctggtc cgggcgctgc acaccgatcg ccggcggcgg tcccggcgct  34860
tggaacgctc ggtgttgaag ttgtaaaaca gccactctct cagaccgtgc agcagatcta  34920
gggcctcagg agtgatgaaa atcccatcat gcctgatagc tctgatcaca tcgaccaccg  34980
tggaatgggc cagacccagc cagatgatgc aattttgttg ggtttcggta acggcggggg  35040
agggaagaac aggaagaacc atgattaact tttaatccaa acggtctcgg agcacttcaa  35100
aatgaagatc gcggagatgg cacctctcgc ccccgctgtg ttggtggaaa ataacagcca  35160
ggtcaaaggt gatacggttc tcgagatgtt ccacggtggc ttccagcaaa gcctccacgc  35220
```

```
gcacatccag aaacaagaca atagcgaaag cgggagggtt ctctaattcc tcaatcatca  35280

tgttacactc ctgcaccatc cccagataat tttcattttt ccagccttga atgattcgaa  35340

ctagttcctg aggtaaatcc aagccagcca tgataaagag ctcgcgcaga gcgccctcca  35400

ccggcattct taagcacacc ctcataattc caagatattc tgctcctggt tcacctgcag  35460

cagattgaca agcggaatat caaactctct gccgcgatcc ctaagctcct ccctcagcaa  35520

taactgtaag tactctttca tatcctctcc gaaattttta gccataggac cgccaggaat  35580

aagattaggg caagccacag tacagataaa ccgaagtcct ccccagtgag cattgccaaa  35640

tgcaagactg ctataagcat gctggctaga cccggtgata tcttccagat aactggacag  35700

aaaatcgccc aggcaatttt taagaaaatc aacaaaagaa aaatcctcca ggtgcacgtt  35760

tagagcctcg ggaacaacga tggagtaaat gcaagcggtg cgttccagca tggttagtta  35820

gctgatctgt agaaaaaaca aaaatgaaca ttaaaccatg ctagcctggc gaacaggtgg  35880

gtaaatcgtt ctttccagca ccaggcaggc cacggggtct ccggcacgac cctcgtaaaa  35940

attgtcgcta tgattgaaaa ccatcacaga gagacgttcc cggtggccgg cgtgaatgat  36000

tcgacaagat gaatacaccc ccggaacatt ggcgtccgcg agtgaaaaaa agcgcccgag  36060

gaagcaataa ggcactacaa tgctcagtct caagtccagc aaagcgatgc catgcggatg  36120

aagcacaaaa ttctcaggtg cgtacaaaat gtaattactc ccctcctgca caggcagcaa  36180

agcccccgat ccctccaggt acacatacaa agcctcagcg tccatagctt accgagcagc  36240

agcagcagca cacaacaggc gcaagagtca gagaaaggct gagctctaac ctgtccaccc  36300

gctctctgct caatatatag cccagatcta cactgacgta aaggccaaag tctaaaaata  36360

cccgccaaat agtcacacac gcccagcaca cgcccagaaa ccggtgacac actcaaaaaa  36420

atacgcgcac ttcctcaaac gcccaaactg ccgtcatttc cgggttccca cgctacgtca  36480

tcaaaacacg actttcaaat tccgtcgacc gttaaaaacg tcacccgccc cgcccctaac  36540

ggtcgcccgt ctctcagcca atcagcgccc cgcatcccca aattcaaaca cctcatttgc  36600

atattaacgc gcaccaaaag tttgaggtat attattgatg atg                   36643
```

<210> SEQ ID NO 15
<211> LENGTH: 540
<212> TYPE: PRT
<213> ORGANISM: Pan troglodytes

<400> SEQUENCE: 15

```
Met Met Arg Arg Val Tyr Pro Glu Gly Pro Pro Pro Ser Tyr Glu Ser
1               5                   10                  15

Val Met Gln Gln Ala Val Ala Ala Ala Met Gln Pro Pro Leu Glu Ala
            20                  25                  30

Pro Tyr Val Pro Pro Arg Tyr Leu Ala Pro Thr Glu Gly Arg Asn Ser
        35                  40                  45

Ile Arg Tyr Ser Glu Leu Ala Pro Leu Tyr Asp Thr Thr Arg Leu Tyr
    50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
            100                 105                 110

Trp Gly Gly Gln Leu Lys Thr Ile Met His Thr Asn Met Pro Asn Val
```

```
        115                 120                 125

Asn Glu Phe Met Tyr Ser Asn Lys Phe Lys Ala Arg Val Met Val Ser
    130                 135                 140

Arg Lys Thr Pro Asn Gly Val Thr Val Gly Asp Asp Tyr Asp Gly Ser
145                 150                 155                 160

Gln Asp Glu Leu Thr Tyr Glu Trp Val Glu Phe Glu Leu Pro Glu Gly
                165                 170                 175

Asn Phe Ser Val Thr Met Thr Ile Asp Leu Met Asn Asn Ala Ile Ile
            180                 185                 190

Asp Asn Tyr Leu Ala Val Gly Arg Gln Asn Gly Val Leu Glu Ser Asp
        195                 200                 205

Ile Gly Val Lys Phe Asp Thr Arg Asn Phe Arg Leu Gly Trp Asp Pro
    210                 215                 220

Val Thr Glu Leu Val Met Pro Gly Val Tyr Thr Asn Glu Ala Phe His
225                 230                 235                 240

Pro Asp Ile Val Leu Leu Pro Gly Cys Gly Val Asp Phe Thr Glu Ser
                245                 250                 255

Arg Leu Ser Asn Leu Leu Gly Ile Arg Lys Arg Gln Pro Phe Gln Glu
            260                 265                 270

Gly Phe Gln Ile Leu Tyr Glu Asp Leu Glu Gly Gly Asn Ile Pro Ala
        275                 280                 285

Leu Leu Asp Val Glu Ala Tyr Glu Glu Ser Lys Glu Lys Ala Glu Ala
    290                 295                 300

Glu Ala Thr Thr Ala Val Ala Thr Ala Ala Thr Val Ala Asp Ala Thr
305                 310                 315                 320

Val Thr Arg Gly Asp Thr Phe Ala Thr Gln Ala Glu Glu Ala Ala Ala
                325                 330                 335

Leu Ala Ala Thr Asp Asp Ser Glu Ser Lys Ile Val Ile Lys Pro Val
            340                 345                 350

Glu Lys Asp Ser Lys Asn Arg Ser Tyr Asn Val Leu Pro Asp Gly Lys
        355                 360                 365

Asn Thr Ala Tyr Arg Ser Trp Tyr Leu Ala Tyr Asn Tyr Gly Asp Pro
    370                 375                 380

Glu Lys Gly Val Arg Ser Trp Thr Leu Leu Thr Thr Ser Asp Val Thr
385                 390                 395                 400

Cys Gly Val Glu Gln Val Tyr Trp Ser Leu Pro Asp Met Met Gln Asp
                405                 410                 415

Pro Val Thr Phe Arg Ser Thr Arg Gln Val Ser Asn Tyr Pro Val Val
            420                 425                 430

Gly Ala Glu Leu Leu Pro Val Tyr Ser Lys Ser Phe Phe Asn Glu Gln
        435                 440                 445

Ala Val Tyr Ser Gln Gln Leu Arg Ala Phe Thr Ser Leu Thr His Val
    450                 455                 460

Phe Asn Arg Phe Pro Glu Asn Gln Ile Leu Val Arg Pro Pro Ala Pro
465                 470                 475                 480

Thr Ile Thr Thr Val Ser Glu Asn Val Pro Ala Leu Thr Asp His Gly
                485                 490                 495

Thr Leu Pro Leu Arg Ser Ser Ile Arg Gly Val Gln Arg Val Thr Val
            500                 505                 510

Thr Asp Ala Arg Arg Arg Thr Cys Pro Tyr Val Tyr Lys Ala Leu Gly
        515                 520                 525

Val Val Ala Pro Arg Val Leu Ser Ser Arg Thr Phe
    530                 535                 540
```

<210> SEQ ID NO 16
<211> LENGTH: 958
<212> TYPE: PRT
<213> ORGANISM: Pan troglodytes

<400> SEQUENCE: 16

```
Met Tyr Val Arg Arg Pro Glu Gly Gly Arg Gly Ala Ser Pro Ser Cys
1               5                   10                  15

Lys Met Ala Thr Pro Ser Met Leu Pro Gln Trp Ala Tyr Met His Ile
            20                  25                  30

Ala Gly Gln Asp Ala Ser Glu Tyr Leu Ser Pro Gly Leu Val Gln Phe
        35                  40                  45

Ala Arg Ala Thr Asp Thr Tyr Phe Ser Leu Gly Asn Lys Phe Arg Asn
    50                  55                  60

Pro Thr Val Ala Pro Thr His Asp Val Thr Thr Asp Arg Ser Gln Arg
65                  70                  75                  80

Leu Thr Leu Arg Phe Val Pro Val Asp Arg Glu Asp Asn Thr Tyr Ser
                85                  90                  95

Tyr Lys Val Arg Tyr Thr Leu Ala Val Gly Asp Asn Arg Val Leu Asp
            100                 105                 110

Met Ala Ser Thr Tyr Phe Asp Ile Arg Gly Val Leu Asp Arg Gly Pro
        115                 120                 125

Ser Phe Lys Pro Tyr Ser Gly Thr Ala Tyr Asn Ser Leu Ala Pro Lys
    130                 135                 140

Gly Ala Pro Asn Thr Ser Gln Trp Lys Asp Ser Asp Ser Lys Met His
145                 150                 155                 160

Thr Phe Gly Val Ala Ala Met Pro Gly Val Val Gly Lys Lys Ile Glu
                165                 170                 175

Ala Asp Gly Leu Pro Ile Gly Ile Asp Ser Ser Ser Gly Thr Asp Thr
            180                 185                 190

Ile Ile Tyr Ala Asp Lys Thr Phe Gln Pro Glu Pro Gln Val Gly Ser
        195                 200                 205

Asp Ser Trp Val Asp Thr Asn Gly Ala Glu Glu Lys Tyr Gly Gly Arg
    210                 215                 220

Ala Leu Lys Asp Thr Thr Asn Met Lys Pro Cys Tyr Gly Ser Phe Ala
225                 230                 235                 240

Arg Pro Thr Asn Lys Glu Gly Gly Gln Ala Asn Ile Lys Asp Ser Glu
                245                 250                 255

Thr Ala Ser Thr Thr Pro Asn Tyr Asp Ile Asp Leu Ala Phe Phe Asp
            260                 265                 270

Ser Lys Asn Ile Ala Ala Asn Tyr Asp Pro Asp Ile Val Met Tyr Thr
        275                 280                 285

Glu Asn Val Glu Leu Gln Thr Pro Asp Thr His Ile Val Phe Lys Pro
    290                 295                 300

Gly Thr Ser Asp Glu Ser Ser Glu Ala Asn Leu Gly Gln Gln Ala Met
305                 310                 315                 320

Pro Asn Arg Pro Asn Tyr Ile Gly Phe Arg Asp Asn Phe Ile Gly Leu
                325                 330                 335

Met Tyr Tyr Asn Ser Thr Gly Asn Met Gly Val Leu Ala Gly Gln Ala
            340                 345                 350

Ser Gln Leu Asn Ala Val Val Asp Leu Gln Asp Arg Asn Thr Glu Leu
        355                 360                 365

Ser Tyr Gln Leu Leu Leu Asp Ser Leu Gly Asp Arg Thr Arg Tyr Phe
```

```
    370                 375                 380

Ser Met Trp Asn Gln Ala Val Asp Ser Tyr Asp Pro Asp Val Arg Ile
385                 390                 395                 400

Ile Glu Asn His Gly Val Glu Asp Glu Leu Pro Asn Tyr Cys Phe Pro
                405                 410                 415

Leu Asn Gly Val Gly Phe Thr Asp Thr Tyr Gln Gly Val Lys Val Lys
            420                 425                 430

Thr Asp Thr Ala Ala Thr Gly Thr Asn Gly Thr Gln Trp Asp Lys Asp
        435                 440                 445

Asp Thr Thr Val Ser Thr Ala Asn Glu Ile His Ser Gly Asn Pro Phe
    450                 455                 460

Ala Met Glu Ile Asn Ile Gln Ala Asn Leu Trp Arg Asn Phe Leu Tyr
465                 470                 475                 480

Ala Asn Val Ala Leu Tyr Leu Pro Asp Ser Tyr Lys Tyr Thr Pro Ala
                485                 490                 495

Asn Ile Thr Leu Pro Thr Asn Thr Asn Thr Tyr Asp Tyr Met Asn Gly
            500                 505                 510

Arg Val Val Ala Pro Ser Leu Val Asp Ala Tyr Ile Asn Ile Gly Ala
        515                 520                 525

Arg Trp Ser Leu Asp Pro Met Asp Asn Val Asn Pro Phe Asn His His
    530                 535                 540

Arg Asn Ala Gly Leu Arg Tyr Arg Ser Met Leu Leu Gly Asn Gly Arg
545                 550                 555                 560

Tyr Val Pro Phe His Ile Gln Val Pro Gln Lys Phe Phe Ala Ile Lys
                565                 570                 575

Ser Leu Leu Leu Leu Pro Gly Ser Tyr Thr Tyr Glu Trp Asn Phe Arg
            580                 585                 590

Lys Asp Val Asn Met Ile Leu Gln Ser Ser Leu Gly Asn Asp Leu Arg
        595                 600                 605

Thr Asp Gly Ala Ser Ile Ala Phe Thr Ser Ile Asn Leu Tyr Ala Thr
    610                 615                 620

Phe Phe Pro Met Ala His Asn Thr Ala Ser Thr Leu Glu Ala Met Leu
625                 630                 635                 640

Arg Asn Asp Thr Asn Asp Gln Ser Phe Asn Asp Tyr Leu Ser Ala Ala
                645                 650                 655

Asn Met Leu Tyr Pro Ile Pro Ala Asn Ala Thr Asn Val Pro Ile Ser
            660                 665                 670

Ile Pro Ser Arg Asn Trp Ala Ala Phe Arg Gly Trp Ser Phe Thr Arg
        675                 680                 685

Leu Lys Thr Arg Glu Thr Pro Ser Leu Gly Ser Gly Phe Asp Pro Tyr
    690                 695                 700

Phe Val Tyr Ser Gly Ser Ile Pro Tyr Leu Asp Gly Thr Phe Tyr Leu
705                 710                 715                 720

Asn His Thr Phe Lys Lys Val Ser Ile Thr Phe Asp Ser Ser Val Ser
                725                 730                 735

Trp Pro Gly Asn Asp Arg Leu Leu Thr Pro Asn Glu Phe Glu Ile Lys
            740                 745                 750

Arg Thr Val Asp Gly Glu Gly Tyr Asn Val Ala Gln Cys Asn Met Thr
        755                 760                 765

Lys Asp Trp Phe Leu Val Gln Met Leu Ala His Tyr Asn Ile Gly Tyr
    770                 775                 780

Gln Gly Phe Tyr Val Pro Glu Gly Tyr Lys Asp Arg Met Tyr Ser Phe
785                 790                 795                 800
```

Phe Arg Asn Phe Gln Pro Met Ser Arg Gln Val Val Asp Glu Val Asn
805 810 815

Tyr Lys Asp Tyr Gln Ala Val Thr Leu Ala Tyr Gln His Asn Asn Ser
820 825 830

Gly Phe Val Gly Tyr Leu Ala Pro Thr Met Arg Gln Gly Gln Pro Tyr
835 840 845

Pro Ala Asn Tyr Pro Tyr Pro Leu Ile Gly Lys Ser Ala Val Ala Ser
850 855 860

Val Thr Gln Lys Lys Phe Leu Cys Asp Arg Val Met Trp Arg Ile Pro
865 870 875 880

Phe Ser Ser Asn Phe Met Ser Met Gly Ala Leu Thr Asp Leu Gly Gln
885 890 895

Asn Met Leu Tyr Ala Asn Ser Ala His Ala Leu Asp Met Asn Phe Glu
900 905 910

Val Asp Pro Met Asp Glu Ser Thr Leu Leu Tyr Val Val Phe Glu Val
915 920 925

Phe Asp Val Val Arg Val His Gln Pro His Arg Gly Val Ile Glu Ala
930 935 940

Val Tyr Leu Arg Thr Pro Phe Ser Ala Gly Asn Ala Thr Thr
945 950 955

<210> SEQ ID NO 17
<211> LENGTH: 425
<212> TYPE: PRT
<213> ORGANISM: Pan troglodytes

<400> SEQUENCE: 17

Met Ser Lys Lys Arg Val Arg Val Asp Asp Asp Phe Asp Pro Val Tyr
1 5 10 15

Pro Tyr Asp Ala Asp Asn Ala Pro Thr Val Pro Phe Ile Asn Pro Pro
20 25 30

Phe Val Ser Ser Asp Gly Phe Gln Glu Lys Pro Leu Gly Val Leu Ser
35 40 45

Leu Arg Leu Ala Asp Pro Val Thr Thr Lys Asn Gly Glu Ile Thr Leu
50 55 60

Lys Leu Gly Glu Gly Val Asp Leu Asp Ser Ser Gly Lys Leu Ile Ser
65 70 75 80

Asn Thr Ala Thr Lys Ala Ala Ala Pro Leu Ser Phe Ser Asn Asn Thr
85 90 95

Ile Ser Leu Asn Met Asp His Pro Phe Tyr Thr Lys Asp Gly Lys Leu
100 105 110

Ser Leu Gln Val Ser Pro Pro Leu Asn Ile Leu Arg Thr Ser Ile Leu
115 120 125

Asn Thr Leu Ala Leu Gly Phe Gly Ser Gly Leu Gly Leu Arg Gly Ser
130 135 140

Ala Leu Ala Val Gln Leu Val Ser Pro Leu Thr Phe Asp Thr Asp Gly
145 150 155 160

Asn Ile Lys Leu Thr Leu Asp Arg Gly Leu His Val Thr Thr Gly Asp
165 170 175

Ala Ile Glu Ser Asn Ile Ser Trp Ala Lys Gly Leu Lys Phe Glu Asp
180 185 190

Gly Ala Ile Ala Thr Asn Ile Gly Asn Gly Leu Glu Phe Gly Ser Ser
195 200 205

Ser Thr Glu Thr Gly Val Asp Asp Ala Tyr Pro Ile Gln Val Lys Leu

```
    210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
                245                 250                 255

Asn Cys Gln Ile Leu Ala Glu Asn Asp Ala Lys Leu Thr Leu Cys Leu
            260                 265                 270

Thr Lys Cys Gly Ser Gln Ile Leu Ala Thr Val Ser Val Leu Val Val
        275                 280                 285

Gly Ser Gly Asn Leu Asn Pro Ile Thr Gly Thr Val Ser Ser Ala Gln
    290                 295                 300

Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
                325                 330                 335

Thr Pro Tyr Thr Asn Ala Val Gly Phe Met Pro Asn Leu Lys Ala Tyr
            340                 345                 350

Pro Lys Ser Gln Ser Ser Thr Thr Lys Asn Asn Ile Val Gly Gln Val
        355                 360                 365

Tyr Met Asn Gly Asp Val Ser Lys Pro Met Leu Leu Thr Ile Thr Leu
    370                 375                 380

Asn Gly Thr Asp Asp Ser Asn Ser Thr Tyr Ser Met Ser Phe Ser Tyr
385                 390                 395                 400

Thr Trp Thr Asn Gly Ser Tyr Val Gly Ala Thr Phe Gly Ala Asn Ser
                405                 410                 415

Tyr Thr Phe Ser Tyr Ile Ala Gln Glu
            420                 425
```

<210> SEQ ID NO 18
<211> LENGTH: 30971
<212> TYPE: DNA
<213> ORGANISM: Artificial Sequence
<220> FEATURE:
<223> OTHER INFORMATION: M72-ChAd63 construct

<400> SEQUENCE: 18

```
catcatcaat aatatacctc aaacttttgg tgcgcgttaa tatgcaaatg aggtgtttga     60

atttggggat gcggggcgct gattggctga gagacgggcg accgttaggg gcggggcggg    120

tgacgttttg atgacgtggc cgtgaggcgg agccggtttg caagttctcg tgggaaaagt    180

gacgtcaaac gaggtgtggt ttgaacacgg aaatactcaa ttttcccgcg ctctctgaca    240

ggaaatgagg tgtttctggg cggatgcaag tgaaaacggg ccattttcgc gcgaaaactg    300

aatgaggaag tgaaaatctg agtaattccg cgtttatggc agggaggagt atttgccgag    360

ggccgagtag actttgaccg attacgtggg ggtttcgatt accgtatttt tcacctaaat    420

ttccgcgtac ggtgtcaaag tccggtgttt ttacggatat cccattgcat acgttgtatc    480

catatcataa tatgtacatt tatattggct catgtccaac attaccgcca tgttgacatt    540

gattattgac tagttattaa tagtaatcaa ttacggggtc attagttcat agcccatata    600

tggagttccg cgttacataa cttacggtaa atggcccgcc tggctgaccg cccaacgacc    660

cccgcccatt gacgtcaata atgacgtatg ttcccatagt aacgccaata gggactttcc    720

attgacgtca atgggtggag tatttacggt aaactgccca cttggcagta catcaagtgt    780

atcatatgcc aagtacgccc cctattgacg tcaatgacgg taaatggccc gcctggcatt    840
```

-continued

```
atgcccagta catgacctta tgggactttc ctacttggca gtacatctac gtattagtca    900
tcgctattac catggtgatg cggttttggc agtacatcaa tgggcgtgga tagcggtttg    960
actcacgggg atttccaagt ctccacccca ttgacgtcaa tgggagtttg ttttggcacc   1020
aaaatcaacg ggactttcca aaatgtcgta acaactccgc cccattgacg caaatgggcg   1080
gtaggcgtgt acggtgggag gtctatataa gcagagctct ccctatcagt gatagagatc   1140
tccctatcag tgatagagat cgtcgacgag ctcgtttagt gaaccgtcag atcgcctgga   1200
gacgccatcc acgctgtttt gacctccata gaagacaccg ggaccgatcc agcctccgcg   1260
gccgggaacg gtgcattgga acgcggattc cccgtgccaa gagtgagatc ttccgtttat   1320
ctaggtacca gatatcgcca ccatgaccgc cgccagcgac aacttccagc tgtctcaggg   1380
cggccagggc ttcgccatcc ctatcggcca agctatggcc attgctggac agatcagaag   1440
cggcggaggc agccctaccg tgcatatcgg ccctaccgcc ttcctgggcc tgggcgtggt   1500
ggacaacaac ggcaacggcg ccagagtgca gcgggtggtc ggatctgccc ctgccgcaag   1560
cctgggcatc agcaccgggg atgtgatcac cgccgtggat ggcgccccta tcaacagcgc   1620
cacagccatg gccgacgccc tgaatggaca ccaccccggc gacgtgatca gcgtgacctg   1680
gcagaccaag agcggaggca ccagaaccgg caacgtgaca ctggccgagg gacctcccgc   1740
cgagttcatg gtggatttcg gcgccctgcc ccccgagatc aactccgcca ggatgtatgc   1800
cggccctggc agcgcctctc tggtggccgc tgctcagatg tgggacagcg tggccagcga   1860
tctgttcagc gccgcctccg ccttccagtc cgtggtctgg ggcctgaccg tgggcagctg   1920
gatcggaagc agtgccggcc tgatggtggc tgccgcctct ccctacgtgg cctggatgtc   1980
agtcacagcc ggccaggccg aactgactgc cgctcaagtg cgagtggctg ctgctgccta   2040
tgagacagcc tacggcctga cagtgccccc acccgtgatc gccgagaacc gggccgagct   2100
gatgatcctg atcgccacca acctgctggg ccagaacacc cccgccattg ccgtgaacga   2160
ggccgagtac ggcgagatgt gggcccagga cgccgctgcc atgtttggct atgccgctgc   2220
tacagccacc gccactgcca ccctgctgcc cttcgaagag gcccccgaga tgacctctgc   2280
cggcggactg ctggaacagg ccgctgccgt ggaagaggcc agcgacacag ccgccgctaa   2340
ccagctgatg aacaacgtgc cccaggccct gcagcagctg gcacagccta cacagggcac   2400
cacccccttct agcaagctcg gcggcctgtg gaaaaccgtg tccccccacc ggtcccccat   2460
cagcaacatg gtgtccatgg ccaacaacca catgagcatg accaacagcg gcgtgtccat   2520
gaccaatacc ctgagcagca tgctgaaggg ctttgcccca gccgctgccg ctcaggctgt   2580
gcagacagct gctcagaatg gcgtgcgggc catgagcagc ctgggcagtt ccctgggcag   2640
ctctggactg ggagggggcg tggccgccaa tctgggcaga gccgctagcg tgggcagcct   2700
gtctgtgcct caagcctggg ctgctgccaa tcaggccgtg acaccagccg ctagagccct   2760
gcctctgacc agcctgacct ctgctgccga gaggggccct ggccagatgc tgggaggact   2820
gcctgtgggc cagatgggag ccagagccgg cggaggactg agcggcgtgc tgagagtgcc   2880
ccccagaccc tacgtgatgc cccactctcc cgccgctggc gatattgccc ctcccgccct   2940
gagccaggac agattcgccg acttccctgc cctgcccctg gatccttctg ccatggtggc   3000
tcaagtggga ccccaggtgg tgaacatcaa caccaagctg ggctacaaca acgccgtggg   3060
agccggcacc ggcatcgtga tcgaccccaa tggcgtggtg ctgaccaaca atcacgtgat   3120
cgctggcgcc accgacatca acgccttcag cgtgggctcc ggccagacct acggcgtgga   3180
cgtggtcgga tacgaccgga cccaggatgt ggccgtgctg cagctgagag gcgctggcgg   3240
```

actgccttct gccgccattg gaggcggagt ggccgtggga gaacctgtgg tggccatggg 3300
caatagcggc ggacagggcg gcacacctag agctgtgcct ggaagagtgg tggccctggg 3360
acagaccgtg caggccagcg atagcctgac aggcgccgag gaaaccctga acggcctgat 3420
ccagttcgac gccgccatcc agcctgggga tgctggcgga cctgtggtga acggactggg 3480
ccaggtggtc ggaatgaata ccgccgcctc ctaatagtga gcggccgcga tctgctgtgc 3540
cttctagttg ccagccatct gttgtttgcc cctcccccgt gccttccttg accctggaag 3600
gtgccactcc cactgtcctt tcctaataaa atgaggaaat tgcatcgcat tgtctgagta 3660
ggtgtcattc tattctgggg ggtggggtgg ggcaggacag caagggggag gattgggaag 3720
acaatagcag gcatgctggg gatgcggtgg gctctagata tcagcgatcg cgtgagtagt 3780
gtttgggggt gggtgggagc ctgcatgatg ggcagaatga ctaaaatctg tgtttttctg 3840
tgtgttgcag cagcatgagc ggaagcgcct cctttgaggg aggggtattc agcccttatc 3900
tgacggggcg tctcccctcc tgggcgggag tgcgtcagaa tgtgatggga tccacggtgg 3960
acggccggcc cgtgcagccc gcgaactctt caaccctgac ctacgcgacc ctgagctcct 4020
cgtccgtgga cgcagctgcc gccgcagctg ctgcttccgc cgccagcgcc gtgcgcggaa 4080
tggccctggg cgccggctac tacagctctc tggtggccaa ctcgagttcc accaataatc 4140
ccgccagcct gaacgaggag aagctgttgc tgctgatggc ccagctcgag gccctgaccc 4200
agcgcctggg cgagctgacc cagcaggtgg ctcagctgca ggcggagacg cgggccgcgg 4260
ttgccacggt gaaaaccaaa taaaaaatga atcaataaat aaacggagac ggttgttgat 4320
tttaacacag agtcttgaat ctttatttga tttttcgcgc gcggtaggcc ctggaccacc 4380
ggtctcgatc attgagcacc cggtggatct tttccaggac ccggtagagg tgggcttgga 4440
tgttgaggta catgggcatg agcccgtccc gggggtggag gtagctccat tgcagggcct 4500
cgtgctcggg ggtggtgttg taaatcaccc agtcatagca ggggcgcagg gcgtggtgct 4560
gcacgatgtc tttgaggagg agactgatgg ccacgggcag ccccttggtg taggtgttga 4620
cgaacctatt gagctgggag ggatgcatgc ggggggagat gagatgcatc ttggcctgga 4680
tcttgagatt ggcgatgttc ccgcccagat cccgccgggg gttcatgttg tgcaggacca 4740
ccagcacggt gtatccggtg cacttgggga atttgtcatg caacttggaa gggaaggcgt 4800
gaaagaattt ggagacgccc ttgtgaccgc ccaggttttc catgcactca tccatgatga 4860
tggcgatggg cccgtgggcg gcggcctggg caaagacgtt tcgggggtcg gacacatcgt 4920
agttgtggtc ctgggtgagc tcgtcatagg ccattttaat gaatttgggg cggagggtac 4980
ccgactgggg gacaaaggtg ccctcgatcc cgggggcgta gttcccctcg cagatctgca 5040
tctcccaggc cttgagctcg gaggggggga tcatgtccac ctgcggggcg atgaaaaaaa 5100
cggtttccgg ggcgggggag atgagctgcg ccgaaagcag gttccggagc agctgggact 5160
tgccgcagcc ggtggggccg tagatgaccc cgatgaccgg ctgcaggtgg tagttgaggg 5220
agagacagct gccgtcctcg cggaggaggg gggccacctc gttcatcatc tcgcgcacat 5280
gcatgttctc gcgcacgagt tccgccagga ggcgctcgcc ccccagcgag aggagctctt 5340
gcagcgaggc gaagtttttc agcggcttga gcccgtcggc catgggcatt ttggagaggg 5400
tctgttgcaa gagttccaga cggtcccaga gctcggtgat gtgctctagg gcatctcgat 5460
ccagcagacc tcctcgtttc gcgggttggg gcgactgcgg gagtagggca ccaggcgatg 5520
ggcgtccagc gaggccaggg tccggtcctt ccagggtcgc agggtccgcg tcagcgtggt 5580

```
ctccgtcacg gtgaaggggt gcgcgccggg ctgggcgctt gcgagggtgc gcttcaggct   5640
catccggctg gtcgagaacc gctcccggtc ggcgccctgc gcgtcggcca ggtagcaatt   5700
gagcatgagt tcgtagttga gcgcctcggc cgcgtggccc ttggcgcgga gcttaccttt   5760
ggaagtgtgt ccgcagacgg gacagaggag ggacttgagg gcgtagagct tgggggcgag   5820
gaagacggac tcgggggcgt aggcgtccgc gccgcagctg gcgcagacgg tctcgcactc   5880
cacgagccag gtgaggtcgg ggcggtcggg gtcaaaaacg aggtttcctc cgtgcttttt   5940
gatgcgtttc ttacctctgg tctccatgag ctcgtgtccc cgctgggtga caaagaggct   6000
gtccgtgtcc ccgtagaccg actttatggg ccggtcctcg agcggggtgc cgcggtcctc   6060
gtcgtagagg aaccccgccc actccgagac gaaggcccgg gtccaggcca gcacgaagga   6120
ggccacgtgg gaggggtagc ggtcgttgtc caccagcggg tccaccttct ccagggtatg   6180
caagcacatg tccccctcgt ccacatccag gaaggtgatt ggcttgtaag tgtaggccac   6240
gtgaccgggg gtcccggccg ggggggtata aaagggggcg ggcccctgct cgtcctcact   6300
gtcttccgga tcgctgtcca ggagcgccag ctgttggggt aggtattccc tctcgaaggc   6360
gggcatgacc tcggcactca ggttgtcagt ttctagaaac gaggaggatt tgatattgac   6420
ggtgccgttg gagacgcctt tcatgagccc ctcgtccatc tggtcagaaa agacgatctt   6480
tttgttgtcg agcttggtgg cgaaggagcc gtagagggcg ttggagagca gcttggcgat   6540
ggagcgcatg gtctggttct ttccttgtc ggcgcgctcc ttggcggcga tgttgagctg   6600
cacgtactcg cgcgccacgc acttccattc ggggaagacg gtggtgagct cgtcgggcac   6660
gattctgacc cgccagccgc ggttgtgcag ggtgatgagg tccacgctgg tggccacctc   6720
gccgcgcagg ggctcgttgg tccagcagag gcgcccgccc ttgcgcgagc agaagggggg   6780
cagcgggtcc agcatgagct cgtcgggggg gtcggcgtcc acggtgaaga tgccgggcag   6840
gagctcgggg tcgaagtagc tgatgcaggt gcccagatcg tccagacttg cttgccagtc   6900
gcgcacggcc agcgcgcgct cgtaggggct gaggggcgtg ccccagggca tggggtgcgt   6960
gagcgcggag gcgtacatgc cgcagatgtc gtagacgtag aggggctcct ggaggacgcc   7020
gatgtaggtg gggtagcagc gcccccgcg gatgctggcg cgcacgtagt cgtacagctc   7080
gtgcgagggc gcgaggagcc ccgtgccgag attggagcgc tgcggctttt cggcgcggta   7140
gacgatctgg cggaagatgg cgtgggagtt ggaggagatg gtgggcctct ggaagatgtt   7200
gaagtgggca tggggcagtc cgaccgagtc cctgatgaag tgggcgtagg agtcctgcag   7260
cttggcgacg agctcggcgg tgacgaggac gtccagggcg cagtagtcga gggtctcttg   7320
gatgatgtcg tacttgagct ggcccttctg cttccacagc tcgcggttga gaaggaactc   7380
ttcgcggtcc ttccagtact cttcgagggg gaacccgtcc tgatcggcac ggtaagagcc   7440
caccatgtag aactggttga cggccttgta ggcgcagcag cccttctcca cggggagggc   7500
gtaagcttgc gcggccttgc gcagggaggt gtgggtgagg gcgaaggtgt cgcgcaccat   7560
gactttgagg aactggtgct tgaagtcgag gtcgtcgcag ccgccctgct cccagagctg   7620
gaagtccgtg cgcttcttgt aggcggggtt gggcaaagcg aaagtaacat cgttgaagag   7680
gatcttgccc gcgcggggca tgaagttgcg agtgatgcgg aaaggctggg gcacctcggc   7740
ccggttgttg atgacctggg cggcgaggac gatctcgtcg aagccgttga tgttgtgccc   7800
gacgatgtag agttccacga atcgcgggcg gcccttgacg tggggcagct tcttgagctc   7860
gtcgtaggtg agctcggcgg ggtcgctgag cccgtgctgc tcgagggccc agtcggcgac   7920
gtgggggttg gcgctgagga aggaagtcca gagatccacg gccagggcgg tctgcaagcg   7980
```

```
gtcccggtac tgacggaact gctggcccac ggccattttt tcgggggtga cgcagtagaa   8040
ggtgcggggg tcgccgtgcc agcggtccca cttgagctgg agggcgaggt cgtgggcgag   8100
ctcgacgagc ggcgggtccc cggagagttt catgaccagc atgaagggga cgagctgctt   8160
gccgaaggac cccatccagg tgtaggtttc cacatcgtag gtgaggaaga gcctttcggt   8220
gcgaggatgc gagccgatgg ggaagaactg gatctcctgc caccagttgg aggaatggct   8280
gttgatgtga tggaagtaga aatgccgacg gcgcgccgag cactcgtgct tgtgtttata   8340
caagcgtccg cagtgctcgc aacgctgcac gggatgcacg tgctgcacga gctgtacctg   8400
ggttcctttg acgaggaatt tcagtgggca gtggagcgct ggcggctgca tctggtgctg   8460
tactacgtcc tggccatcgg cgtggccatc gtctgcctcg atggtggtca tgctgacgag   8520
cccgcgcggg aggcaggtcc agacctcggc tcggacgggt cggagagcga ggacgagggc   8580
gcgcaggccg gagctgtcca gggtcctgag acgctgcgga gtcaggtcag tgggcagcgg   8640
cggcgcgcgg ttgacttgca ggagcttttc cagggcgcgc gggaggtcca gatggtactt   8700
gatctccacg gcgccgttgg tggcgacgtc cacggcttgc agggtcccgt gcccctgggg   8760
cgccaccacc gtgccccgtt tcttcttggg cggcggcggc tccatgctta gaagcggcgg   8820
cgaggacgcg cgccgggcgg caggggcggc tcggggcccg gaggcagggg cggcaggggc   8880
acgtcggcgc cgcgcgcggg caggttctgg tactgcgccc ggagaagact ggcgtgagcg   8940
acgacgcgac ggttgacgtc ctggatctga cgcctctggg tgaaggccac gggacccgtg   9000
agtttgaacc tgaaagagag ttcgacagaa tcaatctcgg tatcgttgac ggcggcctgc   9060
cgcaggatct cttgcacgtc gcccgagttg tcctggtagg cgatctcggt catgaactgc   9120
tcgatctcct cctcctgaag gtctccgcgg ccggcgcgct cgacggtggc cgcgaggtcg   9180
ttggagatgc ggcccatgag ctgcgagaag gcgttcatgc cggcctcgtt ccagacgcgg   9240
ctgtagacca cggctccgtc ggggtcgcgc gcgcgcatga ccacctgggc gaggttgagc   9300
tcgacgtggc gcgtgaagac cgcgtagttg cagaggcgct ggtagaggta gttgagcgtg   9360
gtggcgatgt gctcggtgac gaagaagtac atgatccagc ggcggagcgg catctcgctg   9420
acgtcgccca gggcttccaa gcgctccatg gcctcgtaga agtccacggc gaagttgaaa   9480
aactgggagt tgcgcgccga gacggtcaac tcctcctcca gaagacggat gagctcggcg   9540
atggtggcgc gcacctcgcg ctcgaaggcc ccgggggggct cctcttccat ttcctcctct   9600
tcctcctcca ctaacatctc ttctacttcc tcctcaggag gcggcggcgg gggaggggcc   9660
ctgcgtcgcc ggcggcgcac gggcagacgg tcgatgaagc gctcgatggt ctccccgcgc   9720
cggcgacgca tggtctcggt gacggcgcgc ccgtcctcgc ggggccgcag cgtgaagacg   9780
ccgccgcgca tctccaggtg gccgccgggg gggtctccgt tgggcaggga gagggcgctg   9840
acgatgcatc ttatcaattg acccgtaggg actccgcgca aggacctgag cgtctcgaga   9900
tccacgggat ccgaaaaccg ctgaacgaag gcttcgagcc agtcgcagtc gcaaggtagg   9960
ctgagcccgg tttcttgttc ttcgggtatt tggtcgggag gcgggcgggc gatgctgctg   10020
gtgatgaagt tgaagtaggc ggtcctgaga cggcggatgg tggcgaggag caccaggtcc   10080
ttgggcccgg cttgctggat gcgcagacgg tcggccatgc cccaggcgtg gtcctgacac   10140
ctggcgaggt ccttgtagta gtcctgcatg agccgctcca cgggcacctc ctcctcgccc   10200
gcgcggccgt gcatgcgcgt gagcccgaac ccgcgctgcg gctggacgag cgccaggtcg   10260
gcgacgacgc gctcggcgag gatggcctgc tggatctggg tgagggtggt ctggaagtcg   10320
```

tcgaagtcga cgaagcggtg gtaggctccg gtgttgatgg tgtaggagca gttggccatg 10380
acggaccagt tgacggtctg gtggccgggg cgcacgagct cgtggtactt gaggcgcgag 10440
taggcgcgcg tgtcgaagat gtagtcgttg caggtgcgca cgaggtactg gtatccgacg 10500
aggaagtgcg gcggcggctg gcggtagagc ggccatcgct cggtggcggg ggcgccgggc 10560
gcgaggtcct cgagcatgag gcggtggtag ccgtagatgt acctggacat ccaggtgatg 10620
ccggcggcgg tggtggaggc gcgcgggaac tcgcggacgc ggttccagat gttgcgcagc 10680
ggcaggaagt agttcatggt ggccgcggtc tggcccgtga ggcgcgcgca gtcgtggatg 10740
ctctagacat acgggcaaaa acgaaagcgg tcagcggctc gactccgtgg cctggaggct 10800
aagcgaacgg gttgggctgc gcgtgtaccc cggttcgaat ctcgaatcag gctggagccg 10860
cagctaacgt ggtactggca ctcccgtctc gacccaagcc tgctaacgaa acctccagga 10920
tacggaggcg ggtcgttttt tggccttggt cgctggtcat gaaaaactag taagcgcgga 10980
aagcggccgc ccgcgatggc tcgctgccgt agtctggaga aagaatcgcc agggttgcgt 11040
tgcggtgtgc cccggttcga gcctcagcgc tcggcgccgg ccggattccg cggctaacgt 11100
gggcgtggct gccccgtcgt ttccaagacc ccttagccag ccgacttctc cagttacgga 11160
gcgagcccct ctttttttct tgtgtttttg ccagatgcat cccgtactgc ggcagatgcg 11220
cccccaccct ccaccacaac cgcccctacc gcagcagcag caacagccgg cgcttctgcc 11280
cccgccccag cagcagcagc cagccactac cgcggcggcc gccgtgagcg gagccggcgt 11340
tcagtatgac ctggccttgg aagagggcga ggggctggcg cggctggggg cgtcgtcgcc 11400
ggagcggcac ccgcgcgtgc agatgaaaag ggacgctcgc gaggcctacg tgcccaagca 11460
gaacctgttc agagacagga gcggcgagga gcccgaggag atgcgcgcct cccgcttcca 11520
cgcggggcgg gagctgcggc gcggcctgga ccgaaagcgg gtgctgaggg acgaggattt 11580
cgaggcggac gagctgacgg ggatcagccc cgcgcgcgcg cacgtggccg cggccaacct 11640
ggtcacggcg tacgagcaga ccgtgaagga ggagagcaac ttccaaaaat ccttcaacaa 11700
ccacgtgcgc acgctgatcg cgcgcgagga ggtgaccctg ggcctgatgc acctgtggga 11760
cctgctggag gccatcgtgc agaaccccac gagcaagccg ctgacggcgc agctgtttct 11820
ggtggtgcag cacagtcggg acaacgagac gttcagggag gcgctgctga atatcaccga 11880
gcccgagggc cgctggctcc tggacctggt gaacattctg cagagcatcg tggtgcagga 11940
gcgcgggctg ccgctgtccg agaagctggc ggccatcaac ttctcggtgc tgagcctggg 12000
caagtactac gctaggaaga tctacaagac cccgtacgtg cccatagaca aggaggtgaa 12060
gatcgatggg ttttacatgc gcatgaccct gaaagtgctg accctgagcg acgatctggg 12120
ggtgtaccgc aacgacagga tgcaccgcgc ggtgagcgcc agccgccggc gcgagctgag 12180
cgaccaggag ctgatgcaca gcctgcagcg ggccctgacc ggggccggga ccgaggggga 12240
gagctacttt gacatgggcg cggacctgcg ctggcagccc agccgccggg ccttggaagc 12300
tgccggcggc gtgccctacg tggaggaggt ggacgatgag gaggaggagg gcgagtacct 12360
ggaagactga tggcgcgacc gtatttttgc tagatgcagc aacagccacc gccgccgcct 12420
cctgatcccg cgatgcgggc ggcgctgcag agccagccgt ccggcattaa ctcctcggac 12480
gattggaccc aggccatgca acgcatcatg gcgctgacga cccgcaatcc cgaagccttt 12540
agacagcagc ctcaggccaa ccggctctcg gccatcctgg aggccgtggt gccctcgcgc 12600
tcgaacccca cgcacgagaa ggtgctggcc atcgtgaacg cgctggtgga gaacaaggcc 12660
atccgcggcg acgaggccgg gctggtgtac aacgcgctgc tggagcgcgt ggcccgctac 12720
aacagcacca acgtgcagac gaacctggac cgcatggtga ccgacgtgcg cgaggcggtg 12780
tcgcagcgcg agcggttcca ccgcgagtcg aacctgggct ccatggtggc gctgaacgcc 12840
ttcctgagca cgcagcccgc caacgtgccc cggggccagg aggactacac caacttcatc 12900
agcgcgctgc ggctgatggt ggccgaggtg ccccagagcg aggtgtacca gtcggggccg 12960
gactacttct tccagaccag tcgccagggc ttgcagaccg tgaacctgag ccaggctttc 13020
aagaacttgc agggactgtg gggcgtgcag gccccggtcg gggaccgcgc gacggtgtcg 13080
agcctgctga cgccgaactc gcgcctgctg ctgctgctgg tggcgccctt cacggacagc 13140
ggcagcgtga gccgcgactc gtacctgggc tacctgctta acctgtaccg cgaggccatc 13200
gggcaggcgc acgtggacga gcagacctac caggagatca cccacgtgag ccgcgcgctg 13260
ggccaggagg acccgggcaa cctggaggcc accctgaact tcctgctgac caaccggtcg 13320
cagaagatcc cgccccagta cgcgctgagc accgaggagg agcgcatcct gcgctacgtg 13380
cagcagagcg tggggctgtt cttgatgcag gagggggcca cgcccagcgc cgcgctcgac 13440
atgaccgcgc gcaacatgga gcccagcatg tacgcccgca accgcccgtt catcaataag 13500
ctgatggact acttgcatcg ggcggccgcc atgaactcgg actactttac caacgccatc 13560
ttgaacccgc actggctccc gccgcccggg ttctacacgg gcgagtacga catgcccgac 13620
cccaacgacg ggttcctgtg ggacgacgtg gacagcagcg tgttctcgcc gcggcccacc 13680
accaccaccg tgtggaagaa agagggcggg gaccggcggc cgtcctcggc gctgtccggt 13740
cgcgcgggtg ctgccgcggc ggtgcccgag gctgccagcc ccttcccgag cctgcccttt 13800
tcgctgaaca gcgtgcgcag cagcgagctg ggtcggctga cgcggccgcg cctgctgggc 13860
gaggaggagt acctgaacga ctccttgttg aagcccgagc gcgagaagaa cttccccaat 13920
aacgggatag agagcctggt ggacaagatg agccgctgga agacgtacgc gcacgagcac 13980
agggacgagc cccgagctag cagcgcaggc acccgtagac gccagcggca cgacaggcag 14040
cggggactgg tgtgggacga tgaggattcc gccgacgaca gcagcgtgtt ggacttgggt 14100
gggagtggtg gtggtaaccc gttcgctcac ctgcgccccc gtatcgggcg cctgatgtaa 14160
gaatctgaaa aaataaaaga cggtactcac caaggccatg gcgaccagcg tgcgttcttc 14220
tctgttgttt gtagtagtat gatgaggcgc gtgtacccgg agggtcctcc tccctcgtac 14280
gagagcgtga tgcagcaggc ggtggcggcg gcgatgcagc ccccgctgga ggcgccttac 14340
gtgcccccgc ggtacctggc gcctacggag gggcggaaca gcattcgtta ctcggagctg 14400
gcaccccttgt acgataccac ccggttgtac ctggtggaca acaagtcggc ggacatcgcc 14460
tcgctgaact accagaacga ccacagcaac ttcctgacca ccgtggtgca gaacaacgat 14520
ttcaccccca cggaggccag cacccagacc atcaactttg acgagcgctc gcggtggggc 14580
ggccagctga aaaccatcat gcacaccaac atgcccaacg tgaacgagtt catgtacagc 14640
aacaagttca aggcgcgggt gatggtctcg cgcaagaccc ccaacggggt cacggtaggg 14700
gatgattatg atggtagtca ggacgagctg acctacgagt gggtggagtt tgagctgccc 14760
gagggcaact tctcggtgac catgaccatc gatctgatga acaacgccat catcgacaac 14820
tacttggcgg tggggcggca gaacggggtg ctggagagcg acatcggcgt gaagttcgac 14880
acgcgcaact tccggctggg ctgggacccc gtgaccgagc tggtgatgcc gggcgtgtac 14940
accaacgagg ccttccaccc cgacatcgtc ctgctgcccg gctgcggcgt ggacttcacc 15000
gagagccgcc tcagcaacct gctgggcatc cgcaagcggc agcccttcca ggagggcttc 15060

-continued

```
cagatcctgt acgaggacct ggaggggggc aacatccccg cgctcttgga tgtcgaagcc  15120
tatgaagaaa gtaaggaaaa agcagaggct gaggcaacta cagccgtggc taccgccgcg  15180
actgtggcag atgccactgt caccaggggc gatacattcg ccacccaggc ggaggaagca  15240
gccgccctag cggcgaccga tgatagtgaa agtaagatag tcatcaagcc ggtggagaag  15300
gacagcaaga acaggagcta caacgttcta ccggatggaa agaacaccgc ctaccgcagc  15360
tggtacctgg cctacaacta cggcgacccc gagaagggcg tgcgctcctg gacgctgctc  15420
accacctcgg acgtcacctg cggcgtggag caagtctact ggtcgctgcc cgacatgatg  15480
caagacccgg tcaccttccg ctccacgcga caagttagca actacccggt ggtgggcgcc  15540
gagctcctgc ccgtctactc caagagcttc ttcaacgagc aggccgtcta ctcgcagcag  15600
ctgcgtgcct tcacctcgct cacgcacgtc ttcaaccgct tccccgagaa ccagatcctc  15660
gtccgcccgc ccgcgcccac cattaccacc gtcagtgaaa acgttcctgc tctcacagat  15720
cacgggaccc tgccgctgcg cagcagtatc cggggagtcc agcgcgtgac cgtcactgac  15780
gccagacgcc gcacctgccc ctacgtctac aaggccctgg gcgtagtcgc gccgcgcgtc  15840
ctctcgagcc gcaccttcta aaaaatgtcc attctcatct cgcccagtaa taacaccggt  15900
tggggcctgc gcgcgcccag caagatgtac ggaggcgctc gccaacgctc cacgcaacac  15960
cccgtgcgcg tgcgcgggca cttccgcgct ccctggggcg ccctcaaggg ccgcgtgcgc  16020
tcgcgcacca ccgtcgacga cgtgatcgac caggtggtgg ccgacgcgcg caactacacg  16080
cccgccgccg cgcccgcctc caccgtggac gccgtcatcg acagcgtggt ggccgacgcg  16140
cgccggtacg cccgcgccaa gagccggcgg cggcgcatcg cccggcggca ccggagcacc  16200
cccgccatgc gcgcggcgcg agccttgctg cgcagggcca ggcgcacggg acgcagggcc  16260
atgctcaggg cggccagacg cgcggcctcc ggcagcagca gcgccggcag gacccgcaga  16320
cgcgcggcca cggcggcggc ggcggccatc gccagcatgt cccgcccgcg gcgcggcaac  16380
gtgtactggg tgcgcgacgc cgccaccggt gtgcgcgtgc ccgtgcgcac ccgcccccct  16440
cgcacttgaa gatgctgact tcgcgatgtt gatgtgtccc agcggcgagg aggatgtcca  16500
agcgcaaata caaggaagag atgctccagg tcatcgcgcc tgagatctac ggccccgcgg  16560
cggcggtgaa ggaggaaaga aagccccgca aactgaagcg ggtcaaaaag gacaaaaagg  16620
aggaggaaga tgacggactg gtggagtttg tgcgcgagtt cgccccccgg cggcgcgtgc  16680
agtggcgcgg gcggaaagtg aaaccggtgc tgcggcccgg caccacggtg gtcttcacgc  16740
ccggcgagcg ttccggctcc gcctccaagc gctcctacga cgaggtgtac ggggacgagg  16800
acatcctcga gcaggcggtc gagcgtctgg gcgagtttgc ttacggcaag cgcagccgcc  16860
ccgcgccctt gaaagaggag gcggtgtcca tcccgctgga ccacggcaac cccacgccga  16920
gcctgaagcc ggtgaccctg cagcaggtgc tgccgagcgc ggcgccgcgc cggggcttca  16980
agcgcgaggg cggcgaggat ctgtacccga ccatgcagct gatggtgccc aagcgccaga  17040
agctggagga cgtgctggag cacatgaagg tggaccccga ggtgcagccc gaggtcaagg  17100
tgcggcccat caagcaggtg gccccgggcc tgggcgtgca gaccgtggac atcaagatcc  17160
ccacggagcc catggaaacg cagaccgagc ccgtgaagcc cagcaccagc accatggagg  17220
tgcagacgga tccctggatg ccagcggctt ccaccaccac cactcgccga agacgcaagt  17280
acggcgcggc cagcctgctg atgcccaact acgcgctgca tccttccatc atccccacgc  17340
cgggctaccg cggcacgcgc ttctaccgcg gctacaccag cagccgccgc cgcaagacca  17400
ccacccgccg ccgtcgtcgc agccgccgca gcagcaccgc gacttccgcc ttggtgcgga  17460
```

gagtgtatcg cagcgggcgc gagcctctga ccctgccgcg cgcgcgctac cacccgagca 17520
tcgccattta actaccgcct cctacttgca gatatggccc tcacatgccg cctccgcgtc 17580
cccattacgg gctaccgagg aagaaagccg cgccgtagaa ggctgacggg gaacgggctg 17640
cgtcgccatc accaccggcg gcggcgcgcc atcagcaagc ggttgggggg aggcttcctg 17700
cccgcgctga tccccatcat cgccgcggcg atcggggcga tccccggcat agcttccgtg 17760
gcggtgcagg cctctcagcg ccactgagac acaaaaaagc atggatttgt aataaaaaaa 17820
tggactgacg ctcctggtcc tgtgatgtgt gtttttagat ggaagacatc aatttttcgt 17880
ccctggcacc gcgacacggc acgcggccgt ttatgggcac ctggagcgac atcggcaaca 17940
gccaactgaa cgggggcgcc ttcaattgga gcagtctctg gagcgggctt aagaatttcg 18000
ggtccacgct caaaacctat ggcaacaagg cgtggaacag cagcacaggg caggcgctga 18060
gggaaaagct gaaagagcag aacttccagc agaaggtggt cgatggcctg gcctcgggca 18120
tcaacggggt ggtggacctg gccaaccagg ccgtgcagaa acagatcaac agccgcctgg 18180
acgcggtccc gcccgcgggg tccgtggaga tgccccaggt ggaggaggag ctgcctcccc 18240
tggacaagcg cggcgacaag cgaccgcgtc ccgacgcgga ggagacgctg ctgacgcaca 18300
cggacgagcc gcccccgtac gaggaggcgg tgaaactggg tctgcccacc acgcggcccg 18360
tggcgcctct ggccaccggg gtgctgaaac ccagcagcag cagccagccc gcgaccctgg 18420
acttgcctcc gcctgcttcc cgcccctcca cagtggctaa gcccctgccg ccggtggccg 18480
tcgcgtcgcg cgccccccga ggccgccccc aggcgaactg gcagagcact ctgaacagca 18540
tcgtgggtct gggagtgcag agtgtgaagc gccgccgctg ctattaaaag acactgtagc 18600
gcttaacttg cttgtctgtg tgtgtatatg tatgtccgcc gaccagaagg aggaagaggc 18660
gcgtcgccga gttgcaagat ggccacccca tcgatgctgc cccagtgggc gtacatgcac 18720
atcgccggac aggacgcttc ggagtacctg agtccgggtc tggtgcagtt cgcccgcgcc 18780
acagacacct acttcagtct ggggaacaag tttaggaacc ccacggtggc gcccacgcac 18840
gatgtgacca ccgaccgcag ccagcggctg acgctgcgct tcgtgcccgt ggaccgcgag 18900
gacaacacct actcgtacaa agtgcgctac acgctggccg tgggcgacaa ccgcgtgctg 18960
gacatggcca gcacctactt tgacatccgc ggcgtgctgg atcggggccc cagcttcaaa 19020
ccctactccg gcaccgccta caacagccta gctcccaagg gagcgcccaa cacctcacag 19080
tggaaggatt ccgacagcaa aatgcatact tttggagttg ctgccatgcc cggtgttgtt 19140
ggtaaaaaaa tagaagccga tggtctgcct attggaatag attcatcctc tggaactgac 19200
accataattt atgctgataa aactttccaa ccagagccac aggttggaag tgacagttgg 19260
gtcgacacca atggtgcaga ggaaaaatat ggaggtagag ctcttaagga cactacaaac 19320
atgaagccct gctacggttc ttttgccagg cctaccaaca aagaaggtgg acaggctaac 19380
ataaaagatt ctgaaactgc cagcactact cctaactatg atatagattt ggcattcttt 19440
gacagcaaaa atattgcagc taactacgat ccagatattg taatgtacac agaaaatgtt 19500
gagttgcaaa ctccagatac tcatattgtg tttaagccag gaacttcaga tgaaagttca 19560
gaagccaatt tgggccagca ggccatgccc aacagaccca actacatcgg gttcagagac 19620
aactttatcg ggctcatgta ctacaacagc actggcaata tgggtgtact ggctggtcag 19680
gcctcccagc taaatgctgt ggtggacttg caggacagaa acaccgaact gtcctaccag 19740
ctcttgcttg actctctggg tgacagaacc aggtatttca gtatgtggaa tcaggcggtg 19800

```
gacagctatg accccgatgt gcgcattatt gaaaatcacg gtgtggagga tgaactcccc  19860
aattattgct tccctttgaa tggtgtaggc tttacagata cttaccaggg tgttaaagtt  19920
aagacagata cagccgctac tggtaccaat ggaacgcagt gggacaaaga tgataccaca  19980
gtcagcactg ccaatgagat ccactcaggc aatcctttcg ccatggagat caacatccag  20040
gccaacctgt ggcggaactt cctctacgcg aacgtggcgc tgtacctgcc cgactcctac  20100
aagtacacgc cggccaacat cacgctgccg accaacacca acacctacga ttacatgaac  20160
ggccgcgtgg tggcgccctc gctggtggac gcctacatca acatcggggc gcgctggtcg  20220
ctggacccca tggacaacgt caacccctc aaccaccacc gcaacgcggg cctgcgctac  20280
cgctccatgc tcctgggcaa cgggcgctac gtgcccttcc acatccaggt gccccaaaag  20340
tttttcgcca tcaagagcct cctgctcctg cccgggtcct acacctacga gtggaacttc  20400
cgcaaggacg tcaacatgat cctgcagagc tccctcggca acgacctgcg cacggacggg  20460
gcctccatcg ccttcaccag catcaacctc tacgccacct tcttccccat ggcgcacaac  20520
accgcctcca cgctcgaggc catgctgcgc aacgacacca acgaccagtc cttcaacgac  20580
tacctctcgg cggccaacat gctctacccc atcccggcca acgccaccaa cgtgcccatc  20640
tccatcccct cgcgcaactg ggccgccttc cgcggatggt ccttcacgcg cctcaagacc  20700
cgcgagacgc cctcgctcgg ctccgggttc gacccctact tcgtctactc gggctccatc  20760
ccctacctcg acggcacctt ctacctcaac cacaccttca agaaggtctc catcaccttc  20820
gactcctccg tcagctggcc cggcaacgac cgcctcctga cgcccaacga gttcgaaatc  20880
aagcgcaccg tcgacggaga gggatacaac gtggcccagt gcaacatgac caaggactgg  20940
ttcctggtcc agatgctggc ccactacaac atcggctacc agggcttcta cgtgcccgag  21000
ggctacaagg accgcatgta ctccttcttc cgcaacttcc agcccatgag ccgccaggtc  21060
gtggacgagg tcaactacaa ggactaccag gccgtcaccc tggcctacca gcacaacaac  21120
tcgggcttcg tcggctacct cgcgcccacc atgcgccagg gccagcccta ccccgccaac  21180
taccccctacc cgctcatcgg caagagcgcc gtcgccagcg tcacccagaa aaagttcctc  21240
tgcgaccggg tcatgtggcg catccccttc tccagcaact tcatgtccat gggcgcgctc  21300
accgacctcg gccagaacat gctctacgcc aactccgccc acgcgctaga catgaatttc  21360
gaagtcgacc ccatggatga gtccaccctt ctctatgttg tcttcgaagt cttcgacgtc  21420
gtccgagtgc accagcccca ccgcggcgtc atcgaggccg tctacctgcg cacgcccttc  21480
tcggccggca acgccaccac ctaaagcccc gctcttgctt cttgcaagat gacggcctgt  21540
ggctccggcg agcaggagct cagggccatc ctccgcgacc tgggctgcgg gccctgcttc  21600
ctgggcacct tcgacaagcg cttcccggga ttcatggccc cgcacaagct ggcctgcgcc  21660
atcgtcaaca cggccggccg cgagaccggg ggcgagcact ggctggcctt cgcctggaac  21720
ccgcgctccc acacctgcta cctcttcgac cccttcgggt tctcggacga gcgcctcaag  21780
cagatctacc agttcgagta cgagggcctg ctgcgccgca gcgccctggc caccgaggac  21840
cgctgcatca ccctggaaaa gtccacccag accgtgcagg gtccgcgctc ggccgcctgc  21900
gggctcttct gctgcatgtt cctgcacgcc ttcgtgcact ggcccgaccg ccccatggac  21960
aagaacccca ccatgaactt gctgacgggg gtgcccaacg gcatgctcca gtcgccccag  22020
gtggaaccca ccctgcgccg caaccaggag gcgctctacc gcttcctcaa cgcccactcc  22080
gcctactttc gctcccaccg cgcgcgcatc gagaaggcca ccgccttcga ccgcatgaat  22140
caagacatgt aaactgtgtg tatgtgaatg ctttattcat cataataaac agcacatgtt  22200
```

-continued tatgccacct tctctgaggc tctgacttta tttagaaatc gaaggggttc tgccggctct 22260
cggcgtgccc cgcgggcagg gatacgttgc ggaactggta cttgggcagc cacttgaact 22320
cggggatcag cagcttcggc acggggaggt cggggaacga gtcgctccac agcttgcgcg 22380
tgagttgcag ggcgcccagc aggtcgggcg cggagatctt gaaatcgcag ttgggacccg 22440
cgttctgcgc gcgagagttg cggtacacgg ggttgcagca ctggaacacc atcagggccg 22500
ggtgcttcac gctcgccagc accgtcgcgt cggtgatgcc ctccacgtcc agatcctcgg 22560
cgttggccat cccgaagggg gtcatcttgc aggtctgccg ccccatgctg ggcacgcagc 22620
cgggcttgtg gttgcaatcg cagtgcaggg ggatcagcat catctgagcc tgctcggagc 22680
tcatgcccgg gtacatggcc ttcatgaaag cctccagctg gcggaaggcc tgctgcgcct 22740
tgccgccctc ggtgaagaag accccacagg acttgctaga gaactggttg gtggcgcagc 22800
ccgcgtcgtg cacgcagcag cgcgcgtcgt tgttggccag ctgcaccacg ctgcgccccc 22860
agcggttctg ggtgatcttg gcccggtcgg ggttctcctt cagcgcgcgc tgcccgttct 22920
cgctcgccac atccatctcg atcgtgtgct ccttctggat catcacggtc ccgtgcaggc 22980
accgcagctt gccctcggcc tcggtgcacc cgtgcagcca cagcgcgcag ccggtgcact 23040
cccagttctt gtgggcgatc tgggagtgcg agtgcacgaa gccctgcagg aagcggccca 23100
tcatcgtggt cagggtcttg ttgctggtga aggtcagcgg gatgccgcgg tgctcctcgt 23160
tcacatacag gtggcagatg cggcggtaca cctcgccctg ctcgggcatc agctggaagg 23220
cggacttcag gtcgctctcc acgcggtacc gctccatcag cagcgtcatc acttccatgc 23280
ccttctccca ggccgaaacg atcggcaggc tcagggggtt cttcaccgtc atcttagtcg 23340
ccgccgccga agtcaggggg tcgttctcgt ccagggtctc aaacactcgc ttgccgtcct 23400
tctcggtgat gcgcacgggg ggaaagctga agcccacggc cgccagctcc tcctcggcct 23460
gcctttcgtc ctcgctgtcc tggctgatgt cttgcaaagg cacatgcttg gtcttgcggg 23520
gtttcttttt gggcggcaga ggcggcggcg gagacgtgct gggcgagcgc gagttctcgc 23580
tcaccacgac tatttcttct tcttggccgt cgtccgagac cacgcggcgg taggcatgcc 23640
tcttctgggg cagaggcgga ggcgacgggc tctcgcggtt cggcgggcgg ctggcagagc 23700
cccttccgcg ttcgggggtg cgctcctggc ggcgctgctc tgactgactt cctccgcggc 23760
cggccattgt gttctcctag ggagcaacaa gcatggagac tcagccatcg tcgccaacat 23820
cgccatctgc ccccgccgcc gacgagaacc agcagcagca gaatgaaagc ttaaccgccc 23880
cgccgcccag ccccacctcc gacgccgccg cggccccaga catgcaagag atggaggaat 23940
ccatcgagat tgacctgggc tacgtgacgc ccgcggagca cgaggaggag ctggcagcgc 24000
gcttttcagc cccggaagag aaccaccaag agcagccaga gcaggaagca gagagcgagc 24060
agcagcaggc tgggctcgag catggcgact acctgagcgg ggcagaggac gtgctcatca 24120
agcatctggc ccgccaaagc atcatcgtca aggacgcgct gctcgaccgc gccgaggtgc 24180
ccctcagcgt ggcggagctc agccgcgcct acgagcgcaa cctcttctcg ccgcgcgtgc 24240
cccccaagcg ccagcccaac ggcacctgcg agcccaaccc gcgcctcaac ttctacccgg 24300
tcttcgcggt gcccgaggcc ctggccacct accacctctt tttcaagaac caaaggatcc 24360
ccgtctcctg ccgcgccaac cgcacccgcg ccgacgccct gctcaacctg ggtcccggcg 24420
cccgcctacc tgatatcacc tccttggaag aggttcccaa gatcttcgag ggtctgggca 24480
gcgacgagac tcgggccgcg aacgctctgc aaggaagcgg agaggagcat gagcaccaca 24540
gcgccctggt ggagttggaa ggcgacaacg cgcgcctggc ggtgctcaag cgcacggtcg 24600
agctgaccca cttcgcctac ccggcgctca acctgccccc caaggtcatg agcgccgtca 24660
tggaccaggt gctcatcaag cgcgcctcgc ccctctcaga ggaggagatg caggaccccg 24720
agagctcgga cgagggcaag cccgtggtca gcgacgagca gctggcgcgc tggctgggag 24780
cgagcagcac cccccagagc ctggaagagc ggcgcaagct catgatggcc gtggtcctgg 24840
tgaccgtgga gctggagtgt ctgcgccgct tcttcgccga cgcggagacc ctgcgcaagg 24900
tcgaggagaa cctgcactac ctcttcaggc acgggttcgt gcgccaggcc tgcaagatct 24960
ccaacgtgga gctgaccaac ctggtctcct acatgggcat cctgcacgag aaccgcctgg 25020
ggcagaacgt gctgcacacc accctgcgcg gggaggcccg ccgcgactac atccgcgact 25080
gcgtctacct gtacctctgc cacacctggc agacgggcat gggcgtgtgg cagcagtgcc 25140
tggaggagca gaacctgaaa gagctctgca agctcctgca gaagaacctc aaggccctgt 25200
ggaccgggtt cgacgagcgc accaccgcct cggacctggc cgacctcatc ttccccgagc 25260
gcctgcggct gacgctgcgc aacgggctgc ccgactttat gagccaaagc atgttgcaaa 25320
actttcgctc tttcatcctc gaacgctccg ggatcctgcc cgccacctgc tccgcactgc 25380
cctcggactt cgtgccgctg accttccgcg agtgcccccc gccgctctgg agccactgct 25440
acttgctgcg cctggccaac tacctggcct accactcgga cgtgatcgag gacgtcagca 25500
gcgagggtct gctcgagtgc cactgccgct gcaacctctg cacgccgcac cgctccttgg 25560
cctgcaaccc ccagctgctg agcgagaccc agatcatcgg caccttcgag ttgcaaggcc 25620
ccggcgaggg caagggggt ctcaaactca ccccggggct gtggacctcg gcctacttgc 25680
gcaagttcgt gcccgaggac taccatccct tcgagatcag gttctacgag gaccaatccc 25740
agccgcccaa ggccgagctg tcggcctgcg tcatcaccca gggggccatc ctggcccaat 25800
tgcaagccat ccagaaatcc cgccaagaat ttctgctgaa aaagggccac ggggtctact 25860
tggaccccca gaccggagag gagctcaacc ccagcttccc ccaggatgcc ccgaggaagc 25920
agcaagaagc tgaaagtgga gctgccgctg ccgccggagg atttggagga agactgggag 25980
agcagtcagg cagaggagat ggaagactgg gacagcactc aggcagagga ggacagcctg 26040
caagacagtc tggaggagga agacgaggtg gaggaggagg cagaggaaga agcagccgcc 26100
gccagaccgt cgtcctcggc ggaggagaaa gcaagcagca cggataccat ctccgctccg 26160
ggtcggggtc gcggcggccg ggcccacagt agatgggacg agaccgggcg cttcccgaac 26220
cccaccaccc agaccggtaa gaaggagcgg cagggataca agtcctggcg ggggcacaaa 26280
aacgccatcg tctcctgctt gcaagcctgc gggggcaaca tctccttcac ccggcgctac 26340
ctgctcttcc accgcggggt gaacttcccc cgcaacatct tgcattacta ccgtcacctc 26400
cacagcccct actactgttt ccaagaagag gcagaaaccc agcagcagca gcagaaaacc 26460
agcggcagca gcagcagcta gaaaatccac agcggcggca ggtggactga ggatcgcggc 26520
gaacgagccg gcgcagaccc gggagctgag gaaccggatc tttcccaccc tctatgccat 26580
cttccagcag agtcgggggc aggagcagga actgaaagtc aagaaccgtt ctctgcgctc 26640
gctcacccgc agttgtctgt atcacaagag cgaagaccaa cttcagcgca ctctcgagga 26700
cgccgaggct ctcttcaaca agtactgcgc gctcactctt aaagagtagc ccgcgcccgc 26760
ccacacacgg aaaaaggcgg gaattacgtc accacctgcg cccttcgccc gaccatcatc 26820
atgagcaaag agattcccac gccttacatg tggagctacc agccccagat gggcctggcc 26880
gccggcgccg cccaggacta ctccacccgc atgaactggc tcagtgccgg gcccgcgatg 26940
atctcacggg tgaatgacat ccgcgcccac cgaaaccaga tactcctaga acagtcagcg 27000
atcaccgcca cgccccgcca tcaccttaat ccgcgtaatt ggcccgccgc cctggtgtac 27060
caggaaattc cccagcccac gaccgtacta cttccgcgag acgcccaggc cgaagtccag 27120
ctgactaact caggtgtcca gctggccggc ggcgccgccc tgtgtcgtca ccgccccgct 27180
cagggtataa agcggctggt gatccgaggc agaggcacac agctcaacga cgaggtggtg 27240
agctcttcgc tgggtctgcg acctgacgga gtcttccaac tcgccggatc ggggagatct 27300
tccttcacgc ctcgtcaggc cgtcctgact ttggagagtt cgtcctcgca gccccgctcg 27360
ggcggcatcg gcactctcca gttcgtggag gagttcactc cctcggtcta cttcaacccc 27420
ttctccggct cccccggcca ctacccggac gagttcatcc cgaacttcga cgccatcagc 27480
gagtcggtgg acggctacga ttgaatgtcc catggtggcg cggctgacct agctcggctt 27540
cgacacctgg accactgtta attaatcgcc tctcctacga gctcctgcag cagcgccaga 27600
agttcacctg cctggtcgga gtcaacccca tcgtcatcac ccagcagtcg ggcgatacca 27660
aggggtgcat ccactgctcc tgcgactccc ccgactgcgt ccacactctg atcaagaccc 27720
tctgcggcct ccgcgacctc ctccccatga actaatcacc cccttatcca gtgaaataaa 27780
gatcatattg atgatgattt tacagaaata aagatacaat catattgatg atttgagttt 27840
aataaaaaat aaagaatcac ttacttgaaa tctgatacca ggtctctgtc catgttttct 27900
gccaacacca cttcactccc ctcttcccag ctctggtact gcaggccccg gcgggctgca 27960
aacttcctcc acacgctgaa ggggatgtca aattcctcct gtccctcaat cttcatttta 28020
tcttctatca gatgtccaaa aagcgcgtcc gggtggatga tgacttcgac cccgtctacc 28080
cctacgatgc agacaacgca ccgaccgtgc ccttcatcaa cccccccttc gtctcttcag 28140
atggattcca agagaagccc ctgggggtgc tgtccctgcg actggccgac cccgtcacca 28200
ccaagaacgg ggaaatcacc ctcaagctgg gagagggggt ggacctcgac tcctcgggaa 28260
aactcatctc caacacggcc accaaggccg ccgcccctct cagtttttcc aacaacacca 28320
tttcccttaa catggatcac cccttttaca ctaaagatgg aaaattatcc ttacaagttt 28380
ctccaccatt aaatatactg agaacaagca ttctaaacac actagcttta ggttttggat 28440
caggtttagg actccgtggc tctgccttgg cagtacagtt agtctctcca cttacatttg 28500
atactgatgg aaacataaag cttaccttag acagaggttt gcatgttaca acaggagatg 28560
caattgaaag caacataagc tggggctaaag gtttaaaatt tgaagatgga gccatagcaa 28620
ccaacattgg aaatgggtta gagtttggaa gcagtagtac agaaacaggt gttgatgatg 28680
cttacccaat ccaagttaaa cttggatctg gccttagctt tgacagtaca ggagccataa 28740
tggctggtaa caaagaagac gataaactca ctttgtggac aacacctgat ccatcgccaa 28800
actgtcaaat actcgcagaa aatgatgcaa aactaacact ttgcttgact aaatgtggta 28860
gtcaaatact ggccactgtg tcagtcttag ttgtaggaag tggaaaccta aaccccatta 28920
ctggcaccgt aagcagtgct caggtgtttc tacgttttga tgcaaacggt gttcttttaa 28980
cagaacattc tacactaaaa aaatactggg ggtataggca gggagatagc atagatggca 29040
ctccatatac caatgctgta ggattcatgc ccaatttaaa agcttatcca aagtcacaaa 29100
gttctactac taaaaataat atagtagggc aagtatacat gaatggagat gtttcaaaac 29160
ctatgcttct cactataacc ctcaatggta ctgatgacag caacagtaca tattcaatgt 29220
cattttcata cacctggact aatggaagct atgttggagc aacatttggg gctaactctt 29280
ataccttctc atacatcgcc caagaatgaa cactgtatcc caccctgcat gccaacccctt 29340 cccaccccac tctgtggaaa aaactctgaa acacaaaata aaataaagtt caagtgtttt 29400
attgattcaa cagttttaca ggattcgagc agttattttt cctccaccct cccaggacat 29460
ggaatacacc accctctccc cccgcacagc cttgaacatc tgaatgccat tggtgatgga 29520
catgcttttg gtctccacgt tccacacagt ttcagagcga gccagtctcg ggtcggtcag 29580
ggagatgaaa ccctccgggc acaattggga gaagtactcg cctacatggg ggtagagtca 29640
taatcgtgca tcaggatagg gcggtggtgc tgcagcagcg cgcgaataaa ctgctgccgc 29700
cgccgctccg tcctgcagga atacaacatg gcagtggtct cctcagcgat gattcgcacc 29760
gcccgcagca taaggcgcct tgtcctccgg gcacagcagc gcaccctgat ctcacttaaa 29820
tcagcacagt aactgcagca cagcaccaca atattgttca aaatcccaca gtgcaaggcg 29880
ctgtatccaa agctcatggc ggggaccaca gaacccacgt ggccatcata ccacaagcgc 29940
aggtagatta agtggcgacc cctcataaac acgctggaca taaacattac ctcttttggc 30000
atgttgtaat tcaccacctc ccggtaccat ataaacctct gattaaacat ggcgccatcc 30060
accaccatcc taaaccagct ggccaaaacc tgcccgccgg ctatacactg cagggaaccg 30120
ggactggaac aatgacagtg gagagcccag gactcgtaac catggatcat catgctcgtc 30180
atgatatcaa tgttggcaca acacaggcac acgtgcatac acttcctcag gattacaagc 30240
tcctcccgcg ttagaaccat atcccaggga acaacccatt cctgaatcag cgtaaatccc 30300
acactgcagg gaagacctcg cacgtaactc acgttgtgca ttgtcaaagt gttacattcg 30360
ggcagcagcg gatgatcctc cagtatggta gcgcgggttt ctgtctcaaa aggaggtaga 30420
cgatccctac tgtacggagt gcgccgagac aaccgagatc gtgttggtcg tagtgtcatg 30480
ccaaatggaa cgccggacgt agtcatattt cctgaagtct tggcgcgcca aagtctagaa 30540
gcggtccata gcttaccgag cggcagcagc agcggcacac aacaggcgca agagtcagag 30600
aaaagactga gctctaacct gtccgcccgc tctctgctca atatatagcc cagatctaca 30660
ctgacgtaaa ggccaaagtc taaaaatacc cgccaaatag tcacacacgc ccagcacacg 30720
cccagaaacc ggtgacacac tcaaaaaaat acgcgcactt cctcaaacgc ccaaactgcc 30780
gtcatttccg ggttcccacg ctacgtcatc aaaacacgac tttcaaattc cgtcgaccgt 30840
taaaaacgtc acccgccccg cccctaacgg tcgcccgtct ctcagccaat cagcgccccg 30900
catccccaaa ttcaaacacc tcatttgcat attaacgcgc accaaaagtt tgaggtatat 30960
tattgatgat g 30971

<210> SEQ ID NO 19
<211> LENGTH: 37830
<212> TYPE: DNA
<213> ORGANISM: Pan troglodytes

<400> SEQUENCE: 19
catcatcaat aatatacctt attttggatt gaagccaata tgataatgag atgggcggcg 60
cggggcggga ggcgggtccg ggggcgggcc ggcgggcggg gcggtgtggc ggaagtggac 120
tttgtaagtg tggcggatgt gacttgctag tgccgggcgc ggtaaaagtg acgttttccg 180
tgcgcgacaa cgcccacggg aagtgacatt tttcccgcgg tttttaccgg atgttgtagt 240
gaatttgggc gtaaccaagt aagatttggc cattttcgcg ggaaaactga aacggggaag 300
tgaaatctga ttaatttcgc gttagtcata ccgcgtaata tttgtcgagg gccgagggac 360
tttggccgat tacgtggagg actcgcccag gtgtttttg aggtgaattt ccgcgttccg 420

```
ggtcaaagtc tccgttttat tattatagtc agctgacgcg gagtgtattt ataccctctg    480
atctcgtcaa gtggccactc ttgagtgcca gcgagtagag ttttctcctc tgccgctctc    540
cgctccgctc cgctcggctc tgacaccggg gaaaaaatga gacatttcac ctacgatggc    600
ggtgtgctca ccggccagct ggctgctgaa gtcctggaca ccctgatcga ggaggtattg    660
gccgataatt atcctccctc gactcctttt gagccaccta cacttcacga actctacgat    720
ctggatgtgg tggggcccag cgatccgaac gagcaggcgg tttccagttt ttttccagag    780
tccatgttgt tggccagcca ggagggggtc gaacttgaga cccctcctcc gatcgtggat    840
tcccccgatc cgccgcagct gactaggcag cccgagcgct gtgcgggacc tgagactatg    900
ccccagctgc tacctgaggt gatcgatctc acctgtaatg agtctggttt tccacccagc    960
gaggatgagg acgaagaggg tgagcagttt gtgttagatt ctgtggaaca acccgggcga   1020
ggatgcaggt cttgtcaata tcaccggaaa aacacaggag actcccagat tatgtgttct   1080
ctgtgttata tgaagatgac ctgtatgttt atttacagta agtttatcat ctgtgggcag   1140
gtgggctata gtgtgggtgg tggtctttgg ggggtttttt aatatatgtc aggggttatg   1200
ctgaagactt ttttattgtg atttttaaag gtccagtgtc tgagcccgag caagaacctg   1260
aaccggagcc tgagccttct cgccccagga gaaagcctgt aatcttaact agacccagcg   1320
caccggtagc gagaggcctc agcagcgcgg agaccaccga ctccggtgct tcctcatcac   1380
ccccggagat tcaccccctg gtgcccctgt gtcccgttaa gcccgttgcc gtgagagtca   1440
gtgggcggcg gtctgctgtg gagtgcattg aggacttgct tttgattca caggaacctt   1500
tggacttgag cttgaaacgc cccaggcatt aaacctggtc acctggactg aatgagttga   1560
cgcctatgtt tgcttttgaa tgacttaatg tgtatagata ataaagagtg agataatgtt   1620
ttaattgcat ggtgtgttta acttgggcgg agtctgctgg gtatataagc ttccctgggc   1680
taaacttggt tacacttgac ctcatggagg cctgggagtg tttggagaac tttgccggag   1740
ttcgtgcctt gctggacgag agctctaaca atacctcttg gtggtggagg tatttgtggg   1800
gctctcccca gggcaagtta gtttgtagaa tcaaggagga ttacaagtgg gaatttgaag   1860
agcttttgaa atcctgtggt gagctattgg attctttgaa tctaggccac caggctctct   1920
tccaggagaa ggtcatcagg actttggatt tttccacacc ggggcgcatt gcagccgcgg   1980
ttgcttttct agctttttttg aaggatagat ggagcgaaga gacccacttg agttcgggct   2040
acgtcctgga ttttctggcc atgcaactgt ggagagcatg gatcagacac aagaacaggc   2100
tgcaactgtt gtcttccgtc cgcccgttgc tgattccggc ggaggagcaa caggccgggt   2160
cagaggaccg ggcccgtcgg gatccggagg agagggcacc gaggccgggc gagaggagcg   2220
cgctgaacct gggaaccggg ctgagcggcc atccacatcg ggagtgaatg tcgggcaggt   2280
ggtggatctt tttccagaac tgcggcggat tttgactatt agggaggatg ggcaatttgt   2340
taagggtctt aagagggaga ggggggcttc tgagcataac gaggaggcca gtaatttagc   2400
ttttagcttg atgaccagac accgtccaga gtgcatcact tttcagcaga ttaaggacaa   2460
ttgtgccaat gagttggatc tgttgggtca gaagtatagc atagagcagc tgaccactta   2520
ctggctgcag ccgggtgatg atctggagga agctattagg gtgtatgcta aggtggccct   2580
gcggcccgat tgcaagtaca agctcaaggg gctggtgaat atcaggaatt gttgctacat   2640
ttctggcaac ggggcggagg tggagataga gaccgaagac agggtggctt tcagatgcag   2700
catgatgaat atgtggccgg gggtgctggg catggacggg gtggtgatta tgaatgtgag   2760
```

-continued

```
gttcacgggg cccaacttta acggcacggt gtttttgggg aacaccaacc tggtcctgca   2820
cggggtgagc ttctatgggt ttaacaacac ctgtgtggag gcctggaccg atgtgaaggt   2880
ccgcggttgc gccttttatg gatgttggaa ggccatagtg agccgcccta agagcaggag   2940
ttccattaag aaatgcttgt ttgagaggtg caccttgggg atcctggccg agggcaactg   3000
cagggtgcgc cacaatgtgg cctccgagtg cggttgcttc atgctagtca agagcgtggc   3060
ggtaatcaag cataaatatgg tgtgcggcaa cagcgaggac aaggcctcac agatgctgac   3120
ctgcacggat ggcaactgcc acttgctgaa gaccatccat gtaaccagcc acagccggaa   3180
ggcctggccc gtgttcgagc acaacttgct gacccgctgc tccttgcatc tgggcaacag   3240
gcggggggtg ttcctgccct atcaatgcaa ctttagtcac accaagatct tgctagagcc   3300
cgagagcatg tccaaggtga acttgaacgg ggtgtttgac atgaccatga agatctggaa   3360
ggtgctgagg tacgacgaga ccaggtcccg gtgcagaccc tgcgagtgcg gggcaagca   3420
tatgaggaac cagcccgtga tgctggatgt gaccgaggag ctgaggacag accacttggt   3480
tctggcctgc accagggccg agtttggttc tagcgatgaa gacacagatt gaggtgggtg   3540
agtgggcgtg gcctggggtg gtcatgaaaa tatataagtt gggggtctta gggtctcttt   3600
atttgtgttg cagagaccgc cggagccatg agcgggagca gcagcagcag cagtagcagc   3660
agcgccttgg atggcagcat cgtgagccct tatttgacga cgcggatgcc ccactgggcc   3720
ggggtgcgtc agaatgtgat gggctccagc atcgacggcc gacccgtcct gcccgcaaat   3780
tccgccacgc tgacctatgc gaccgtcgcg gggacgccgt tggacgccac cgccgccgcc   3840
gccgccaccg cagccgcctc ggccgtgcgc agcctggcca cggactttgc attcctggga   3900
ccactggcga caggggctac ttctcgggcc gctgctgccg ccgttcgcga tgacaagctg   3960
accgccctgc tggcgcagtt ggatgcgctt actcgggaac tgggtgacct ttctcagcag   4020
gtcatggccc tgcgccagca ggtctcctcc ctgcaagctg gcgggaatgc ttctcccaca   4080
aatgccgttt aagataaata aaaccagact ctgtttggat taaagaaaag tagcaagtgc   4140
attgctctct ttatttcata attttccgcg cgcgataggc cctagaccag cgttctcggt   4200
cgttgagggt gcggtgtatc ttctccagga cgtggtagag gtggctctgg acgttgagat   4260
acatgggcat gagcccgtcc cgggggtgga ggtagcacca ctgcagagct tcatgctccg   4320
gggtggtgtt gtagatgatc cagtcgtagc aggagcgctg ggcatggtgc ctaaaaatgt   4380
ccttcagcag caggccgatg gccagggga ggcccttggt gtaagtgttt acaaaacggt   4440
taagttggga agggtgcatt cggggagaga tgatgtgcat cttggactgt atttttagat   4500
tggcgatgtt tccgcccaga tcccttctgg gattcatgtt gtgcaggacc accagtacag   4560
tgtatccggt gcacttgggg aatttgtcat gcagcttaga gggaaaagcg tggaagaact   4620
tggagacgcc tttgtggcct cccagatttt ccatgcattc gtccatgatg atggcaatgg   4680
gcccgcggga ggcagcttgg gcaaagatat ttctggggtc gctgacgtcg tagttgtgtt   4740
ccagggtgag gtcgtcatag gccattttta caaagcgcgg gcggagggtg cccgactggg   4800
ggatgatggt cccctctggc cctggggcgt agttgccctc gcagatctgc atttcccagg   4860
ccttaatctc ggagggggga atcatatcca cctgcggggc gatgaagaaa acggtttccg   4920
gagccgggga gattaactgg gatgagagca ggtttctaag cagctgtgat tttccacaac   4980
cggtgggccc ataaataaca cctataaccg gttgcagctg gtagtttaga gagctgcagc   5040
tgccgtcgtc ccggaggagg ggggccacct cgttgagcat gtccctgacg cgcatgttct   5100
ccccgaccag atccgccaga aggcgctcgc cgcccaggga cagcagctct tgcaaggaag   5160
```

caaagttttt cagcggcttg aggccgtccg ccgtgggcat gtttttcagg gtctggctca 5220
gcagctccag gcggtcccag agctcggtga cgtgctctac ggcatctcta tccagcatat 5280
ctcctcgttt cgcgggttgg ggcgactttc gctgtagggc accaagcggt ggtcgtccag 5340
cggggccaga gtcatgtcct tccatgggcg cagggtcctc gtcagggtgg tctgggtcac 5400
ggtgaagggg tgcgctccgg gctgagcgct tgccaaggtg cgcttgaggc tggttctgct 5460
ggtgctgaag cgctgccggt cttcgccctg cgcgtcggcc aggtagcatt tgaccatggt 5520
gtcatagtcc agcccctccg cggcgtgtcc cttggcgcgc agcttgccct tggaggtggc 5580
gccgcacgag gggcagagca ggctcttgag cgcgtagagc ttgggggcga ggaagaccga 5640
ttcgggggag taggcgtccg cgccgcagac cccgcacacg gtctcgcact ccaccagcca 5700
ggtgagctcg gggcgcgccg ggtcaaaaac caggtttccc ccatgctttt tgatgcgttt 5760
cttacctcgg gtctccatga ggtggtgtcc ccgctcggtg acgaagaggc tgtccgtgtc 5820
tccgtagacc gacttgaggg gtcttttctc caggggggtc cctcggtctt cctcgtagag 5880
gaactcggac cactctgaga cgaaggcccg cgtccaggcc aggacgaagg aggctatgtg 5940
ggaggggtag cggtcgttgt ccactagggg gtccaccttc tccaaggtgt gaagacacat 6000
gtcgccttcc tcggcgtcca ggaaggtgat tggcttgtag gtgtaggcca cgtgaccggg 6060
ggttcctgac ggggggtat aaaagggggt gggggcgcgc tcgtcgtcac tctcttccgc 6120
atcgctgtct gcgagggcca gctgctgggg tgagtattcc ctctcgaagg cgggcatgac 6180
ctccgcgctg aggttgtcag tttccaaaaa cgaggaggat ttgatgttca cctgtcccga 6240
ggtgatacct ttgagggtac ccgcgtccat ctggtcagaa aacacgatct ttttattgtc 6300
cagcttggtg gcgaacgacc cgtagagggc gttggagagc agcttggcga tggagcgcag 6360
ggtctggttc ttgtccctgt cggcgcgctc cttggccgcg atgttgagct gcacgtactc 6420
gcgcgcgacg cagcgccact cggggaagac ggtggtgcgc tcgtcgggca ccaggcgcac 6480
gcgccagccg cggttgtgca gggtgaccag gtccacgctg gtggcgacct cgccgcgcag 6540
gcgctcgttg gtccagcaga gacggccgcc cttgcgcgag cagaaggggg gcagggggtc 6600
gagctgggtc tcgtccgggg ggtccgcgtc cacggtgaaa accccggggc gcaggcgcgc 6660
gtcgaagtag tctatcttgc aaccttgcat gtccagcgcc tgctgccagt cgcgggcggc 6720
gagcgcgcgc tcgtaggggt tgagcggcgg gccccagggc atggggtggg tgagtgcgga 6780
ggcgtacatg ccgcagatgt catagacgta gaggggctcc cgcaggaccc cgatgtaggt 6840
ggggtagcag cggccgccgc ggatgctggc gcgcacgtag tcatacagct cgtgcgaggg 6900
ggcgaggagg tcggggccca ggttggtgcg ggcggggcgc tccgcgcgga agacgatctg 6960
cctgaagatg gcatgcgagt tggaagagat ggtggggcgc tggaagacgt tgaagctggc 7020
gtcctgcagg ccgacggcgt cgcgcacgaa ggaggcgtag gagtcgcgca gcttgtgtac 7080
cagctcggcg gtgacctgca cgtcgagcgc gcagtagtcg agggtctcgc ggatgatgtc 7140
atatttagcc tgccccttct tttccacag ctcgcggttg aggacaaact cttcgcggtc 7200
tttccagtac tcttggatcg ggaaaccgtc cggttccgaa cggtaagagc ctagcatgta 7260
gaactggttg acggcctggt aggcgcagca gcccttctcc acggggaggg cgtaggcctg 7320
cgcggccttg cggagcgagg tgtgggtcag ggcgaaggtg tccctgacca tgactttgag 7380
gtactggtgc ttgaagtcgg agtcgtcgca gccgccccgc tcccagagcg agaagtcggt 7440
gcgcttcttg gagcgggggt tgggcagagc gaaggtgaca tcgttgaaga ggattttgcc 7500

```
cgcgcggggc atgaagttgc gggtgatgcg gaagggcccc ggcacttcag agcggttgtt   7560
gatgacctgg gcggcgagca cgatctcgtc gaagccgttg atgttgtggc ccacgatgta   7620
gagttccagg aagcggggcc ggccctttac ggtgggcagc ttctttagct cttcgtaggt   7680
gagctcctcg ggcgaggcga ggccgtgctc ggccagggcc cagtccgcga ggtgcgggtt   7740
gtctctgagg aaggacttcc agaggtcgcg ggccaggagg gtctgcaggc ggtctctgaa   7800
ggtcctgaac tggcggccca cggccatttt ttcgggggtg atgcagtaga aggtgagggg   7860
gtcttgctgc cagcggtccc agtcgagctg cagggcgagg tcgcgcgcgg cggtgaccag   7920
gcgctcgtcg cccccgaatt tcatgaccag catgaagggc acgagctgct ttccgaaggc   7980
ccccatccaa gtgtaggtct ctacatcgta ggtgacaaag aggcgctccg tgcgaggatg   8040
cgagccgatc gggaagaact ggatctcccg ccaccagttg gaggagtggc tgttgatgtg   8100
gtggaagtag aagtcccgtc gccgggccga acactcgtgc tggcttttgt aaaagcgagc   8160
gcagtactgg cagcgctgca cggctgtac ctcatgcacg agatgcacct ttcgcccgcg   8220
cacgaggaag ccgaggggaa atctgagccc cccgcctggc tcgcggcatg gctggttctc   8280
ttctactttg gatgcgtgtc cgtctccgtc tggctcctcg aggggtgtta cggtggagcg   8340
gaccaccacg ccgcgcgagc cgcaggtcca gatatcggcg cgcggcggtc ggagtttgat   8400
gacgacatcg cgcagctggg agctgtccat ggtctggagc tcccgcggcg gcggcaggtc   8460
agccgggagt tcttgcaggt tcacctcgca gagtcgggcc agggcgcggg gcaggtctag   8520
gtggtacctg atctctaggg gcgtgttggt ggcggcgtcg atggcttgca ggagcccgca   8580
gccccggggg gcgacgacgg tgccccgcgg ggtggtggtg gtggtggcgg tgcagctcag   8640
aagcggtgcc gcgggcgggc ccccggaggt aggggggggct ccggtcccgc gggcaggggc   8700
ggcagcggca cgtcggcgtg gagcgcgggc aggagttggt gctgtgcccg gaggttgctg   8760
gcgaaggcga cgacgcggcg gttgatctcc tggatctggc gcctctgcgt gaagacgacg   8820
ggcccggtga gcttgaacct gaaagagagt tcgacagaat caatctcggt gtcattgacc   8880
gcggcctggc gcaggatctc ctgcacgtct cccgagttgt cttggtaggc gatctcggcc   8940
atgaactgct cgatctcttc ctcctggagg tctccgcgtc cggcgcgttc cacggtggcc   9000
gccaggtcgt tggagatgcg ccccatgagc tgcgagaagg cgttgagtcc gccctcgttc   9060
cagactcggc tgtagaccac gccccccctgg tcatcgcggg cgcgcatgac cacctgcgcg   9120
aggttgagct ccacgtgccg cgcgaagacg gcgtagttgc gcagacgctg gaagaggtag   9180
ttgagggtgg tggcggtgtg ctcggccacg aagaagttca tgacccagcg gcgcaacgtg   9240
gattcgttga tgtcccccaa ggcctccagc cgttccatgg cctcgtagaa gtccacggcg   9300
aagttgaaaa actgggagtt gcgcgccgac acggtcaact cctcctccag aagacggatg   9360
agctcggcga cggtgtcgcg cacctcgcgc tcgaaggcta tggggatctc ttcctccgct   9420
agcatcacca cctcctcctc ttcctcctct tctggcactt ccatgatggc ttcctcctct   9480
tcgggggggtg gcggcggcgg cggtggggga gggggcgctc tgcgccggcg gcggcgcacc   9540
gggaggcggt ccacgaagcg cgcgatcatc tccccgcggc ggcggcgcat ggtctcggtg   9600
acggcgcggc cgttctcccg gggggcgcagt tggaagacgc cgccggacat ctggtgctgg   9660
ggcgggtggc cgtgaggcag cgagacggcg ctgacgatgc atctcaacaa ttgctgcgta   9720
ggtacgccgc cgagggacct gagggagtcc atatccaccg gatccgaaaa cctttcgagg   9780
aaggcgtcta accagtcgca gtcgcaaggt aggctgagca ccgtggcggg cggcgggggg   9840
tggggggagt gtctggcgga ggtgctgctg atgatgtaat tgaagtaggc ggacttgaca   9900
```

-continued

```
cggcggatgg tcgacaggag caccatgtcc ttgggtccgg cctgctggat gcggaggcgg    9960
tcggctatgc cccaggcttc gttctggcat cggcgcaggt ccttgtagta gtcttgcatg   10020
agcctttcca ccggcacctc ttctccttcc tcttctgctt cttccatgtc tgcttcggcc   10080
ctggggcggc gccgcgcccc cctgcccccc atgcgcgtga ccccgaaccc cctgagcggt   10140
tggagcaggg ccaggtcggc gacgacgcgc tcggccagga tggcctgctg cacctgcgtg   10200
agggtggttt ggaagtcatc caagtccacg aagcggtggt aggcgcccgt gttgatggtg   10260
taggtgcagt tggccatgac ggaccagttg acggtctggt ggcccggttg cgacatctcg   10320
gtgtacctga gtcgcgagta ggcgcgggag tcgaagacgt agtcgttgca agtccgcacc   10380
aggtactggt agcccaccag gaagtgcggc ggcggctggc ggtagagggg ccagcgcagg   10440
gtggcggggg ctccgggggc caggtcttcc agcatgaggc ggtggtaggc gtagatgtac   10500
ctggacatcc aggtgatacc cgcggcggtg gtggaggcgc gcgggaagtc gcgcacccgg   10560
ttccagatgt tgcgcagggg cagaaagtgc tccatggtag gcgtgctctg tccagtcaga   10620
cgcgcgcagt cgttgatact ctagaccagg gaaaacgaaa gccggtcagc gggcactctt   10680
ccgtggtctg gtgaatagat cgcaagggta tcatggcgga gggcctcggt tcgagccccg   10740
ggtccgggcc ggacggtccg ccatgatcca cgcggttacc gcccgcgtgt cgaacccagg   10800
tgtgcgacgt cagacaacgg tggagtgttc cttttggcgt tttctggcc gggcgccggc    10860
gccgcgtaag agactaagcc gcgaaagcga aagcagtaag tggctcgctc cccgtagccg   10920
gagggatcct tgctaagggt tgcgttgcgg cgaaccccgg ttcgaatccc gtactcgggc   10980
cggccggacc cgcggctaag gtgttggatt ggcctccccc tcgtataaag accccgcttg   11040
cggattgact ccggacacgg ggacgagccc cttttatttt tgctttcccc agatgcatcc   11100
ggtgctgcgg cagatgcgcc ccccgcccca gcagcagcaa caacaccagc aagagcggca   11160
gcaacagcag cgggagtcat gcagggcccc ctcacccacc ctcggcgggc cggccacctc   11220
ggcgtccgcg gccgtgtctg gcgcctgcgg cggcggcggg gggccggctg acgaccccga   11280
ggagcccccg cggcgcaggg ccagacacta cctggacctg gaggagggcg agggcctggc   11340
gcggctgggg gcgccgtctc ccgagcgcca cccgcgggtg cagctgaagc gcgactcgcg   11400
cgaggcgtac gtgcctcggc agaacctgtt cagggaccgc gcgggcgagg agcccgagga   11460
gatgcgggac aggaggttca gcgcagggcg ggagctgcgg caggggctga accgcgagcg   11520
gctgctgcgc gaggaggact ttgagcccga cgcgcggacg gggatcagcc ccgcgcgcgc   11580
gcacgtggcg gccgccgacc tggtgacggc gtacgagcag acggtgaacc aggagatcaa   11640
cttccaaaag agtttcaaca accacgtgcg cacgctggtg gcgcgcgagg aggtgaccat   11700
cgggctgatg cacctgtggg actttgtaag cgcgctggtg cagaacccca acagcaagcc   11760
tctgacggcg cagctgttcc tgatagtgca gcacagcagg gacaacgagg cgtttaggga   11820
cgcgctgctg aacatcaccg agcccgaggg tcggtggctg ctggacctga ttaacatcct   11880
gcagagcata gtggtgcagg agcgcagcct gagcctggcc gacaaggtgg cggccatcaa   11940
ctactcgatg ctgagcctgg gcaagtttta cgcgcgcaag atctaccaga cgccgtacgt   12000
gcccatagac aaggaggtga agatcgacgg tttttacatg cgcatggcgc tgaaggtgct   12060
caccctgagc gacgacctgg gcgtgtaccg caacgagcgc atccacaagg ccgtgagcgt   12120
gagccggcgg cgcgagctga gcgaccgcga gctgatgcac agcctgcagc gggcgctggc   12180
gggcgccggc agcggcgaca gggaggcgga gtcctacttc gatgcggggg cggacctgcg   12240
```

ctgggcgccc agccggcggg ccctggaggc cgcgggggtc cgcgaggact atgacgagga 12300
cggcgaggag gatgaggagt acgagctaga ggagggcgag tacctggact aaaccgcggg 12360
tggtgtttcc ggtagatgca agacccgaac gtggtggacc cggcgctgcg ggcggctctg 12420
cagagccagc cgtccggcct taactcctca gacgactggc gacaggtcat ggaccgcatc 12480
atgtcgctga cggcgcgtaa cccggacgcg ttccggcagc agccgcaggc caacaggctc 12540
tccgccatcc tggaggcggt ggtgcctgcg cgctcgaacc ccacgcacga gaaggtgctg 12600
gccatagtga acgcgctggc cgagaacagg gccatccgcc cggacgaggc cgggctggtg 12660
tacgacgcgc tgctgcagcg cgtggcccgc tacaacagcg gcaacgtgca gaccaacctg 12720
gaccggctgg tgggggacgt gcgcgaggcg gtggcgcagc gcgagcgcgc ggatcggcag 12780
ggcaacctgg gctccatggt ggcgctgaat gccttcctga gcacgcagcc ggccaacgtg 12840
ccgcgggggc aggaagacta caccaacttt gtgagcgcgc tgcggctgat ggtgaccgag 12900
accccccaga gcgaggtgta ccagtcgggc ccggactact tcttccagac cagcagacag 12960
ggcctgcaga cggtgaacct gagccaggct ttcaagaacc tgcgggggct gtggggcgtg 13020
aaggcgccca ccggcgaccg ggcgacggtg tccagcctgc tgacgcccaa ctcgcgcctg 13080
ctgctgctgc tgatcgcgcc gttcacggac agcggcagcg tgtcccggga cacctacctg 13140
gggcacctgc tgaccctgta ccgcgaggcc atcgggcagg cgcaggtgga cgagcacacc 13200
ttccaggaga tcaccagcgt gagccgcgcg ctggggcagg aggacacgag cagcctggag 13260
gcgactctga actacctgct gaccaaccgg cggcagaaga ttccctcgct gcacagcctg 13320
acctccgagg aggagcgcat cttgcgctac gtgcagcaga gcgtgagcct gaacctgatg 13380
cgcgacgggg tgacgcccag cgtggcgctg gacatgaccg cgcgcaacat ggaaccgggc 13440
atgtacgccg cgcaccggcc ttacatcaac cgcctgatgg actacctgca tcgcgcggcg 13500
gccgtgaacc ccgagtactt taccaacgcc atcctgaacc cgcactggct cccgccgccc 13560
gggttctaca gcgggggctt cgaggtcccg gagaccaacg atggcttcct gtgggacgac 13620
atggacgaca gcgtgttctc ccccgcggccg caggcgctgg cggaagcgtc cctgctgcgt 13680
cccaagaagg aggaggagga ggaggcgagt cgccgccgcg gcagcagcgg cgtggcttct 13740
ctgtccgagc tgggggcggc agccgccgcg cgcccccgggt ccctgggcgg cagcccccttt 13800
ccgagcctgg tggggtctct gcacagcgag cgcaccaccc gccctcggct gctgggcgag 13860
gacgagtacc tgaataactc cctgctgcag ccggtgcggg agaaaaacct gcctcccgcc 13920
ttccccaaca acgggataga gagcctggtg gacaagatga gcagatggaa gacctatgcg 13980
caggagcaca gggacgcgcc tgcgctccgg ccgcccacgc ggcgccagcg ccacgaccgg 14040
cagcgggggc tggtgtggga tgacgaggac tccgcggacg atagcagcgt gctggacctg 14100
ggagggagcg gcaacccgtt cgcgcacctg cgcccccgcc tggggaggat gttttaaaaa 14160
aaaaaaaaaa aagcaagaag catgatgcaa aaattaaata aaactcacca aggccatggc 14220
gaccgagcgt tggtttcttg tgttcccttc agtatgcggc gcgcggcgat gtaccaggag 14280
ggacctcctc cctcttacga gagcgtggtg ggcgcggcgg cggcggcgcc ctcttctccc 14340
tttgcgtcgc agctgctgga gccgccgtac gtgcctccgc gctacctgcg gcctacgggg 14400
gggagaaaca gcatccgtta ctcggagctg gcgccccctgt tcgacaccac ccgggtgtac 14460
ctggtggaca acaagtcggc ggacgtggcc tccctgaact accagaacga ccacagcaat 14520
tttttgacca cggtcatcca gaacaatgac tacagcccga gcgaggccag cacccagacc 14580
atcaatctgg atgaccggtc gcactggggc ggcgacctga aaaccatcct gcacaccaac 14640
atgcccaacg tgaacgagtt catgttcacc aataagttca aggcgcgggt gatggtgtcg 14700
cgctcgcaca ccaaggaaga ccgggtggag ctgaagtacg agtgggtgga gttcgagctg 14760
ccagagggca actactccga gaccatgacc attgacctga tgaacaacgc gatcgtggag 14820
cactatctga aagtgggcag gcagaacggg gtcctggaga gcgacatcgg ggtcaagttc 14880
gacaccagga acttccgcct ggggctggac cccgtgaccg ggctggttat gcccggggtg 14940
tacaccaacg aggccttcca tcccgacatc atcctgctgc ccggctgcgg ggtggacttc 15000
acttacagcc gcctgagcaa cctcctgggc atccgcaagc ggcagccctt ccaggagggc 15060
ttcaggatca cctacgagga cctggagggg ggcaacatcc ccgcgctcct cgatgtggag 15120
gcctaccagg atagcttgaa ggaaaatgag gcgggacagg aggataccgc ccccgccgcc 15180
tccgccgccg ccgagcaggg cgaggatgct gctgacaccg cggccgcgga cggggcagag 15240
gccgaccccg ctatggtggt ggaggctccc gagcaggagg aggacatgaa tgacagtgcg 15300
gtgcgcggag acaccttcgt cacccggggg gaggaaaagc aagcggaggc cgaggccgcg 15360
gccgaggaaa agcaactggc ggcagcagcg gcggcggcgg cgttggccgc ggcggaggct 15420
gagtctgagg ggaccaagcc cgccaaggag cccgtgatta agcccctgac cgaagatagc 15480
aagaagcgca gttacaacct gctcaaggac agcaccaaca ccgcgtaccg cagctggtac 15540
ctggcctaca actacggcga cccgtcgacg gggtgcgct cctggaccct gctgtgcacg 15600
ccggacgtga cctgcggctc ggagcaggtg tactggtcgc tgcccgacat gatgcaagac 15660
cccgtgacct tccgctccac gcggcaggtc agcaacttcc cggtggtggg cgccgagctg 15720
ctgcccgtgc actccaagag cttctacaac gaccaggccg tctactccca gctcatccgc 15780
cagttcacct ctctgaccca cgtgttcaat cgctttcctg agaaccagat tctggcgcgc 15840
ccgcccgccc ccaccatcac caccgtcagt gaaaacgttc ctgctctcac agatcacggg 15900
acgctaccgc tgcgcaacag catcggagga gtccagcgag tgaccgttac tgacgccaga 15960
cgccgcacct gcccctacgt ttacaaggcc ttgggcatag tctcgccgcg cgtcctttcc 16020
agccgcactt tttgagcaac accaccatca tgtccatcct gatctcaccc agcaataact 16080
ccggctgggg actgctgcgc gcgcccagca agatgttcgg aggggcgagg aagcgttccg 16140
agcagcaccc cgtgcgcgtg cgcgggcact tccgcgcccc ctggggagcg cacaaacgcg 16200
gccgcgcggg gcgcaccacc gtggacgacg ccatcgactc ggtggtggag caggcgcgca 16260
actacaggcc cgcggtctct accgtggacg cggccatcca gaccgtggtg cggggcgcgc 16320
ggcggtacgc caagctgaag agccgccgga agcgcgtggc ccgccgccac cgccgccgac 16380
ccggggccgc cgccaaacgc gccgccgcgg ccctgcttcg ccgggccaag cgcacgggcc 16440
gccgcgccgc catgagggcc gcgcgccgct tggccgccgg catcaccgcc gccaccatgg 16500
ccccccgtac ccgaagacgc gcggccgccg ccgccgccgc cgccatcagt gacatggcca 16560
gcaggcgccg gggcaacgtg tactgggtgc gcgactcggt gaccggcacg cgcgtgcccg 16620
tgcgcttccg cccccccgcgg acttgagatg atgtgaaaaa acaacactga gtctcctgct 16680
gttgtgtgta tcccagcggc ggcggcgcgc gcagcgtcat gtccaagcgc aaaatcaaag 16740
aagagatgct ccaggtcgtc gcgccggaga tctatgggcc cccgaagaag gaagagcagg 16800
attcgaagcc ccgcaagata aagcgggtca aaaagaaaaa gaaagatgat gacgatgccg 16860
atggggaggt ggagttcctg cgcgccacgg cgcccaggcg cccggtgcag tggaagggcc 16920
ggcgcgtaaa gcgcgtcctg cgccccggca ccgcggtggt cttcacgccc ggcgagcgct 16980
ccacccggac tttcaagcgc gtctatgacg aggtgtacgg cgacgaagac ctgctggagc 17040
aggccaacga gcgcttcgga gagtttgctt acgggaagcg tcagcgggcg ctggggaagg 17100
aggacctgct ggcgctgccg ctggaccagg gcaaccccac ccccagtctg aagcccgtga 17160
ccctgcagca ggtgctgccg agcagcgcac cctccgaggc gaagcggggt ctgaagcgcg 17220
agggcggcga cctggcgccc accgtgcagc tcatggtgcc caagcggcag aggctggagg 17280
atgtgctgga gaaaatgaaa gtagaccccg gtctgcagcc ggacatcagg gtccgcccca 17340
tcaagcaggt ggcgccgggc ctcggcgtgc agaccgtgga cgtggtcatc ccccaccggca 17400
actcccccgc cgccgccacc actaccgctg cctccacgga catggagaca cagaccgatc 17460
ccgccgcagc cgcagccgca gccgccgccg cgacctcctc ggcggaggtg cagacggacc 17520
cctggctgcc gccggcgatg tcagctcccc gcgcgcgtcg cgggcgcagg aagtacggcg 17580
ccgccaacgc gctcctgccc gagtacgcct tgcatccttc catcgcgccc acccccggct 17640
accgaggcta tacctaccgc ccgcgaagag ccaagggttc cacccgccgt ccccgccgac 17700
gcgccgccgc caccacccgc cgccgccgcc gcagacgcca gcccgcactg gctccagtct 17760
ccgtgaggaa agtggcgcgc gacggacaca ccctggtgct gcccagggcg cgctaccacc 17820
ccagcatcgt ttaaaagcct gttgtggttc ttgcagatat ggccctcact tgccgcctcc 17880
gtttcccggt gccgggatac cgaggaggaa gatcgcgccg caggaggggt ctggccggcc 17940
gcggcctgag cggaggcagc cgccgcgcgc accggcggcg acgcgccacc agccgacgca 18000
tgcgcggcgg ggtgctgccc ctgttaatcc ccctgatcgc cgcggcgatc ggcgccgtgc 18060
ccgggatcgc ctccgtggcc ttgcaagcgt cccagaggca ttgacagact tgcaaacttg 18120
caaatatgga aaaaaaaacc ccaataaaaa agtctagact ctcacgctcg cttggtcctg 18180
tgactatttt gtagaatgga agacatcaac tttgcgtcgc tggccccgcg tcacggctcg 18240
cgcccgttcc tgggacactg gaacgatatc ggcaccagca acatgagcgg tggcgccttc 18300
agttggggct ctctgtggag cggcattaaa agtatcgggt ctgccgttaa aaattacggc 18360
tcccgggcct ggaacagcag cacgggccag atgttgagag acaagttgaa agagcagaac 18420
ttccagcaga aggtggtgga gggcctggcc tccggcatca acggggtggt ggacctggcc 18480
aaccaggccg tgcagaataa gatcaacagc agactggacc cccggccgcc ggtggaggag 18540
gtgccgccgg cgctggagac ggtgtccccc gatgggcgtg gcgagaagcg cccgcggccc 18600
gatagggaag agaccactct ggtcacgcag accgatgagc cgcccccgta tgaggaggcc 18660
ctgaagcaag gtctgcccac cacgcggccc atcgcgccca tggccaccgg ggtggtgggc 18720
cgccacaccc ccgccacgct ggacttgcct ccgcccgccg atgtgccgca gcagcagaag 18780
gcggcacagc cgggcccgcc cgcgaccgcc tcccgttcct ccgccggtcc tctgcgccgc 18840
gcggccagcg gcccccgcgg gggggtcgcg aggcacggca actggcagag cacgctgaac 18900
agcatcgtgg gtctgggggt gcggtccgtg aagcgccgcc gatgctactg aatagcttag 18960
ctaacgtgtt gtatgtgtgt atgcgcccta tgtcgccgcc agaggagctg ctgagtcgcc 19020
gccgttcgcg cgcccaccac caccgccact ccgcccctca agatggcgac cccatcgatg 19080
atgccgcagt ggtcgtacat gcacatctcg ggccaggacg cctcggagta cctgagcccc 19140
gggctggtgc agttcgcccg cgccaccgag agctacttca gcctgagtaa caagtttagg 19200
aaccccacgg tggcgcccac gcacgatgtg accaccgacc ggtctcagcg cctgacgctg 19260
cggttcattc ccgtggaccg cgaggacacc gcgtactcgt acaaggcgcg gttcaccctg 19320
gccgtgggcg acaaccgcgt gctggacatg gcctccacct actttgacat ccgcggggtg 19380
ctggaccggg gtcccacttt caagccctac tctggcaccg cctacaactc cctggccccc 19440
aagggcgctc ccaactcctg cgagtgggag caagaggaaa ctcaggcagt tgaagaagca 19500
gcagaagagg aagaagaaga tgctgacggt caagctgagg aagagcaagc agctaccaaa 19560
aagactcatg tatatgctca ggctcccctt tctggcgaaa aaattagtaa agatggtctg 19620
caaataggaa cggacgctac agctacagaa caaaaaccta tttatgcaga ccctacattc 19680
cagcccgaac cccaaatcgg ggagtcccag tggaatgagg cagatgctac agtcgccggc 19740
ggtagagtgc taaagaaatc tactcccatg aaaccatgct atggttccta tgcaagaccc 19800
acaaatgcta atggaggtca gggtgtacta acggcaaatg cccagggaca gctagaatct 19860
caggttgaaa tgcaattctt ttcaacttct gaaaacgccc gtaacgaggc taacaacatt 19920
cagcccaaat tggtgctgta tagtgaggat gtgcacatgg agaccccgga tacgcacctt 19980
tcttacaagc ccgcaaaaag cgatgacaat tcaaaaatca tgctgggtca gcagtccatg 20040
cccaacagac ctaattacat cggcttcaga gacaacttta tcggcctcat gtattacaat 20100
agcactggca acatgggagt gcttgcaggt caggcctctc agttgaatgc agtggtggac 20160
ttgcaagaca gaaacacaga actgtcctac cagctcttgc ttgattccat gggtgacaga 20220
accagatact ttttccatgtg gaatcaggca gtggacagtt atgacccaga tgttagaatt 20280
attgaaaatc atggaactga agacgagctc cccaactatt gtttccctct gggtggcata 20340
ggggtaactg acacttacca ggctgttaaa accaacaatg gcaataacgg gggccaggtg 20400
acttggacaa aagatgaaac ttttgcagat cgcaatgaaa taggggtggg aaacaatttc 20460
gctatggaga tcaacctcag tgccaacctg tggagaaact tcctgtactc caacgtggcg 20520
ctgtacctac cagacaagct taagtacaac ccctccaatg tggacatctc tgacaacccc 20580
aacacctacg attacatgaa caagcgagtg gtggccccgg ggctggtgga ctgctacatc 20640
aacctgggcg cgcgctggtc gctggactac atggacaacg tcaacccctt caaccaccac 20700
cgcaatgcgg gcctgcgcta ccgctccatg ctcctgggca acgggcgcta cgtgcccttc 20760
cacatccagg tgccccagaa gttctttgcc atcaagaacc tcctcctcct gccgggctcc 20820
tacacctacg agtggaactt caggaaggat gtcaacatgg tcctccagag ctctctgggt 20880
aacgatctca gggtggacgg ggccagcatc aagttcgaga gcatctgcct ctacgccacc 20940
ttcttcccca tggcccacaa cacggcctcc acgctcgagg ccatgctcag gaacgacacc 21000
aacgaccagt ccttcaatga ctacctctcc gccgccaaca tgctctaccc catacccgcc 21060
aacgccacca acgtccccat ctccatcccc tcgcgcaact gggcggcctt ccgcggctgg 21120
gccttcaccc gcctcaagac caaggagacc ccctccctgg gctcgggatt cgacccctac 21180
tacacctact cgggctccat tccctacctg gacggcacct tctacctcaa ccacactttc 21240
aagaaggtct cggtcacctt cgactcctcg gtcagctggc cgggcaacga ccgtctgctc 21300
acccccaacg agttcgagat caagcgctcg gtcgacgggg agggctacaa cgtggcccag 21360
tgcaacatga ccaaggactg gttcctggtc cagatgctgg ccaactacaa catcggctac 21420
cagggcttct acatcccaga gagctacaag gacaggatgt actccttctt caggaacttc 21480
cagcccatga gccggcaggt ggtggaccag accaagtaca aggactacca ggaggtgggc 21540
atcatccacc agcacaacaa ctcgggcttc gtgggctacc tcgcccccac catgcgcgag 21600
ggacaggcct accccgccaa cttccccctat ccgctcatag gcaagaccgc ggtcgacagc 21660
atcacccaga aaaagttcct ctgcgaccgc accctctggc gcatcccctt ctccagcaac 21720
ttcatgtcca tgggtgcgct ctcggacctg ggccagaact tgctctacgc caactccgcc 21780
cacgccctcg acatgacctt cgaggtcgac cccatggacg agcccaccct tctctatgtt 21840
ctgttcgaag tctttgacgt ggtccgggtc caccagccgc accgcggcgt catcgagacc 21900
gtgtacctgc gtacgccctt ctcggccggc aacgccacca cctaaagaag caagccgcag 21960
tcatcgccgc ctgcatgccg tcgggttcca ccgagcaaga gctcagggcc atcgtcagag 22020
acctgggatg cgggccctat tttttgggca ccttcgacaa gcgcttccct ggctttgtct 22080
ccccacacaa gctggcctgc gccatcgtca acacggccgg ccgcgagacc gggggcgtgc 22140
actggctggc cttcgcctgg aacccgcgct ccaaaacatg cttcctcttt gaccccttcg 22200
gcttttcgga ccagcggctc aagcaaatct acgagttcga gtacgagggc ttgctgcgtc 22260
gcagcgccat cgcctcctcg cccgaccgct gcgtcaccct cgaaaagtcc acccagaccg 22320
tgcaggggcc cgactcggcc gcctgcggtc tcttctgctg catgtttctg cacgcctttg 22380
tgcactggcc tcagagtccc atggaccgca accccaccat gaacttgctg acgggggtgc 22440
ccaactccat gctccagagc cccaggtcg agcccaccct gcgccgcaac caggagcagc 22500
tctacagctt cctggagcgc cactcgcctt acttccgccg ccacagcgca cagatcagga 22560
gggccacctc cttctgccac ttgcaagaga tgcaagaagg gtaataacga tgtacacact 22620 tttttctca ataaatggca tctttttatt tatacaagct ctctggggta ttcatttccc 22680
accaccaccc gccgttgtcg ccatctggct ctatttagaa atcgaaaggg ttctgccggg 22740
agtcgccgtg cgccacgggc agggacacgt tgcgatactg gtagcgggtg ccccacttga 22800
actcgggcac caccaggcga ggcagctcgg ggaagttttc gctccacagg ctgcgggtca 22860
gcaccagcgc gttcatcagg tcgggcgccg agatcttgaa gtcgcagttg gggccgccgc 22920
cctgcgcgcg cgagttgcgg tacaccgggt tgcagcactg gaacaccaac agcgccgggt 22980
gcttcacgct ggccagcacg ctgcggtcgg agatcagctc ggcgtccagg tcctccgcgt 23040
tgctcagcgc gaacggggtc atcttgggca cttgccgccc caggaagggc gcgtgccccg 23100
gtttcgagtt gcagtcgcag cgcagcggga tcagcaggtg cccgtgcccg gactcggcgt 23160
tggggtacag cgcgcgcatg aaggcctgca tctggcggaa ggccatctgg gccttggcgc 23220
cctccgagaa gaacatgccg caggacttgc ccgagaactg gtttgcgggg cagctggcgt 23280
cgtgcaggca gcagcgcgcg tcggtgttgg cgatctgcac cacgttgcgc ccccaccggt 23340
tcttcacgat cttggccttg gacgattgct ccttcagcgc gcgctgcccg ttctcgctgg 23400
tcacatccat ctcgatcaca tgttccttgt tcaccatgct gctgccgtgc agacacttca 23460
gctcgccctc cgtctcggtg cagcggtgct gccacagcgc gcagcccgtg ggctcgaaag 23520
acttgtaggt cacctccgcg aaggactgca ggtacccctg caaaaagcgg cccatcatgg 23580
tcacgaaggt cttgttgctg ctgaaggtca gctgcagccc gcggtgctcc tcgttcagcc 23640
aggtcttgca cacggccgcc agcgcctcca cctggtcggg cagcatcttg aagttcacct 23700
tcagctcatt ctccacgtgg tacttgtcca tcagcgtgcg cgccgcctcc atgcccttct 23760
cccaggccga caccagcggc aggctcacgg ggttcttcac catcaccgtg gccgccgcct 23820
ccgccgcgct ttcgctttcc gccccgctgt tctcttcctc ttcctcctct tcctcgccgc 23880
cgcccactcg cagcccccgc accacggggt cgtcttcctg caggcgctgc accttgcgct 23940
tgccgttgcg cccctgcttg atgcgcacgg gcgggttgct gaagcccacc atcaccagcg 24000
cggcctcttc ttgctcgtcc tcgctgtcca gaatgacctc cggggagggg gggttggtca 24060
tcctcagtac cgaggcacgc ttcttttct tcctgggggc gttcgccagc tccgcggctg 24120

```
cggccgctgc cgaggtcgaa ggccgagggc tgggcgtgcg cggcaccagc gcgtcctgcg  24180
agccgtcctc gtcctcctcg gactcgagac ggaggcgggc ccgcttcttc gggggcgcgc  24240
ggggcggcgg aggcggcggc ggcgacggag acggggacga gacatcgtcc agggtgggtg  24300
gacggcgggc cgcgccgcgt ccgcgctcgg gggtggtctc gcgctggtcc tcttcccgac  24360
tggccatctc ccactgctcc ttctcctata ggcagaaaga gatcatggag tctctcatgc  24420
gagtcgagaa ggaggaggac agcctaaccg ccccctctga gccctccacc accgccgcca  24480
ccaccgccaa tgccgccgcg gacgacgcgc ccaccgagac caccgccagt accaccctcc  24540
ccagcgacgc acccccgctc gagaatgaag tgctgatcga gcaggacccg ggttttgtga  24600
gcggagagga ggatgaggtg gatgagaagg agaaggagga ggtcgccgcc tcagtgccaa  24660
aagaggataa aaagcaagac caggacgacg cagataagga tgagacagca gtcgggcggg  24720
ggaacggaag ccatgatgct gatgacggct acctagacgt gggagacgac gtgctgctta  24780
agcacctgca ccgccagtgc gtcatcgtct gcgacgcgct gcaggagcgc tgcgaagtgc  24840
ccctggacgt ggcggaggtc agccgcgcct acgagcggca cctcttcgcg ccgcacgtgc  24900
cccccaagcg ccgggagaac ggcacctgcg agcccaaccc gcgtctcaac ttctacccgg  24960
tcttcgcggt acccgaggtg ctggccacct accacatctt tttccaaaac tgcaagatcc  25020
ccctctcctg ccgcgccaac cgcacccgcg ccgacaaaac cctgaccctg cggcagggcg  25080
cccacatacc tgatatcgcc tctctggagg aagtgcccaa gatcttcgag ggtctcggtc  25140
gcgacgagaa acgggcggcg aacgctctgc acggagacag cgaaaacgag agtcactcgg  25200
gggtgctggt ggagctcgag ggcgacaacg cgcgcctggc cgtactcaag cgcagcatag  25260
aggtcaccca ctttgcctac ccggcgctca acctgccccc caaggtcatg agtgtggtca  25320
tgggcgagct catcatgcgc cgcgcccagc ccctggccgc ggatgcaaac ttgcaagagt  25380
cctccgagga aggcctgccc gcggtcagcg acgagcagct ggcgcgctgg ctggagaccc  25440
gcgaccccgc gcagctggag gagcggcgca agctcatgat ggccgcggtg ctggtcaccg  25500
tggagctcga gtgtctgcag cgcttcttcg cggaccccga gatgcagcgc aagctcgagg  25560
agaccctgca ctacaccttc cgccagggct acgtgcgcca ggcctgcaag atctccaacg  25620
tggagctctg caacctggtc tcctacctgg gcatcctgca cgagaaccgc ctcgggcaga  25680
acgtcctgca ctccaccctc aaaggggagg cgcgccgcga ctacatccgc gactgcgcct  25740
acctcttcct ctgctacacc tggcagacgg ccatgggggt ctggcagcag tgcctggagg  25800
agcgcaacct caaggagctg gaaaagctcc tcaagcgcac cctcagggac ctctggacgg  25860
gcttcaacga gcgctcggtg gccgccgcgc tggcggacat catctttccc gagcgcctgc  25920
tcaagaccct gcagcagggc ctgcccgact tcaccagcca gagcatgctg cagaacttca  25980
ggactttcat cctggagcgc tcgggcatcc tgccggccac ttgctgcgcg ctgcccagcg  26040
acttcgtgcc catcaagtac agggagtgcc cgccgccgct ctggggccac tgctacctct  26100
tccagctggc caactacctc gcctaccact cggacctcat ggaagacgtg agcggcgagg  26160
gcctgctcga gtgccactgc cgctgcaacc tctgcacgcc ccaccgctct ctagtctgca  26220
acccgcagct gctcagcgag agtcagatta tcggtacctt cgagctgcag ggtccctcgc  26280
ctgacgagaa gtccgcggct ccagggctga aactcactcc ggggctgtgg acttccgcct  26340
acctacgcaa atttgtacct gaggactacc acgcccacga gatcaggttc tacgaagacc  26400
aatcccgccc gcccaaggcg gagctcaccg cctgcgtcat cacccagggg cacatcctgg  26460
```

-continued

```
gccaattgca agccatcaac aaagcccgcc gagagttctt gctgaaaaag ggtcgggggg  26520
tgtacctgga cccccagtcc ggcgaggagc taaacccgct acccccgccg ccgccccagc  26580
agcgggacct tgcttcccag gatggcaccc agaaagaagc agcagccgcc gccgccgccg  26640
cagccataca tgcttctgga ggaagaggag gaggactggg acagtcaggc agaggaggtt  26700
tcggacgagg agcaggagga gatgatggaa gactgggagg aggacagcag cctagacgag  26760
gaagcttcag aggccgaaga ggtggcagac gcaacaccat cgccctcggt cgcagccccc  26820
tcgccggggc ccctgaaatc ctccgaaccc agcaccagcg ctataacctc cgctcctccg  26880
gcgccggcgc cacccgcccg cagacccaac cgtagatggg acaccacagg aaccggggtc  26940
ggtaagtcca agtgcccgcc gccgccaccg cagcagcagc agcagcagcg ccagggctac  27000
cgctcgtggc gcgggcacaa gaacgccata gtcgcctgct tgcaagactg cgggggcaac  27060
atctctttcg cccgccgctt cctgctattc caccacgggg tcgcctttcc ccgcaatgtc  27120
ctgcattact accgtcatct ctacagcccc tactgcagcg gcgacccaga ggcggcagcg  27180
gcagccacag cggcgaccac cacctaggaa gatatcctcc gcgggcaaga cagcggcagc  27240
agcggccagg agacccgcgg cagcagcggc gggagcggtg ggcgcactgc gcctctcgcc  27300
caacgaaccc ctctcgaccc gggagctcag acacaggatc ttccccactt tgtatgccat  27360
cttccaacag agcagaggcc aggagcagga gctgaaaata aaaaacagat ctctgcgctc  27420
cctcacccgc agctgtctgt atcacaaaag cgaagatcag cttcggcgca cgctggagga  27480
cgcggaggca ctcttcagca aatactgcgc gctcactctt aaagactagc tccgcgccct  27540
tctcgaattt aggcgggaga aaactacgtc atcgccggcc gccgcccagc ccgcccagcc  27600
gagatgagca aagagattcc cacgccatac atgtggagct accagccgca gatgggactc  27660
gcggcgggag cggcccagga ctactccacc cgcatgaact acatgagcgc gggaccccac  27720
atgatctcac aggtcaacgg gatccgcgcc cagcgaaacc aaatactgct ggaacaggcg  27780
gccatcaccg ccacgccccg ccataatctc aacccccgaa attggcccgc cgccctcgtg  27840
taccaggaaa ccccctccgc caccaccgta ctacttccgc gtgacgccca ggccgaagtc  27900
cagatgacta actcaggggc gcagctcgcg ggcggctttc gtcacggggc gcggccgctc  27960
cgaccaggta taagacacct gatgatcaga ggccgaggta tccagctcaa cgacgagtcg  28020
gtgagctctt cgctcggtct ccgtccggac ggaactttcc agctcgccgg atccggccgc  28080
tcttcgttca cgccccgcca ggcgtacctg actctgcaga cctcgtcctc ggagccccgc  28140
tccggcggca tcggaaccct ccagttcgtg gaggagttcg tgccctcggt ctacttcaac  28200
cccttctcgg gacctcccgg acgctacccc gaccagttca ttccgaactt tgacgcggtg  28260
aaggactcgg cggacggcta cgactgaatg tcaggtgtcg aggcagagca gcttcgcctg  28320
agacacctcg agcactgccg ccgccacaag tgcttcgccc gcggttctgg tgagttctgc  28380
tactttcagc tacccgagga gcataccgag ggccggcgc acggcgtccg cctgaccacc  28440
cagggcgagg ttacctgttc cctcatccgg gagtttaccc tccgtcccct gctagtggag  28500
cgggagcggg gtccctgtgt cctaactatc gcctgcaact gccctaaccc tggattacat  28560
caagatcttt gctgtcatct ctgtgctgag tttaataaac gctgagatca gaatctactg  28620
gggctcctgt cgccatcctg tgaacgccac cgtcttcacc caccccgacc aggcccaggc  28680
gaacctcacc tgcggtctgc atcggagggc caagaagtac ctcacctggt acttcaacgg  28740
cacccccttt gtggtttaca acagcttcga cggggacgga gtctccctga aagaccagct  28800
ctccggtctc agctactcca tccacaagaa caccaccctc caactcttcc ctccctacct  28860
```

gccgggaacc tacgagtgcg tcaccggccg ctgcacccac ctcacccgcc tgatcgtaaa 28920
ccagagcttt ccgggaacag ataactccct cttccccaga acaggaggtg agctcaggaa 28980
actccccggg gaccagggcg gagacgtacc ttcgaccctt gtggggttag gattttttat 29040
taccgggttg ctggctcttt taatcaaagt ttccttgaga tttgttcttt ccttctacgt 29100
gtatgaacac ctcaacctcc aataactcta ccctttcttc ggaatcaggt gacttctctg 29160
aaatcgggct tggtgtgctg cttactctgt tgattttttt ccttatcata ctcagccttc 29220
tgtgcctcag gctcgccgcc tgctgcgcac acatctatat ctactgctgg ttgctcaagt 29280
gcaggggtcg ccacccaaga tgaacaggta catggtccta tcgatcctag gcctgctggc 29340
cctggcggcc tgcagcgccg ccaaaaaaga gattaccttt gaggagcccg cttgcaatgt 29400
aactttcaag cccgagggtg accaatgcac caccctcgtc aaatgcgtta ccaatcatga 29460
gaggctgcgc atcgactaca aaaacaaaac tggccagttt gcggtctata gtgtgtttac 29520
gcccggagac ccctctaact actctgtcac cgtcttccag ggcggacagt ctaagatatt 29580
caattacact ttcccttttt atgagttatg cgatgcggtc atgtacatgt caaaacagta 29640
caacctgtgg cctccctctc cccaggcgtg tgtggaaaat actgggtctt actgctgtat 29700
ggctttcgca atcactacgc tcgctctaat ctgcacggtg ctatacataa aattcaggca 29760
gaggcgaatc tttatcgatg aaaagaaaat gccttgatcg ctaacaccgg ctttctatct 29820
gcagaatgaa tgcaatcacc tccctactaa tcaccaccac cctccttgcg attgcccatg 29880
ggttgacacg aatcgaagtg ccagtggggt ccaatgtcac catggtgggc cccgccggca 29940
attccaccct catgtgggaa aaatttgtcc gcaatcaatg ggttcatttc tgctctaacc 30000
gaatcagtat caagcccaga gccatctgcg atgggcaaaa tctaactctg atcaatgtgc 30060
aaatgatgga tgctgggtac tattacgggc agcggggaga aatcattaat tactggcgac 30120
cccacaagga ctacatgctg catgtagtcg aggcacttcc cactaccacc cccactacca 30180
cctctcccac caccaccacc actactacta ctactactac tactactact actaccacta 30240
ccgctgcccg ccatacccgc aaaagcacca tgattagcac aaagcccct cgtgctcact 30300
cccacgccgg cgggcccatc ggtgcgacct cagaaaccac cgagctttgc ttctgccaat 30360
gcactaacgc cagcgctcat gaactgttcg acctggagaa tgaggatgtc cagcagagct 30420
ccgcttgcct gacccaggag gctgtggagc ccgttgccct gaagcagatc ggtgattcaa 30480
taattgactc ttcttctttt gccactcccg aataccctcc cgattctact ttccacatca 30540
cgggtaccaa agaccctaac ctctctttct acctgatgct gctgctctgt atctctgtgg 30600
tctcttccgc gctgatgtta ctggggatgt tctgctgcct gatctgccgc agaaagagaa 30660
aagctcgctc tcagggccaa ccactgatgc ccttccccta ccccccggat tttgcagata 30720
acaagatatg agctcgctgc tgacactaac cgctttacta gcctgcgctc taacccttgt 30780
cgcttgcgac tcgagattcc acaatgtcac agctgtggca ggagaaaatg ttactttcaa 30840
ctccacggcc gatacccagt ggtcgtggag tggctcaggt agctacttaa ctatctgcaa 30900
tagctccact tcccccggca tatccccaac caagtaccaa tgcaatgcca gcctgttcac 30960
cctcatcaac gcttccaccc tggacaatgg actctatgta ggctatgtac cctttggtgg 31020
gcaaggaaag acccacgctt acaacctgga agttcgccag cccagaacca ctacccaagc 31080
ttctcccacc accaccacca ccaccaccat caccagcagc agcagcagca gcagccacag 31140
cagcagcagc agattattga ctttggtttt ggccagctca tctgccgcta cccaggccat 31200
ctacagctct gtgcccgaaa ccactcagat ccaccgccca gaaacgacca ccgccaccac 31260
cctacacacc tccagcgatc agatgccgac caacatcacc cccttggctc ttcaaatggg 31320
acttacaagc cccactccaa aaccagtgga tgcggccgag gtctccgccc tcgtcaatga 31380
ctgggcgggg ctgggaatgt ggtggttcgc cataggcatg atggcgctct gcctgcttct 31440
gctctggctc atctgctgcc tccaccgcag gcgagccaga ccccccatct atagacccat 31500
cattgtcctg aaccccgata atgatgggat ccatagattg gatggcctga aaaacctact 31560
tttttctttt acagtatgat aaattgagac atgcctcgca ttttcttgta catgttcctt 31620
ctcccacctt ttctggggtg ttctacgctg gccgctgtgt ctcacctgga ggtagactgc 31680
ctctcaccct tcactgtcta cctgctttac ggattggtca ccctcactct catctgcagc 31740
ctaatcacag taatcatcgc cttcatccag tgcattgatt acatctgtgt gcgcctcgca 31800
tacttcagac accacccgca gtaccgagac aggaacattg cccaacttct aagactgctc 31860
taatcatgca taagactgtg atctgccttc tgatcctctg catcctgccc accctcacct 31920
cctgccagta caccacaaaa tctccgcgca aaagacatgc ctcctgccgc ttcacccaac 31980
tgtggaatat acccaaatgc tacaacgaaa agagcgagct ctccgaagct tggctgtatg 32040
gggtcatctg tgtcttagtt ttctgcagca ctgtctttgc cctcataatc taccccctact 32100
ttgatttggg atggaacgcg atcgatgcca tgaattaccc cacctttccc gcacccgaga 32160
taattccact gcgacaagtt gtacccgttg tcgttaatca acgcccccca tcccctacgc 32220
ccactgaaat cagctacttt aacctaacag gcggagatga ctgacgccct agatctagaa 32280
atggacggca tcagtaccga gcagcgtctc ctagagaggc gcaggcaggc ggctgagcaa 32340
gagcgcctca atcaggagct ccgagatctc gttaacctgc accagtgcaa aagaggcatc 32400
ttttgtctgg taaagcaggc caaagtcacc tacgagaaga ccggcaacag ccaccgcctc 32460
agttacaaat tgcccaccca gcgccagaag ctggtgctca tggtgggtga gaatcccatc 32520
accgtcaccc agcactcggt agagaccgag gggtgtctgc actccccctg tcggggtcca 32580
gaagacctct gcaccctggt aaagaccctg tgcggtctca gagatttagt cccctttaac 32640
taatcaaaca ctggaatcaa taaaaagaat cacttactta aaatcagaca gcaggtctct 32700
gtccagttta ttcagcagca cctccttccc ctcctcccaa ctctggtact ccaaacgcct 32760
tctggcggca aacttcctcc acaccctgaa gggaatgtca gattcttgct cctgtccctc 32820
cgcacccact atcttcatgt tgttgcagat gaagcgcacc aaaacgtctg acgagagctt 32880
caaccccgtg taccccctatg acacggaaag cggccctccc tccgtccctt tcctcacccc 32940
tcccttcgtg tctcccgatg gattccaaga aagtcccccc ggggtcctgt ctctgaacct 33000
ggccgagccc ctggtcactt cccacggcat gctcgccctg aaaatgggaa gtggcctctc 33060
cctggacgac gctggcaacc tcacctctca agatatcacc accgctagcc ctcccctcaa 33120
aaaaaccaag accaacctca gcctagaaac ctcatccccc ctaactgtga gcacctcagg 33180
cgccctcacc gtagcagccg ccgctcccct ggcggtggcc ggcacctccc tcaccatgca 33240
atcagaggcc cccctgacag tacaggatgc aaaactcacc ctggccacca aaggccccct 33300
gaccgtgtct gaaggcaaac tggccttgca aacatcggcc ccgctgacgg ccgctgacag 33360
cagcaccctc acagtcagtg ccacaccacc ccttagcaca agcaatggca gcttgggtat 33420
tgacatgcaa gcccccattt acaccaccaa tggaaaacta ggacttaact ttggcgctcc 33480
cctgcatgtg gtagacagcc taaatgcact gactgtagtt actggccaag gtcttacgat 33540
aaacggaaca gccctacaaa ctagagtctc aggtgccctc aactatgaca catcaggaaa 33600

```
cctagaattg agagctgcag ggggtatgcg agttgatgca aatggtcaac ttatccttga  33660
tgtagcttac ccatttgatg cacaaaacaa tctcagcctt aggcttggac agggacccct  33720
gtttgttaac tctgcccaca acttggatgt taactacaac agaggcctct acctgttcac  33780
atctggaaat accaaaaagc tagaagttaa tatcaaaaca gccaagggtc tcatttatga  33840
tgacactgct atagcaatca atgcgggtga tgggctacag tttgactcag gctcagatac  33900
aaatccatta aaaactaaac ttggattagg actggattat gactccagca gagccataat  33960
tgctaaactg ggaactggcc taagctttga caacacaggt gccatcacag taggcaacaa  34020
aaatgatgac aagcttacct tgtggaccac accagaccca tcccctaact gtagaatcta  34080
ttcagagaaa gatgctaaat tcacacttgt tttgactaaa tgcggcagtc aggtgttggc  34140
cagcgtttct gttttatctg taaaaggtag ccttgcgccc atcagtggca cagtaactag  34200
tgctcagatt gtcctcagat ttgatgaaaa tggagttcta ctaagcaatt cttcccttga  34260
ccctcaatac tggaactaca gaaaaggtga ccttacagag ggcactgcat ataccaacgc  34320
agtgggattt atgcccaacc tcacagcata cccaaaaaca cagagccaaa ctgctaaaag  34380
caacattgta agtcaggttt acttgaatgg ggacaaatcc aaacccatga ccctcaccat  34440
taccctcaat ggaactaatg aaacaggaga tgccacagta agcacttact ccatgtcatt  34500
ctcatggaac tggaatggaa gtaattacat taatgaaacg ttccaaacca actccttcac  34560
cttctcctac atcgcccaag aataaaaagc atgacgctgt tgatttgatt caatgtgttt  34620
ctgttttatt ttcaagcaca acaaaatcat tcaagtcatt cttccatctt agcttaatag  34680
acacagtagc ttaatagacc cagtagtgca aagccccatt ctagcttata gatcagacag  34740
tgataattaa ccaccaccac caccatacct tttgattcag gaaatcatga tcatcacagg  34800
atcctagtct tcaggccgcc ccctccctcc caagacacag aatacacagt cctctccccc  34860
cgactggctt taaataacac catctggttg gtcacagaca tgttcttagg ggttatattc  34920
cacacggtct cctgccgcgc caggcgctcg tcggtgatgt tgataaactc tcccggcagc  34980
tcgctcaagt tcacgtcgct gtccagcggc tgaacctccg gctgacgcga taactgtgcg  35040
accggctgct ggacgaacgg aggccgcgcc tacaaggggg tagagtcata atcctcggtc  35100
aggatagggc ggtgatgcag cagcagcgag cgaaacatct gctgccgccg ccgctccgtc  35160
cggcaggaaa acaacacgcc ggtggtctcc tccgcgataa tccgcaccgc ccgcagcatc  35220
agcttcctcg ttctccgcgc gcagcacctc acccttatct cgctcaaatc ggcgcagtag  35280
gtacagcaca gcaccacgat gttattcatg atcccacagt gcagggcgct gtatccaaag  35340
ctcatgccgg gaaccaccgc ccccacgtgg ccatcgtacc acaagcgcac gtaaatcaag  35400
tgtcgacccc tcatgaacgc gctggacaca aacattactt ccttgggcat gttgtaattc  35460
accacctccc ggtaccagat aaacctctgg ttgaacaggg caccttccac caccatcctg  35520
aaccaagagg ccagaacctg cccaccggct atgcactgca gggaacccgg gttggaacaa  35580
tgacaatgca gactccaagg ctcgtaaccg tggatcatcc ggctgctgaa ggcatcgatg  35640
ttggcacaac acagacacac gtgcatgcac tttctcatga ttagcagctc ttccctcgtc  35700
aggatcatat cccaaggaat aacccattct tgaatcaacg taaaacccac acagcaggga  35760
aggcctcgca cataactcac gttgtgcatg gtcagcgtgt tgcattccgg aaacagcgga  35820
tgatcctcca gtatcgaggc gcgggtctcc ttctcacagg gaggtaaagg gtccctgctg  35880
tacggactgc gccgggacga ccgagatcgt gttgagcgta gtgtcatgga aaagggaacg  35940
```

-continued

```
ccggacgtgg tcatacttct tgaagcagaa ccaggttcgc gcgtggcagg cctccttgcg  36000

tctgcggtct cgccgtctag ctcgctccgt gtgatagttg tagtacagcc actcccgcag  36060

agcgtcgagg cgcaccctgg cttccggatc tatgtagact ccgtcttgca ccgcggccct  36120

gataatatcc accaccgtag aataagcaac acccagccaa gcaatacact cgctctgcga  36180

gcggcagaca ggaggagcgg gcagagatgg gagaaccatg ataaaaaact tttttaaag  36240

aatattttcc aattcttcga aagtaagatc tatcaagtgg cagcgctccc ctccactggc  36300

gcggtcaaac tctacggcca aagcacagac aacggcattt ctaagatgtt ccttaatggc  36360

gtccaaaaga cacaccgctc tcaagttgca gtaaactatg aatgaaaacc catccggctg  36420

attttccaat atagacgcgc cggcagcgtc caccaaaccc agataatttt cttctctcca  36480

gcggtttacg atctgtctaa gcaaatccct tatatcaagt ccgaccatgc caaaaatctg  36540

ctcaagagcg ccctccacct tcatgtacaa gcagcgcatc atgattgcaa aaattcaggt  36600

tcttcagaga cctgtataag attcaaaatg ggaacattaa caaaaattcc tctgtcgcgc  36660

agatcccttc gcagggcaag ctgaacataa tcagacaggt ccgaacggac cagtgaggcc  36720

aaatccccac caggaaccag atccagagac cctatactga ttatgacgcg catactcggg  36780

gctatgctga ccagcgtagc gccgatgtag gcgtgctgca tgggcggcga gataaaatgc  36840

aaagtgctgg ttaaaaaatc aggcaaagcc tcgcgcaaaa aagctaacac atcataatca  36900

tgctcatgca ggtagttgca ggtaagctca ggaaccaaaa cggaataaca cacgattttc  36960

ctctcaaaca tgacttcgcg gatactgcgt aaaacaaaaa attataaata aaaaattaat  37020

taaataactt aaacattgga agcctgtctc acaacaggaa aaaccacttt aatcaacata  37080

agacgggcca cgggcatgcc ggcatagccg taaaaaaatt ggtccccgtg attaacaagt  37140

accacagaca gctccccggt catgtcgggg gtcatcatgt gagactctgt atacacgtct  37200

ggattgtgaa catcagacaa acaaagaaat cgagccacgt agcccggagg tataatcacc  37260

cgcaggcgga ggtacagcaa aacgaccccc ataggaggaa tcacaaaatt agtaggagaa  37320

aaaaatacat aaacaccaga aaaaccctgt tgctgaggca aaatagcgcc ctcccgatcc  37380

aaaacaacat aaagcgcttc cacaggagca gccataacaa agacccgagt cttaccagta  37440

aaagaaaaaa gatctctcaa cgcagcacca gcaccaacac ttcgcagtgt aaaaggccaa  37500

gtgccgagag agtatatata ggaataaaaa gtgacgtaaa cgggcaaagt ccaaaaaacg  37560

cccagaaaaa ccgcacgcga acctacgccc cgaaacgaaa gccaaaaaac actagacact  37620

cccttccggc gtcaacttcc gctttcccac gctacgtcac ttcccccggt caaacaaact  37680

acatatcccg aacttccaag tcgccacgcc caaaacaccg cctacacctc cccgcccgcc  37740

ggcccgcccc cggacccgcc tcccgccccg cgccgcccat ctcattatca tattggcttc  37800

aatccaaaat aaggtatatt attgatgatg                                  37830
```

```
<210> SEQ ID NO 20
<211> LENGTH: 593
<212> TYPE: PRT
<213> ORGANISM: Pan troglodytes

<400> SEQUENCE: 20

Met Arg Arg Ala Ala Met Tyr Gln Glu Gly Pro Pro Pro Ser Tyr Glu
1               5                   10                  15

Ser Val Val Gly Ala Ala Ala Ala Ala Pro Ser Ser Pro Phe Ala Ser
            20                  25                  30

Gln Leu Leu Glu Pro Pro Tyr Val Pro Pro Arg Tyr Leu Arg Pro Thr
```

```
        35                  40                  45

Gly Gly Arg Asn Ser Ile Arg Tyr Ser Glu Leu Ala Pro Leu Phe Asp
    50                  55                  60

Thr Thr Arg Val Tyr Leu Val Asp Asn Lys Ser Ala Asp Val Ala Ser
65                  70                  75                  80

Leu Asn Tyr Gln Asn Asp His Ser Asn Phe Leu Thr Thr Val Ile Gln
                85                  90                  95

Asn Asn Asp Tyr Ser Pro Ser Glu Ala Ser Thr Gln Thr Ile Asn Leu
            100                 105                 110

Asp Asp Arg Ser His Trp Gly Gly Asp Leu Lys Thr Ile Leu His Thr
        115                 120                 125

Asn Met Pro Asn Val Asn Glu Phe Met Phe Thr Asn Lys Phe Lys Ala
    130                 135                 140

Arg Val Met Val Ser Arg Ser His Thr Lys Glu Asp Arg Val Glu Leu
145                 150                 155                 160

Lys Tyr Glu Trp Val Glu Phe Glu Leu Pro Glu Gly Asn Tyr Ser Glu
                165                 170                 175

Thr Met Thr Ile Asp Leu Met Asn Asn Ala Ile Val Glu His Tyr Leu
            180                 185                 190

Lys Val Gly Arg Gln Asn Gly Val Leu Glu Ser Asp Ile Gly Val Lys
        195                 200                 205

Phe Asp Thr Arg Asn Phe Arg Leu Gly Leu Asp Pro Val Thr Gly Leu
    210                 215                 220

Val Met Pro Gly Val Tyr Thr Asn Glu Ala Phe His Pro Asp Ile Ile
225                 230                 235                 240

Leu Leu Pro Gly Cys Gly Val Asp Phe Thr Tyr Ser Arg Leu Ser Asn
                245                 250                 255

Leu Leu Gly Ile Arg Lys Arg Gln Pro Phe Gln Glu Gly Phe Arg Ile
            260                 265                 270

Thr Tyr Glu Asp Leu Glu Gly Gly Asn Ile Pro Ala Leu Leu Asp Val
        275                 280                 285

Glu Ala Tyr Gln Asp Ser Leu Lys Glu Asn Glu Ala Gly Gln Glu Asp
    290                 295                 300

Thr Ala Pro Ala Ala Ser Ala Ala Ala Glu Gln Gly Glu Asp Ala Ala
305                 310                 315                 320

Asp Thr Ala Ala Ala Asp Gly Ala Glu Ala Asp Pro Ala Met Val Val
                325                 330                 335

Glu Ala Pro Glu Gln Glu Glu Asp Met Asn Asp Ser Ala Val Arg Gly
            340                 345                 350

Asp Thr Phe Val Thr Arg Gly Glu Glu Lys Gln Ala Glu Ala Glu Ala
        355                 360                 365

Ala Ala Glu Glu Lys Gln Leu Ala Ala Ala Ala Ala Ala Ala Ala Leu
    370                 375                 380

Ala Ala Ala Glu Ala Glu Ser Glu Gly Thr Lys Pro Ala Lys Glu Pro
385                 390                 395                 400

Val Ile Lys Pro Leu Thr Glu Asp Ser Lys Lys Arg Ser Tyr Asn Leu
                405                 410                 415

Leu Lys Asp Ser Thr Asn Thr Ala Tyr Arg Ser Trp Tyr Leu Ala Tyr
            420                 425                 430

Asn Tyr Gly Asp Pro Ser Thr Gly Val Arg Ser Trp Thr Leu Leu Cys
        435                 440                 445

Thr Pro Asp Val Thr Cys Gly Ser Glu Gln Val Tyr Trp Ser Leu Pro
    450                 455                 460
```

Asp Met Met Gln Asp Pro Val Thr Phe Arg Ser Thr Arg Gln Val Ser
465 470 475 480

Asn Phe Pro Val Val Gly Ala Glu Leu Leu Pro Val His Ser Lys Ser
485 490 495

Phe Tyr Asn Asp Gln Ala Val Tyr Ser Gln Leu Ile Arg Gln Phe Thr
500 505 510

Ser Leu Thr His Val Phe Asn Arg Phe Pro Glu Asn Gln Ile Leu Ala
515 520 525

Arg Pro Pro Ala Pro Thr Ile Thr Thr Val Ser Glu Asn Val Pro Ala
530 535 540

Leu Thr Asp His Gly Thr Leu Pro Leu Arg Asn Ser Ile Gly Gly Val
545 550 555 560

Gln Arg Val Thr Val Thr Asp Ala Arg Arg Arg Thr Cys Pro Tyr Val
565 570 575

Tyr Lys Ala Leu Gly Ile Val Ser Pro Arg Val Leu Ser Ser Arg Thr
580 585 590

Phe

<210> SEQ ID NO 21
<211> LENGTH: 964
<212> TYPE: PRT
<213> ORGANISM: Pan troglodytes

<400> SEQUENCE: 21

Met Ala Thr Pro Ser Met Met Pro Gln Trp Ser Tyr Met His Ile Ser
1 5 10 15

Gly Gln Asp Ala Ser Glu Tyr Leu Ser Pro Gly Leu Val Gln Phe Ala
20 25 30

Arg Ala Thr Asp Ser Tyr Phe Ser Leu Ser Asn Lys Phe Arg Asn Pro
35 40 45

Thr Val Ala Pro Thr His Asp Val Thr Thr Asp Arg Ser Gln Arg Leu
50 55 60

Thr Leu Arg Phe Ile Pro Val Asp Arg Glu Asp Thr Ala Tyr Ser Tyr
65 70 75 80

Lys Ala Arg Phe Thr Leu Ala Val Gly Asp Asn Arg Val Leu Asp Met
85 90 95

Ala Ser Thr Tyr Phe Asp Ile Arg Gly Val Leu Asp Arg Gly Pro Thr
100 105 110

Phe Lys Pro Tyr Ser Gly Thr Ala Tyr Asn Ser Leu Ala Pro Lys Gly
115 120 125

Ala Pro Asn Ser Cys Glu Trp Glu Gln Glu Glu Thr Gln Thr Ala Glu
130 135 140

Glu Ala Gln Asp Glu Glu Glu Asp Glu Ala Glu Ala Glu Glu Glu Met
145 150 155 160

Pro Gln Glu Glu Gln Ala Pro Val Lys Lys Thr His Val Tyr Ala Gln
165 170 175

Ala Pro Leu Ser Gly Glu Lys Ile Thr Lys Asp Gly Leu Gln Ile Gly
180 185 190

Thr Asp Ala Thr Ala Thr Glu Gln Lys Pro Ile Tyr Ala Asp Pro Thr
195 200 205

Phe Gln Pro Glu Pro Gln Ile Gly Glu Ser Gln Trp Asn Glu Ala Asp
210 215 220

Ala Ser Val Ala Gly Gly Arg Val Leu Lys Lys Thr Thr Pro Met Lys
225 230 235 240

```
Pro Cys Tyr Gly Ser Tyr Ala Arg Pro Thr Asn Ala Asn Gly Gly Gln
                245                 250                 255

Gly Val Leu Val Glu Lys Asp Gly Gly Lys Met Glu Ser Gln Val Asp
            260                 265                 270

Met Gln Phe Phe Ser Thr Ser Glu Asn Ala Arg Asn Glu Ala Asn Asn
        275                 280                 285

Ile Gln Pro Lys Leu Val Leu Tyr Ser Glu Asp Val His Met Glu Thr
    290                 295                 300

Pro Asp Thr His Ile Ser Tyr Lys Pro Ala Lys Ser Asp Asp Asn Ser
305                 310                 315                 320

Lys Val Met Leu Gly Gln Gln Ser Met Pro Asn Arg Pro Asn Tyr Ile
                325                 330                 335

Gly Phe Arg Asp Asn Phe Ile Gly Leu Met Tyr Tyr Asn Ser Thr Gly
            340                 345                 350

Asn Met Gly Val Leu Ala Gly Gln Ala Ser Gln Leu Asn Ala Val Val
        355                 360                 365

Asp Leu Gln Asp Arg Asn Thr Glu Leu Ser Tyr Gln Leu Leu Leu Asp
    370                 375                 380

Ser Met Gly Asp Arg Thr Arg Tyr Phe Ser Met Trp Asn Gln Ala Val
385                 390                 395                 400

Asp Ser Tyr Asp Pro Asp Val Arg Ile Ile Glu Asn His Gly Thr Glu
                405                 410                 415

Asp Glu Leu Pro Asn Tyr Cys Phe Pro Leu Gly Gly Ile Gly Val Thr
            420                 425                 430

Asp Thr Tyr Gln Ala Ile Lys Thr Asn Gly Asn Gly Asn Gly Gly Gly
        435                 440                 445

Asn Thr Thr Trp Thr Lys Asp Glu Thr Phe Ala Asp Arg Asn Glu Ile
    450                 455                 460

Gly Val Gly Asn Asn Phe Ala Met Glu Ile Asn Leu Ser Ala Asn Leu
465                 470                 475                 480

Trp Arg Asn Phe Leu Tyr Ser Asn Val Ala Leu Tyr Leu Pro Asp Lys
                485                 490                 495

Leu Lys Tyr Asn Pro Ser Asn Val Glu Ile Ser Asp Asn Pro Asn Thr
            500                 505                 510

Tyr Asp Tyr Met Asn Lys Arg Val Val Ala Pro Gly Leu Val Asp Cys
        515                 520                 525

Tyr Ile Asn Leu Gly Ala Arg Trp Ser Leu Asp Tyr Met Asp Asn Val
    530                 535                 540

Asn Pro Phe Asn His His Arg Asn Ala Gly Leu Arg Tyr Arg Ser Met
545                 550                 555                 560

Leu Leu Gly Asn Gly Arg Tyr Val Pro Phe His Ile Gln Val Pro Gln
                565                 570                 575

Lys Phe Phe Ala Ile Lys Asn Leu Leu Leu Leu Pro Gly Ser Tyr Thr
            580                 585                 590

Tyr Glu Trp Asn Phe Arg Lys Asp Val Asn Met Val Leu Gln Ser Ser
        595                 600                 605

Leu Gly Asn Asp Leu Arg Val Asp Gly Ala Ser Ile Lys Phe Glu Ser
    610                 615                 620

Ile Cys Leu Tyr Ala Thr Phe Phe Pro Met Ala His Asn Thr Ala Ser
625                 630                 635                 640

Thr Leu Glu Ala Met Leu Arg Asn Asp Thr Asn Asp Gln Ser Phe Asn
                645                 650                 655
```

Asp Tyr Leu Ser Ala Ala Asn Met Leu Tyr Pro Ile Pro Ala Asn Ala
660 665 670

Thr Asn Val Pro Ile Ser Ile Pro Ser Arg Asn Trp Ala Ala Phe Arg
675 680 685

Gly Trp Ala Phe Thr Arg Leu Lys Thr Lys Glu Thr Pro Ser Leu Gly
690 695 700

Ser Gly Phe Asp Pro Tyr Tyr Thr Tyr Ser Gly Ser Ile Pro Tyr Leu
705 710 715 720

Asp Gly Thr Phe Tyr Leu Asn His Thr Phe Lys Lys Val Ser Val Thr
725 730 735

Phe Asp Ser Ser Val Ser Trp Pro Gly Asn Asp Arg Leu Leu Thr Pro
740 745 750

Asn Glu Phe Glu Ile Lys Arg Ser Val Asp Gly Glu Gly Tyr Asn Val
755 760 765

Ala Gln Cys Asn Met Thr Lys Asp Trp Phe Leu Ile Gln Met Leu Ala
770 775 780

Asn Tyr Asn Ile Gly Tyr Gln Gly Phe Tyr Ile Pro Glu Ser Tyr Lys
785 790 795 800

Asp Arg Met Tyr Ser Phe Phe Arg Asn Phe Gln Pro Met Ser Arg Gln
805 810 815

Val Val Asp Glu Thr Lys Tyr Lys Asp Tyr Gln Gln Val Gly Ile Ile
820 825 830

His Gln His Asn Asn Ser Gly Phe Val Gly Tyr Leu Ala Pro Thr Met
835 840 845

Arg Glu Gly Gln Ala Tyr Pro Ala Asn Phe Pro Tyr Pro Leu Ile Gly
850 855 860

Lys Thr Ala Val Asp Ser Val Thr Gln Lys Lys Phe Leu Cys Asp Arg
865 870 875 880

Thr Leu Trp Arg Ile Pro Phe Ser Ser Asn Phe Met Ser Met Gly Ala
885 890 895

Leu Thr Asp Leu Gly Gln Asn Leu Leu Tyr Ala Asn Ser Ala His Ala
900 905 910

Leu Asp Met Thr Phe Glu Val Asp Pro Met Asp Glu Pro Thr Leu Leu
915 920 925

Tyr Val Leu Phe Glu Val Phe Asp Val Val Arg Val His Gln Pro His
930 935 940

Arg Gly Val Ile Glu Thr Val Tyr Leu Arg Thr Pro Phe Ser Ala Gly
945 950 955 960

Asn Ala Thr Thr

<210> SEQ ID NO 22
<211> LENGTH: 578
<212> TYPE: PRT
<213> ORGANISM: Pan troglodytes

<400> SEQUENCE: 22

Met Lys Arg Thr Lys Thr Ser Asp Glu Ser Phe Asn Pro Val Tyr Pro
1 5 10 15

Tyr Asp Thr Glu Ser Gly Pro Pro Ser Val Pro Phe Leu Thr Pro Pro
20 25 30

Phe Val Ser Pro Asp Gly Phe Gln Glu Ser Pro Pro Gly Val Leu Ser
35 40 45

Leu Asn Leu Ala Glu Pro Leu Val Thr Ser His Gly Met Leu Ala Leu
50 55 60

-continued

```
Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
        195                 200                 205

Gly Ala Pro Leu His Val Val Asp Ser Leu Asn Ala Leu Thr Val Val
    210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
            260                 265                 270

Ala Tyr Pro Phe Asp Ala Gln Asn Asn Leu Ser Leu Arg Leu Gly Gln
        275                 280                 285

Gly Pro Leu Phe Val Asn Ser Ala His Asn Leu Asp Val Asn Tyr Asn
    290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Ala Gly Asp Gly Leu Gln Phe Asp Ser Gly Ser Asp Thr Asn
            340                 345                 350

Pro Leu Lys Thr Lys Leu Gly Leu Gly Leu Asp Tyr Asp Ser Ser Arg
        355                 360                 365

Ala Ile Ile Ala Lys Leu Gly Thr Gly Leu Ser Phe Asp Asn Thr Gly
    370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
        435                 440                 445

Val Thr Ser Ala Gln Ile Val Leu Arg Phe Asp Glu Asn Gly Val Leu
    450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
```

-continued

```
                485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Thr
        515                 520                 525

Leu Thr Ile Thr Leu Asn Gly Thr Asn Glu Thr Gly Asp Ala Thr Val
    530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu
```